US007087383B2

(12) United States Patent
Nakagawara

(10) Patent No.: US 7,087,383 B2
(45) Date of Patent: Aug. 8, 2006

(54) NUCLEIC ACID SEQUENCES SHOWING ENHANCED EXPRESSION IN BENIGN NEUROBLASTOMA COMPARED WITH ACRITICAL HUMAN NEUROBLASTOMA

(75) Inventor: Akira Nakagawara, Chiba (JP)

(73) Assignees: Hisamitsu Pharmaceutical Co., Inc., Saga (JP); Chiba-Perfecture, Chiba (JP)

( * ) Notice: Subject to any disclaimer, the term of this patent is extended or adjusted under 35 U.S.C. 154(b) by 0 days.

(21) Appl. No.: 10/220,891

(22) PCT Filed: Mar. 2, 2001

(86) PCT No.: PCT/JP01/01631

§ 371 (c)(1),
(2), (4) Date: Mar. 7, 2003

(87) PCT Pub. No.: WO01/66733

PCT Pub. Date: Sep. 13, 2001

(65) Prior Publication Data

US 2003/0207286 A1 Nov. 6, 2003

(51) Int. Cl.
*C12Q 1/68* (2006.01)
*C07H 21/04* (2006.01)

(52) U.S. Cl. ...................... 435/6; 536/23.5; 536/24.31; 536/24.33

(58) Field of Classification Search .................... 435/6; 536/23.5, 24.31, 24.33
See application file for complete search history.

(56) References Cited

U.S. PATENT DOCUMENTS

| | | | | |
|---|---|---|---|---|
| 4,683,202 | A * | 7/1987 | Mullis | 435/91.2 |
| 5,424,186 | A | 6/1995 | Fodor et al. | |
| 5,807,522 | A | 9/1998 | Brown et al. | |
| 6,255,468 | B1 * | 7/2001 | Southan et al. | 536/23.1 |
| 6,426,186 | B1 * | 7/2002 | Jones et al. | 435/6 |
| 6,756,212 | B1 * | 6/2004 | Curtis et al. | 435/69.1 |

OTHER PUBLICATIONS

1996 SIGMA Catalog, p. 1513.*

Holmes et al., J. Biol. Chem. 274(33), 23491-23498 (1999).*

Accession No. AA046951 (1997).*

Accession No. AI802048 (1999).*

Accession No. AI056359 (1998).*

Database EMBL Online, "mRNA for KIAA0327", Database Accession No. AB002325—Document No. XP002283249 (Jul. 1, 1997).

Database EMBL Online, "EST", Database Accession No. AA578755—Document No. XP002283250 (Sep. 11, 1997).

Database EMBL Online, "EST", Database Accession No. AA999664—Document No. XP002283251 (Jun. 8, 1998).

Tang et al., "High-Level Expression of *EPHB6, EFNB2,* and *EFNB3* Is Associated with Low Tumor Stage and High *TrkA* Expression in Human Neuroblastomas", Clinical Cancer Research, vol. 5, pp. 1491-1496—Document No. XP-002283248 (Jun. 1999).

Database EMBL Online, "Microsatellite Sequence From Clon TGLA357", Database Accession No. AAQ33965—Document No. XP002283252 (Feb. 2, 1993).

Database EMBL Online, "Sequence 415," Database Accession No. I31503—Document No. XP002283253 (Feb. 13, 1997).

Database EM_HUM, EMBL, "*Homo sapiens* Clone 25048", Database Accession No. AF131776—Document No. XP002296850 (Mar. 15, 1999).

Database EM_EST, EMBL, "*Homo sapiens* mRNA", Database Accession No. HSM016129, Document No. XP002296851 (Feb. 20, 2000).

Database EM_EST, EMBL, "*Homo sapiens* mRNA", Database Accession No. HSM018419, Document No. XP002296852 (Feb. 20, 2000).

Database EM_EST, EMBL, "*Homo sapiens* cDNA", Database Accession No. HSAA45741, Document No. XP002296853 (Mar. 3, 2000).

Database EM_EST, EMBL, "IB 467 Infant Brain", Database Accession No. HST03555, Document No. XP002296854 (Mar. 4, 2000).

Database GSN, EMBL, "Human Nervous Sstem Related Polynucleotide Seq ID No. 1205", Database Accession No. ABA12198, Document No. XP002296855 (Jan. 17, 2001).

Database EM_PAT, EMBL, "Sequence 3 From Patent WO9720068", Database Accession No. A62991, Document No. XP002297150 (Mar. 12, 1998).

Nakagawara, Shinkeigashu no Hassel to Sono Bunshi Kiko [Neuroblastoma Development and Molecular Mechanism], Shoni Naika 30, 143, 1998.

Kundson et al., "Regression of Neuroblastoma IV-S: A Genetic Hypothesis," The New England Journal of Medicine, 302, pp. 1254-1256, May 29, 1980.

Nakagawara, Akira, "The NGF Story and Neuroblastoma," Medical and Pediatric Oncology, vol. 31, pp. 113-115 (1998).

Nakagawara et al., Shinkeigasarboushu ni Okeru Neutrophin Juyoutai no Hatsugen to Yogo, [Expression of Neurotrophin Receptors and Prognosis I Neuroblastomal], Shoni Geka (Pediatric Surgery), vol. 29, pp. 425-432 (1997).

(Continued)

*Primary Examiner*—Kenneth R. Horlick
(74) *Attorney, Agent, or Firm*—Fitch, Even, Tabin & Flannery

(57) ABSTRACT

There are disclosed a nucleic acid which is derived from the gene expressed in human neuroblastoma, and which comprises any sequence selected from the group consisting of the nucleic acid sequences set forth SEQ ID NO:1 to NO:104 in the Sequence Listing, or its complementary nucleic acid; a fragment of the nucleic acid; their use as probes or primers; and the diagnosis of neuroblastoma prognosis using any of the foregoings.

14 Claims, 4 Drawing Sheets

OTHER PUBLICATIONS

Nakagawara, Nou-shinkeishuyo no Tadankai Hatsugan [Multistage Oncogenesis of Cerebral and Neural Tumors]. Molecular Medicine, vol. 36, No. 4, pp. 366-372 (1999).

Naldini et al., "In Vivo Gene Delivery and Stable Transduction of Nondividing Cells by a Lentiviral Vector," Science, vol. 272, pp. 263-267 (Apr. 12, 1996).

Nagase et al., "Prediction of the Coding Sequences of Unidentified Human Genes. VII. The Complete Sequences of 100 New cDNA Clones from Brain Which Can Code for Large Proteins *in vitro*," DNA Research, vol. 4, pp. 141-150 (1997).

* cited by examiner nbla-00106 nbla-00219 nbla-03145

NUCLEIC ACID SEQUENCES SHOWING ENHANCED EXPRESSION IN BENIGN NEUROBLASTOMA COMPARED WITH ACRITICAL HUMAN NEUROBLASTOMA

CROSS-REFERENCED APPLICATIONS

This application is a National phase of International Application PCT/JP01/01631, filed Mar. 2, 2001, which designated the U.S. and that International Application was not published under PCT Article 21(2) in English.

TECHNICAL FIELD

This invention relates to nucleic acids derived from genes expressed in human neuroblastomas. More specifically, the invention relates to nucleic acids and their fragments derived from the genes whose expression is enhanced in human neuroblastoma with favorable prognosis based on comparison between human neuroblastoma with favorable prognosis and human neuroblastoma with unfavorable prognosis as well as to their utility in the diagnosis of prognosis for human neuroblastomas.

BACKGROUND ART

Individual tumors exhibit distinct characteristic natures, and their biological properties are not necessarily identical even though the basic principle of oncogenesis is the same. Rapid advances in the understanding of cancer from a molecular biological and molecular genetic perspective in recent years have opened the way to an explanation of oncogenesis and tumor cell biology on the genetic level.

(Neuroblastomas)

Neuroblastoma is a pediatric cancer occurring in sympathetic gangliocytes and adrenal medullary cells which originate from cells of the peripheral sympathetic nervous system. Of these sympathetic nervous system cells, neural crest cells in the initial stage of development migrate to the abdomen, differentiating and maturing at sites where sympathetic ganglia are formed. Some of these cells migrate further to the adrenal bodies, penetrating through the adrenal cortex which is already in the process of formation, and reaching the medulla and forming medullary substance there. The neural crest cells also serve as a source of other peripheral nerve cells, differentiating into dorsal root ganglia (sensory nerves), skin pigment cells, thyroid C cells, some pulmonary cells, intestinal gangliocytes, and the like.

(Prognosis for Neuroblastoma)

Neuroblastoma is characterized by a varied clinical profile (Nakagawara, Shinkeigashu no Hassei to Sono Bunshi Kiko [Neuroblastoma Development and Molecular Mechanism], Shoni Naika 30, 143, 1998). For example, neuroblastomas occurring at less than one year of age have very favorable prognosis, with the majority undergoing differentiation and cell death, and spontaneous regression. Currently, most neuroblastomas discovered by a positive result in the commonly performed mass screening of 6-month-old infant urine are of the type which tend to undergo this spontaneous regression. On the other hand, neuroblastomas occurring at age 1 or higher are highly malignant and lead to death of the infant in the majority of cases. It is also hypothesized that a somatic mutation occurs in highly malignant neuroblastomas in infants older than one year of age, which are of monoclonal nature, whereas in naturally regressing neuroblastomas, the genetic mutation remains at only a germline mutation. See Knudson A G, et al.: Regression of neuroblastoma IV-S: A genetic hypothesis, N. Engl. J. Med. 302, 1254 (1980)).

(Tumor Markers which Allow the Diagnosis of Prognosis for Neuroblastoma)

With recent advances in molecular biology research, it has become clear that expression of the high affinity nerve growth factor (NGF) receptor TrkA is closely connected with control of differentiation and cell death. See Nakagawara A., The NGF story and neuroblastoma, Med. Pediatr. Oncol., 31, 113 (1998). Trk is a membrane-spanning receptor, existing as the three main types, Trk-A, -B and -C. These Trk family receptors play an important role in specific nerve cell differentiation and survival in the central nervous and peripheral nervous systems. See Nakagawara, et al., Shinkeigasaiboushu ni Okeru Neurotrophin Juyoutai no Hatsugen to Yogo [Expression of Neurotrophin Receptors and Prognosis in Neuroblastoma], Shoni Geka (Pediatric Surgery), 29:425–432, 1997. The survival and differentiation of tumor cells is controlled by signals from Trk tyrosine kinase and Ret tyrosine kinase. In particular, the role of TrkA receptor is most significant, with TrkA expression being notably high in neuroblastomas with favorable prognosis, and its signals exerting a powerful control over survival and differentiation of tumor cells, and cell death (apoptosis). In neuroblastomas with unfavorable prognosis, on the other hand, TrkA expression is significantly suppressed, while tumor development is aided by a mechanism in which survival is promoted by signals from TrkB and Ret.

It has become clear that amplification of the neural oncogene N-myc has become clearly associated with the prognosis of neuroblastoma. See Nakagawara, Noushinkeishuyo no Tadankai Hatsugan [Multistage Oncogenesis of Cerebral and Neural Tumors], Molecular Medicine, 364, 366(1999). This gene, first cloned in neuroblastoma, is ordinarily only present in a single copy per haploid set in normal cells and neuroblastomas with favorable prognosis, whereas it has been found to be amplified several dozen times in neuroblastomas with unfavorable prognosis. Thus, amplification of N-myc is closely linked to tumor progression.

Up till the present time, however, no oncogene other than N-myc is known to be expressed in neuroblastomas, and absolutely no genetic information other than that of N-myc has been known in relation to favorable or unfavorable prognosis.

DISCLOSURE OF THE INVENTION

This invention has been accomplished in light of the circumstances described above, and its object is to identify the information of genes which are expressed in neuroblastomas, to further identify the information of the genes which is related to favorable or unfavorable prognosis, and to allow the diagnosis for favorable or unfavorable prognosis of neuroblastoma based on that genetic information.

In the course of conducting diligent research in line with the aforementioned object, the present inventors have examined the prognoses of neuroblastomas and have succeeded in constructing cDNA libraries from clinical tissues with favorable prognosis and unfavorable prognosis. Approximately 2400 clones were respectively obtained from these two types of cDNA libraries and were classified according to the prognosis of neuroblastoma (whether favorable or unfavorable).

The present inventors further determined the partial or whole sequences of these cloned genes, and upon performing a homology search, selected suitable genes.

Moreover, upon comparing the classified gene groups as described above against the selected genes, the present inventors found that the expression of a considerable number of the genes is enhanced only in clinical tissues of neuroblastoma with favorable prognosis.

Based on such knowledge, the present inventors have succeeded in providing genetic information (nucleic acid sequence information etc.) for the detection and cloning of the genes only expressed in human neuroblastomas with favorable prognosis. Furthermore, based on the aforementioned nucleic acid sequence information it has been made possible to carry out the method for detection of prognosis and to design tumor markers which can be used therefor, and this invention has thereupon been completed.

Specifically, this invention provides the nucleic acids and nucleic acid fragments described under 1. to 8. below. The invention further provides uses for those nucleic acids and nucleic acid fragments as described under 9 to 11. below.

1. A nucleic acid derived from a gene expressed in human neuroblastoma, the nucleic acid comprising a sequence selected from the group consisting of the nucleic acid sequences set forth in SEQ ID NO:1 to NO:104 in the Sequence Listing, or its complementary nucleic acid.

2. The nucleic acid according to 1. above, characterized in that the nucleic acid is DNA.

3. A nucleic acid derived from a gene whose expression is enhanced in human neuroblastoma with favorable prognosis based on comparison between human neuroblastoma with favorable prognosis and human neuroblastoma with unfavorable prognosis, the nucleic acid comprising a sequence selected from the group consisting of the nucleic acid sequences set forth in SEQ ID NO:1 to NO:104 in the Sequence Listing, or its complementary nucleic acid.

4. The nucleic acid according to 3. above, characterized in that the nucleic acid is DNA.

5. A fragment of the nucleic acid according to any one of 1. to 4. above.

6. An isolated nucleic acid which can hybridize to the nucleic acid according to any one of 1. to 4. above under stringent conditions.

7. The isolated nucleic acid according to 6. above, characterized in that the nucleic acid is DNA.

8. A PCR primer comprising the nucleic acid according to 7. above.

9. A method of diagnosing the prognosis of human neuroblastoma, the method comprising detecting the nucleic acid according to 3. above from clinical tissue of human neuroblastoma.

10. A diagnosis kit for the prognosis of human neuroblastoma, containing a pair of PCR primers according to 8. above.

Accordingly, preferred as the nucleic acid described above is nucleic acid derived from a gene whose expression is enhanced only in human neuroblastoma with favorable prognosis, upon comparison between human neuroblastoma with favorable prognosis and human neuroblastoma with unfavorable prognosis, as information relating to the sequence of said nucleic acid will allow the diagnosis for prognosis of human neuroblastoma.

BEST MODE FOR CARRYING OUT THE INVENTION

Figure 1:
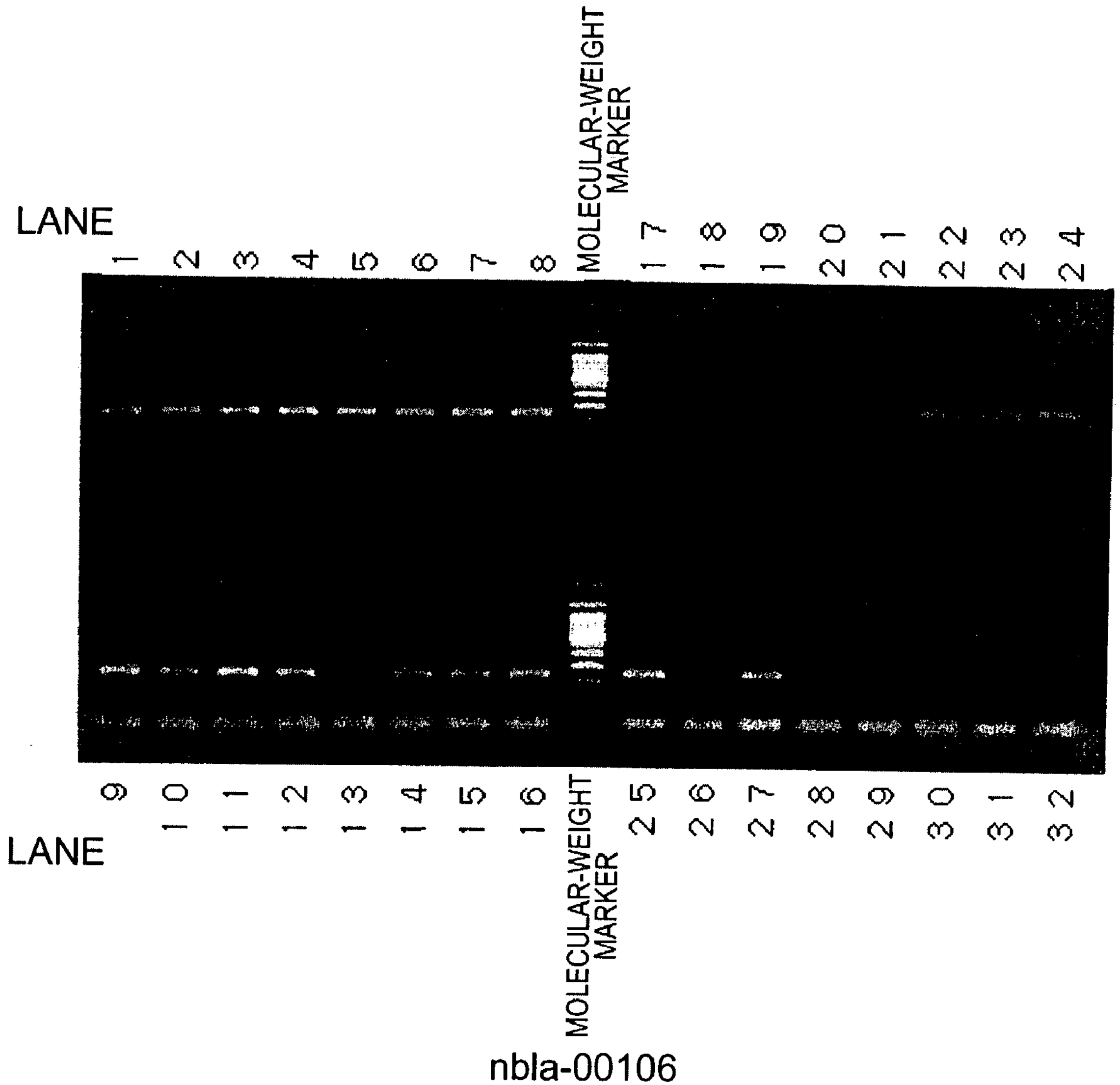
FIG. 1 is an illustration corresponding to an electrophoregram showing an example of a gene whose expression was found enhanced in human neuroblastomas with favorable prognosis (the result from nucleic acid sequence nbla-00106), as a result of examining the level of gene expression in human neuroblastomas with favorable prognosis and with unfavorable prognosis by semi-quantitative PCR. In the figure, Lanes 1–16 are clinical tissue specimens of human neuroblastomas with favorable prognosis. On the other hand, Lanes 17–32 are clinical tissue specimens of human neuroblastomas with unfavorable prognosis.

The nucleic acids derived from the genes expressed in human neuroblastomas according to this invention (hereinafter referred to as "genes of the invention") and their related nucleic acid fragments (hereinafter referred to respectively as "nucleic acids of the invention" and "nucleic acid fragments of the invention", or where distinction between the nucleic acids and their fragments is not particularly necessary in description, they will be collectively referred to as "nucleic acids of the invention") will now be explained in greater detail, with reference to preferred embodiments of the invention.

The nucleic acids of the invention are derived from the genes of the invention as mentioned above, and they either constitute the genes or are obtained from the genes by in vivo or in vitro procedures. The term "nucleic acids" as used throughout the present specification refers to, for example, DNA or RNA, or polynucleotides derived therefrom which are active as DNA or RNA, and preferably they are DNA or RNA. Particularly preferred nucleic acids either have sequences identical to the human cDNA sequences disclosed in the present specification or have sequences complementary thereto.

The term "hybridize under stringent conditions" as used in the present specification means that two nucleic acids (or fragments) hybridize to each other under the hybridization conditions described by Sambrook, J. et al. in "Expression of cloned genes in *E. coli*", Molecular Cloning: A Laboratory Manual (1989), Cold Spring Harbor Laboratory Press, New York, USA, 9.47–9.62 and 11.45–11.61.

More specifically, the "stringent conditions" refers to hybridization at approximately 45° C., 6.0×SSC, followed by washing at 50° C., 2.0×SSC. The stringency may be selected by choosing a salt concentration in the washing step from approximately 2.0×SSC, 50° C. as low stringency to approximately 0.2×SSC, 50° C. as high stringency. Also, the temperature in the washing step may be increased from room temperature, or approximately 22° C. as low stringency conditions, to approximately 65° C. as high stringency conditions.

The term "isolated nucleic acid" as used throughout the present specification refers to a nucleic acid or a polynucleotide containing substantially no cellular substances or culture medium, if prepared by recombinant DNA techniques, or containing substantially no precursor chemical substances or other chemical substances, if prepared by chemical synthesis.

The term "favorable prognosis" as used throughout the present specification refers to a condition of human neuroblastoma in which the tumor is localized or has become a regressing or benign sympathetic ganglion neoplasm, and is judged by a physician to have low malignancy based on N-myc or other tumor markers (TrkA, chromosomal aberration, etc.). According to a preferred embodiment of the invention, a favorable prognosis is a case of stage 1 or 2, with an onset age of less than one year and survival without recurrence for 5 or more years after surgery, and with no amplification of N-myc in the clinical tissue; however, there is no limitation to such specific cases. The term "unfavorable prognosis" as used throughout the present specification refers to a condition of human neuroblastoma in which progression of the tumor has been observed, and it is judged by a physician to have high malignancy based on N-myc or other tumor markers. According to a preferred embodiment of the invention, an unfavorable prognosis is a case of stage 4, with an onset age of greater than one year, death within 3 years after surgery and amplification of N-myc in the clinical tissue; however, there is no limitation to such specific cases.

Neuroblastoma is a tumor consisting of actual nerve cells, of which only two types of tumor are known in humans, and analysis of the genes expressed therein is expected to provide very useful knowledge for understanding the biology of nerve cells. Specifically, it is extremely difficult, and practically impossible, to obtain site-specific homogeneous tissue from the brain or peripheral nerves. On the other hand, a neuroblastoma consists of an almost homogeneous nerve cell population (though tumorized) derived from peripheral sympathetic nerve cells, and thus offers a high possibility of obtaining homogeneous expression of neuro-related genes. Furthermore, since neuroblastoma is a type of cancer, it will characteristically have many important genes expressed in the immature stage of neurogenesis.

Clinically and biologically, neuroblastoma can be neatly classified into favorable prognosis and unfavorable prognosis types. Cancer cells from neuroblastoma with favorable prognosis are characterized by having a very slow rate of proliferation, with spontaneous regression beginning at some point. Findings to date have confirmed that nerve cell differentiation and apoptosis (nerve cell death) occur in the spontaneous regression, and that the differentiation which occurs in the maturation stages of normal nerve cells and programmed cell death are phenomena very closely resembling each other. Consequently, it is highly probable that the analysis of genes expressed in such tumors will lead to obtaining important genetic information relating to nerve cell differentiation and apoptosis.

Neuroblastomas with unfavorable prognosis are tumors consisting of cancer cells which continue to exhibit definitely malignant proliferation. The probability is very high, therefore, that they have a large number of important genes connected with nerve cell proliferation or genes expressed in undifferentiated nerve cells. In other words, it is highly probable that these will allow the obtainment of genetic information completely different from the profile of genes expressed in neuroblastomas with favorable prognosis.

It is commonly reported that nerve cells contain more expressed gene types than cells derived from other organs. Neuroblastoma cell lines are derived from clinical tissues with unfavorable prognosis, and it is believed that the gene expression profile in the case of tumor development and progression is substantially altered from that of normal nerve cells.

Neuroblastoma is characteristically a pediatric tumor, and because of the very low possibility of effects by acquired factors, it is expected that analysis of the mechanism of cancerization will also yield embryological information with high probability. More surprisingly, the nucleic acids of the invention include nucleic acids of genes whose expression is enhanced only in specific cell cycle phases, and this further suggests the very strong possibility of obtaining genetic information highly useful for the analysis of cancerization mechanisms and related to development and differentiation.

The nucleic acids of the invention, having the various characteristics mentioned above and derived from the genes which can yield useful genetic information, are obtained from human neuroblastoma clinical tissues and have any of the nucleic acid sequences set forth in SEQ ID NO:1 to NO:104 in the Sequence Listing, or a portion thereof.

As a result of comparing levels of expression of the genes according to this invention in clinical tissues from human neuroblastomas with favorable prognosis and with unfavorable prognosis, a highly significant difference was found in the genes corresponding to the nucleic acid sequences set forth I SEQ ID NO:1 to NO:104 in the Sequence Listing. That is, expression of these genes was enhanced in human neuroblastomas with favorable prognosis. Thus, in addition to providing the useful genetic information described above, the nucleic acid sequences set forth in SEQ ID NO:1 to NO:104 can also be utilized as data for tumor markers to diagnose favorable or unfavorable prognosis of neuroblastoma, by detecting the nucleic acid having any of these nucleic acid sequences.

Specifically, this invention will make it possible to obtain various gene information on or relating to human neuroblastoma through the following means.

(1) Probes for Hybridization

According to one embodiment of this invention, the nucleic acids of the invention or their fragments may be used as probes for hybridization in order to detect genes expressed in human neuroblastoma. The nucleic acids of the invention or their fragments may also be used as probes for hybridization in order to determine gene expression in various tumors and normal tissues, to identify the distribution of the gene expression.

When the nucleic acids of this invention or their fragments are used as probes for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization, the nucleic acid of this invention or its fragment may be used as a probe for Northern hybridization to measure the length of mRNA or to quantitatively detect gene expression in a sample to be examined.

As another application example, the nucleic acid of the invention or its fragment may be used as a probe for Southern hybridization to detect the presence or absence of the DNA sequence in genomic DNA of a sample to be examined.

As still another application example, the nucleic acid of the invention or its fragment may be used as a probe for fluorescence in situ hybridization (FISH) to identify the location of the gene on a chromosome.

As yet another application example, the nucleic acid of the invention or its fragment may be used as a probe for in situ hybridization to identify the tissue distribution of gene expression.

When the nucleic acid of the invention or its fragment is used as a probe for hybridization, a nucleic acid residue length of at least 40 is necessary; and among the nucleic acids and their fragments of the invention, the one with 40 or more contiguous residues or its fragment is preferably used. More preferably, the one with 60 or more residues is used.

Nucleic acid probe techniques for the types of hybridization mentioned above are well known to one skilled in the art, and for example, conditions suitable for hybridization between a nucleic acid probe of various lengths according to the invention and target polynucleotide may be readily determined. For example, Sambrook et al. described in "Molecular Cloning: A Laboratory Manual, loc. cit. may be followed for such manipulations which are well known to one skilled in the art.

A probe according to this invention is preferably labeled in an easily detectable fashion. The detectable label may be an element or compound, of any type which can be detected either visually or using devices. As commonly used detectable labels there may be mentioned radioactive isotopes, avidin or biotin, and fluorescent substances (FITC, rhodamine, and the like). The radioactive isotopes include $^{32}P$, $^{14}C$, $^{125}I$, $^{3}H$ and $^{35}S$. Biotin-labeled probes are detected after hybridization using labeling means such as avidin/streptavidin, fluorescent labels, enzymes, gold colloidal complexes or the like. A probe according to the invention may also be labeled by binding with a protein. Radioactive or fluorescent histone single-stranded DNA binding protein may be used for this purpose.

(2) Primers for use in PCR

In addition to hybridization for the detection of target genes (e.g., the genes according to this invention), any nucleic acid sequence included in the nucleic acid of the invention or its fragment may be used as a primer in a polymerase chain reaction (PCR). For example, mRNA may be extracted from a sample to be examined, and the gene expression may be semi-quantitatively measured by RT-PCR. This may be carried out by a method well known to one skilled in the art. See, for example, Sambrook et al. described in "Molecular Cloning: A Laboratory Manual," loc. cit. and Idenshibyo Nyumon [Introduction to Genetic Diseases] (Takahisa, S.: Nankodo Publishing).

When the nucleic acid of this invention or its fragment is used as a PCR primer, a nucleic acid residue length of 10 to 60 is necessary; and among the nucleic acids of the invention and their fragments, the one with 10 to 60 contiguous residues or its fragment is preferably used. More preferably, the one with 15 to 30 residues is used. In most cases, a primer sequence with a GC content of 40–60% is preferred. Also, there is preferably no difference in the Tm values of the two primers used for amplification. Preferably there is no annealing at the 3' ends of the primers and no secondary structure is formed in the primers.

(3) Gene Screening

A nucleic acid of the invention or its fragment may also be used to detect the expression distribution of a target gene which is expressed in various tissues or cells. This may be accomplished, for example, by using the nucleic acid of the invention or its fragment as a probe for hybridization or as a primer for PCR, as described above.

Expression distribution of a target gene can also be detected using a DNA chip, microarray or the like. That is, the nucleic acid of the invention or its fragment may be directly attached to the chip or array. For this purpose, methods for spotting such a nucleic acid (DNA) onto plates using a high precision dispenser are known (see, for example, U.S. Pat. No. 5,807,522). mRNA extracted from cells of a tissue specimen may be labeled there with a fluorescent substance or the like, hybridized, and an analysis may be made of the type of tissue cells with high expression of the gene. The DNA attached to the chip or array may be the reaction product of PCR using the nucleic acid of the invention or its fragment as the primer. Alternatively, nucleic acid fragments of the invention may be directly synthesized on a substrate to prepare a DNA chip or array (see, for example, U.S. Pat. No. 5,424,186).

(4) Gene Cloning

The nucleic acid of this invention or its fragment may be used for cloning a gene which is expressed in human neuroblastoma. For example, by using the nucleic acid of the invention or its fragment as a probe for northern hybridization or southern hybridization, or as a primer for PCR, cloning of a gene containing the nucleic acid of the invention or its fragment is possible. As the genes subjected to such cloning there may be mentioned genes with differing levels of expression particularly between neuroblastoma with favorable prognosis and neuroblastoma with unfavorable prognosis, genes whose forms of expression differ in other tissues or cancer cells, genes whose expression is cell cycle phase-dependent, genes induced upon neurodifferentiation and genes whose expression is regulated by oncogenes or tumor suppressor genes. The cloning may be carried out according to ordinary gene recombination techniques, by incorporating the nucleic acid of the invention or its fragment into an appropriate plasmid or bacteriophage to construct an expression vector, introducing this into host cells for transformation (or transduction), and culturing the transformants. The individual manipulations for this procedure are described in detail by Sambrook et al. in "Molecular Cloning: A Laboratory Manual," loc. cit., as well as in other well-known literature.

(5) Methods of Diagnosing Tumor Prognosis and Tumor Markers to be Used Therefor

As mentioned above, the genes related to the nucleic acids of this invention have their expression enhanced in human neuroblastomas with favorable prognosis. The nucleic acid (DNA) of the invention or its fragment may therefore be used as a probe for hybridization, or as a primer for PCR to allow the identification of prognosis. Specifically, this may be accomplished by examining whether the expression of the gene is enhanced in a clinical tissue containing sample taken from a subject. The methods of detecting the gene include Northern blotting hybridization, in situ hybridization and RT-PCR, as mentioned above among others.

When hybridization is employed, prognosis may be diagnosed as favorable if the amount of nucleic acid hybridizing to the probe is increased in the sample. When RT-PCR is employed, mRNA is extracted from the sample and reverse transcribed into DNA, amplification is performed using the aforementioned primer, and the gene expression is semi-quantitatively measured. The prognosis may be diagnosed as favorable if the gene expression is then found to be enhanced. For the purpose of such specific diagnosis it is preferred to utilize a diagnosis kit containing a pair of such primers as essential components. In addition to the primer components, the diagnosis kit also include known components such as PCR buffer, detergent solution and enzymes.

(6) Antisense Oligonucleotides

According to another embodiment of this invention there are provided antisense oligonucleotides to the nucleic acids of the invention. The antisense oligonucleotides are capable of hybridizing to the nucleic acids of the invention, and include antisense DNAs and antisense RNAS. Antisense DNA inhibits transcription of mRNA from DNA, while antisense RNA inhibits translation of mRNA. Native types of such antisense oligonucleotides may be synthesized using an automated synthesizer or by PCR using the nucleic acid of the invention as templates. The antisense oligonucleotides also encompass antisense oligonucleotide derivatives having improved binding affinity for the target DNA or mRNA, tissue selectivity, cell permeability, nuclease resistance and intracellular stability. Such derivatives may be synthesized using antisense technology known in the art.

Antisense oligonucleotides having sequences complementary to the sequences near the translation initiation codon of the mRNA, those of the ribosome-binding site, and those of the capping site or the splicing site are capable of inhibiting synthesis of the RNA and therefore will exhibit a particularly notable inhibitory effect on gene expression. This invention therefore encompasses such antisense oligonucleotides.

(7) Gene Therapy

According to a further embodiment of this invention, there are provided nucleic acid sequences encoding the therapeutic genes to be used in gene therapy. Thus, the nucleic acid of the invention can be transferred into a vector for use in gene transportation, whereby the transgene (i.e., the gene of the invention) can be expressed by an arbitrary expression promoter and can be used for the gene therapy of cancers, for example.

1. Vectors

The transferable viral vectors may be prepared from DNA viruses or RNA viruses. They may be any viral vector of an MoMLV vector, a herpes virus vector, an Adenovirus vector, an AAV vector, a HIV vector, a Seidai virus vector and the like. One or more proteins among the constituent protein group of a viral vector are substituted by the constituent proteins of a different species of virus, or alternatively a part of the nucleic acid sequence constituting genetic information is substituted by the nucleic acid sequence of a different species of virus to form a viral vector of the pseudo-type which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science 272, 263–267, 1996). Further, virues having a host spectrum other than human is usable as the viral vector insofar as they are efficacious. As for the vectors other than those of viral origin, there may be used complexes of calcium phosphate and nucleic acid, ribosomes, cation-lipid complexes, Seidai virus liposomes, polymer carriers having polycation as the main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SR α, a heat shock protein, and an elongation factor; chimera type promoters such as a CAG promoter; and the promoters whose expression can be induced by tetracyclines, steroids and the like.

The gene group discovered by this invention as being expressed in human neuroblastomas with favorable prognosis will now be explained in greater detail by way of the examples; however, the technical scope of the invention will not be restricted to those example.

EXAMPLES

Production Example 1 Construction of cDNA Library from Human Neuroblastoma

1. Obtaining Samples

Human neuroblastoma clinical tissue specimens were quasi-aseptically frozen immediately after surgical extraction and then preserved at −80° C.

2. Selecting Samples with Favorable Prognosis

Prognosis of the samples obtained in 1. above was carried out based on the following criteria.

| Favorable prognosis | Unfavorable prognosis |
|---|---|
| Stage 1 or 2 | Stage 4 |
| Age of onset: <1 | Age of onset: ≧1 |
| Survival for ≧5 years after surgery without recurrence | Death within 3 years after surgery |
| No amplification of N-myc | Amplification of N-myc |

Amplification of N-myc in the aforementioned two sample types was confirmed in the following manner.

The clinical tissue specimen obtained in 1. above was thinly sliced with a scalpel and then thoroughly homogenized after addition of 5 ml of TEN buffer (50 mM Tris-HCl (pH=8.0)/1 mM EDTA/100 mM NaCl). Upon adding 750 μl of SDS (10%) and 125 μl of proteinase K (20 mg/ml) to the mixture, it was gently stirred and allowed to stand at 50° C. for 8 hours. This was followed by phenol/chloroform treatment and finally ethanol precipitation to obtain purified genomic DNA. A 5 μg portion of the obtained genomic DNA was completely digested with the restriction endonuclease EcoRI (NEB Inc.), and an N-myc probe was used to determine amplification of N-myc by Southern hybridization.

3. Preparation of mRNA from Clinical Tissue of Human Neuroblastoma with Favorable Prognosis A 2–3 g portion of the clinical tissue samples of human neuroblastoma judged to have favorable prognosis in 2. above was treated using a Total RNA Extraction Kit (QIAGEN Inc.) and the total RNA was extracted. The extracted total RNA was purified using an oligo dT cellulose column (Collaborative Research, Inc.) to obtain a pool of mRNA with a polyA structure.

4. Dephosphorylation of mRNA

A 100–200 μg portion of the mRNA pool prepared in 3. above was dissolved in 67.3 μl of distilled sterile water containing 0.1% diethyl pyrocarbonate (DEPC), and then 20 μl of 5×BAP buffer (Tris-HCl (500 mM, pH=7.0)/mercaptoethanol (50 mM)), 2.7 μl of RNasin (40 unit/μl: Promega Inc.) and 10 μl of BAP (0.25 unit/μl, bacteria-derived alkali phosphatase: Takara Shuzo Co. Ltd.) were added. The mixture was reacted at 37° C. for 1 hour to effect dephosphorylation of the 5' end of the mRNA. This was followed by phenol/chloroform treatment two times, and finally ethanol precipitation to obtain a purified dephosphorylated mRNA pool.

5. Decapping of Dephosphorylated mRNA

The total amount of the dephosphorylated mRNA pool prepared in 4. above was dissolved in 75.3 μl of distilled sterile water containing 0.1% DEPC, and then 20 μl of 5×TAP buffer (sodium acetate (250 mM, pH=5.5)/mercaptoethanol (50 mM), EDTA (5 mM, pH=8.0)), 2.7 μl of RNasin (40 unit/μl) and 2 μl of TAP (tobacco acid pyrophosphatase:20 unit/μl) were added. The mixture was reacted at 37° C. for 1 hour to effect decapping treatment of the 5' end of the dephosphorylated mRNA. The dephosphorylated mRNA of incomplete length with no capped structure remained without decapping, and with the 5' end dephosphorylated. This was followed by phenol/chloroform treatment and ethanol precipitation to obtain a purified decapped mRNA pool.

6. PreDaration of OliQo-Capped mRNA

The total amount of the decapped mRNA pool prepared in 5. above was dissolved in 11 il of distilled sterile water containing 0.1% DEPC, and then 4 il of 5'-oligo RNA (5'-AGCAUCGAGUCGGCCUUGGCCUACUGG-3': 100 ng/il) (SEQ ID NO: 105), 10 il of 10×ligation buffer (Tris-HCl (500 mM, pH=7.0)/mercaptoethanol (100 mM)), 10 il of magnesium chloride (50 mM), 2.5 il of ATP (24 mM), 2.5il of RNasin (40 unit/il), 10 il of T4 RNA ligase (25 unit/il: Takara Shuzo Co. Ltd.) and 50 il of polyethylene glycol (50% w/v, PEG8000: Sigma Corporation) were added. The mixture was reacted at 20° C. for 3 hours for ligation of the 5'-oligo RNA to the 5' end of the decapped mRNA. The dephosphorylated mRNA of incomplete length with no capped structure resulted in no ligation to the 5'-oligo RNA. This was followed by phenol/chloroform treatment and ethanol precipitation to obtain a purified oligo-capped mRNA pool.

7. Removal of DNA from Oligo-Capped mRNA

The oligo-capped mRNA pool prepared in 6. above was dissolved in 70.3 μl of distilled sterile water containing 0.1% DEPC, and then 4 μl of Tris-HCl (1 M, pH=7.0), 5.0 μl of DTT (0.1 M), 16 μl of magnesium chloride (50 mM), 2.7 μl of RNasin (40 unit/μl) and 2 μl of DNaseI (5 unit/μl: Takara Shuzo Co. Ltd.) were added. The mixture was reacted at 37° C. for 10 minutes to dissolve the excess DNA. This was followed by phenol/chloroform treatment and ethanol precipitation and column purification (S-400HR: Pharmacia Biotech Inc.), to obtain a purified DNA(−) oligo-capped mRNA pool.

8. Preparation of 1st Strand cDNA

The DNA(−) oligo-capped mRNA pool prepared in 7. above was reverse transcribed using SuperScript II (kit by Life Tech Oriental, Inc.) to obtain a pool of 1st strand cDNA. The pool of DNA(−) oligo-capped mRNA was dissolved in 21 il of sterile distilled water, and then 10 il of 10× First Strand buffer (kit accessory), 8 il of dNTP mix (5 mM, kit accessory), 6 il of DTT (0.1 M, kit accessory), 2.5 il of oligo-dT adapter primer (5 pmol/il, 5'-GCGGCTGAAGACGGCCTATGTGGCC TTTTTTTTTTTTTTTTT-3'), (SEQ ID NO: 106) 2.0 il of RNasin (40 unit/il) and 2 il of SuperScript II RTase (kit accessory) were added. The mixture was reacted at 42° C. for 3 hours to effect reverse transcription. This was followed by phenol/chloroform treatment, alkali treatment and neutralization treatment to dissolve all the RNA and purification was carried out by ethanol precipitation.

9. Preparation of 2nd Strand cDNA

The 1st strand cDNA pool prepared in 8. above was subjected to PCR amplification using Gene Amp (kit by Perkin Elmer Inc.). The pool of 1st strand cDNA was dissolved in 52.4 il of sterile distilled water, and then 30 il of 3.3× Reaction buffer (kit accessory), 8 il of dNTP mix (2.5 mM, kit accessory), 4.4 il of magnesium acetate (25 mM, kit accessory), 1.6 il of Primer F (10 pmol/il, 5'-AGCATCGAGTCGGCCTTGTTG-3'), (SEQ ID NO: 107), 1.6 il of Primer R (10 pmol/il, 5'-GCGCTGAAGACGGCCTATGT-3') (SEQ ID NO: 108) and 2 il of rTth (kit accessory) were added. A 100 il portion of mineral oil was gently added to the mixture and overlayed thereon. After denaturing the reaction solution at 94° C. for 5 minutes, a cycle of 94° C. for 1 minute, 52° C. for 1 minute and 72° C. for 10 minutes was repeated 12 times, and then the solution was allowed to stand at 72° C. for 10 minutes to complete the PCR reaction. This was followed by phenol/chloroform treatment and ethanol precipitation to obtain a 2nd strand cDNA pool.

10. SfiI Treatment of 2nd Strand cDNA

The 2nd strand cDNA pool prepared in 9. above was dissolved in 87 μl of sterile distilled water, and then 10×NEB buffer (NEB Inc.), 100×BSA (bovine serum albumin available from NEB Inc.) and 2 μl of SfiI (restriction endonuclease, 20 unit/μl, NEB Inc.) were added. The mixture was reacted overnight at 50° C. to effect SfiI restriction endonuclease treatment. This was followed by phenol/chloroform treatment and ethanol precipitation to obtain a pool of cDNA which had been SfiI-treated at both ends.

11. Size Fractionation of SfiI-Treated cDNA

The SfiI-treated cDNA pool prepared in 10. above was electrophoresed on 1% agarose gel and a fraction with >2 kb was purified using Geneclean II (Bio101 Inc.). The purified cDNA pool was dissolved in 100 μl of sterile distilled water and allowed to stand at 37° C. for 6 hours. This was followed by phenol/chloroform treatment and ethanol precipitation to obtain a long-chain cDNA pool.

12. cDNA Library

The long-chain cDNA pool prepared in 11. above was ligated into the cloning vector pME18S-FL3 (provided by Prof. Sumio Kanno of the Institute of Medical Science, Tokyo University) using a DNA Ligation Kit ver. 1 (kit by Takara Shuzo Co. Ltd.). The long-chain cDNA pool was dissolved in 8 μl of sterile distilled water, and then 1 μl of pME18S-FL3 pretreated with restriction endonuclease DraIII, 80 μl of Solution A (kit accessory) and 10 μl of Solution B (kit accessory) were added and reaction was conducted at 16° C. for 3 hours. This was followed by phenol/chloroform treatment and ethanol precipitation for purification to obtain a cDNA library.

Example 2 Transformation into *E. coli*

1. Cloning

The cDNA library prepared in Example 1, 12. above was used for transformation into *E. coli* (TOP-10: Invitrogen Corporation). The cDNA library was dissolved in 10 μl of sterile distilled water and mixed with TOP-10. The mixture was then incubated on ice for 30 minutes, at 40° C. for 1 minute and on ice for 5 minutes. After adding 500 μl of SOB medium, shake culturing was performed at 37° C. for 60 minutes. Appropriate amounts thereof were seeded onto ampicillin-containing agar media and culturing was continued at 37° C. for a day and a night to obtain *E. coli* clones.

2. Preservation of *E. coli* Clones (Preparation of Glycerol Stock)

The *E. coli* clones on agar media obtained in 1. above were collected with toothpick and suspended in 120 μl of LB medium prepared in a 96-well plate. The 96-well plate was then allowed to stand overnight at 37° C. for culturing of the *E. coli.* A 72 μl portion of 60% glycerol solution was then added and preserved at −20° C. (glycerol stock)

Example 3 Nucleic Acid Sequence Determination

1. Preparation of Plasmid

The 10 μl of glycerol stock prepared in Example 2, 2. above was transferred to a 15 ml centrifugation tube, and then 3 ml of LB medium and 50 g g/ml of ampicillin were added and shaking was carried out overnight at 37° C. for culturing of the *E. coli.* A QIAprep Spin Miniprep Kit (QIAGEN Inc.) was then used to extract and purify a plasmid DNA from the *E. coli.*

2. Analysis of Both End Sequences

Both end sequences of the plasmid DNA prepared in 1. above were determined using a DNA Sequencing Kit (kit by ABI). There were combined 600 ng of plasmid DNA, 8 μl of premix (kit accessory) and 3.2 pmol of primers, and sterile distilled water was added to a total of 20 μl After denaturing the mixture at 96° C. for 2 minutes, a cycle of 96° C. for 10 seconds, 50° C. for 5 seconds and 60° C. for 4 minutes was repeated 25 times for reaction. The product was then purified by ethanol precipitation. Sequence determination was carried out by polyacrylamide gel electrophoresis under denaturing conditions, using ABI377 (ABI).

Example 4

Homology Search of Database

An internet nucleic acid sequence homology search was conducted for the nucleic acid sequence data obtained from the both end-sequence analysis in Example 3. The search was conducted using the BLAST database of the NCBI (National Center of Biotechnology Information, http://www.ncbi.nblm.nih.gov/BLAST).

Example 5

Comparison of Gene Expression Levels in Human Neuroblastomas with Favorable Prognosis and Unfavorable Prognosis by Semi-Quantitative PCR PCR primers were synthesized from the nucleic acid sequences of portions of the gene group obtained in Example 4, and the expression levels in the clinical tissues of human neuroblastomas with favorable prognosis and unfavorable prognosis were comparatively quantitated. mRNA was extracted from the human neuroblastoma clinical tissues by the method described in Examples 1–3, and rTaq (Takara Shuzo Co. Ltd.) was used for PCR reaction. Specifically, 5 μl of sterile distilled water, 2 μl of mRNA, 1 μl of 10×rTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 55° C. for 15 seconds and 72° C. for 20 seconds was repeated 35 times, and then the mixture was allowed to stand at 72° C. for 6 minutes for PCR reaction. The reaction solution was subjected to 1% agarose gel electrophoresis. Consequently, when the PCR primers based on the nucleic acid sequences set forth in SEQ ID NO:1 to NO:104 in the Sequence Listing were used in amplification, the genes whose expression was enhanced only in neuroblastomas with favorable prognosis were identified. Tables 1 and 2 show the information on the nucleic acid sequences set forth in SEQ ID NO:1 to NO:104, including the results of the homology search shown in Example 4 (73 nucleic acid sequences among 104 nucleic acid sequences had no homology).

Figure 2:
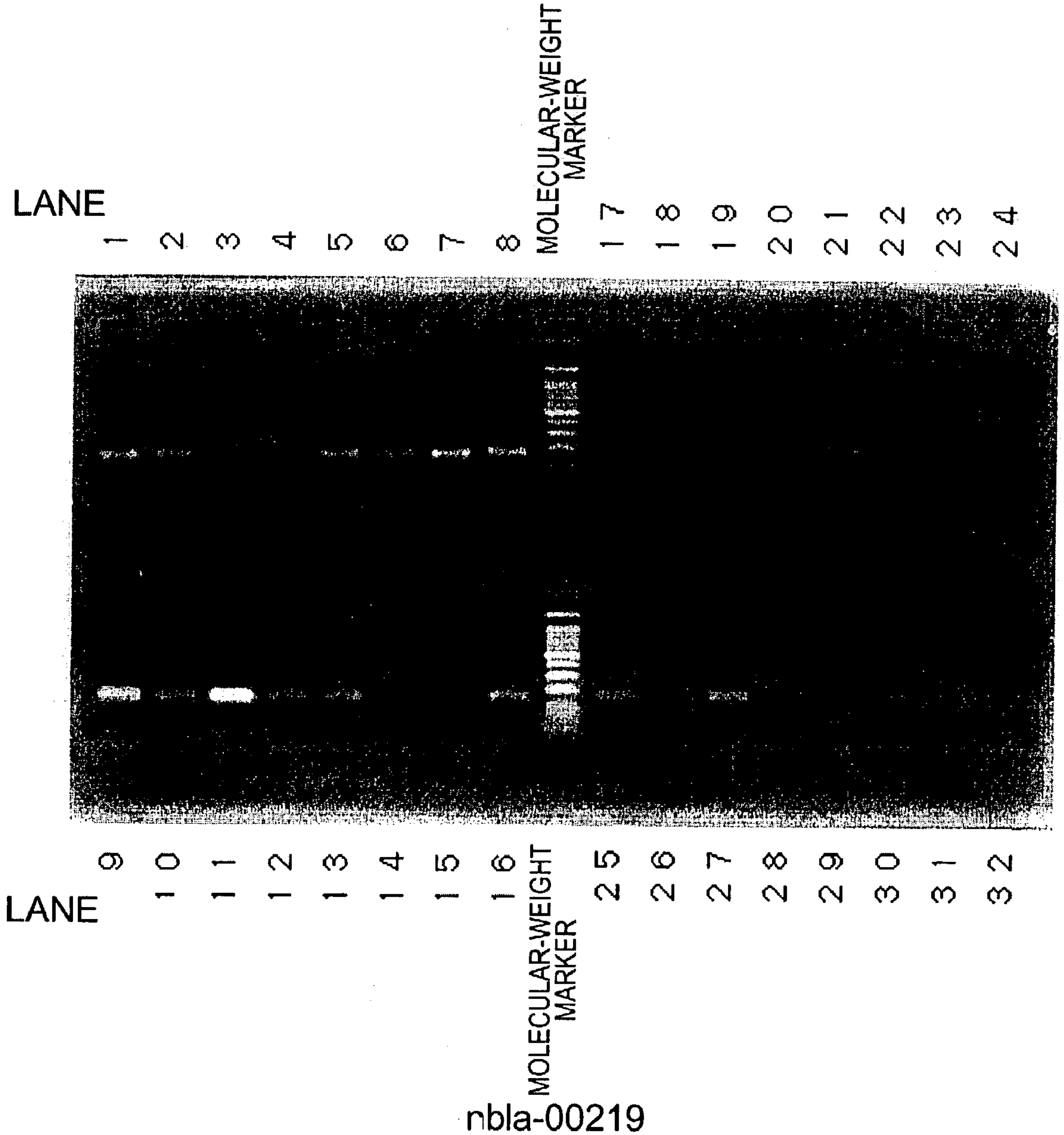
FIG. 2 is an illustration corresponding to an electrophoregram showing another example of a gene whose expression was found enhanced in human neuroblastomas with favorable prognosis (the result from nucleic acid sequence nbla-00219), as a result of examining the level of gene expression in human neuroblastomas with favorable prognosis and with unfavorable prognosis by semi-quantitative PCR. In the figure, Lanes 1–16 are clinical tissue specimens of human neuroblastomas with favorable prognosis. On the other hand, Lanes 17–32 are clinical tissue specimens of human neuroblastomas with unfavorable prognosis.
Figure 3:
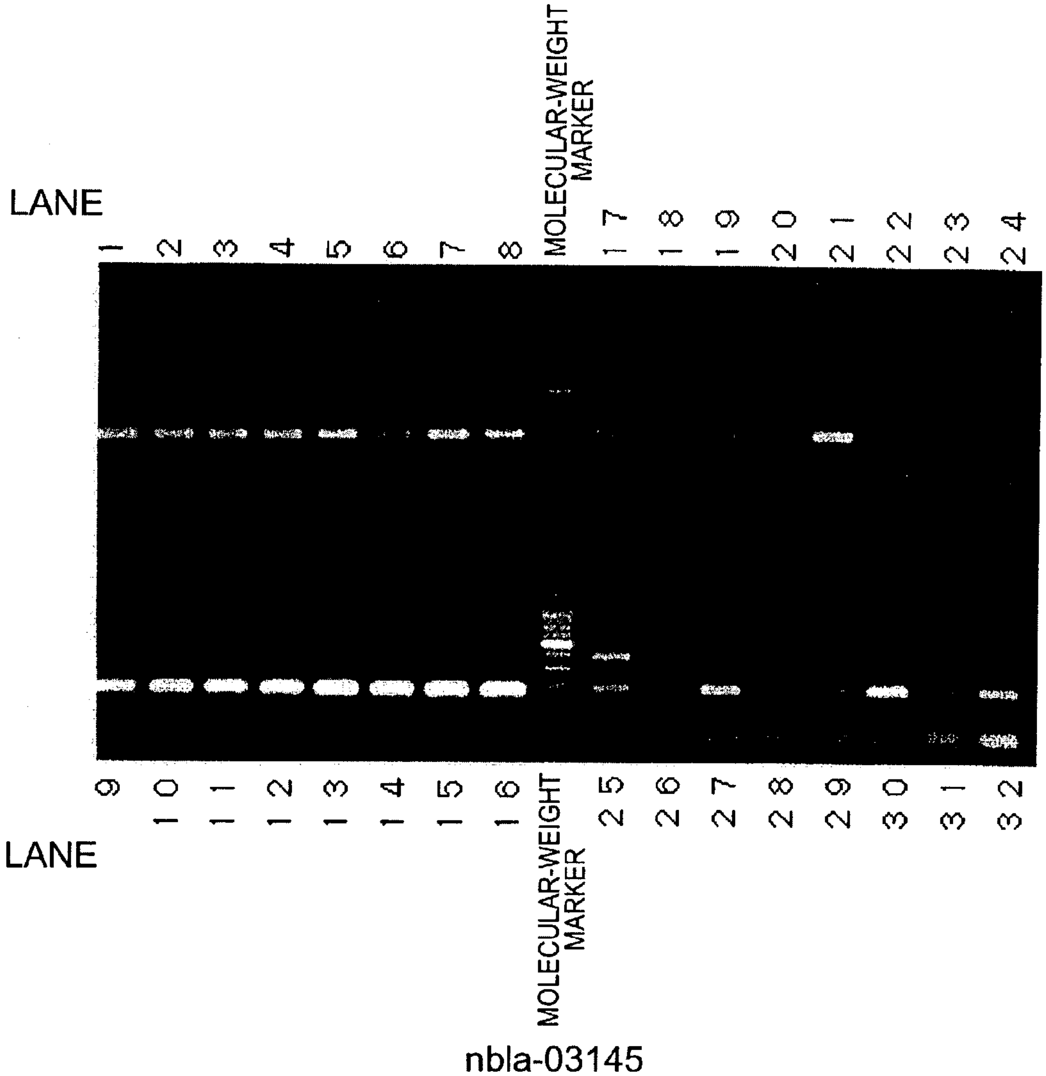
FIG. 3 is an illustration corresponding to an electrophoregram showing still another example of a gene whose expression was found enhanced in human neuroblastoma with favorable prognosis (the result from nucleic acid sequence nbla-03145), as a result of examining the level of gene expression in human neuroblastomas with favorable prognosis and with unfavorable prognosis by semi-quantitative PCR. In the figure, Lanes 1–16 are clinical tissue specimens of human neuroblastomas with favorable prognosis. On the other hand, Lanes 17–32 are clinical tissue specimens of human neuroblastomas with unfavorable prognosis.

Examples of the measurements of gene expression levels in human neuroblastomas with favorable prognosis and unfavorable prognosis by semi-quantitative PCR (Nucleic acid sequences nbla-00106, nbla-00219 and nbla-03145) are shown in FIGS. 1–3.

TABLE 1

| Nucleic acid sequences whose expression is enhanced in neuroblastomas with favorable prognosis | | | |
|---|---|---|---|
| SEQ ID | CLONE NAME | CELL CYCLE PHASE SPECIFICITY | HOMOLOGY (ACCESSION No.) |
| 1 | nbla-00002 | | KIAA0327(AB002325) |
| 2 | nbla-00012 | S PHASE | — |
| 3 | nbla-00052 | | — |
| 4 | nbla-00067 | | — |
| 5 | nbla-00078 | S PHASE | KIAA0322(AB002320) |
| 6 | nbla-00086-f | | GTPaseRAB6B(AF166492) |
| 7 | nbla-00086-r | | — |
| 8 | nbla-00100 | G2/M PHASE | KIAA0632(AB014532) |
| 9 | nbla-00106 | — | |
| 10 | nbla-00113 | | KIAA0874(AB020681) |
| 11 | nbla-00118 | | — |
| 12 | nbla-00126 | | MAB21L1(NM_005584) |
| 13 | nbla-00137 | | — |
| 14 | nbla-00150 | G2/M PHASE | SART-3(AB020880) |
| 15 | nbla-00158 | | — |
| 16 | nbla-00172 | G2/M PHASE | — |
| 17 | nbla-00177 | S PHASE | — |
| 18 | nbla-00204 | | — |
| 19 | nbla-00219 | | KIAA0367(AB002365) |
| 20 | nbla-00235 | G2/M PHASE | — |
| 21 | nbla-00237 | | — |
| 22 | nbla-00271 | | KIAA0886(AB020693) |
| 23 | nbla-00343 | | KIAA1145(AB032971) |
| 24 | nbla-00371 | S PHASE | — |
| 25 | nbla-00375 | | — |
| 26 | nbla-00418 | | — |
| 27 | nbla-00433 | | — |
| 28 | nbla-00437 | S PHASE AND G2/M PHASE | — |
| 29 | nbla-00490 | G2/M PHASE | T1-227H(D50525) |
| 30 | nbla-00538-f | | DKFZp586D1146(AL080222) |
| 31 | nbla-00538-r | | DKFZp566D1146(AL080222) |
| 32 | nbla-00613 | | — |
| 33 | nbla-00650 | | — |
| 34 | nbla-00652 | S PHASE AND G2/M PHASE | FLJ10739 fis(AK001601) |
| 35 | nbla-00660 | G2/M PHASE | — |
| 36 | nbla-00693 | | DKFZp434G0827(AL122107) |
| 37 | nbla-00697 | G1 PHASE AND S PHASE | — |
| 38 | nbla-00715 | | — |
| 39 | nbla-00744 | | — |
| 40 | nbla-00761 | S PHASE | KIAA0751(AB018294) |
| 41 | nbla-00830-f | | — |
| 42 | nbla-00830-r | | — |
| 43 | nbla-00831-f | | KIAA0868(AB020675) |
| 44 | nbla-00831-r | | KIAA0868(AB020675) |
| 45 | nbla-00832-f | | — |
| 46 | nbla-00832-r | | (AF140710) |
| 47 | nbla-02942 | | (NM_001788) |
| 48 | nbla-02975 | G1 PHASE | FLJ10103 fis(AK000965) |
| 49 | nbla-02981 | | — |
| 50 | nbla-02999 | G2/M PHASE | (AF182814) |
| 51 | nbla-03010 | G1 PHASE | — |
| 52 | nbla-03103 | G1 PHASE | — |
| 53 | nbla-03107-f | | KIAA1309(AB037730) |
| 54 | nbla-03107-r | | KIAA1309(AB037730) |

TABLE 2

| Nucleic acid sequences whose expression is enhanced in neuroblastomas with favorable prognosis | | | |
|---|---|---|---|
| 55 | nbla-03139 | S PHASE AND M PHASE | FOG2(NM_012082) |
| 56 | nbla-03145 | G1 PHASE | XCE(Y16187) |
| 57 | nbla-03199-f | S PHASE | — |
| 58 | nbla-03199-r | S PHASE | — |
| 59 | nbla-03212-f | S PHASE | — |

TABLE 2-continued

| Nucleic acid sequences whose expression is enhanced in neuroblastomas with favorable prognosis | | | |
|---|---|---|---|
| 60 | nbla-03212-r | S PHASE | — |
| 61 | nbla-03219-f | | — |
| 62 | nbla-03219-r | | — |
| 63 | nbla-03301-f | S PHASE | NF-L(X05608) |
| 64 | nbla-03301-r | S PHASE | — |
| 65 | nbla-03461-f | | — |
| 66 | nbla-03461-r | | — |
| 67 | nbla-03539-f | S PHASE | — |
| 68 | nbla-03539-r | S PHASE | — |
| 69 | nbla-03575-f | S PHASE AND G2/M PHASE | KIAA0517(AB011089) |
| 70 | nbla-03575-r | S PHASE AND G2/M PHASE | — |
| 71 | nbla-03646-f | | KIAA0018(D13643) |
| 72 | nbla-03646-r | | KIAA0018(D13643) |
| 73 | nbla-03684-f | | — |
| 74 | nbla-03755-r | S PHASE | — |
| 75 | nbla-03759-f | | — |
| 76 | nbla-03759-r | | — |
| 77 | nbla-03761-f | | — |
| 78 | nbla-03761-r | | — |
| 79 | nbla-03771-f | | — |
| 80 | nbla-03771-r | | — |
| 81 | nbla-03777-f | | — |
| 82 | nbla-03777-r | | — |
| 83 | nbla-03779-f | | — |
| 84 | nbla-03779-r | | — |
| 85 | nbla-03781-f | | — |
| 86 | nbla-03781-r | | DKFZp434C035(AL137633) |
| 87 | nbla-03831-f | | — |
| 88 | nbla-03831-r | | — |
| 89 | nbla-03851-f | | — |
| 90 | nbla-03851-r | | — |
| 91 | nbla-03862-f | | — |
| 92 | nbla-03862-r | | — |
| 93 | nbla-03898-f | | — |
| 94 | nbla-03898-r | | — |
| 95 | nbla-03911-f | | — |
| 96 | nbla-03911-r | | — |
| 97 | nbla-03914-f | | — |
| 98 | nbla-03914-r | | — |
| 99 | nbla-04021-f | | — |
| 100 | nbla-04021-r | | — |
| 101 | nbla-04055-f | | — |
| 102 | nbla-04055-r | | — |
| 103 | nbla-04061-f | | — |
| 104 | nbla-04061-r | | — |

Example 6

Measurement of Cell Cycle Phase-Dependent Gene Expression Levels by Semi-Quantitative PCR PCR primers were synthesized from the nucleic acid sequences of portions of the gene group obtained in Example 4, and HeLa cells were used for comparative quantitation of cell cycle phase-dependent gene expression levels. The HeLa cells used were treated in each of the following manners.

(1) Untreated (2) Treated with 400 μM of mimosine for 18 hours, with 65% of the cells arrested in the G1 phase.

(3) Treated with 2 mM thymidine for 20 hours, with 100% of the cells arrested in the S phase.

Figure 4:
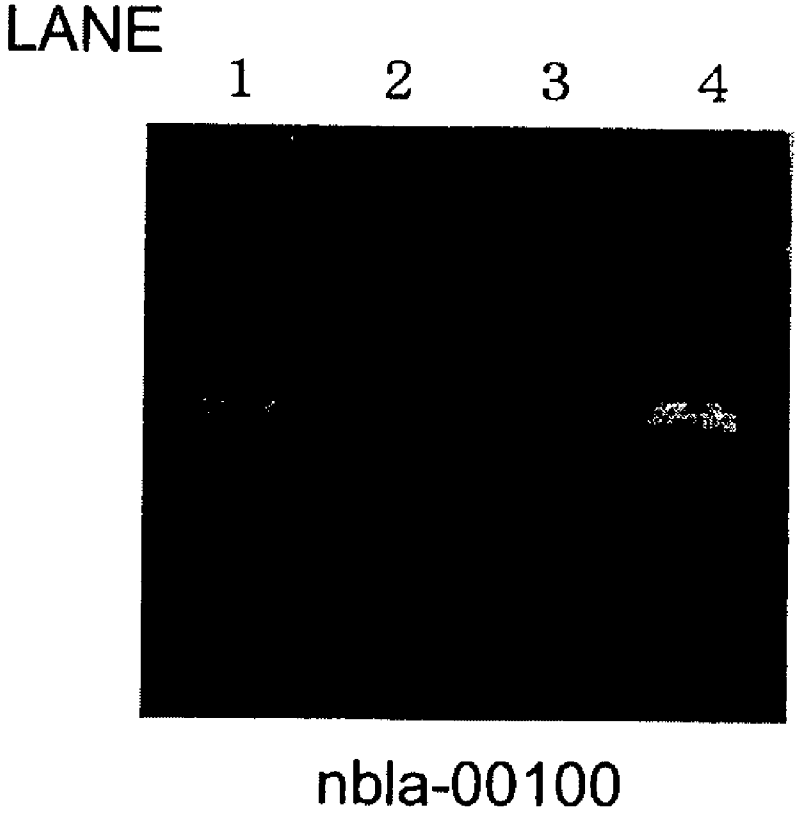
FIG. 4 is an illustration corresponding to an electrophoregram showing an example of a gene whose expression was noted (the result from nucleic acid sequence nbla-00100), as a result of examining the level of cell cycle phase-specific gene expression by semi-quantitative PCR. In the figure, Lane 1 represents untreated HeLa cells (60–70% confluent). Lane 2 represents HeLa cells treated with 400 μM of mimosine for 18 hours, with 65% arrested in the G1 phase. Lane 3 represents HeLa cells treated with 2 mM thymidine for 20 hours, with 100% arrested in the S phase. Lane 4 represents HeLa cells treated with 0.6 μg/ml of nocodazole for 18 hours, with 85% arrested in the G2/M phase.

(4) Treated with 0.6 μg/ml of nocodazole, with 85% of the cells arrested in the G2/M phase.

mRNA was extracted from the aforementioned 4 types of HeLa cells by the method described in Examples 1–3, and rTaq (Takara Shuzo Co. Ltd.) was used for PCR reaction. Specifically, 5 μl of sterile distilled water, 2 μl of mRNA, 1 μl of 10×rTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 55° C. for 15 seconds and 72° C. for 20 seconds was repeated 35 times, and then the mixture was allowed to stand at 72° C. for 6 minutes for PCR reaction. The reaction solution was subjected to 1% agarose gel electrophoresis. Consequently, when the PCR primers based on the nucleic acid sequences set forth in SEQ ID NO:1 to NO:104 in the Sequence Listing were used in amplification, it was found that the gene expression was specific for cell cycle phase in 31 nucleic acid sequences. An example of the electrophoresis results (Nucleic acid sequence nbla-00100) is shown in FIG. 4. Also, Tables 1 and 2 have displayed a tabulation of the cell cycle phase specificities and individual nucleic acid sequences that were discovered in the manner presented herein.

INDUSTRIAL APPLICABILITY

The nucleic acids of this invention provide information relating to the genes expressed in neuroblastoma.

The nucleic acids of the invention or their fragments may be used as probes or primers for various types of hybridization or PCR, and permit detection of the expression of the aforementioned genes in other tissues and cells, as well as analysis of their structure and functions. Production of the human proteins encoded by the genes through genetic engineering is also possible.

The nucleic acids of the invention are those derived from a gene whose expression is enhanced in human neuroblastoma with favorable prognosis based on comparison between human neuroblastoma with favorable prognosis and human neuroblastoma with unfavorable prognosis, and therefore allow the diagnosis for prognosis of neuroblastoma based on this genetic information from these nucleic acids. Unlike the N-myc gene which is a factor for unfavorable prognosis, these genes are considered factors for favorable prognosis, similar to the TrkA gene, and therefore can serve as markers (tumor markers) for neuroblastoma malignancy and sensitivity to anti-cancer agents.

The invention claimed is:

1. An isolated nucleic acid comprising a sequence selected from the group consisting of nucleic acid sequences set forth in SEQ ID NO:3, SEQ ID NO:5, SEQ ID NO:9, SEQ ID NO:19, SEQ ID NO:22, SEQ ID NO:32, SEQ ID NO:40, SEQ ID NO:55, SEQ ID NO:56 and SEQ ID NO:74, in the Sequence Listing or a complementary nucleic acid thereof.

2. The nucleic acid according to claim 1, wherein the nucleic acid is DNA.

3. The nucleic acid according to claim 1, wherein the nucleic acid is derived from a gene expressed in human neuroblastoma.

4. A method of diagnosising the prognosis of human neuroblastoma, said method comprising extracting a neuroblastoma specimen from a subject;

detecting at least one nucleic acid in the specimen, the nucleic acid comprising a sequence selected from the group consisting of nucleic acid sequences set forth in SEQ ID NO:3, SEQ ID NO:5, SEQ ID NO:9, SEQ ID NO:19, SEQ ID NO:22, SEQ ID NO:32, SEQ ID NO:40, SEQ ID NO:55, SEQ ID NO:56 and SEQ ID NO:74, in the Sequence Listing or a complementary nucleic acid thereof; and diagnosing the prognosis of the human neuroblastoma as favorable if said nucleic acid is detected.

5. The isolated nucleic acid according to claim 1, wherein the nucleic acid sequence is SEQ ID NO:3 in the Sequence Listing.

6. The isolated nucleic acid according to claim 1, wherein the nucleic acid sequence is SEQ ID NO:5 in the Sequence Listing.

7. The isolated nucleic acid according to claim 1, wherein the nucleic acid sequence is SEQ ID NO:9 in the Sequence Listing.

8. The isolated nucleic acid according to claim 1, wherein the nucleic acid sequence is SEQ ID NO:19 in the Sequence Listing.

9. The isolated nucleic acid according to claim 1, wherein the nucleic acid sequence is SEQ ID NO:22 in the Sequence Listing.

10. The isolated nucleic acid according to claim 1, wherein the nucleic acid sequence is SEQ ID NO:32 in the Sequence Listing.

11. The isolated nucleic acid according to claim 1, wherein the nucleic acid sequence is SEQ ID NO:40 in the Sequence Listing.

12. The isolated nucleic acid according to claim 1, wherein the nucleic acid sequence is SEQ ID NO:55 in the Sequence Listing.

13. The nucleic acid according to claim 1, wherein the nucleic acid sequence is SEQ ID NO:56 in the Sequence Listing.

14. The isolated nucleic acid according to claim 1, wherein the nucleic acid sequence is SEQ ID NO:74 in the Sequence Listing.

* * * * *

SEQUENCE LISTING

```
<160> NUMBER OF SEQ ID NOS: 108

<210> SEQ ID NO 1
<211> LENGTH: 2187
<212> TYPE: DNA
<213> ORGANISM: Homo sapiens

<400> SEQUENCE: 1

tgttggccta ctggtaatgc tcactgccta cccatttctc catattcaca agaaaatata     60

catatttgca ggaaaatata taatttttag atgtcatgga tcattttagg aaagttgtag    120

tcagttaaaa agctgtcata tcattctaca aaggaggagt aaagtaggag caattgtgtg    180

gcccaacatt tgtttgtttt ttagccaagc ttagatttat aaagcaatga gggtgtggtt    240

ttaaccacaa agtgaaagtg ttagacagtt gttggctctc tcctaaaaag tgaatgagat    300

ttttcctata cattttcctt cttgttgact aatatatgat gaatactttt ttcagcttgg    360

atataccata aatataaaaa taataaagcc aaagaattta agctaaaatt caacactttt    420

cttaactaat ttaactggta tggtctccat agtagtccac tgttttgttt cctgtgttaa    480

cttccctttt gtttcgaaag ctcttagaat aaggagtcaa ctggattttt atgtccatgg    540

acccccttgtg attatatgca gtgtacgctg tgtgtgcgtg tgtgtgtgtg tgtgtgtgag   600

agagatcctt ttacttagaa aaaggtctac tatgctcatt agaagatcaa aagcagattc    660

tccttacttg taacatagga gtttcaggat taatctgtat tcaagctcat tctatatcct    720

tcatcaaaga aaagacaatg ttttgtgtct gttgtccctc tcacacacag ccctaatata    780

taatgtgtaa ctgccttatc tgcagcccta aactaatata gctagaggtc ttctaatcat    840

tctcctacct ctaggaaaga aatatagtct tgaaaactgc caatctggtg tgcatacaaa    900

atatatacaa aataccaagg aacattatat gagccttttg ctaggtatat ctaagcaact    960

gcttcagtta atggccactt tacaaattgc tgaaagaagg aaacgtcttt cgattctttt   1020

ttttttcttt ttttttttg agacagagtc tctgtctgtt actcaggctg tagtgcagtg    1080

gcacaatgat agctccctcc agcctcaaac tcctgggctc aagcattcct tctgcatcag   1140
```

-continued

```
cctcctgact agctggaact caggctcatg ccaccagacc tggctaattt ttctgttttc   1200
agtagagaaa atattttctt tcactaattt aactggtatg gtttccattg tctacccagt   1260
tttccatatg cataagaaaa tatattcaca ggaaaatata aagttttcag atttcatgag   1320
tggttttaag aaagttttag tcagtgaaaa aactatcata ccagtcttca aaggaagggt   1380
gaaataagtt catctgctac gttgcccagg ctggtcttga agggaaacag actttttttgc   1440
agtcatactt atcctttggc ttcttagtaa gtattatata gtcattactt tttgcagttt   1500
tttagatcaa agtgttaatg taggtaaagt taattttaga atatatgtaa aagtcaagtc   1560
tgctttaaat ttaatcatct ctttggtgaa agggatggga tggagctttg ctttttatca   1620
tatattcatc tgtacctttc aagtattcaa atagaaaaat ataaacaatg taaataaaat   1680
agcaaaacaa tgtaatatct cataaaactg caatggtaaa agcatttatc ctattgaaat   1740
tccacaattt ttatttgaaa atattatcga catgtaattc aagtggcatt tagaagaata   1800
atttaaaagc aacaactcta tagaaagctt gtaaaatgat taagtagttt aaaccaaata   1860
aaacaatttc tgagtcagtc atctccagta ggtctatttt agtctcaaga taaattcatt   1920
tctggtgaca actgaagttc ttagttattt gttagtatat attggagaca tttacaataa   1980
agcttagagc acaatgggaa atgaaagtat catgtttttt ttaagaccaa atgtattgca   2040
gaaatgtgag taatttaatc cgatgctaca atctgatcat tctgatctaa tctgatcatt   2100
taataacact aaataaaacc ttcatctcaa aaaaaaaaaa aaaaggccac atgtgctcga   2160
gctgcaggtc gcggccgcta gactagt                                        2187
```

<210> SEQ ID NO 2
<211> LENGTH: 2238
<212> TYPE: DNA
<213> ORGANISM: Homo sapiens

<400> SEQUENCE: 2

```
gaattcctcg agcactgttg gcctactggc tgaccattta gatgcttaca agatgctttt     60
ctctgacttc ttcagctcca actgctcctt tccattaccc taaagctgtg gatcataaag    120
agtgttctcc agaccagcag tatctgcacc acctggatct tgttagaaat gcagattttc    180
aaaccccacc catgagctac tgaaacagaa ctctgaaggt gaggcctaga aaccggtttt    240
aaccaatgtg ccaagtgatt ctaatgcctg ctatcaatca tttgggaacc attgtcctaa    300
actcagctgc tgcttctgct tcatctccag ttgattcagt ttccttaatt gttaccatta    360
taaaaacaaa ataaagcaaa acaagacatt tacctatatt attaatcaca aataagttcc    420
ctaccctgtg ggtcacaaat ttgggctttg gatatctaat tctgcatcaa gtacatatct    480
ctgtctttac aatctcaaca aattattaga tatatcagta acttccatat atgctctcat    540
tttgtagttg cagtgtcact atctccattt aatggatagg gaaatagggg ctcaggaaag    600
agaagtgtat tatccatgac ggaggtaaca tgggctgcat tcaattaggg tttctcattt    660
ccagctaaga cactttgcac catattgaag cagcttgtaa ctaaatttgc cataaaaata    720
tatctaaaat cctaattaag tttgaatagc ttgatcttag ttgaaagtta ttcctaattc    780
attcacaagt agcttttaaa agggatatgt ttatgttaaa caatagaagg tctccaaatc    840
ctatcagata actgtatcct gtctttaaaa atgtaatttt ttatatctac tgcctgaatt    900
aaattgctta gttgtacttt ccagagaaat agaatggacc aaagcagttc aaatatttta    960
atattcttct ggagtttgac tgctgagatg taaagaacta ttgatatcac tagtaaataa   1020
```

-continued

```
ataatgtata tttattgagg tttagtcaat agagcgatta cttataagag gcatgtagta   1080

cttaattatc atcctcttca cgaaactcca acttaacctt ggacaataca attaagagtt   1140

gtgttcagat ggctttaaaa acaggtgcat ggtacaacat gctcttgttg ttaaccattt   1200

tgcttaatgg ccaaacttct cttgggtcag ttttgataac tcctctgcaa tttcatcaac   1260

aatgagggaa atgtaatttc aaggtgagca ttgagactga gtatattagg caagagtggg   1320

gcttgcttat ttttggcctt gcagctccca gaaatagaat gtttacaagg tgtaatcata   1380

tttcagtacc ttgtttttcc agaattgttt tcttttccca gaaatttttt actctctatt   1440

tatttgtatt tagctcttct ttactaaagt ataactctat cagagcagaa gactgtgtct   1500

tcttcttcat ctttatatct tacattctta gcatggtaga tgtttaattg gaatgtgatt   1560

tcagagagtg gctgtgttcc agtcttgatc caatattgat gaactgaatg tgttagtcta   1620

ttataagcaa agattttcag gtcaaacttg gtttgaaata cagactgtat gttcctcaca   1680

gaaaatgtga ctttgagcaa ccaagtctgc ttaaagtcag ctattaaaag tatgtatttc   1740

atgcatctag tttttttctta atatatttta taaagtcttt aaagtgatat gtggaagaat   1800

gtggtaaagc acttagttag agcaaaaagg gttgttttcc ctatcagccc aaaataccat   1860

atgtctagaa tcattaggaa ttaactgtaa catagtggac aagcattatt actatgtgct   1920

agtgtttcat gacttcctca gattattcaa atggtatcca atctacttgg tccaatccaa   1980

ctcttctttt cttccacaaa cctttcactt attttacatg gatgactttt gtttctcaac   2040

ttttatacaa ttacagtttc ataatagaat ttgacattga ttttatactg cctacaatat   2100

tgtttattta atgtaattct tagcataaaa ataataaaaa tgagcaagtc aaaaaaaaaa   2160

aaaaaaaaaa aaaaaaaaaa aaaaaaaaaa aaaaaggcca catgtgctcg agctgcaggt   2220

cgcggccgct agactagt                                                 2238
```

<210> SEQ ID NO 3
<211> LENGTH: 1861
<212> TYPE: DNA
<213> ORGANISM: Homo sapiens

<400> SEQUENCE: 3

```
cactgttggc ctactggatg cgaccgatcc ccttctcccg gaccccagga gccggcgccc     60

ccgccctgta gggttacgac tcactgatta aaaagaggga ctttttcaaa tactttgcac    120

ttttgattgt gtattatgga taccaaggaa gagaagaagg aacggaaaca aagttatttt    180

gctcgatgac aatcaaaaca aaacacatga taaaaaagag aagaagatgg tggttcagaa    240

gccccatggg actatggaat acactgctgg aaaccaggac accctaaact ccatagcact    300

gaaatttgac atcactccca ataaattggt ggaactgaat aaacttttca cacatactat    360

tgttccaggc caggtccttt ttgtgccaga tgccaactct ccttccagta ccttaaggct    420

atcatcatcc agtcctggtg ctactgtctc tccttcatca tcagatgcag aatatgataa    480

attgcctgat gctgacttag cgcgaaaggc cttgaaaccc attgaaagag tcttatcgtc    540

tacttctgaa gaagatgagc caggtgtggt gaaattttta aaaatgaatt gtcgatactt    600

caccgatgga aagggtgtgg ttggcggtgt tatgatagtg actcctaaca acatcatgtt    660

tgaccctcat aaatctgatc ctctggttat tgaaaatggg tgtgaggagt atggtctcat    720

ctgccccatg gaagaggttg tttccattgc gctctacaat gacatttctc acatgaagat    780

caaagatgcc ttgccatcgc ctggagaatg ggaagacctg gcttcagaaa aggatatcaa    840

cccattcagt aagttcaaat ctatcaacaa ggaaaaacga cagcagaatg gagagaaaat    900
```

-continued

```
tatgacttcg gattccagac caatagtacc tttggagaag tccacaggac atacacctac     960
aaagccctca ggcagctctg tgtcagagaa attaaagaaa ctggactcct ctagggagac    1020
atcccatggt tctcccacag tgactaagct cagcaaggaa ccttccgaca cttcttctgc    1080
atttgaatct acagccaaag aaaactttct aggggaagat gatgattttg ttgacttgga    1140
agaactttct tctcaaactg gtggtggaat gcacaaaaaa gacaccttga aggagtgcct    1200
ttctcttgac ccagaggaac gaaagaaagc tgagtcacaa ataaacaatt ctgccgtgga    1260
aatgcaggtg cagtcagccc tagccttttt gggaacagag aatgatgttg aactgaaggg    1320
ggcgctagat ttagaaacct gtgagaagca agatataatg ccagaagtgg acaagcagtc    1380
tggttcgcca gaaagccgag tagaaaacac actgaacata catgaagatt tagataaagt    1440
taaactcatt gaatattacc tgactaagaa caaagaaggg ccacaggtat ctgaaaattt    1500
gcagaaaaca gaattaagtg atggaaaaag tattgaacca gggggaatag acattaccct    1560
tagtagttct ctttcccagg cgggtgatcc cataactgag ggcaataaag agccagataa    1620
gacctgggtg aaaaagggag agcccctccc ggtaaaactg aactcttcta cagaagcaaa    1680
tgtgattaaa gaggctctag actcctcttt ggaatctact ctggacaacg gctgtcaagg    1740
tgcacaaatg gataataaat ctgaagttca gttgtggctg ttaaagagaa ttcaggtacc    1800
cattgaagat atacttcctt caaaaaaaaa aaaaaaaagg ccacatgtgc tcgagctgca    1860
g                                                                    1861
```

<210> SEQ ID NO 4
<211> LENGTH: 2481
<212> TYPE: DNA
<213> ORGANISM: Homo sapiens

<400> SEQUENCE: 4

```
gaattcctcg agcactgttg gcctactggt tcagcagctt tttaactggc gttgttttta      60
tgctgatgta ttatgccttc tttcatccca atggacccag attcgggcag tcaccaagtt     120
gtgcttgtga ggacccagcc gctgccttca ctttgccccc agacgtggcc acaagcaccc     180
tacggtccat ctccaacaac cgcagtgttg tcagcgaccg cgatcagaaa ttcgcagagc     240
gggatgggtg tgtacctgtc tttcaagtga ggcccactgc cccatccacc ccatcatctc     300
gcccaccacg gattgaagaa tcagtcatta aaattgactt gttcaggaat aggtacccag     360
catgggagag acatgttttg gaccgaagcc tccgaaaggc tattttagct tttgaatgtt     420
ccccatctcc tccaaggctg cagtacaaag atgatgccct tattcaggag cggttggagt     480
acgaaaccac tttataaagc aaaaggagtt gcaggaccca caacatccag atgaaggggt     540
gacagcaggg ctgtggccat aatgacactt catcctagag cagggcagtg agccgtgaag     600
ttcctagtgg gaccgtcatc accattatca tttgatcctg tcggctgggg gcggctggtc     660
tccttccaaa gcagctgcac ccgagagtct ctgactccac ctgaaagaat gacgctggct     720
taataggact ctccattgct accaaactcc tcctgcacgg tcttgggtgc acccaccaga     780
gggtactact attatggaaa aattttgcct ccaatcatta gggtgtcttg atggcgttaa     840
ctgatctttc cataaaaata gattcagtca tacacacata cacacactaa cacacataag     900
ttacaccagt cctctgtcaa aaaagcttag gtgacttttc ttgatgcaaa gctctgattc     960
ccacaggaat ataaaaacaa agaaagaggg aaacatccct cgagaaaaaa aatagtattg    1020
cttagaaaag aaaccatttt ctcatttgga aatccatacc atgtgtgaaa atcctatcca    1080
```

-continued

```
acggacagca aacccaaatg ttgtctacac atgtgttagc attgatggag tggttcattt   1140
tctacacatt tcaggatttg ttttatattt taaattttca gttgcgaaca tcctttttga   1200
cagaaatcct atgcagccca tgtacggctt tcaacaagac caaggagctc aataacttca   1260
tgatgtaaat taaatagtaa tcatgattca gtattcaatt gcaaaaatgt aacaggtaca   1320
caaagaggaa gtggggaaaa aggcaaaatg agagtctgat tcccaggcat gtgcagcgcc   1380
cattgggaca taacggcagt gcggcgcgag ccagaggaat gggctggaac cggatctgtt   1440
tccagacgca gaatgagtgg ctctgtgtga ccataggcag atgctgactc tggaagactc   1500
cgtgccactc ctttctagtg ccaaacacca tccaaccaca ggactgacgt ggaagcccca   1560
aacaactgag aatgagtggc atgagccccc taaaagcagg cgagagaacg agcaatcaag   1620
ttctccactg tgtacagact tttcctcccc ccaatccaag gtcaaagtga tgtgtctttt   1680
agaggctttg ggacactttt tagtaagtat gagcagacaa atgcaatgaa tatgctatga   1740
aaaaaccctt ctgaactgag agagggctta tcactatatc cagctaagat ttgtatttga   1800
atcatctgta aagtcgcact cttacaacaa gcttctgggt tttaaatacc tccgtacagc   1860
aagtaaacgt tccccgcttt ctgttctcag tgtcctcggt catggtgctt ttcgttgcat   1920
taaaagtgcc ggtcaaactt tgatagtatt tttttatagt tggtgcagag tggaataact   1980
catggattat ttcaatattt ctgtaataaa aaatataggg tatacacata ggcatcatca   2040
catttttat agacctggaa tcgtttaaaa tactttaagc atcataatta cttgggatgt   2100
cagaaactgg tccacaaatt ccatcagcct gcctcagcag attgaaaaca tttgtctctt   2160
gcaagatcac cctactttgc aagttggtgc ccccaggaac ctggccaggg gtgctatcag   2220
aatatcaggt gaagagagaa tcagcttaaa tagaaagggc ttgtcaagac tggccaatgt   2280
ttcccaggaa atcaaagatg taaatgatta ctttcatcca tccattgtaa caaacctgac   2340
cacagtggaa gctgtcttaa acttccttcc ctggttttat attaacccaa ctgatagatt   2400
aagtattagt caaaccacta aaaaagaaaa aaaaaaaggc cacatgtgct cgagctgcag   2460
gtcgcggccg ctagactagt c                                              2481
```

<210> SEQ ID NO 5
<211> LENGTH: 3208
<212> TYPE: DNA
<213> ORGANISM: Homo sapiens

<400> SEQUENCE: 5

```
gaattcctcg agcactgttg gcctactggt actgggttgc gagggctgtg acgcgtcctg     60
ctgcagcccc tcgtgctaca gctcctcgtg ctacagcacg tcctgctaca gcagctcgtg    120
ctacagcgcc tcgtgctaca gcccctcctg ctacaacggc aacaggttcg ccagccacac    180
gcgcttctcc tccgtggaca gcgccaagat ctccgagagc acggtcttct cctcgcaaga    240
cgacgaggag gaggagaaca gcgcgttcga gtcggtaccc gactccatgc agagccctga    300
gctggacccg gagtccacga acggcgctgg gccgtggcaa gacgagctgg ccgcccctag    360
cgggcacgtg gaaagaagcc cggaaggtct ggaatccccc gtggcaggtc caagcaatcg    420
gagagaaggt gaatgtccta tactccataa ttcccagcca gtaagccagc ttccttccct    480
gaggcctgaa catcatcact acccaacaat cgatgagcct cttccaccaa actgggaagc    540
tcgaattgac agccacgggc gggtctttta tgtggaccac gtgaaccgca caaccacctg    600
gcagcgtccg acggcagcag ccaccccgga tggcatgcgg agatcggggt ccatccagca    660
gatggagcaa ctcaacaggc ggtatcaaaa cattcagcga accattgcaa cagagaggtc    720
```

-continued

```
cgaagaagat tctggcagcc aaagctgcga gcaagcccca gcaggaggag gcggaggtgg    780
agggagtgac tcagaagccg aatcttccca gtccagctta gatctaagga gagaggggtc    840
actttctcca gtgaactcac aaaaaatcac cttgctgctg cagtccccag cggtcaagtt    900
catcaccaac cccgagttct tcactgtgct acacgccaat tatagtgcct accgagtctt    960
caccagtagc acctgcttaa agcacatgat tctgaaagtc cgacgggatg ctcgcaattt   1020
tgaacgctac cagcacaacc gggacttggt gaatttcatc aacatgttcg cagacactcg   1080
gctggaactg ccccggggct gggagatcaa aacggaccag cagggaaagt ctttttcgt    1140
ggaccacaac agtcgagcta ccactttcat tgacccccga atccctcttc agaacggtcg   1200
tcttcccaat catctaactc accgacagca cctccagagg ctccgaagtt acagcgctgg   1260
agaggcctca gaagtttcta gaaacagagg agcctcttta ctggccaggc caggacacag   1320
cttagtagct gctattcgaa gccaacatca acatgagtca ttgccactgg catataatga   1380
caagattgtg gcatttcttc gccagccaaa catttttgaa atgctgcaag agcgtcagcc   1440
aagcttagca agaaaccaca cactcaggga gaaaatccat tacattcgga ctgagggtaa   1500
tcacgggctt gagaagttgt cctgtgatgc ggatctggtc attttgctga gtctctttga   1560
agaagagatt atgtcctacg tccccctgca ggctgccttc caccctgggt atagcttctc   1620
tccccgatgt tcaccctgtt cttcacctca gaactcccca ggtttacaga gagccagtgc   1680
aagagcccct tcccccctacc gaagagactt tgaggccaag ctccgcaatt tctacagaaa  1740
actggaagcc aaaggatttg gtcagggtcc ggggaaaatt aagctcatta ttcgccggga   1800
tcatttgttg gagggaacct tcaatcaggt gatggcctat tcgcggaaag agctccagcg   1860
aaacaagctc tacgtcacct ttgttggaga ggagggcctg gactacagtg gcccctcgcg   1920
ggagttcttc ttccttctgt ctcaggagct cttcaaccct tactatggac tctttgagta   1980
ctcggcaaat gatacttaca cggtgcagat cagccccatg tccgcatttg tagaaaacca   2040
tcttgagtgg ttcaggttta gcggtcgcat cctgggtctg gctctgatcc atcagtacct   2100
tcttgacgct ttcttcacga ggcccttcta caaggcactc ctgagactgc cctgtgattt   2160
gagtgacctg gaatatttgg atgaggaatt ccaccagagt ttgcagtgga tgaaggacaa   2220
caacatcaca gacatcttag acctcacttt cactgttaat gaagaggttt ttggacaggt   2280
cacggaaagg gagttgaagt ctggaggagc caacacacag gtgacggaga aaaacaagaa   2340
ggagtacatc gagcgcatgg tgaagtggcg ggtggagcgc ggcgtggtac agcagaccga   2400
ggcgctggtg cgcggcttct acgaggttgt agactcgagg ctggtgtccg tgtttgatgc   2460
cagggagctg gagctggtga tagctggcac cgcggaaatc gacctaaatg actggcggaa   2520
taacactgag taccggggag gttaccacga tgggcatctt gtgatccgct ggttctgggc   2580
tgcggtggag cgcttcaata atgagcagag gctgagatta ctgcagtttg tcacgggaac   2640
atccagcgtg ccctacgaag gcttcgcagc cctccgtggg agcaatgggc ttcggcgctt   2700
ctgcatagag aaatggggga aaattacttc tctccccagg gcacacacat gcttcaaccg   2760
actggatctt ccaccgtatc cctcgtactc catgttgtat gaaaagctgt taacagcagt   2820
agaggaaacc agcacctttg gacttgagtg aggacatgga acctcgcctg acattttcct   2880
ggccagtgac atcacccttc ctgggatgat ccccttttcc ctttccctta atcaactctc   2940
ttttgatttt ggtattccat gatttttatt ttcaaaccaa atcaggattg acaaaagctg   3000
tgcatgaaga actgccttct tctaagatct aaccttcagg cttctctcct ctgttttcaa   3060
```

-continued

```
tgaactgcta gcctgtatgc aatattaaaa aacagctgtc tcaaggtctg tgtatatctc   3120

cacatacctc cattactaac aatgaaatat gaatgcaagt taagctacac ttgaccaaat   3180

ggtaataaat gtttacttcc atttctat                                      3208


<210> SEQ ID NO 6
<211> LENGTH: 818
<212> TYPE: DNA
<213> ORGANISM: Homo sapiens
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (749)..(749)
<223> OTHER INFORMATION: a, t, c, g, unknown or other
<220> FEATURE:
<221> NAME/KEY: modified_base
<222> LOCATION: (779)..(779)
<223> OTHER INFORMATION: a, t, c, g, unknown or other
<220> FEATURE:
<221> NAME/KEY: modified_base
<222> LOCATION: (789)..(789)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other
<220> FEATURE:
<221> NAME/KEY: modified_base
<222> LOCATION: (817)..(817)
<223> OTHER INFORMATION: a, t, c, g, unknown or other

<400> SEQUENCE: 6

cctcgagcac tgttggccta ctgggtcgac gtgtggcgtc ggctctaccc ggaatggaga     60

atatccagga gaaaagcaaa gaagggatga tcgacatcaa gctgggcaaa ccccaggagc    120

ccccggccag cgagggcggc tgctcctgct aatgcagagc cgacctgtgg cttcccatga    180

cactccttgc ttgttgtgtt gcttcctatt ggctagcttc ctaagggggg agggaaccga    240

gttatcaaga tgggaggatt tttcttttct ctctgtcttt aggagtaggg tgggatgggg    300

agggaggctg ggcatcaggg atcacatcac tcttaacggc tgttacttaa acaactattt    360

tttggtttgg ttgtaatata ttgtacttta ttaagattgc caaaaactgt taaaatttaa    420

aaaaaattta aatcatgtgt atacaatttt ttgccagata aaaatgtagt catttttatt    480

tgaaagatgt gctttttgtt tttgtatatt tgtaaactta tagagaacct tttccacaca    540

cctcctcctt cctgttctct ttgaaccgtt catcacctct gccttcctcc tatccccaac    600

ccaataaatt aaaacaatta actgagcaaa ttaattaggc ttcaatctgg ggccatctgg    660

cccactctct anggcctact ccagttaaat caaacattgg gttgacacat caacctctga    720

aaaggtactc cgantcctgn cnttccaang gcaaaatggg tcgtcaacct cctgttganc    780
```

-continued tgaaacaang nccgttggct ccaaggaacc ccggnana 818

<210> SEQ ID NO 7
<211> LENGTH: 821
<212> TYPE: DNA
<213> ORGANISM: Homo sapiens
<220> FEATURE:
<221> NAME/KEY: modified_base
<222> LOCATION: (504)..(504)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (711)..(711)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (751)..(751)
<223> OTHER INFORMATION: a, t, c, g, unknown or other
<220> FEATURE:
<221> NAME/KEY: modified_base
<222> LOCATION: (766)..(766)
<223> OTHER INFORMATION: a, t, c, g, unknown or other
<220> FEATURE:
<221> NAME/KEY: modified_base
<222> LOCATION: (774)..(774)
<223> OTHER INFORMATION: a, t, c, g, unknown or other
<220> FEATURE:
<221> NAME/KEY: modified_base
<222> LOCATION: (783)..(783)
<223> OTHER INFORMATION: a, t, c, g, unknown or other
<220> FEATURE:
<221> NAME/KEY: modified_base
<222> LOCATION: (793)..(793)
<223> OTHER INFORMATION: a, t, c, g, unknown or other
<220> FEATURE:
<221> NAME/KEY: modified_base
<222> LOCATION: (797)..(797)
<223> OTHER INFORMATION: a, t, c, g, unknown or other
<220> FEATURE:
<221> NAME/KEY: modified_base
<222> LOCATION: (800)..(800)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other

<400> SEQUENCE: 7
ggcttttttt tttttttttt tttttttttt gagaattagg acagtttatt gtttgaccaa 60
catgctgagt cttttccaca ttttacacag tttaatgtga aatcaacatg gcggctatgt 120
cttctgagcc cataacagat ggaattgcca ccctctgtgc tcctcacagc caatcacttt 180
aaagggatgg gtgaggggaa agtgagggga gaagtggaca cacaccgcga gatgcaggct 240

-continued

```
ggccttcaat gctatggagg cttcccacct cctgaaggaa ccatctaaac ccctgctgca    300

aggatttcct gatgaaacca cacactgctg ggagtgccaa ccagacaggg gtctggagtc    360

caaggagttt gcacattgag atcccaaggt tttggaacac ctaaatagtt catgtcaaac    420

aaaaattcaa agggtgtcct gatctgtgtg ggtgcccatg acaatcaatc agagtagact    480

tggggactgg cccttgtgca gtanaggagc ccaaaatacc accaatattc tcactcatat    540

gctgggaaaa acctagtgtc ctaaccaaaa agagtanaga tggtctgagg aacacaccct    600

cacacagcan tccttgctgt gtaataaata tggagtcaca tttgttcaca cacanggcaa    660

caatgggntg aaaaatggga acttcactct gtgccaaatt ctacctgcaa ncaaggggac    720

aaggatggtg cctgctcaan acaaaaatca nggaaccaac aaattntgaa aaanaggcct    780

ggntgccttg gantttnttn ccccgaaaaa ggaantgatt t                        821
```

<210> SEQ ID NO 8
<211> LENGTH: 3591
<212> TYPE: DNA
<213> ORGANISM: Homo sapiens

<400> SEQUENCE: 8

```
aattcctcga gcactgttgg cctactgggg tagaggccga cctgacattc tttaacacgc     60

tggtgagaaa gaagagcaag ctgggagacc tggagggggc caaggcgctg ttgccggtcc    120

tggcaaagag ggcctcgtc cccaacctgc agacattctg caacctggcc atcgggtgcc    180

acaggccgaa ggacggtcta cagcttctca cagacatgaa gaagtcccag gtgaccccca    240

acactcacat ctacagtgcc ctcatcaacg cggccatcag gaagctgaac tacacctatc    300

tcatcagcat cttgaaggac atgaagcaga acagggtccc ggtgaacgaa gtggtcatcc    360

gccagctgga gtttgcagcc cagtaccctc ccacctttga ccggtaccaa gggaagaaca    420

cctacctgga gaagattgac ggcttccgag cctattacaa gcagtggctg acagtgatgc    480

ccgcagagga aaccccgcac ccctggcaga agttccggac caagccccag ggggaccagg    540

acaccggcaa ggaggctgat gacggatgtg cccttggggg caggtgatgg gagcacagct    600

ggaacaatgt gctcggcccc cagtgctctg tgggagcccc aggacaagtg agctggtgtc    660

acctcctgcc tgggggaaga gccaggccct gaggaacagc cgcagcgtgt cacaggtgtt    720

ggtgaggaca cacactaggc ccaaggtgcc tgtgctccca gcaggtccaa gtgcagctcc    780

agccaccttt gcgtgtcacc ttcacgggac ttccagctcc agctaccttt gtgcgtcacc    840

tcacacacca caaggggggct ggggcatctg gtccctgggg cctgggccgc cccgccgggt    900

tccataggcc gatgctctga aagaagagac gtggggctcg agagatttaa agattttatt    960

tttacaaatc acagctgata gacagcgaag ccttccccat agagaccgtg ctccaactcg   1020

ggcctggggc actgctcgct gctcccagga aggggggtggc gtgacaggca ggaacctgcg   1080

aagtccagag tccagggtgg agcgcgccag cctcagccag agcagccacg acagccacag   1140

tgtgtgcact cgatgatgcg gccctgcaac ggaggaggac agtgagacga tgccactgcg   1200

ccacgctcgc ccctgcacac tcacatatgt ggcaaccctc ccacgaagga cctgccacca   1260

tgccatatag ggacacacct cagaaaccct tccttgacag ctctggacag ggaaaatttg   1320

gctccctcat gaaggtagga ccagctgctg ttgacaccga ggttacatct gtatgtctat   1380

ttataatatg ttctgcaaat ccaacacacg tttgccaatc aagaaaaaga aatcggtgtg   1440

aatgagtctc gttattctgc taagtgagca tgacagaccc tgcgatgagc agaggtggct   1500

ctgctactgt ttggggactt caggggggcc tctgggctgg tacactctgg tgggggaaga   1560
```

-continued

```
gggcaggaga ctatgcactt gagtcacacc cttctggccc agagcccccc cagaaagaag   1620
ggtcttgtcc cccaggcctg gtgcggccca acacttggcc agccagaaag ccctagaaca   1680
gtggcttgtg tttattttac tttttcaagt tcttttttttg gaagaacaag accatagttt   1740
aagtaaacag gatcctctgg tgaaacccag gtaagtctac agcgggctgt tttggccaca   1800
gggctgaagc agcaccccag cccaccagcc cctgacctgg actccttgtg gaatctgggc   1860
actcagagga agggggcttc tgccactctg ccacctgtcc ctgcctccat cagaaagcca   1920
acaccccagt cttccgtcgg ggaggcggcc cttgctcgcc cccactgctc agtacccaag   1980
tcctcagcat ccagccacag ctctccattg tcagtctcac tgcagcataa aggggactca   2040
tgtgaagagg cccctgtgtg gagctgggga aaagaaggcc aggctggcag atgggcggtg   2100
gggccaacaa ctgtgctgag ggctgcact gagcggccac tgctgtgact ctgcctcggg   2160
ccacagctgc ctttcagagg ggcttggaac cggatggagc tcagctcctg tccctcagca   2220
ccactcctga ggcgcctggc ctaggagtgg tacttggaac agaaagttct gaaagaagaa   2280
acacagtggg ctgggtgcag tagctcatgc ctgtaatccc ggcactttgg gaggctgagg   2340
caggtggatc acctgaggtc gggagttcga gaccagcctg agcaacattg agaaaccccg   2400
tctctactaa aaatacaaaa ttagccaggc gtggtggtgc atgcctgtag tcccagctac   2460
tcaggaggat gaggcaggag aaccgcttga acccgggagg tggaggttgc agtgagccaa   2520
gatggcatca ctgcactcca gcctgggcga caaagcaaga ctccgtcttg gggggggcggg   2580
aaagatagtg atggtaatgt taaagtatca ctgtgaggac tgaaagggac aggaactcac   2640
tggttgtcct tccctgatgt caccctgcca ccaccttggg attagggctc cccaccacca   2700
tttcctaagt gaggaaaggg gttcagtaat ttgcccaaaa gtggagttga gattgacccc   2760
agacctaaca aacacacagc cacacgctgc ctcacatgga ttcctgaata cagggaccca   2820
ctcccacgag ggagagccag caggacatcc agggacaaaa cgacattcca gcccaaccaa   2880
ataacataag atcccttgca gtcgactaag gcagaatttt gagctgaaaa caacaccaag   2940
cttgagtgtc agacattacc acttccagct tgcttttggg cacgcggcag atgcagttcg   3000
tcccgaagtt ggtgtcccgt gtctgaatgc accgcaggca gcacaagttc tcatatcctt   3060
gctttttcca ttttgcaatc aggtttttgt ctgcatagcc ttctttaata caatattcat   3120
agagttctgt caaaaagatg gggaaagagc atcaggccat ggtctaaaaa ccttccccac   3180
ccttgatcaa aaaaagcatt caggccgggt gcagtggctc acacctgtaa tcccagcact   3240
ttgggaggcc gaggcaggcg gatcacctga ggtcaggagt tcaggaccag cccggccaac   3300
atggtaaaac cccgtctcta ctaaaaatac aaaaattact cgggcgtggt agcagctgta   3360
atcccagcta cttaggaggc tgaggcagga gaatcacttg aacccaggag gcggaggttg   3420
tagtgacctg aggtcgtgcc actggactcc agcctgggtg acagcgaaac tccatctcaa   3480
aaaaaaaaag gcattcagta ttgcaacggg acagtccttg gaggaggaac aaaaaaaaaa   3540
aaaaaaaggc cacatgtgct cgagctgcag gtcgcggccg ctagactagt c            3591
```

<210> SEQ ID NO 9
<211> LENGTH: 2954
<212> TYPE: DNA
<213> ORGANISM: Homo sapiens

<400> SEQUENCE: 9

```
gaattcctcg agcactgttg gcctactggg aagctcttct agttcatctg ctggccggct     60
```

-continued

```
ctcagtcccc gtggcgcccc ctttcctctt gtcccagagc gctctcgact ccaccatgcc    120
aaggggattc ctggtgaagc gaactaaacg gacaggcggc ttgtaccgag ttcgccttgc    180
ggagcgtgtc ttccctctgc tggggcccca gggggcgccg cccttcttgg aggaggctcc    240
cagcgcctcc ttgcccggcg cggagcgggc gacacccccc acccgagagg aaccaggaaa    300
ggggttgacg gcggaggcgg cccgggaaca gtcggggtcg ccatgtcggg cggctggggt    360
gagcccgggg acgggcgggc gggaaggcgc ggagtggcgg gcgggtggca gggaaggtcc    420
cgggcccagc cccagcccca gccccagtcc agcgaagccg gcaggcgcag agctgcgtcg    480
ggcgttcctg gagcgctgcc tcagctcgcc cgtctccgcc gagtctttcc ccgggggcgc    540
cgccgccgtg gccgctttct cctgctccgt ggcgccagca gccgcaccga ccccgggggga   600
gcagtttctg ctgccgcttc gggcgccgtt cccagagccc gcgcttcagc cggaccctgc    660
gcccctctcg gccgcccttc agagtctgaa gcgggcggcc ggcggcgggc gccgcggcaa    720
ggcacccacg ggctgcgcgt ctggacccgc ggccgcggga atcaagaagc caaaggccat    780
gaggaagttg agctttgccg atgaggtgac cacatcccct gtcctgggcc tgaagatcaa    840
ggaggaggag cccggagcgc cgtcccgggg cttgggggc agccgcacgc cactggggga     900
gttcatctgc cagctgtgca aggagcagta cgcagacccc ttcgcgctgg cccagcaccg    960
ctgctcccgc atcgtgcgcg tagagtaccg ctgccctgag tgcgacaagg tgttcagctg   1020
tcctgcgaac ctggcctccc atcgccgctg gcataagccg cgtcctgcgg ctgcaaacgc   1080
cgccacagtc tcctccgccg acgggaagcc gccttcttcg tcgtcttcgt cctcccggga   1140
ctccggggcc attgcatctt ttctggcgga gggaaaggag aacagccgaa tagagcggac   1200
tgcggatcag cacccgcagg ccagggacag ctccggggcg gatcagcacc cggacagcgc   1260
cccgaggcag ggcctccagg tgctgacgca tccagagcca ccgctgcctc agggccccta   1320
cacggagggg gtgttggggc gccgggtacc tgtgccgggc agtaccagtg gtggcagggg   1380
atccgagatt ttcgtgtgcc catattgcca caaaaagttt cgtcgccaag cctatctgcg   1440
caagcacctg agcactcacg aggcgggctc ggcccgtgcg ctagcgccgg gctttggctc   1500
cgaacgcggt gccccacttg ccttcgcttg cccattgtgc ggagcgcact tccctacagc   1560
agatatcagg gagaagcacc ggctgtggca tgctgtccgc gaggagctgc tcctgcccgc   1620
tctggcgggg gctcctcccg aaacgtcggg ccctagcggg ccatctgacg ggagtgccca   1680
gcaaatttc tcgtgcaagc actgcccgtc cacttttttt agctctccag ggctgacccg    1740
gcacatcaat aagtgccacc cctcagaaag ccggcaagtg ctgctgctgc agatgccact   1800
gcggcctggc tgctgaggga cgagagacca ggatgatttc gaggttggcc ttagaggaaa   1860
cagatcatgg gaatttctgt ggggctttct tcaacttgca agtttacttt cattccttcc   1920
tatgttttaa tcccctaaaa ttctccctgt agtcaatgtt ccaccagagg agcggacagt   1980
gaaatgtaat atccctctct agagcaggta tgtatatggt ataaaccttg agatcaaaga   2040
ctgtcagctt taaatccttc tcactttccc cactaaaata ggatttttcc ccttaaaact   2100
ctggagaccc taacgaatcc tatatgattt gtaattccta tggaaagtcg cggtgaatgc   2160
gtgcatgtct caatgtccac aaaggattct ggctaccctt tggtagccaa tgtttttttt   2220
gtcttgtcat cacaggcgcc tatacagctt ctgtctcaat agggtcagat attttgcaca   2280
tattctgtga attaaaagtt atgtgattgg tgccaaactt aaggagattc aagacctggc   2340
agaaaatgta agaggatttt tgctgctttt ggggtgcatg gggatctccc ctgtaaactt   2400
tcctttgccc aattatatgt acatgtccat tcttaagttg gtgtttggag gtggggagga   2460
```

-continued

```
tgctacttta ctggagttga gacaccccct aaaattctca ccctcagcta ttttgtgggc   2520
agtattcagg aagagctact tcaaaccttt ctttaaatgg ctttttggaa atacagaagt   2580
cgtttcctca agtttgactg ttttaatggg gtttcaccca aattgtttaa tgcttctgct   2640
gtaaatgtca tactgtgtat tcattatgaa aatatgtaca gcttaaggaa gatgttaaca   2700
cctgtaatcc actaaggaac tgaatggcaa tttgctcaat attcagtatt ttcttttcag   2760
cggcaacttg tttttgattt ttttaaaaaa ccatttcagt gtacattgtg tactaattcc   2820
ctactagcca gtttgggaca ttggctgagc actgcctgac agaaagcccg tatttgtaag   2880
atgcttacca ccaaataaat gtacatagac tgtgaaaaaa aaaaaaaaaa aggccacatg   2940
tgctcgagct gcag                                                     2954
```

<210> SEQ ID NO 10
<211> LENGTH: 2269
<212> TYPE: DNA
<213> ORGANISM: Homo sapiens

<400> SEQUENCE: 10

```
tgttggccta ctggtaagcc tgggaacatt aaaagctaat ttataaaagc aatacttttt     60
aatatgaaaa cttactgcaa agtttgttta tacttttgcc taaaaaggaa attggatggg    120
atactgtggc aaatcataaa aaaccagata attgaacttt gaagttatag aaaatcagag    180
aggggtaagt ttatagggca ttttgttctg atggttcaac cagaggtctg ggaaatagca    240
ctgttggccc aaacagaaca ggcttttaga agataaaagc gacaagaagg aatctggtga    300
attttagtca tcccagcttt ttagtcttaa ccacagttct cactctctta aatggtacct    360
caaaaagctg gagcctctct gccatgatta tgcttctaca aatttctttt ataaagagac    420
tcaaagctaa tgatagctta aaagaaaagt taatgccttc tcattggaaa tgtataatca    480
aataagtagt taagggcttt tggtattaaa gatattctga agctctgaaa tgctagaaaa    540
aaatttggaa tggagtatat gcctgaaaag gttttggatt cagaaagaaa aaggatggtt    600
agtttaatca gtgattcttt ttaaactctt caaatatcat gaacaagata ctaaattgta    660
cctaaggatt tgtatttctt tacaatttgt tctaaatatc tgtttaatga ctagttgata    720
tttgtgcatg ttatttaata aagagttata tttttataga aaaaaagagt gaaatgtgtg    780
ctaactgttt ttttacttaa ttttacttgg gcagctagca aaattgcaga aatatgcatc    840
ctgggaaaag aaacagcctt tgaagaatta gcctttcaag ttcaaatcta tttaataatg    900
agaagtctca caagtgaatt tttaagtaca ggcatacctc agacgtactt taggttccag    960
accatctcag taaagcaaat accacaacaa agcgagtcag gaggaatttt ttggtttccc   1020
agtgcatata aaagttttgt ttatactata ttaagtgtgc aatagcatta tgtctaaaaa   1080
tatgtacata agtttaaaaa tattttattg ctaaaaatgg taacaaagtg agcacatgct   1140
gttggaaaaa gagcaccaat agacttgctt gaagcagggt tgccacaaac cttcaatttg   1200
taaaaaacgc caatatgtac aaagcacaat aaagcaaagc acaatagaac aggattgcct   1260
gtattagaca tgctacaaac ttcataactg gaaacatctc aaagacccca tgaagctcat   1320
ttgaatggga cttaacaatt agacagttat tttagaaatt gagtgcagac ctaaatacat   1380
agttttccaa aaagaaaatt attgtctctg atatcttaaa acataaaaac ccaaaatttt   1440
atatagaaga aattgactct gtaaaacgca atgaaatagt cctcttttta aacagtttaa   1500
aggaagcatt ttcaccgttt gtaaaaatta tttttaaata tttagggcaa aatttttgtt   1560
```

-continued

```
agataataat ggaaaagctt gtgtgagttt agtggttaaa atatcttgta attcatcatt   1620

atttaagtga cttcttggga gccgtctttg tacctaaaat ggagtttttt ttttaagcct   1680

ccacagagat agtcacccaa agtatttcca gtcagtaaaa gtagaattca tagaaaaaac   1740

tgaggcaaat taaaacaatt ccattaatca aaatggcttt aaacaaatta agtattagca   1800

taaaaatagc aaaaagtaca actaaaaaaa tggttgggtt ttcccagtgg ttaaatgcta   1860

tataataact gcaaataaaa gttttttttgt acatggacag cgtcctcata aaagaaaata   1920

ggccaggcca ggcgcagtgg ctcgcgcctg taatcccagc actttgggag gccaaggcgg   1980

gcggatcacg aggtcaggag atcgagacca tcctggctaa cacggtgaaa ccccgtctct   2040

actaaacaaa atgcaaaaaa tcagccgggt gtggccgcgg gcgcctgtag ttccagctac   2100

tcgggaggct gaggcaggag aatggcgtga gcctgggagg cggagcttgc agtgagccga   2160

gatcgtgcca ctgcactcca gcctgggcga cagagcgaga ctccgtctca aaaaaaaaaa   2220

aaaaaaggcc acatgtgctc gagctgcagg tcgcggccgc tagactagt               2269


<210> SEQ ID NO 11
<211> LENGTH: 2260
<212> TYPE: DNA
<213> ORGANISM: Homo sapiens

<400> SEQUENCE: 11

aattcctcga gcactgttgg cctactggtt tcagcacatg atgatgtttt caggtttgcg     60

aggagcgatc gcatttgcct tagctattcg gaacacagaa tctcagccca aacaaatgat    120

gtttaccact acgctgctcc tcgtgttctt cactgtctgg gtatttggag gaggaacaac    180

ccccatgttg acttggcttc agatcagagt tggcgtggac ctggatgaaa atctgaagga    240

ggacccctcc tcacaacacc aggaagcaaa taacttggat aaaaacatga cgaaagcaga    300

gagtgctcgg ctcttcagaa tgtggtatag ctttgaccac aagtatctga aaccaatttt    360

aacccactct ggtcctccgc tgactacaac attacctgaa tggtgtggtc cgatttccag    420

gctgcttacc agtcctcaag cctatgggga acagctaaaa gaggatgatg tggaatgcat    480

tgtaaaccag gatgaactag ccataaatta ccaggagcaa gcctcctcac cctgcagtcc    540

tcctgcaagg ctaggtctgg accagaaagc ttcaccccag acgccaggca aggaaaacat    600

ttatgaggga gacctcggcc tgggaggcta tgaactcaag cttgagcaaa ctttgggtca    660

atcccagttg aattaattgg catgaagagt acagatgtaa tcacaagtaa tgcaagactc    720

actgaggaat acaagccaag ctgatgaggc agtacagggg agaggctgga aaacatatta    780

agagcataaa ttggagagaa tcaaagcctt gtcacatgga tcctctggtg cctgaagaaa    840

tgagatttta ttatccctct ctattatgca aatgaattta gttttttgac agcagccatt    900

ctgattactg gattggctgg ggtggggatg gaggtatcag gagtctagct gctggaggat    960

gggacagctg tgctgggtct tcagggcatt tctgctgcga atgcggctct ccaggccctt   1020

cacttctatt ctggatttta ttccctccat taaggagagt ttaaaaataa aagaaagctt   1080

ctgagagtaa acattttgct cctaagctga agggaatgcc cagctattta gtaagtgata   1140

agtttcttat tttgaggact tgactcccat ttgctctcag tgaccccagg gcagagccca   1200

gagaagtgtt ccgtacccac tgctgatggt ttcccagagc ccacactgag ttgaagaacc   1260

tattgttctt cttggcatcc ttcttatgct acttctccca tcgctcaaag ggggttgccta   1320

tggctgggtg tgccctgccc taaatgcagc accactttca agcttagtag gaccattcca   1380

agaaaaccag gtttcttctc cccataccac gttgtgcctg aagaacaagc cttcccgtcc   1440
```

-continued

```
ttgcctgcat gtgagtcact tcttggctgt gcagcaggtc ccccctccc cgcgatatgc   1500

tggagggtag gattctgcag cctgtgttgc tctctacctg gcagcagact gtgcaggagc   1560

cccaacctgt cctccaattc cagcattcac agctgatgag cagtgcagga gcagggcgag   1620

aggaacagag ccaatgatgt gtgggttaca ctgaggagcc aaggacaggg cctcaggtct   1680

ccccttaca aggcgtggct catggcctgc attccagaga ccaacatgat agcttttaat   1740

tcagctgcat gacctgtgcc ttttaagcca taaagatacc tcaagcctag cacctcttga   1800

aatccagatg ttcatattag actcgaaaaa ataggctcca ggcctaggtg cccaggctat   1860

gatgagtctg cttttgaagg aggtagggaa tgacatcttc cttggaccca aagcttaaaa   1920

gtaatgtatg ctttgctgac cactgtttgt taggccttaa acaacattca ctgtggtggt   1980

atcaggcaca ctgctatgtg catcaattat ttttttgctt tccaaacaga atctctgggg   2040

cacaagtttt acacttaagc taagtataac tttgtcattt caggtaaata tgacaagtgg   2100

tggagcatga agttttctaa tttgacttaa tcctaataaa tttttgttac aaagtaaaaa   2160

aaaaaaaaaa aaaaaaaaaa aaaaaaaaaa aaaaaaaaaa aaaaaaaaaa aaaaaaaaaa   2220

aaaaaaaaaa aaaaaaaaaa aaaaaaaaaa aaaaaaaaaa                         2260
```

<210> SEQ ID NO 12
<211> LENGTH: 2561
<212> TYPE: DNA
<213> ORGANISM: Homo sapiens

<400> SEQUENCE: 12

```
cactgttggc ctactggtta gacaaaccaa cagcagcttc ttctgacata tacacacgca     60

cactcacccc ggacacacac tcagcacact tttcctccat tcgattaaca gtgctgcaca    120

cacaatgatt acgggaaagc gcaaataaat acggaaaggg gtgcttattt tgactactgg    180

aagagctttg ctgggtctca gcgcaacttt tgttttttat tcctgagaag gtgatctctc    240

catgcggttc tctcacacaa ggattcttta aaagaggaag agagacaagc agaggggga    300

ggacagtctt tcactttaag aacggctggg ctcaaagata aaaggaaggg aaaagcagca    360

gcagcagcag cagcagcagc agcagcagca gcagcagcag cagcagggaa accaacgctg    420

cagcacttcc gaaaggcatt tttgatccat ttctgagtgt tgcggcccgt ttctccaccg    480

aagttggctc cagctctagc agccgcattg gatcccacag cttactgcga gactccggtg    540

tacaatccgg atctctgccc caacatgatt gcggcccagg ccaagctggt ctaccatctg    600

aataaatact acaacgaaaa atgccaagcc aggaaagctg ccattgccaa aactatccgg    660

gaagtctgca aagtagtttc cgacgtactg aaggaagtgg aagtgcagga gccgcggttc    720

atcagctctc tcaacgagat ggacaatcgc tacgagggcc tcgaggtcat ctccccacc    780

gaatttgaag tggtgcttta tctcaaccaa atgggggtgt tcaacttcgt ggacgatggc    840

tcactgcccg gctgcgcggt gctgaagttg agcgacgggc gcaagaggag catgtccctc    900

tgggtggaat tcattaccgc ctccggctac ctctcggcgc gcaaaatccg gtccaggttt    960

cagacgctgg tggctcaagc ggtagacaaa tgtagctacc gggatgtggt aaagatggtg   1020

gcagacacca gcgaagtgaa actgagaatc cgagataggt acgtggtgca gatcacgccg   1080

gcctttaaat gcaccgggat ctggccgagg agtgctgccc actggccact tccccacatc   1140

ccctggccgg gacccaaccg ggtggcggag gtcaaggcgg aaggtttcaa tctcttgtcc   1200

aaggagtgcc actccttggc cggcaagcag agctcggcgg agagcgacgc ctgggtgctg   1260
```

-continued

```
cagttcgcgg aggcagagaa cagactgcag atggggggct gcagaaagaa gtgcctctcc   1320

atcctcaaaa ccttaaggga tcgtcacctt gaactgccgg gccagccctt gaacaattac   1380

catatgaaga ctctggtttc ctacgagtgt gaaaagcatc cccgagagtc ggactgggac   1440

gagtcttgcc tgggtgatcg gctgaacggg attttgctgc aacttatctc ctgcctgcag   1500

tgccggcggt gtccccacta ctttctaccg aacttagatc tgtttcaagg caaacctcac   1560

tcagctctgg aaaacgctgc caaacaaacg tggcgactgg caagagagat cctgaccaac   1620

ccgaaaagtt tggaaaaact ttagaggatg atttaatcaa gagccgaaat tattaccctt   1680

ctcaaagtcc ttattaagtg taaacttctg ctcaattcct aatattccac tccgcagtgc   1740

aaacaatctc ttcctttaaa aaggaataat aatacaatat ttaaacatca tctcacccac   1800

ccccacaagg ggagaaaaag taggggaagc ggatggagaa aaacccaaag ccactagtat   1860

tagaagactt ctttccacac gatttcctat ctcccttgaa aagtacaccg taacactccg   1920

taaacagccc agctgtaacg ccagaccgag acgaacactc tgcctaacta tcaaaggatt   1980

atagcaatcc tggtgattta ggtgcatctg tctgtgagta aacacgattt ggatatgcca   2040

tctgaaagaa actgtaatgt atattttgat ttgtaacaaa tattgtgatc tcacattgtc   2100

tttgaaagtg tggatgttgg tgttttgtga tttggtgaac agaacttaaa ttgccattct   2160

ggatacttcc agacattttc cactaacaaa gatatcattt aaaggtagat ttcttcctgg   2220

tacttttatc tgtctttgaa agtgtctgaa ctttaaaaag tttacatttt gtttcaaata   2280

ttgcttgttc tatttctaac attccataaa tatacttgaa atgttattta aatatattca   2340

aagaaatttg aattcagctt atataataac gcttgaatat ctgaattata tatttgaaaa   2400

atgcacttga aatacactgg ataattactt ttgtgattta gattttaatt tgttgctggt   2460

ttttatttaa ttagatggta ataaatgaag taaaataaaa gttaaaaaaa aaaaaaaaaa   2520

aaaaggccac atgtgctcga gctgcaggtc gcggccgcta g                         2561
```

<210> SEQ ID NO 13
<211> LENGTH: 2952
<212> TYPE: DNA
<213> ORGANISM: Homo sapiens

<400> SEQUENCE: 13

```
gaattcctcg agcactgttg gcctactggt gtttcattaa gaggcagtct gttctgtgga     60

cctgggaggg agagacaggg agcgtttttc accaacaact tacaactcca cagtaagttg    120

agaggagtcc cgactccatg ctgtatgaag tccagcactg acacaccatg gccagcgacc    180

aacttgctaa gtcaaaaaaa tctaactcag aaccctttga ctgaggaaca gttttcacac    240

tccagaaaat tctaaatgac tttcatttgc tgttggttca catgccctcg tggaagactt    300

tgcttgctgc tttgttttca taagcagctt gaaggaaact caggcaggaa ctatggaact    360

ccagctgctg ctgtaactgc atcttgacga tgcaaaatga cgatggaaat atagaagcat    420

gtacatcata tctatcatga attgagcatg tgggtctgtt ccctcgaatg aaaaatacat    480

gcaaataaaa atatttggct ataggtggtg caacttttaa cagttgttct agaacttaca    540

catccaaata tgtgttttca ctttgcacag ggtggcctat ggagttttat gcttgctcta    600

gtaatgttgt agtggaaaac attttggaag tattttaatg tattaaccac attgtttaat    660

atctttaacc tcattaaatc acagtccttt aaggaatgat atgtgtgcac tcttgtatgt    720

gtatgagtgt atgtatgtgt gtgtgcagtt gcatgtgtgg gagtggggat gcacgtgtgt    780

gttcggtgtg tgtatatgag catgtgtgag tatgtgtgta tatgtgtgtg caattgcatg    840
```

-continued

```
tgtatgtatg tgtatgtatg tgtgtttgtt gtgtggtatg tatatgggca tgtgtgtgta    900
tatatgtgtg tgtgcagttg atgtgtttgg gggatacctg tgcttgttgt gtggtatgtg    960
tatgtatggg catgtgtgtg tatatatgtg tgtgtgcagc tgatgtgtgt gtggggatgc   1020
atgtgtgtgc attgtgtata tgtgtctggg catgtgtgtg tatctatgtg tgtgtgcagt   1080
ttggggatgc atgtgtggtg tgcatatgta tatggacatg tgtgagtatg tgagtatatg   1140
gtgtatgcac acatacttat atatgcatgt acatatttat cccttataaa cacatataca   1200
cacatgtaca cacacatatg tgcacataca tatatatgtg catgtatata tcccttacat   1260
atacacacat atacatgcac acatatatgc acacatacat atatatgtgt gtgtatatat   1320
ttatccctta taaacacata tacacacgta tatgcacaca tacatatata tgtgtgtgta   1380
tatatttatc ccttataaac acatatacac acgtatatgc acacatacat atatatgtgt   1440
gtgtatatat ttatccctta taaacacata tacacacgta tatgcacaca tacatatata   1500
tgtgtgtgta tatatttatc ccttataaac acatatacac acgtatatgc acacgtacat   1560
atttatgtgt gtgtatatat ttatccctta taaacacgta tacacacgta tatgcacaca   1620
tacatattta tgtgcatgta tatatttatc ccttatgaac aaaagctctt tggggtcctc   1680
aatagcttct aaaggtgcaa agggtttctg agaccaacat gtctgaaagc cactgaatta   1740
ccttaacagc tcctaggtct gaaagtttat ggttctaaaa aatgcccagc acttgctgtt   1800
tctatgagga ataaaagtga ttgtctcacc gtcaacactg tctacaacac tgttagggag   1860
acaaagctta tctacatcaa gatgatggat tagctacttt tcttagttct ttctagctcc   1920
cacaacaaaa taccgtaaac tgggtggctt ataaacaaga gaaatgtatt gctcacggtt   1980
ctggaacttg gaagtccaag atcaaagtgg aaacagattc agcatctggt gagggcccgt   2040
tcctcattga cagtcatctt gctgtattct catatggtgg atgggactag aggtctccct   2100
ctgggatttc ctttataagg gcattaatcc tattcaggag gtaacattca tgacctaacc   2160
ccttccggag gccttgcctc ctaacaccat cacactgaag gttaggattc tgacataggg   2220
attttggatg gatgcatgca ttcagaccac agtgacagcc tacaatcaag ttctaaattg   2280
tgtagttcaa actaggagaa ctgtgaggag atggttttgg ggaaagtgac ttctgcattt   2340
gcctcaatga ttttccctgc gatgacacgt ggcctgctct gaacagtgtt tgttccacaa   2400
aatgctgctg tcctttattc agaaactttc tattgaaacc aatttttatc tcaataacct   2460
gatttttaat ctcacaaaac tggacctggt gactttgagt tactatatta gaaccttgta   2520
aattgccttg tttactgatt gttttaacac aagatcctgt catctcacta gactatgtaa   2580
atttgcagat aaaaatgccc atctggccgg gcgcggtggc tcacgcctgt aatcccagca   2640
ctttgggagg ccgaggcggg cggatcacga ggccaggaga tcgagaccat tctggctaac   2700
acggtgaaac cccgtctcta ctaaaaatac aaaaaattag ccgggcgtgg tagcgggcgc   2760
ctgtagtccc agctactcgg gaggctgagg caggagaatg gcgtgaaccc gggaggcgga   2820
gcttgcagtg agccgagatc gagccactgc actccagcct gggcgacaga gcgagactcc   2880
gtctcaaaaa aaaaaaaaaa aaaaaaaaag gccacatgtg ctcgagctgc aggtcgcggc   2940
cgctagacta gt                                                       2952
```

<210> SEQ ID NO 14
<211> LENGTH: 1403
<212> TYPE: DNA
<213> ORGANISM: Homo sapiens -continued

<400> SEQUENCE: 14

```
cctactgggt ttccccctgt gtggataaga gcaaaaaccc cgattttaag gtgttcaggt     60
acagcacttc cctagagaaa cacaagctgt tcatctcagg cctgcctttc tcctgtacta    120
aagaggaact agaagaaatc tgtaaggctc atggcaccgt gaaggacctc aggctggtca    180
ccaaccgggc tggcaaacca aagggcctgg cctacgtgga gtatgaaaat gagtcccagg    240
cgtcgcaggc tgtgatgaag atggacggca tgactatcaa agagaacatc atcaaagtgg    300
caatcagcaa ccctcctcag aggaaagttc cagagaagcc agagaccagg aaggcaccag    360
gtggccccat gcttttgccg cagacataca gagcgagggg gaagggaagg acgcagctgt    420
ctctactgcc tcgtgccctg cagcgcccaa gtgctgcagc tcctcaggct gagaacggcc    480
ctgccgcggc tcctgcagtt gccgccccag cagccaccga ggcacccaag atgtccaatg    540
ccgattttgc caagctgttt ctgagaaagt gaacgggacg ctgggagaca ggaaatgcct    600
tacttcactc tggcccggcg gacctcccac cacccagcag tgcactgggg atggacaggc    660
ctggtgtgct gcgtgctcgc aaccacagat ggctcctcgg ctttagacag aaaggggaag    720
gggttctaag tcaagagcct ttcagtgctc cctcatattg agggcagtgg cagaaaagtg    780
accactcagc aggctgggcc caggatgtgg tgtcctgaga tagttttgta tcttaaagac    840
tgaggcacag aagcgaaacg agaacacact gtttttgaga cacagttgtc caaatgtttc    900
tggccagctc cggccccttt ttgtatgaca cttctcttcc accctgcaca gcacatgtgc    960
ccgtcattct tttaatttta aaagatgaaa tggcagatgc tagtaattca cagaatggcc   1020
tcttgtgggg gtgggtctga gggaagtcag ctataaaaca tttgctggag ttttgttcaa   1080
tggggctgtg catttttata ttatgtgttt gtaaatgaca tgtcagccct tgtttcatgt   1140
ttcctaaaag cagaatattt gcaacatttg ttttgtatag gaattatttg tgccacctgc   1200
tgtggactgt ttctttgcc  tagtgactag tgacctgtgt tgtctaaaca tgagtttcag   1260
ccctttggtt ttgtttaata ccatgtcaaa tgcaaacttc aattctcccc atttagcttt   1320
attaaactga cgttctcttc aaaaaaaaaa aaaaaaaaaa aaaaaaaaaa aaaaaaaaaa   1380
ggccacatgt gctcgagctg cag                                             1403
```

<210> SEQ ID NO 15
<211> LENGTH: 2144
<212> TYPE: DNA
<213> ORGANISM: Homo sapiens

<400> SEQUENCE: 15

```
cactgttggc ctactggtgt gtcaatttta tctcttagaa ttgtggattt tattgtcaag     60
acagaatggc tgttcattta ttttataaaa gcatctcctt ctataactca aaatggtctt    120
taagtgtcat ataaaagtgt acattttact tttaagcaac taatttagat acctaagaaa    180
aactatgtgc attaggaaaa gtcatgtttt tcttctcaga aaggttgatc acatgatatg    240
tctactaaga attttcacct ctgtacttgt atgtatattt tattgttact caatcttgta    300
ttttatttac aaattcaaca ctgtcaaccc tgggaattct aaaataccaa tgtattttta    360
ggttgtagct aatgttgtat tcactttcaa ttctcagttg tccacactgg tgatataaga    420
ggaacaaatc agaatcatta aatactttgt aatgccatca taaactcata tattcatcct    480
caaactccct tgtttaatgc taattggtgg cctggaactt cactgagatg caaaatcaag    540
aactgaagcc tagttgctag ataacaaaaa gctataaatg tttatgtatg tgaattttaa    600
attagaataa ccgtcttaaa ctcctacttg ccatttctaa ggcaaagcat tcattttaat    660
```

-continued

```
attgtacttt gccttttcat tcagttagtg gagtaagtca tgaaaccctt aggaagaaaa    720
acaagttatg acttattcac taaaattgat gcaagacagt tggttctaga tgaccatggc    780
catgtgttca tcatataaaa ccttcagttc tctctatggt gcttggctgg agattgacat    840
gtgaggatgt gccaatcata ttaaatggat ttggtctatg tgggtgatat gtggcctgaa    900
tgtaactgtg atagactgaa atttgttctt agctctcaaa atccactgaa gaagtcaagt    960
gaaggtgggt aaaataggga gattagtgac aactttgtgc caaatttttt aaaaaatgga   1020
agcaggtagc caatattaga atgataattt aagggtgtgg ttgaatttta gttagttgtc   1080
acatagttat tgaacctcat atgctcagtg ctgtgggaat caaacatgga agaggtatgg   1140
ctcctgcccc taatgagaac aagggggaaa aatccagata taatctaaat gctaggttat   1200
gtcagggtat aggaacacag agaatggggg acctgtaaga actggaagag tcagagaggg   1260
ctccattgaa gaggtcaaac ataattccgg aaagaattag gtagtgagga gattgtgcca   1320
ggaaaataag tgggaaaggc cacagttatg cttcctttga atggaagaga gacaaagcta   1380
tcagctatag atcattgttt tcttaagaca gccaaactgg ccctttgaaa ccattcaaat   1440
taccccagtt tagctcccta ccttttagtc tccgtgagga agacaagctg ttgcattatc   1500
atattcctct gtgctgagca gctcaagact cagccacaat atgcaaattg ctttaatgcc   1560
atattacggc agttgattta gacatttgcc agtgcaccaa accatgagag attgtccgac   1620
ctaatgccac ctggcagatg tgtacccaga gatttttctg tagctccatg tttcccataa   1680
agggcattgg aaatgcacag atgaagatct tcctttggaa ccaggcacat ttggcccctt   1740
ctcagtgact gcactgtgga actcttctta agaaaatatt gaaaacagct taatgctttc   1800
atatagtgac cgacatttag ttgaaaacta ctgctgcata gcaaatattg tgactcttcg   1860
tgtgtccaca ggagctcttg tgtgggttta aagctatgaa gtgtattcac attgtgaagt   1920
tttaattatc tttattgaaa ttaattgtgt aaaaatggta tgtgctctat taggtattca   1980
gtttgtatgt gaattctata aagaaagtgg tttttgttct ttgagtttgt tttgtttctt   2040
gaagattaca ataaatatct aagagactat attcctgaaa aaaaaaaaaa aaaaaaaaaa   2100
ggccacatgt gctcgagctg caggtcgcgg ccgctagact agtc                    2144
```

```
<210> SEQ ID NO 16
<211> LENGTH: 2995
<212> TYPE: DNA
<213> ORGANISM: Homo sapiens

<400> SEQUENCE: 16
```

```
gaattcctcg agcactgttg gcctactggc accccaagtt tgtcttgtga acttttgagt     60
taagttatta atcctcttac attcagctgg catagtggtt tctttaaagg gttgctacaa    120
agactacagt tgagaagtcc ttttataacc atgtccaaat acatagtatt ctctatactt    180
gtgtttaatt gtcttatttt tgctaggaaa taaaatttct gaatgagatc tgaaaatgga    240
ccttagaacc tgaatactca cacttttgat acctatgcag tgttatatga atttccttaa    300
acccactgtt gtttgcaata agttgattca tgacagtgtt ccttggaagg taatggtcag    360
aagctatgta gtttttcata aaatattcca tcttgagtaa aactgtaaag gttcttcacg    420
gttcaacctt acatttggca gatctaacat atttctgttc tattcaacat tttaaataga    480
tatagctaat ctccccatat gctctaatgc tgcttcttat gaactatcaa atgccttggc    540
ttttgggaaa acccggaagc atgcatttgg tttgcctata aataaataag acatgtacag    600
```

-continued

```
agtattttcc tggaaaagta ttacttatcc tcgtgacaag tcttaacacc tggtaagact    660
tgttcactta acatttttta agtttggttg ctttttcccc ctgctggctg ttgaatttga    720
atcctgaaac agttgtagta tatcttgctt gcctgcttgc acgcttcctc tctttccacc    780
ttttgttcca tcttaaagct aatttaggaa aagtctggtt ataaactagt ctttatataa    840
aaattatctt ttatcactaa tgtagttttt tttccagaac catcagctaa taggaatata    900
agaccattgc tctccataat tactggatta cttctacatc tttcattagt atttaaagag    960
ccaaagagct aacaatatat tccagatttt ttacgtggac atgccttcct tttggactca   1020
tcataaattc ataggactgt aaggacagtt gagtatgatg gttctgggca cctttaggta   1080
ataacatctt cttcctactt ttctctctat ctgtgctttg ctccttttcc tgaacctgct   1140
tttggctttc ttcaactgct cctctggcac tcttgtgtgt aaaaccaatc acctgcaccc   1200
tagttatccc catttgtcct cgttcagcat cttgcagccc catcatcatg ccctacaaag   1260
ctgcacactc tagaaattcg atggatcgac caaaactctt tgtaacacca cctgagggct   1320
cttctcgcag gaggatcatt catggcacag cggtgagtag ctgttgggag cagctgggca   1380
agtctgggag ccagtgctgt tcctgtgcag actgtacatg accctgagct gtggtgtggg   1440
cgtaagaggg ggagaccgtg acatccacca tcccatcttt cccattgatc atgaatctgg   1500
ctagctgggc agtagtgtcc cctcacttcc tcttcacttg gggattttgc tctccctaaa   1560
catttgaatt tgaagatgaa agctgttctt tgttcaagca tgtatgagtg gacgccctac   1620
cctcctggag cgtccataca cataagtaca atgccagaat actttcattt ttgaaagtag   1680
gaaaaccaaa tggcctttga aggggaagtg ggcttggact gctgccttgg cattttattt   1740
caaccatatc cagaagctgg ctgaactcta aatgtggttc actcaaaagc aagataaaga   1800
atttttatcc tgcttggcta atccctgtca aggccctgtc aagggatctt aaaatttagt   1860
caaaaaagta ttttgaaaac attagtcatt tgctatatca ctaattcgta aaaggctgtt   1920
aggctgtgct ataaattctg attttgtaag tgaaaaatat aatttgtact tattattacg   1980
ggctgaggta atgttaattt tcaccatgct ataaatgcaa tgaggtaatt tgtatgtctc   2040
caggaatctt cttctttgtt ttaaatcttg tgtttatttg gtgtcagttg aaagatataa   2100
accttgttct gtggtcttta gacattgtac tttagtctta aaggactcac cagtgaacta   2160
gaagatctca ttgcctctct ccaggataac agtatgaccc ttttgatgaa aggctgaaac   2220
agtttcttaa aatcgtaact tcccagagca attcagattt ataaacctga tgaacactta   2280
aaaggatttt gcttaaagga taattcaggg ttgtgagagc ttgatggctt tgcctacagc   2340
ctgtttttct ttcaagctcc atcggccttt ctggaatcag tgtttgattc atgattgagt   2400
caggcctcca accctctaag ccacaggtga aacaatcttt gatgtctgga aagttttaat   2460
ttattagagt gttggtgttt cagagatcct ccttagctgt agacagaaag ccgtagttaa   2520
acagaacagc ttggccccaa agttgggtac tcactgggca ggggaaaaga gcatttacca   2580
tggaaaaact atcttgttct gggtaaaaac aaaaattaac actccttgag agaaggttga   2640
gggccacctg tggctgacag gttaaatgag agatttgtca tcacatgatc cagagccttg   2700
ttttgttttg tttttattac cttcctcttt ctctatttaa tcacatagct gtctttttac   2760
ctctttacaa ccaagtattt aggcaaatac taacagaaaa cgactcagag tcatttatac   2820
cctggagctg cactgtggaa ttcagtagtg actggccaca gtgagcactt ggaaagtggc   2880
tactgaaact gacaagctaa attttaagtt tttaaaaaat atttagttgt gttaaaaaaa   2940
aaaaaaaaaa aggccacatg tgctcgagct gcaggtcgcg gccgctagac tagtc        2995
```

-continued

<210> SEQ ID NO 17
<211> LENGTH: 1877
<212> TYPE: DNA
<213> ORGANISM: Homo sapiens

<400> SEQUENCE: 17
gaattcctcg agcactgttg gcctactggt aagattttta tagttaagtg aggcatttgt 60
tgattacaca aaacatgtta ttgatatttg tatcacatat gcacattttt ttccttttaa 120
gtatggtata ccgtgttctc agcaattatt tcattatcgt ttctctgcaa cctttcttca 180
atggtactaa gcaagacaca tctggggagg cctactttct atgttgtggc ataaaagtat 240
gtattgaagc tttagtagag atctcaaaaa tggttggatg gtagcaaatt actaagaact 300
ctcaaagttt ctaaagcctt agtttcagct tgctagaaaa cctatgttga gtattatggc 360
tagttccata gttgagttgg gaaatgtctt tgaggagaca ctttttcact ttgtattcat 420
ctgtacattt tctgttactt gcattctgtc atgctcaggc tattagagca ggtacatttt 480
tataactgga atgtttatgt gtagtgaagc tctgagagga ctttgcatta gatctcagca 540
gcataatcag aaggttgtcc tttgtctcag caatttttaa gctaatagta gcagaaattg 600
cagtggaaat agactgcttt gccacaacat tcagaaaatc atttatcttt ttattgcagt 660
tcttgtcacc aaacaataca ttttagtact tctcaaattg cagaactctc atagggctgg 720
gaaaatgcct gtagacacat acatactatg aatgtgctaa tgttttttgt attttcatag 780
cccatcaaag ctcctgagtc agtttccact ataatcactg cagaatcaat cttctacaag 840
ggagtatatt accaaattgg tgatgttgtt tctgtgattg atgaacaaga tggaaagccc 900
tactatgctc aaatcagagg ttttatccag gaccagtatt gcgagaagag tgcagcactg 960
acgtggctca ttcctaccct ctctagcccc agagaccaat ttgatcccgc ctcctatatc 1020
atagggccag aggaagatct tccaaggaag atggaatact tggaatttgt ttgtcatgca 1080
ccttctgagt atttcaagtc acggtcatca ccatttccca cagttcccac cagaccagag 1140
aagggctaca tatggactca tgttgggcct actcctgcaa taacaattaa ggaatcagtt 1200
gccaaccatt tgtagttcac aaattaaaac tgggtttcca ggcctggtgt ggtggctcac 1260
gcctgtagcc ccagctattg caccactgct ctccaagctg ggcaatggag tcagattctc 1320
tttcttaaaa aaccacaaaa aaactggatt tccagttctc taatattctt agtaccacaa 1380
gatatgtcat aggtatcttt aaatgaaatt cttagctgga aaagtgacta aaaagttttt 1440
ctcctgctac ctagtaataa acaaatcatt gtttattact ggtcacttag aaaattaaaa 1500
gggatagggc caggcacagt ggcttatgcc tgtaattgca gcacttttag aggccgaggc 1560
aggcggatca cctgaggtcg ggaagtggat cgcctgaggt caggagttcg agaccagcct 1620
ggccaacatg gcgaaacccc gtcgctacta aaaatacaaa aattagccag gtgtggtggc 1680
atgtgcctgt aatcccagct atttgggagg ctgaggcagg agaatcgcct aaacccagga 1740
ggtggaggtt gtagtgagcc aagattgcac cgctgtgctc cagcctgggc aacagagtga 1800
gactcttgtc tcggaaaaaa aaaaaaaaaa aaaaggccac atgtgctcga gctgcaggtc 1860
gcggccgcta gactagt 1877

<210> SEQ ID NO 18
<211> LENGTH: 2290
<212> TYPE: DNA
<213> ORGANISM: Homo sapiens -continued

<400> SEQUENCE: 18

```
gaattcctcg agcactgttg gcctactgga gttcccaccg ctggggctgg cggcgaccaa     60
ctgtaagaga aactcactgg gaggcgaggc agggggggtgc ggaggatggg aaggcgactc    120
tgaagggtgg gaagtgaatg ctggacttga tcgtctttct ctttctttca gcgcagacct    180
gtcgcagcca gagagctgtc atttcagtac cgggattcag aattgatcca gtccgcagcg    240
gagggggcac atcccagcta ccgagctgct gagtgtctct ggctgggaca atagtatttt    300
tttctctgcg aggctgcaat taacatctta tttgttctgg ctccatacag gctttgtcag    360
gatcgcggtg cggcgaccga cgttgggctc ttgcattgct ttgtgcttgg caatggaatc    420
atggtttcgg ggtctaaact tttgtttcgt tttgtagtct taatgtatct gattcttttt    480
caagtttccc tagtaacagg tttggggacg gggtgggaag aagcgagaaa aggggtgaag    540
agaaaaaacc agattatata gaaaggaaaa agggaaaagg gatgtttccc cacctttttaa    600
tctaactatc tatctgtctg tctatctatc atcatagata gtcattttgc ctcctggaca    660
gttggctgac gaagtgtctg ataaaccagc ttcagataca tgctacaaaa ggtcattcgc    720
ctcctgatta tgtttctact tgtaaacgca gttggtggtt tgcaaaacaa gtgctaaaat    780
agtgcagtga tgtggtggga ggaaaccata atgggtaatt catataaagt gctggaatct    840
tcgtaagggt gagtttctcg agcggcaggt gaagttgaat aaagcaattt tccatcattt    900
gttcccctca ctcttgcatt tttttcctcc gcttgtttct ctcccctggg gcgattatgg    960
atagccaaga acaccatttt aaaagagatt gatagtgaaa acaggaagtt tatggtctgt   1020
tatccactgg agttgtttga aatattaaaa ttggtccttt acttcttaat gcatattaat   1080
agagtgaccc tcttcaaggc tttcccgtct taaacgaatg cctgggataa acactgtaag   1140
gggaaacagt taataattcc ccagcaggct ttaactattt tcccagtaac aaatcaccgg   1200
caagagagca gcctgggtgg cattttggtt ttgtgtcatt ttggttcttt acaatatttt   1260
ttattcattt aaggaaatgt taaaaggaaa taattagggt ttatgtccag aacaaatttt   1320
gaaacaccgt ttaagcaaca cattttcttt taaaaacaaa gaacattgag caacacaaag   1380
gagaaaaaca ttttatttat ttcaacttcc ctagagatcg taattatgat tttcgcaagg   1440
caatttggtc agttctgtta ctttatccag aggaaaaaaa agcatgacag atgtggaata   1500
aaaacggagg aaaaaatgct ttggatggtt tatacataaa aaggaaagaa tgtaatgtga   1560
ggttcagtta tacctctatt ttgcatctag tgatttctca tattatcttg taacactgat   1620
tttgatgttt cttagaaatt cttaaagtca tgacacagtg gcataagaat aacagctgaa   1680
agggacaatt taaaagccta aatcctaaat ggaaaggttc acttactccc aggatcattt   1740
atattcaagt agaagtcagg gcagggtcag aaaagaaagc caccccttaat aaagcgcttc   1800
acccttcaca ttgtttctca taaccttcat aaattgcagg ctactgagct ggcctgatga   1860
tgatccttct gagatatatt tatagcagat gatttgtgga tgataactac gccaagcaag   1920
acactgtctc cagtaacccc aggctcgtct gacttcctca ggggattata ataaagaatc   1980
acaaaaagaa ccctatatga acagtctggt ctctggacac taacaacagc acaatccaaa   2040
ggcaaagaaa ggaggaacca ccttgtttca tgtctgcaag ctgctccata tgaaagcatt   2100
gctgacatgt tgacccaaca gcaaaaagag agcagcagtt tacgcaccct cagctctctg   2160
tcctttcctt tctattgatg ttggtccact tttatgactg aatacatatt aaaatcacca   2220
tttcaaatta taaaaaaaaa aaaaaaaggc cacatgtgct cgagctgcag gtcgcggccg   2280
```

-continued ctagactagt 2290

<210> SEQ ID NO 19
<211> LENGTH: 2347
<212> TYPE: DNA
<213> ORGANISM: Homo sapiens

<400> SEQUENCE: 19
ttcctcgagc actgttggcc tactggcaga atacaaggaa gaaagatgca cagagaagaa 60
tgaagatcgt catgcactac acatggatta catacttgta aaccgtgaag aaaattcaca 120
ctcaaagcca gagacctgtg aagaaagaga aagcatagct gaattagaat tgtatgtagg 180
ttccaaagaa acagggctgc agggaactca gttagcaagc ttcccagaca catgtcagcc 240
agcctcctta aatgaaagaa aaggtctctc tgcagagaaa atgtcttcta aaggcgatac 300
gagatcatct tttgaaagcc ctggcaagac tgtggagccg ttctctgaac tcggcttggg 360
tgagggtccc cagctgcaga ttctggaaga aatgaagcct ctagaatctt tagcactaga 420
ggaagcctct ggtccagtca gccaatcaca gaagagtaag agccgaggca gggctggccc 480
ggatgcagtt acccatgata atgaatggga aatgctttca ccacagcctg ttcagaaaaa 540
catgatccct gacacggaaa tggaggagga gacagagttc cttgagctcg gaaccaggat 600
atcaagacca aatggactac tgtcagagga tgtaggaatg gacatcccct ttgaagaggg 660
cgtgctgagt cccagtgctg cagacatgag gcctgaacct cctaattctc tggatcttaa 720
tgacactcat cctcggagaa tcaagctcac agccccaaat atcaatcttt ctctggacca 780
aagtgaagga tctattctct ctgatgataa cttggacagt ccagatgaaa ttgacatcaa 840
tgtggatgaa cttgataccc ccgatgaagc agattctttt gagtacactg gccatgatcc 900
cacagccaac aaagattctg gccaagagtc agagtctatt ccagaatata cggccgaaga 960
ggaacgggag gacaaccggc tttggaggac agtggtcatt ggagaacaag agcagcgcat 1020
tgacatgaag gtcatcgagc cctacaggag agtcatttct cacggaggag attcaggata 1080
ctatggggac ggtctaaatg ccatcattgt gtttgccgcc tgttttctgc cagacagcag 1140
tcgggcggat taccactatg tcatggaaaa tcttttccta tatgtaataa gtactttaga 1200
gttgatggta gctgaagact atatgattgt gtacttgaat ggtgcaaccc caagaaggag 1260
gatgccaggg ctaggctgga tgaagaaatg ctaccagatg attgacggac ggttgaggaa 1320
gaatttgaaa tcattcatca ttgttcatcc atcttggttc atcagaacaa tccttgctgt 1380
gacacgacct tttataagtt caaaattcag cagtaaaatt aaatatgtca atagcttatc 1440
agaactcagt gggctgatcc caatggattg catccacatt ccagagagca tcatcaagta 1500
cgatgaagag agatcttata agagaagtgt gaggtaaaat ctcctgatct cctattcatg 1560
ctggaccctg tgtgtgtaca ccagtgtttt acttgtgggt gacctcaaca agctaccaga 1620
gcaagaggtc actgtatcag tcttttgtat gccattttca gtctttgtcc tgtgtgtaaa 1680
gctgttgagg tcaacctaat ttgcaactga aacctactaa accagataca tccctgactt 1740
ggcccaggct gcaagctaac ttgaactgta cccaccagac tgacgtggat gttttcagct 1800
ttattcagcc agcatgtttc tgatcccttt gcaacttatg tctacatttt atgaaggaat 1860
ttgcaaagta aatgtacata aacactgaat gggaggcaat gacaacatat ttaatggaag 1920
gagtacgtct cagggctcca gaagacagtt tcgaaaagca catatgcacc actttcattt 1980
ggccctgctt tgctgagtga ctgtctcatg ctgtgcttgc ttctcttttg tttcttttcc 2040
acaccaataa tttttgctcc tgcagactgg atgaagaact gagggaagca tcagaggcag 2100

-continued

```
ctaagtaaga cttggttttc gtttagcggc tggcatgatg ttggcttgca tttcagaact   2160

gaattgggaa aatctgcatg cctggtgttt tattcctgct tcctgataat aatgcacttt   2220

agaaattctc tttctcctat gatagatgta atctctatta ttcttactac aatctatttt   2280

tccccatgaa aaaaaaaaaa aaaggccaca tgtgctcgag ctgcaggtcg cggccgctag   2340

actagtc                                                             2347
```

```
<210> SEQ ID NO 20
<211> LENGTH: 2267
<212> TYPE: DNA
<213> ORGANISM: Homo sapiens

<400> SEQUENCE: 20

gaattcctcg agcactgttg gcctactggt tccagatgtc cagcacattt ttaataggaa     60

agtattggga acagatgtca ttattttcag cctaggtttt aaaacatttt agtatgtcat    120

gaattatctt caaaaggatc ataaatcttt tttaaaggtc cattttattt aaaatatata    180

aaaataatca ctgcactgca gcctgggtga cagagagtct gtttccaaaa aaaaaaaaaa    240

aaaaaaacta tagcatcagt cttttctagg ttattttcag aaatttcaaa caatgggaaa    300

agaatggaag aacttttgag gggagttgag gaacacgaaa aaagatcagt tcacagtcat    360

ataaataaaa agtcatgtta cttgtttttt ctcttttgac ggaaatatgt aatacattta    420

tccagtttta aaatcaaagt atgtgcttag aatgtaaaga caaggaatgc taaaagtaca    480

tttatcactt aatggcaggg ataagttatg gtaagtgcaa tgttaagtga ttttgttgtg    540

cgaacatcat aaagtatact tatacaaacc tagatggtct agccttctcc acacctacgc    600

tacaaagctg tacagtatgt tactgtacta aacactgtag ggaattgtaa cacagtggta    660

agtatttgtg tatctaaaca tcgaaaaagt aaaaacagag tataaaagat ttttagccca    720

ggcacagtgg ctcacgcctg taatcccagc actttgggag gccaaggtgg gtggatcact    780

tgaggttagg agtttgtgac cagcctggcc aacatgttaa aacccggtct ctactgaaaa    840

tacaaaaatt ggctgagcgc agtggctcac acctataatc ccagcacttt aggaggccaa    900

ggcaggcaga tcacctgagg tcaggagttc gagatcagcc tgaccaacgt ggagaaaccc    960

cgtctttact aaaaatacaa aattagccag gcctggtggc aggtgcctat aatcccagct   1020

actcaggagg ctgaggcagg agaattgctt gaactcaggc agcagaggtt gcggtgagcc   1080

aaaatcgcac cattgtcatg ccatcgcact ccagcctgag caacaagagt gaaactcatc   1140

tcaaaaaaaa aaaaaaaaaa aaaaaagtac acctgtatgg aacacttaac catgactgga   1200

gcttgcagga ccggaagttg ctctggatga gtcagtgagt gagtggtgag tgaatgtgaa   1260

agcctaggac actactctac catagactgt agaaacactg tacacttagg ctacactaaa   1320

tttatcttta aaatttttgt ttcttcaata ataaatcagc caggcatggt ggctcatggc   1380

ttaatcccag cacttcggga gtccaaggtg ggcggattac ttgaggccag gagtctcaga   1440

ctggtttggc caacatagtg aaacactgtc tctacaaaat aaaaaaatta gccaggcgtg   1500

gtggtgcatg cctgtaattc cagttactca ggaggctgag gcacaagaat tgcttgaacc   1560

tgtaggcaga ggttgtggtg agccaagatt gcaccactgc actccagcct gggtgacaga   1620

gtgagactct gtctcagaaa aaaaaaataa ataaataaat acaaataata aattagctta   1680

ctgtaacttt tttactttat gaactttttg atttttttaa ctttttgact gttgtaataa   1740

cataactcaa aaggcaaaca tgttgcacag ctatacaaaa acatttttta tccccctatt   1800
```

-continued

```
ctataggggt ttttctagtt aaaaaaattt ttattttata ctttttaagc tttttttgtt   1860
aaaaattcat acaccctcca agctaggcaa cagagcaaaa ctccatctca aaaaaaaaaa   1920
aaaggccagg cgcagtggcc cacgcctcta atcctggcac tttgggaggc gaaggtgggc   1980
aaatcacttg aggtcaggag ttcaagacca gcctggccaa catggcgaaa cgccgtctgt   2040
actaaaaata caaaaattag ttggttgtgg tggtgtacac ctgtaatcgc agctactcag   2100
gaggctgaga cacaagaacg cttgaacccg ggaggtggag gttgcagcaa accaagatgg   2160
ctcctctgca ctccagcctg ggcgacagag caacactcat ctcaaaaaaa aaaaaaaaaa   2220
aaaaggccac atgtgctcga gctgcaggtc gcggccgcta gactagt                2267
```

<210> SEQ ID NO 21
<211> LENGTH: 2475
<212> TYPE: DNA
<213> ORGANISM: Homo sapiens

<400> SEQUENCE: 21

```
gaattcctcg agcactgtgg cctttttttt tttttttttt tggaaagcaa ggatcacact     60
tccccctccc tgttccttaa tcccttttct aaaaaggggg gaaaatccgg atggatttta    120
gggattggtc tggtgtcagc tgtgttttat tgcacaccta aatcctgatt ataggctttt    180
catttctccg caaagccttt attttggcag ttaagccaaa tgtgttttcc agaaagttag    240
ttattttctc ctctttcttt cctttctttc ctcccttttt cccgtctgac cccaaacgtt    300
attgtccaaa catgactgga cagcagcttt tgtttcttga ccctgtaata tgacagtctg    360
ctaatattga cagaaggtgc agtttttggg ttatagtcgt gattttcgct aatcaatcat    420
attagcagga aaaaaaatga cttgtttctg ttgtacttga gtcttaagaa aaagtgccca    480
tagtttagtg acaatttcca aaggctttag taccacctgt atttcaaaat gggggaccca    540
aactcccgga agaaacaagc tctgaacaga ctacgtgctc agcttagaaa gaaaaaaagaa   600
tctctagctg accagtttga cttcaagatg tatattgcct ttgtattcaa ggagaagaag    660
aaaaagtcag cactttttga agtgtctgag gttataccag tcatgacaaa taattatgaa    720
gaaaatatcc tgaaaggtgt gcgagattcc agctattcct tggaaagttc cctagagctt    780
ttacagaagg atgtggtaca gctccatgct cctcgatatc agtctatgag aagggatgta    840
attggctgta ctcaggagat ggatttcatt ctttggcctc ggaatgatat tgaaaaaatc    900
gtctgtctcc tgttttctag gtggaaagaa tctgatgagc cttttaggcc tgttcaggcc    960
aaatttgagt ttcatcatgg tgactatgaa aaacagtttc tgcatgtact gagccgcaag   1020
gacaagactg gaatcgttgt caacaatcct aaccagtcag tgtttctctt cattgacaga   1080
cagcacttgc agactccaaa aaacaaagct acaatcttca agttatgcag catctgcctc   1140
tacctgccac aggaacagct cacccactgg gcagttggca ccatagagga tcacctccgt   1200
ccttatatgc cagagtaggg tactgaccag caaaatggag aagatcagag aatgcagcag   1260
cagttttttt tcttgttttc ttaccacttt attctttcag agtttaaaga aaatggactc   1320
atgcacagaa cactatgcat tttgaaactt gttcatcctg gattttttta aatcattttt   1380
atctcagaac ttaaacaaaa attagatgtc gtgcacggac tgtgtgaaag aagatgcttt   1440
gcatatttgc tgcactgcat cagtatctta ctaaaaatgt gaaatgaaag gactattgta   1500
cactgaaatg cttaaatgta tctgaaagca caaggtgata ctcattttta tggtcttccc   1560
atttgtgctg gtttttgcct ctttgacatc tgtcatcagt atttagaggg tgagaagtga   1620
atgtaacagg tataaataac atttttaaaa acaataactt tgctataatc acagttgttc   1680
```

-continued

```
cagagcactg tcagatacat tctaatgacc agaactggtt taaaaaaaga aaatataacc   1740
atgggaaaga aatcttaaat gaaaaacgca tctcattgta ggcatttttg cctcatattt   1800
tactgggcca tgtttgtttc ctggtactca tgtatttttt ttttccagat ctctttcccc   1860
aagttgctat tgtaagagta ttctgctgcg tgtggatgca gttatacaca ttaaagcaga   1920
tctggagtct gaagtagcta taaagcagct ataaaacaga aatacatgca tagctgcaga   1980
aaccatgata ggtagaggac ttttcttttg gttttgtttt gttttgtttt gttttgtttt   2040
tggttttaca gagaagagat ttttattaca aagaaaaaaa ttccagtgaa ttgtgcagaa   2100
atgctggttt ttacaccatc ctaaagaaaa actttacaag ggtgttttgg agtagaaaaa   2160
aggttataaa gttggaatct taaattgtaa aattaaccat tgagtgtcaa agttctaaaa   2220
gcagaactca ttttgtgcaa tgaacataag gaaagactac tgtataggtt tttttttttt   2280
ctccttttaa atgaagaaaa gctttgctta agggttgcat acttttattg gagtaaatct   2340
gaatgatcct actcctttgg agtaaaacta gtgcttacca gtttccaatt gtatttagct   2400
tctggttgga atttgaaaaa aaaaaaaaaa aaggccacat gtgctcgagc tgcaggtcgc   2460
ggccgctaga ctagt                                                      2475
```

<210> SEQ ID NO 22
<211> LENGTH: 1980
<212> TYPE: DNA
<213> ORGANISM: Homo sapiens

<400> SEQUENCE: 22

```
ttcctcgagc actgttggcc tactggtaaa gagcctgaaa atattaatgc agctcttcaa     60
gaaacagaag ctccttatat atctattgca tgtgatttaa ttaaagaaac aaagctttct    120
gctgaaccag ctccggattt ctctgattat tcagaaatgg caaaagttga acagccagtg    180
cctgatcatt ctgagctagt tgaagattcc tcacctgatt ctgaaccagt tgacttattt    240
agtgatgatt caatacctga cgttccacaa aaacaaggtg aaactgtgat gcttgtgaaa    300
gaaagtctca ctgagacttc atttgagtca atgatagaat atgaaaataa ggaaaaactc    360
agtgctttgc cacctgaggg aggaaagcca tatttggaat cttttaagct cagtttagat    420
aacacaaaag ataccctgtt acctgatgaa gtttcaacat tgagcaaaaa ggagaaaatt    480
cctttgcaga tggaggagct cagtactgca gtttattcaa atgatgactt atttatttct    540
aaggaagcac agataagaga aactgaaacg ttttcagatt catctccaat tgaaattata    600
gatgagttcc ctacattgat cagtcctaaa actgattcat tttctaaatt agccagggaa    660
tatactgacc tagaagtatc ccacaaaagt gaaattgcta atgccccgga tggagctggg    720
tcattgcctt gcacagaatt gccccatgac ctttctttga agaacataca acccaaagtt    780
gaagagaaaa tcagtttctc agatgacttt tctaaaaatg ggtctgctac atcaaaggtg    840
ctcttattgc ctccagatgt ttctgctttg gccactcagg cagagataga gagcatagtt    900
aaacccaaag ttcttgtgaa agaagctgag aaaaaacttc cttccgatac agaaaaagag    960
gacagatcac catctgctat attttcagca gagctgagta aaacttcagt tgttgacctc   1020
ctgtactgga gagacattaa gaagactgga gtggtgtttg gtgccagcct attccagctg   1080
ctttcattga cagtattcag cattgtgagc gtaacagcct acattgcctt ggccctgctc   1140
tctgtgacca tcagctttag gatatacaag ggtgtgatcc aagctatcca gaaatcagat   1200
gaaggccacc cattcagggc atatctggaa tctgaagttg ctatatctga ggagttggtt   1260
```

-continued

```
cagaagtaca gtaattctgc tcttggtcat gtgaactgca cgataaagga actcaggcgc   1320
ctcttcttag ttgatgattt agttgattct ctggagtttg cagtgttgat gtgggtattt   1380
acctatgttg gtgccttgtt taatggtctg acactactga ttttggctct catttcactc   1440
ttcagtgttc ctgttattta tgaacggcat caggcacaga tagatcatta tctaggactt   1500
gcaaataaga atgttaaaga tgctatggct aaaatccaag caaaaatccc tggattgaag   1560
cgcaaagctg aatgaaaacg cccaaaataa ttagtaggag ttcatcttta aaggggatat   1620
tcatttgatt atacgggggga gggtcaggga agaacgaacc ttgacgttgc agtgcagttt   1680
cacagatcgt tgttagatct ttatttttag ccatgcactg ttgtgaggaa aaattacctg   1740
tcttgactgc catgtgttca tcatcttaag tattgtaagc tgctatgtat gggtttaaac   1800
cgtaatcata tctttttcct atctatctga ggcactggtg gaataaaaaa cctgtatatt   1860
ttactttgtt gcagatagtc ttgccgcatc ttggcaagtt gcagagatgg tggagctaga   1920
aaaaaaaaaa aaaaaaaggc cacatgtgct cgagctgcag gtcgcggccg ctagactagt   1980
```

<210> SEQ ID NO 23
<211> LENGTH: 3305
<212> TYPE: DNA
<213> ORGANISM: Homo sapiens

<400> SEQUENCE: 23

```
gaattcctcg agcactgttg gcctactgga ttttgtaaaa actgggacca tatcctgtgt     60
gccatagaaa ggatgataat accaagatga agccactggt tcctgccttc aagttctttc    120
aagtttttat tttaaagaaa actctgtgca tactaccaaa ttttacagtg aatgattgtg    180
cggactcgtg tgtaagaaaa actaggactg tgtggtgtaa ataactacaa ttctcttaac    240
tccgtagcag ttgccaactc agtccttgta cttcgttaac acgaatctgt ttcagagctc    300
tcctaccttg ctcactgcct taatcagacc gatttcctgc ccacctgacc agcccagcgt    360
ggtaaacctc tgtatattga gaccttggca taattggtga tcctgaagaa agaggtctct    420
ctcctaagtc tctgtcagaa ttgagcttca caattgctaa tggttgtttt ctgtgagtcc    480
tataaaaagc aaggatatgc atgattcagg gaatgaagaa tcacaggctt gggcagtgtt    540
aaacactgtg gcctatggtc cccgtgtgat ccaccctgct tctctccagg ggaccatagg    600
tcccgtcatg tactcagtgt ccacagcagt cagtcgtgta tgaccctgta acgtggaaat    660
cttatcacac acctgttatc caacaagtct acctgagggg ttttgttaca ctttaaatgg    720
gaaggcatag ggatttatga atggggcttt caccttctca tacccaggca accaacacct    780
gattttgtct caactggcta gcaaatgccc agccttcaga gtgtgcagga atgttttcaa    840
atccctcatc agactgtgac tttaacatta atttggaatc ctgtgagcac tactctgaag    900
gtttgtgttt tggcaaatct tttttctttt ttgagacagg gctctgctaa atattgctca    960
ggctggttgc aaactccttg cttcaaggga tcctcccacc tcagcctccc aagcagccgg   1020
gactgcaggc acaagccacc atgcctggct gttttttggc aaatcttgat tgtgataagc   1080
ccccctggag gatatgattc actttatgtg attcatctta ttcacaggtc tgtgagggac   1140
tgcaaagctt actcaggaaa tgaaaacaaa tgatggtcat gttgcagttt tttccttgaa   1200
ggacaaccga accatagcct ctaaagttca agtgcactga ggtgtcggaa cgctgaaagc   1260
atgaggaaac gaggacgtag ggtgtgactg aatggtggct agattagtgg gagcagttca   1320
cctggatgaa gattgagagc atcgtctttg agaagtgaaa gactagcaag aataaaataa   1380
attaagtcca gtgtttgagc caaggttgcc acctgtctct taacatctca ctgaacataa   1440
```

-continued

```
gtcctgaggt attaggacga ccatactgcc tctgagctga aaacattcaa aagttcacat   1500

ccctgtttgg gggataccat tcaccgcctt cagcccagat gatactttcc tttaaatctg   1560

tgtctctgtg tgtataacaa agaggaagat ggaaacaatg ttcatggaaa ctgctgttga   1620

gccccttgtc ccaccactcc cgccatctgc tgcaggcagg aaggcatgtg agtgtacgtt   1680

ttcttccagg agacatcagg tccccctgga ttcaaattaa gtgcaatatt ttgcaaacag   1740

ctcttcttag ggaaatctcc tgaaggaaaa aaatgtgaca gaatgttcca tagtctgaga   1800

gaatggaatc gttgagcatt tagtacaagt ccagtgtgtg tgagcgggac ttaggcagct   1860

caagcttgct ttttttttta agcgtacaat tgagtggttt tagtaaattc acaaacttgt   1920

tcaaccatca ccactatcta attccagact cacgcatttt taaacaataa atgtcatttc   1980

atgaaatctt tggtgataaa gtattttgga ttcagagaag agctccctta ccagtcccac   2040

cctgatctca tggctgtctc tcctttcatt gtcagactcc ccctggtcta ccgcgttgat   2100

gtgtatacac tgatctttca agtctgggag acagataagg aggccaggtg caaggcaggg   2160

aggcagagag aatgttgtgc ttcctttagc ttttgtattt cgatggccag cattaccctt   2220

tacctgtggg catcagactc agcgtgggct gagtgctgag tgtaacttac actcctaaat   2280

caagctgggg cctgggtggg cccctcttgg tatctgtgaa tctttccaag caccacttcg   2340

gacacaccag ggattgagtg ctgctgttag tttagagaag gagagatgtc taacccttga   2400

ggtgaagggc tctgggaggg tccaagaaga cgtaggcttc attttcacac cagcccacac   2460

cattccagtg ctcagcctag caaatgtgct ttaatgcaca cttctcagac ctgtgatccg   2520

tgtatcttct ccccagtgac agaagtagag aagagaatgg aaagcagcac actccgtccc   2580

ctctagtctg gagctgttaa cagaatctgc tagaaactag ctttattcta acataccgta   2640

ggatctaaat cctcctacct ggatcatgaa ttcctttgaa ataattcata ttttcattga   2700

ctctcactaa atgtcaaata accttgtttt cacttggata ggctcagcct acctggcata   2760

tttattttgc agtcttgttg aaagttcatg aaactttgta ctttttaata agatgataca   2820

ctcgaaggaa acttttaatc tctgcagttt attctctctt aaggaataaa cactcccact   2880

gtttgttctc ttcaatgtgt aaggagatta aatgacattt tagaaatatt acaattaaaa   2940

atagtgatgt agctgtaaca tatgctggaa ttggatattt aatttatgtt tgtgtcaact   3000

ataatccttt ccccacccct ttcatttatg gtaaacatct tgggcaaacc caaagatgga   3060

aagtgcttgt tgggtgggta agcaccacct ggtctctcag caaacactcc tgagtggttg   3120

aagatgctgg acattggatt ctagcactgg gtttatctgg tgacatagtc tcctgtgggt   3180

cttgagttgg ttatttcaag ctcaaactct gaatatgatt aaaccagaac accccacccc   3240

caactgccaa aaaaaaaaaa aaggccacat gtgctcgagc tgcaggtcgc ggccgctaga   3300

ctagt                                                               3305
```

<210> SEQ ID NO 24
<211> LENGTH: 2254
<212> TYPE: DNA
<213> ORGANISM: Homo sapiens

<400> SEQUENCE: 24

```
atattatagt gggaatcaga tctaaattaa tatgaaacgt atgcttcttt ttatttacca     60

ctcctccaaa tggttttact atgattttgc tggtcatgtt cactgagcgg actgcccagt    120

tcatttaagt atttcttatt tgataaacaa tgacagggga cacctaattt gataccaaaa    180
```

-continued

```
atcttaaatt tcttggtact ttgttttgat atctgtaacc ttaaacatct cgagagagcg    240
aattcaaata ctccaccggt cctaatattg taatatcacc ctcctctttc tctgttctgc    300
tatatcccat atcagtaaaa caagcgtaag cagggacccc cgagggactc ctgctgtcct    360
ccctggcctt ttcctccttt tgctatttca taatttacat cagcccccat taagtcactg    420
aagacttcta acaccccatc gtgttttaaa gcgtgtgctg ttcttgctat agcccagcat    480
ctcggtatct gaaaccttaa atcctgtacc ttcctatgtc aaaagcaagc catcacgtgg    540
cgtactaagg tacgggagat aatccagagg agtgtgcaaa cacgagtgga tgtctcactg    600
attggggcac agagaaaact gggaggggat cgattttggt gttttctgcc tttcagccta    660
ttcccattct gtctggacat taggcctcca ggtagttact gtttggccgc aaacagagaa    720
atggtgggaa atgaggcgta ggagagaagc agagatcaaa ttatggaggg actgaggagg    780
gaaaggtcaa ggtgaaattt ttttagagaa agttattctg taaagggttt tgatggtaca    840
cttttgaagg gggatgggag tgggtccagg aggctgggaa acatgctata tggaaccctc    900
caggcaggaa acatggcctg aaatacgtca gtaccagggg aaggcagact caagatgatc    960
ttatccagcg ttctgactgc cagtcagagg gacagagaat gtcgtccggg ggagccttcg   1020
attctgacct aggtgatggg tgcccttgag aacgcaagga taagaacaac gttgaatgga   1080
aaacctggct tagaaactct tgagcttgag gggtgtgaac aggacctctg agcctctcca   1140
aacagaacgg aacttaggcc aaagcagtat tcacaccgcg agcagctccc gtcgtcactt   1200
tggacgcagt agcacgcagt ggtagaggca tcagacatgg ggaagggagt gacatggtac   1260
atgtgcgttc tgacgtggat tttactaggg ctgtgtgtgt tcagcccaaa agaacaagag   1320
caataaccag tgcaggcagt tccacccaca ttctactcag ccagagcagg ggctggcctg   1380
gaggcctggc tctacaggag cctctgcagg ctggggtaca cacgcctctt gtggtgtgag   1440
catgacacca gcggagatgt gtgcataaca ttgtgtgtgt tcacagaaca cactccccaa   1500
atataagcca actactccat ctggtgctca gccagaggaa gaatcttttc taaggctggc   1560
agagaaatct ggctgttgga cctaatgagg ggggacttga ctggttataa cttttgagtg   1620
tcttcgtatt tagatgttat taaaaaccct cgataggaag aaatcgccag gggcacatgc   1680
acagtaaaaa ggataggtgg cctagaaata gtctgtaatg tcaacagaga aaaataagct   1740
aataatggag ccggtgagag aaggcccagg gcagtcacag gtaaataaga gtaggacctt   1800
caaggtccaa gcagaagagt ggggcggggc agggcagtga gtgtgcacct ggcagcgttg   1860
ctgaacagga agatgcagga agtatgtggg gctgcctctt ccaattaatt tttgtgataa   1920
aatctacata aaatttatct aaaattggcc aggtatagtg cctcagcctg taatcccagc   1980
actttggaag gctgaggcgg gtggatcacc tgaggtcagg agttcgagac cagcttggcc   2040
aacacggcga gaccctgtct ctactaaaaa tacaaaaatt agccgggcat ggtggcatct   2100
gcctgtaatt ccagctactt gggaggctga ggtgggagaa ttgcttgaac ccgggaggtg   2160
gaggtggcag tgagccgaga tcacgctact gcacttcagc ctgggtgaca gagcgagact   2220
ctgtctcaat ttaaaaaaaa aaaaaaaaaa aaaa                                2254
```

<210> SEQ ID NO 25
<211> LENGTH: 2393
<212> TYPE: DNA
<213> ORGANISM: Homo sapiens

<400> SEQUENCE: 25

```
cctactggtc aatttgagat gagatttggg ttgggacaga gccaagccat atcacccagc     60
```

-continued

```
attgtagtaa cagtctcact ggtgacagta acggaggtaa tggtagtggt aataaaatat    120
atatttttta ctgtgcttgt tttttgagac agggtttcac cctgttgccc aggctggagt    180
gcagtggcat gatcatagct cactgcagct ttgaactcct ggcttcaagc aatcctcctg    240
ccagcctggg attacaggta taataacagt aattactgag agcctgacag tcattatgct    300
aagtactttt aatttacatt atttctaatc ttcaaaacaa cagtggcagg tgggaattat    360
tttcctgagt taataggtga ggggggccat aaaagactga cttcacaaat aaatagtatt    420
tcaactaggc atactgattt aaaagggcac taatattctg ctcaatgctt cttttttttt    480
tttttagata agcaaaagaa cttatatgag aaaaatggct tacttaaaaa ttacggggct    540
gggcatggtg gctcatatct gtaattccca gtactttgga aggccaagat gggaagatta    600
cctgagccta ggagttggag aacagcctag gcaatatggc aagccctcat ctctaaaata    660
aataaacaaa caatttttttt aaattgtggt cccagaaaca ccattttgag gaaattttcc    720
aagagccagg ggatctttga aaggaggcta ctgaggtagc taaacacaac cccaacaaag    780
ataaaaggtt taagtaatac tggaagacag gcaaacagta cctacaatct tttaacttcc    840
catcagccta gagatcctca gctctacact agatccccca tcacaggcct tgagaccaac    900
tcaagttctc cacattcctc tcaagacact ttagggatgc ttggaacttc ctgttatacc    960
ttgttggcag accatcttca ggcaatacag aggctaatgt ctgcatcata actatgattc   1020
caccttggga aagtgggaat cacaatttgc agactatcca aatgtgaagg ggggaagggg   1080
tgctcagaag attctgggga gctgcaaatg acagatgtcc acctagcatc cctctgacaa   1140
atagggcccc tctacatatt aatccatgtg actttggaaa tgcatagttt tactgagtaa   1200
gaggtgatct tcctggaaat gaaagaaaga accaaacaac agaaggccag atgagttggt   1260
gttacactgt aacatcttca attagcaatt tattaagtcc tgattactct gccatggaca   1320
gctaaggaag tagagtagat tttcttaaaa aaggaactct aaagaaatta aaacagaaaa   1380
tttaaaacta tttgtcaact tatttaaaaa tagtaataaa cgattacagc cgggcacagt   1440
ggctcacgcc tgtaatccca gcactttgga aggccgaggt gggcaaacac gaggtcaaga   1500
gagcgagacc atcctggcca acatggtgaa accccgactc tactaaaaat acaaaaatta   1560
gctgggcgtg gtggcgtgtg cctgtagtcc cagctactgg ggaggctgag gcaggagaat   1620
cgcttgaacc cagaaggcgg agagtgcagt gagccaagat cacgccactg tactccagcc   1680
tggtgacaga gcgagactcc gtttcaaaat aaataaataa ataataaaca attacatgtt   1740
aacataacat tttaataaac aactgggccg ggcacggtgg cttacacctg taaaactagc   1800
accttgggag gcctaggtgg gaggatcagt tgagcccagg agttcaagac cagcctgggc   1860
aacgtagtga gattctatat aacaaaaaga aaaaagttat ttaaaaaata aataaatagt   1920
ttccaaaaac ataagagggg tattgtttta tattttggca ttaagagaag acaactggat   1980
tctcatattt gcttctgcat tcaggcttgt ggtatcacac attgcacggc ctactccatg   2040
cactccactc tacattcatg aaagaatgag taaaaaaagg cctggtgcag tagctcatgc   2100
ctgtaatctc agcacttttg gaggtccagg tgggcagatc acttgaggcc aggagtttgc   2160
gaccagcttg gccaacatgg tgaaaccctg cctctactaa aaatgcaaaa attagtcagg   2220
tgtggtggca catgcctgta gtctcagcta ctcgggaggc gaggcatatg agaattgctt   2280
ggacccagga ggtggaggtt gcagtgagcc aagactgtac cactgcactc tagtctgcgc   2340
gatagtatga gactctcaaa aaaaaaaaaa aaaaaaaagg ccacatgtgc tcg          2393
```

-continued

<210> SEQ ID NO 26
<211> LENGTH: 718
<212> TYPE: DNA
<213> ORGANISM: Homo sapiens

<400> SEQUENCE: 26
cactgttggc ctactggcaa aaaataaaat aaaatatata ctatcttgct cctcagaacc 60
agtggggaag aagagggaag gcaaagaaag aaactgagca tagtaaacac agcatttttt 120
tgtaggctct tatttaaaat gtgtgtgtgt gtgtgtatgt gtgtgtttct gagtaagtat 180
tgactgggaa aaagagagaa gtcaatcaaa agtatactgt gcaattgaga gaggctggcc 240
caagatttaa aacttcctgt gggtaatcta actgtgagta gataggaatc ggccatatga 300
cgaaatgaga tcaataggaa atgtgctttt tgaggaaatt ttattttagt accaaatgtt 360
gccagtgaca atcttcagtt aagaagtaag ttattctgac ctaaaattct tatctctgcc 420
actttggttt aaaaacaaaa acccttatat acatggaata gttatatttt aattaagcat 480
ttattttagt tgttttcatc cattcaagca aaatgaataa gcagcatttt tcattgcact 540
taaaaatgta aaatacctgc atgccactaa tctgtaacat tttaccagtt cagatgcctg 600
taatgtgtga ctttatgtgt gtctgtgttg ttttgaagag aataaaggaa ataatacttt 660
gcaaaaaaaa aaaaaaaaaa aaggccacat gtgctcgagc tgcaggtcgc ggccgcta 718

<210> SEQ ID NO 27
<211> LENGTH: 2214
<212> TYPE: DNA
<213> ORGANISM: Homo sapiens

<400> SEQUENCE: 27
gagcatccag taagaagacc tgcctcaaga ggtgcactgc ggtgaccagt ggaggtgact 60
ggttggagcc tggaattgga aacagattcc aagctctggt ggacaaactc tccaggcctg 120
gtgggaatca cagctggggc agacctcatc ctggctgcct ggccacaggc ccccactctc 180
tgccactggt ggtaggacga tgcctgtgtg gagagctggc ttctctgctc ccgcctggtc 240
caccacttgg ctagagttca gagacaggaa gtgattggtc taagctaaca cagcaagttg 300
gtggcagacc tggttctaga ggcaaaacct tcttccagat gtgaatgaaa cctgcaggct 360
tcattttcct ttctgagcag tgcttcttag ctctttggag acacgaagcc cttggaaaat 420
ctgatgaagg ttacggacct tccctaggaa aacagataac tgacgtagac tcaaaaaccc 480
caagcaattt caggagccac tggactccct gaatgaaacc catccctgga ctccaggcta 540
agaacctcag ccctggggac ttcacctgct gccctttcct tacctgtcac acattgagcc 600
ccgagtcaag gccactgtac aagtagtgcc cctccctccc cctggccaag cctccttccc 660
ttgttcagga ataaagaatt ccgaggagcc ctttttagtc attcccttct cccagaccta 720
acgaatggtg cgtcaggttt ctggagcctc atttcccttc cccagacatt ggcagaggtc 780
ccttgggcta gattttctct tctggttttg tttcttgttc tgcctgactg gccgctggct 840
tccacaaagg agccctttgc tcctggcctg ggctctgatt tcactgtgtg gtctcagggg 900
aagctggact gctgtggacg ctggtgggag cttgagtctg gtctgagtct gccccaggaa 960
gaaagaatcc tgcttccacc aaccaagccc agtcagcggt tcctcccaac tggccaagtg 1020
ttcagcccag tgggctgggg aggaagagga tgagggcctc gctcctggtg cctgtggctc 1080
tgggcagggt gagaggtcgg tggaggatct ttctgtgtgt tctctgagta tgcagcagtg 1140
cagttgaagg gaacagggcc caggcaggca gcaggacgag gactcctccc atcttcacac 1200

-continued

```
ctgaaccagt cagcctggaa gctacaagtt ctcacctgcc tccccagaat gaacatcaga   1260
aaaggcaaaa ctgaccaggg ctgggatggg tttgggtcag cgtggttgga gggcagcctg   1320
tggatccctg cactggagtc ctgctgtctt cgatgcaggt tggatcatac attgttacct   1380
cctactgtat gcctcaccct ggaatagcag aatgctcagg gggagatccg agaacgagaa   1440
ggtgctccca gccccaggag cttccagtct ggctctgatc cttggccgac ctagaggaaa   1500
cctccacaca cgcccctttt gtgctaatgg tgcagtttgt gtccccctct gcccatcact   1560
gtgctgtgct tgttcctgcc tctgtgcctt ccccatatact gctcggacat gtcccctttc   1620
ctctcctcta cccagctaag cccttctgat ccacggggcc cggcttccca aaccacccag   1680
cccacattcc tccttcctgc tccgaacagg tcccgtgtga gcccctgccc ccgaattgca   1740
tgctgtccca tggacgctcc agtctcttcc gtgtgtgtct tgagtcccta actagacagt   1800
tagctccctg agggcaaggg actgtcattt cctcttgagt cctaccaggg tctagcacag   1860
gactgggctc ctaactctca ggaaacactt gtcggctgac tggtgcctca agcgctggag   1920
cttgtcggtg gccggtaatg ggcagtgcac gtggggagag ggtatgtgag ttaactcaag   1980
ggtgcctttt cttgggctgt gggctggctc ccctgggtca aaagtggatg tcggaggcct   2040
caggctctta cctccttggg gcagtgggag catcagggac cccccaccccc accccggctc   2100
tgcaggagtg cacggaagtg gtcgtccagc ctggatattt ctacaggttg ctgactcctg   2160
cgggagctga ctgagtggaa taaatgttct ctcaacaaaa aaaaaaaaaa aaaa         2214
```

<210> SEQ ID NO 28
<211> LENGTH: 2016
<212> TYPE: DNA
<213> ORGANISM: Homo sapiens

<400> SEQUENCE: 28

```
aacacatcta gacataggga aataaggttc caaagaaaac cttacacttt tattcagatt     60
ttatgttggc ctcagttgta ctagaaaagc gtttcagtat gtgtctcttg ggaatctgc     120
accttcttgg tcactgcact tcatagcccg gcatatcact gagaattcag aaatctgact    180
ctttacccag ggacgaatac atcgttatga gttcaggtgc actaaataca taggaacacc    240
cagagaaaat gagcccgaaa caatggttct ttttattttg gaagtttcag acaaactctt    300
tggaaaattg aagaaatcta tggatccttt tcctgggaag actgtacaga catacgtatt    360
cgtgtggttt ctgtgggtgt agggactggc cctggtcatg tgtcaggaag ccccaatcca    420
gaagatcgtc ttcattttac cttggccggt gatctgactc tgttctcgcg cccatctgtg    480
gttgattctc tgtcgccttg gaatggagca tcagatcttg aaggtcgctc attgcttttc    540
cacgcataga actgagccac atggcaagag cttcctaatg aaatggacgg aaactctctg    600
caaagggctg ccccagaagc acgggtgata gaaatagagt ccaaggcact aaggccgctg    660
agccacagtc ctcctaggca atgcctcctg ctggcttagt gggtttattt cataagttga    720
gtactaatgt cctgtttttt aaatgaacat atttcttcta acatttctaa caattatgaa    780
gattttctcc ctaagtgtga ctttttctta tgtcttgggg tatcagattt acagcgtaac    840
atgtgtactt caaattgtag tagtgactgg aaatttagga ttctgttgtt tcataacact    900
taaatctgca gcagattttc aggaaaatgg tcaagattca cagataattc cttccttatt    960
ccttacagat tttacaattg tatggttatt tctgaatttg gttaatttgt ttataagtgt   1020
agtggacatt taacagaaca gatgcacccg attatctgat tagaaatgtg tttcaacaca   1080
```

-continued

```
cgggtccctt tgcgtgtttc caatctctgt tttcggatct gggattctcc acctgttaca   1140

tcgttcactg gaactttcct acaaaataca gcctcgctga gaggcgcatc gtggaaaaat   1200

gaagcagcct gaagaaactc taatattggg accgagtgga gagatggaag agcatcatca   1260

gagtggtgcc gccgcacatg cgggaggcgt cccaggcagc attgctcttt gtacatgaga   1320

caggatacca ctgtctttta tgcattagac tggtaaccag ataaaataac cttgtaaaac   1380

agatctttta tgtaagaaaa atacaactct cacctcgcaa acattcctgt ctgttgcgga   1440

tgaacctagc agcaggagag gagccagggt cagtccactt ggcctgaaag ttaacgtcat   1500

atattcagat gtcaaggggt ttctgtgcat gcttttgaag tattgtgttt gggcttttac   1560

aacatgtgcc tcactgtttc gcatctacag agagagtgcc gctgagagag gagcctgagt   1620

ggatccgtgc ccagatctgc attctctgtc ctcaccactt ctccctgctg gttgatataa   1680

atgtggggat aacgtcgagc acaaaggagt caaaaattga tcagggctgg gtgtggtggc   1740

tcacgcctaa aatcctagca ctctgggagg ccgaggcagg aggactgccc aaggccagga   1800

gttaacatag caggaccctg tctctacaaa aaaataaaaa aaatcagctg ggcatggtgg   1860

tgtgcacttg tagtctcagc tgtttgagag gctgaggcag gaggatctct tgagcccagg   1920

agtttgagca tgcagtgagc tgtgatcgtg ccactgcact tcatcccggg cgatggagtg   1980

agaccccatc tcttatttaa aaaaaaaaaa aaaaaa                             2016
```

<210> SEQ ID NO 29
<211> LENGTH: 2730
<212> TYPE: DNA
<213> ORGANISM: Homo sapiens

<400> SEQUENCE: 29

```
cactgttggc ctactggtga aaaccactgc cccagacagc aatatgtttg acctgaatgg     60

cattccaatc ttttctgtac ctccactcag cacagttcat gttcagtaga tgctgaacat    120

tcttagaaat actgtgtgtg aacttagaaa agtgcaagaa gacaggcatg tctttgaccc    180

caggaatgat catttgctga agatggtgtc aagtgaacct agattaacag ccctccactc    240

cagatggata tccagtgatt cctagaatgg gatatagcca gagaacaatt ctatgcaccc    300

tacactgaca gactccctta agcaacacca gatgctctac tggtacttga agtacatgac    360

tttgaagtct tgaccctcca tgaatacctg aattatcagc aagcgggttt tgaagctggt    420

gcctcattga ggccatatta gagcaacttg tacatttgac ctcttgttat cagccatggt    480

actctacttc gtgtgcaaga gataactatg aaagccaaat tcaaatactg gcaacatttc    540

ctaaaggggc tcaatatcta tcattcgtct tcttttccaa actacacatc actgtatgac    600

tcaaccagta gcagttatat tgccccttgg tttttattca gtttaactac tgtttccaag    660

ataaatgagc taataagctt taaaaaaaaa aaaaaaaaaa ggctgaattc ttttttcttc    720

atcactggca tatctgccta ttctccagaa ttattatgac tattcagctc actttaacag    780

ttgaacttca agcgacaatc tttgaacacc ccttctcatg tgatttaaaa tgaaaccatt    840

tggaaaagtt tcttctagcc agtaatagat ttttttttta attgctctgc cttgtgccga    900

gagatgttct tttaagatga atcttttgat gtctgatacc accaaatata ggtggtaggg    960

agagttggag gctggccctt tgagcaggcc attagcttac ttgctgggca tttccgatag   1020

cttattgcct accttttttgc tggaaacaaa ctgatttgaa aaacaaaatc tatgaagact   1080

gcagctaagg attttatcgg tagacttaag agcttttgtc cttgtggata ttttagtgga   1140

accacatcag tctcaatact gtcattttac actgactcag agcagctgac ttcattcctt   1200
```

-continued

```
gccatgatat atatttaagg caggcattgt aacagacata aagacaactt atctgtttca   1260

gcaggaagga ttcagtttat gaactctcag accagatcat gttgaacaag gagactttga   1320

tgtgtgtcat gagaaaactc attctttact tcccagtcaa tttaaaggcc agctatcctg   1380

agctactcga atgaatgcac tggttaaaca ttggaaatag tttgtttata tccttgtctc   1440

tctctaggcc aattgtgatt acatgactcg actctacatc tcgtcaaaca aggcctaggt   1500

ctggttgctg tagactgctc gccctcaaca aataaaatct ggttgactag cctccttgta   1560

tatacaacta ttatttgtta agaagaaatt atcgtcaatt ttctactacc ttccaattgt   1620

cagctctttt tttcctctct ggtttttcct atactttaca gaaaaagaca ttgatctata   1680

ctgccattcc ctctaatcct gccatactca gtcaaaagga atgacttaag atgaagatga   1740

tcatctgctc gagtctaaaa tatacattgt atataagaat tggtgattag aaaagcaaaa   1800

aacctaaaac ttaaatctag gagtctgtat actgtctcca tgtctccatg cctcaggtct   1860

catctaaatc tttgaacagc accattcaac caatctgagg ccttgacttg cttgtaagat   1920

gattctcaga gatcggctga gttaaaaaag atgacgactt gattaccaaa gaaagtaggg   1980

ccaactttga caaatctggc tctgctgacc ctgtcactcc cagatgtagc atagactcct   2040

aaacagaacc tcaagtctga ttgaggataa ggccttctcc tgagctgaaa gttctttggc   2100

agatgagcaa gaaactgaaa gctgatgtac ctgactggct ctgtaagatc agaaaactgt   2160

atccagaata agccctatgg attaacccct gagtacccag agtaaaaact aatttacaga   2220

acttccttat tgatctgctg gttcttccag atcatattct ggctattggt atggctggcc   2280

tttctgaagg taccctgctt gtctattttc ctgactcagc tcttgcctgc ctttttcaca   2340

tgttgctgca attagactca ccgtgaggac tacagtcaat ttcagtctat cttgtgccca   2400

atacaacaag gatttttaat agtaacaacc cacacctcac ccactaggac tcaatgttca   2460

caacaggaag gaccattgct gcatactcct tgaccagcaa ctttttttgaa gatattttta   2520

agtgcagagt aggcctctat tcctgtatgt aattgttcat tttcagcacc tggaacctca   2580

tctatcgggt ctggaaggaa tacagcagtt cgaaagccgc gtccatttct ctccttcagt   2640

agtgcagaaa tgagtccgat tcaccagtac acacagaact gtaccagttc aacctagcaa   2700

aaaaaaaaaa aaaaggccac atgtgctcga                                    2730
```

<210> SEQ ID NO 30
<211> LENGTH: 865
<212> TYPE: DNA
<213> ORGANISM: Homo sapiens
<220> FEATURE:
<221> NAME/KEY: modified_base
<222> LOCATION: (1)..(2)
<223> OTHER INFORMATION: a, t, c, g, unknown or other
<220> FEATURE:
<221> NAME/KEY: modified_base
<222> LOCATION: (4)..(9)
<223> OTHER INFORMATION: a, t, c, g, unknown or other
<220> FEATURE:
<221> NAME/KEY: modified_base
<222> LOCATION: (11)..(16)
<223> OTHER INFORMATION: a, t, c, g, unknown or other
<220> FEATURE:
<221> NAME/KEY: modified_base
<222> LOCATION: (21)..(22)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
<220> FEATURE:

-continued

<221> NAME/KEY: modified_base
<222> LOCATION: (41)..(42)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (674)..(674)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (745)..(745)
<223> OTHER INFORMATION: a, t, c, g, unknown or other
<220> FEATURE:
<221> NAME/KEY: modified_base
<222> LOCATION: (756)..(756)
<223> OTHER INFORMATION: a, t, c, g, unknown or other
<220> FEATURE:
<221> NAME/KEY: modified_base
<222> LOCATION: (770)..(770)
<223> OTHER INFORMATION: a, t, c, g, unknown or other
<220> FEATURE:
<221> NAME/KEY: modified_base
<222> LOCATION: (773)..(773)
<223> OTHER INFORMATION: a, t, c, g, unknown or other
<220> FEATURE:
<221> NAME/KEY: modified_base
<222> LOCATION: (798)..(798)
<223> OTHER INFORMATION: a, t, c, g, unknown or other
<220> FEATURE:
<221> NAME/KEY: modified_base
<222> LOCATION: (819)..(819)
<223> OTHER INFORMATION: a, t, c, g, unknown or other
<220> FEATURE:
<221> NAME/KEY: modified_base
<222> LOCATION: (834)..(834)
<223> OTHER INFORMATION: a, t, c, g, unknown or other
<220> FEATURE:
<221> NAME/KEY: modified_base
<222> LOCATION: (843)..(843)
<223> OTHER INFORMATION: a, t, c, g, unknown or other
<220> FEATURE:
<221> NAME/KEY: modified_base
<222> LOCATION: (845)..(845)
<223> OTHER INFORMATION: a, t, c, g, unknown or other
<220> FEATURE:
<221> NAME/KEY: modified_base
<222> LOCATION: (853)..(853)
<223> OTHER INFORMATION: a, t, c, g, unknown or other
<220> FEATURE:
<221> NAME/KEY: modified_base
<222> LOCATION: (857)..(857)
<223> OTHER INFORMATION: a, t, c, g, unknown or other
<220> FEATURE:
<221> NAME/KEY: modified_base
<222> LOCATION: (860)..(860)
<223> OTHER INFORMATION: a, t, c, g, unknown or other
<220> FEATURE:
<221> NAME/KEY: modified_base
<222> LOCATION: (864)..(864)
<223> OTHER INFORMATION: a, t, c, g, unknown or other

<400> SEQUENCE: 30
nngnnnnnnt nnnnnnggcc nngnatcctc gagcacggtg nngcctactg ctagcaaaac 60
ttgtttagct tagcaaaaac aaacacacaa aaaaactgag aactctgctg tttcagatat 120
gccataacat acatctgaaa cacatgtgta acaatcaaaa tggtgggctc tagaatggtt 180
ttggagctcg agatcttcat gggttagact tgctggtcag acccaggagc acctgtggct 240
cacaccttct gttcccctcc tggcctgtgc agaatgtaaa cagcagactc atactcaatg 300

-continued

```
ggcactacag gccttatcag acgttttata caagcctgga ttgcttagta ggggaataag    360

gcattctctg agggggcttt ccacttagat tgagaatttt atttgaaaag aatctggttt    420

aaatggcatt gtggtccgag gtagctgctc tccccactga gagctgagcc gaaatataag    480

aataatatat ttgtgcttcg agttggtgtt tctttcagtg taatgcatgc agtggtcaca    540

acccagttac tcataatatt tggattgtat ttgttcgtaa gatatgccca agaagactag    600

agaattagtg ttatatacca tatagaactt actgtcagtc aactataaac anggccaatt    660

aaaaactgtt ccantactac gcaaacacat attaaaggcc nttgctgatg acacattaac    720

tggatctaac caacccaaaa agggnttgat ttgaanctga ttgttgccan tangcatatt    780

ggatcccacc taccaaantt cctccgaagg ggattttgna atttgaaaag ggtntaggaa    840

atntncctaa aancaanttn tggng                                          865
```

<210> SEQ ID NO 31
<211> LENGTH: 876
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(4)
<223> OTHER INFORMATION: a, t, c, g, unknown or other
<220> FEATURE:
<221> NAME/KEY: modified_base
<222> LOCATION: (7)..(12)
<223> OTHER INFORMATION: a, t, c, g, unknown or other
<220> FEATURE:
<221> NAME/KEY: modified_base
<222> LOCATION: (27)..(27)
<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (383)..(383)
<223> OTHER INFORMATION: a, t, c, g, unknown or other
<220> FEATURE:
<221> NAME/KEY: modified_base
<222> LOCATION: (597)..(597)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (717)..(717)
<223> OTHER INFORMATION: a, t, c, g, unknown or other
<220> FEATURE:

-continued

<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (775)..(775)
<223> OTHER INFORMATION: a, t, c, g, unknown or other
<220> FEATURE:
<221> NAME/KEY: modified_base
<222> LOCATION: (786)..(786)
<223> OTHER INFORMATION: a, t, c, g, unknown or other
<220> FEATURE:
<221> NAME/KEY: modified_base
<222> LOCATION: (795)..(795)
<223> OTHER INFORMATION: a, t, c, g, unknown or other
<220> FEATURE:
<221> NAME/KEY: modified_base
<222> LOCATION: (809)..(809)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other
<220> FEATURE:
<221> NAME/KEY: modified_base
<222> LOCATION: (827)..(828)
<223> OTHER INFORMATION: a, t, c, g, unknown or other
<220> FEATURE:
<221> NAME/KEY: modified_base
<222> LOCATION: (834)..(834)
<223> OTHER INFORMATION: a, t, c, g, unknown or other
<220> FEATURE:
<221> NAME/KEY: modified_base
<222> LOCATION: (843)..(843)
<223> OTHER INFORMATION: a, t, c, g, unknown or other
<220> FEATURE:
<221> NAME/KEY: modified_base
<222> LOCATION: (862)..(862)
<223> OTHER INFORMATION: a, t, c, g, unknown or other
<220> FEATURE:
<221> NAME/KEY: modified_base
<222> LOCATION: (871)..(871)
<223> OTHER INFORMATION: a, t, c, g, unknown or other

<400> SEQUENCE: 31
gngntgnnnn nntgtggctt ttttttnggc ttttnaaaga aaaatgttaa gacttattca 60
agatgtgtat caggcattat aacaaaacag cagaacttca acctttggga atactgtaat 120
tttacatccc tttgatgcac aagtccaagt atactatttt attacagatc attctatagg 180
ggactacaag acatgaacta agaggaaatg tgcacagtca caatccaaga atatcagctc 240
tgggagtgta cactgtttgt tagaggatga agcacatcct ttgccatttc aaatactgtg 300
ccaggtggag gactaggaag gctcaaagat ggtcatggtt gacaagcact cttatcacaa 360
acacatggat agcttatcac ggngaacaca tttcaaaggg cagcaaagtg agcaagctat 420
tcacacaaag ccaggaggga ttatgactaa actctccagt ttataagcac aagtccacat 480
ctcaactcct caagaacagg tgctcaatgg caattaacta aaagttatga catgaacatt 540
acaagacttt ccagctagca ttttgttaac agcctgtgtc tgtaagtcag caaattnaaa 600
acattcagtt gtatcctcca gacagaacac cacaccacta catgtncacn tacanggctt 660
cacattttat gtcaagttca tacacaaaat gtncaacntg tcaagtactt aacacanttt 720
gccaaaaata tggcaactgc ttcaattgtc aattgagtgt ccttaanana gaaancggct 780
ccctantcaa cactngaggg aaaatagtnc cattncatta agacaanntt gggnacctta 840
aantttcaac ctgaagggaa antataatca ncaagt 876

-continued

<210> SEQ ID NO 32
<211> LENGTH: 2274
<212> TYPE: DNA
<213> ORGANISM: Homo sapiens

<400> SEQUENCE: 32
cactgttggc ctactggtag ttggttttag ataatatctt ctactgccaa acttctggca 60
aatttacctg tgaatttcaa aatgttataa aatctcttga tatgcttttg tttttccttt 120
tagccatttt ctcttcaatt tcttagtccc tctgccctct gtaaatgtgt tgagtgatat 180
agctatcaga tgtattgaag gcaaagttct cgcagaggtc tctgttccag ctctgtaaag 240
gtcacaggaa tcgtgaagga gctgagaaat cttcctctcc ggcccactgt ctgtggccca 300
ttgtcattgt ttcctcatga aacattgcag agtttgaatc ctcagtaact ctcattgact 360
ggattagagg tgatggccac agcaaatggg agagcaaaat gttggcctac agagaatgac 420
acaattttat tcgcctttgg tgttagttgc catagtgctg tatttgaaaa tcgatgcttt 480
agccaaaagc tgaatgacca ccgtttccgt agtttccact gttttgtctg catagaattt 540
tcctgaacta caagcaaaaa tgtattttgt ccaatgtcac aaaagtgaaa atgttactaa 600
tcttagatgt gttgcatatt ttgtgttttt acgttccaaa ctctttcaaa agctgccgtt 660
acaaagctgt ttggctgtat tgacagcatg tggtgttttt acaaaagcaa ttctaggaga 720
gccagtgtct accatgaact cctgacatcc ccactccagg gtcattcatg acattgaaat 780
ggcaacttgt acactgtaat tcttcgaaaa gtaacagggg atggaaatca gacctggccg 840
ttagtcacta gtgtgtagta ccgtgatctg aagtaggaaa tttaactgac atagaataat 900
tgtggttttt gaagcagcta ctcattgctt tttcctttg ctgtggagat catggattgg 960
gaatgtcctc gtgaggtgga cctaaggcag taacatttaa acttcatgtc ctagcacccg 1020
ccctccatct gacccaaaga taaaaaaggc atcaagcttc atggttatgc ctaagcttaa 1080
aaattccctt ccccactact aatattgagt tcagcagggc cccatcttac ttatttttca 1140
aaaaagttat agctttgaat tatagactat attactaaat ttggtaaggt agttctttgc 1200
atgaatggga atgtgtgtca aaatactttc acaaaaggca tgattacaat ggaaatgccc 1260
ctttgcctcc agttttgcta accctaaaaa gtatttcact aatttcaagc actgtttaca 1320
ctcaaatccc aaaattggcc aaattatata attctcttaa attttcattt ctgtaggtgg 1380
agatttaact atggttctgg tgaatcatag aagggagaga caatatttga ggggagttta 1440
tcagcagaat atcatgcctt atgaccccat tactgaaaca cagacattac aatcagaaat 1500
agacctaata attccaatat ccctccatta actagttcca gtgatgctga gagacacagc 1560
accctgtgcc aggtatcaga aatataagcc tcagcagagg gtaactgaaa actttcaatc 1620
agaaacactc tccaaggctt atggctagat tatgtaggtc actaccattc aaaacttttc 1680
tatacaaagg tggaaaagca ctcagaatct gggaattttc tggttggaag aacaatgttc 1740
tccttttcca aattggaata aagactcaga attacccatt cttcataatc atgtctgatt 1800
ggtacataca ctccaggaag tctcaaccta gaaacatttc caacctaagc atttaaagga 1860
aaactggctc attcttctga cccaaactca aaaaatatga gtacttgcgt acctccattt 1920
ctgcatgaag attttaaaac agatttcatt tttttctgtt tattttggga aggtgcgtgg 1980
gggtgttctt tcaagtgatt cacatctcaa acccatacca ctctcaactt ttatttgatg 2040
tgttcaaagc caaaaaataa aataaaataa agcagggctg aacacttaat ttgacatgaa 2100

-continued

```
gctgaaggac tgagcaagcc agaggagaga ggttgaatga agcatagcct tggcttcata   2160
ccacactttt tgtgccttgt attatcaatg taaattctga atgttgtaca gtaaacctgg   2220
atggacttct tagaaaaaaa aaaaaaaaaa aggccacatg tgctcgagct gcag         2274
```

<210> SEQ ID NO 33
<211> LENGTH: 2465
<212> TYPE: DNA
<213> ORGANISM: Homo sapiens

<400> SEQUENCE: 33

```
cactgttggc ctactggcaa atggatcaac atcggctatg agggtgagga gttgaagcca     60
tacacagagc ccgaggagga cttcggggac accaagagaa ttgaggtgat ggtgggtatg    120
ggctacacac gggaagaaat caaagagtcc ttgaccagcc agaagtacaa cgaagtgacc    180
gccacctacc tcctgctggg caggaagact gaggagggtg gggaccgggg cgccccaggg    240
ctggccctgg cacgggtgcg ggcgcccagc gacaccacca acggaacaag ttccagcaaa    300
ggcaccagcc acagcaaagg gcagcggagt tcctcttcca cctaccaccg ccagcgcagg    360
catagcgatt tctgtggccc atcccctgca cccctgcacc ccaaacgcag cccgacgagc    420
acgggggagg cggagctgaa ggaggagcgg ctgccaggcc ggaaggcgag ctgcagcacc    480
gcggggagtg ggagtcgagg gctgcccccc tccagcccca tggtcagcag cgcccacaac    540
cccaacaagg cagagatccc agagcggcgg aaggacagca cgagcacccc caacaacctc    600
cctcctagca tgatgacccg cagaaacacc tacgtttgca cagaacgccc gggggctgag    660
cgcccgtcac tgttgccaaa tgggaaagaa aacagctcag gcaccccacg ggtgcccccct    720
gcctcccccct ccagtcacag cctggcaccc ccatcagggg agcggagccg cctggcacgc    780
ggttccacca tccgcagcac cttccatggt ggccaggtcc gggaccggcg ggcaggggggt    840
gggggtggtg ggggtgtgca gaatgggccc cctgcctctc ccacactggc ccatgaggct    900
gcacccctgc ccgccgggcg gccccgcccc accaccaacc tcttcaccaa gctgacctcc    960
aaactgaccc gaagggttac cctcgatccc tctaaacggc agaactctaa tcgctgtgtt   1020
tcgggcgcct ctctgcccca gggatccaag atcaggtcgc agacgaacct gagagaatcg   1080
gggggacctga ggtcacaagt tgccatctac cttgggatca aacggaaacc gcccccccggc   1140
tgctccgatt cccctggagt gtgaagctga ccagctcgcg ccctcctgag gccctgatgg   1200
cagctctgcg ccaggccaca gcagccgccc gctgccgctg ccgccagcca cagccgttcc   1260
tgctggcctg cctgcacggg ggtgcgggcg ggcccgagcc cctgtcccac ttcgaagtgg   1320
aggtctgcca gctgccccgg ccaggcttgc ggggagttct cttccgccgt gtggcgggca   1380
ccgccctggc cttccgcacc ctcgtcaccc gcatctccaa cgacctcgag ctctgagcca   1440
ccacggtccc agggccctta ctcttcctct cccttgtcgc cttcacttct acaggagggg   1500
aaggggccag ggaggggatt ctccctttat catcacctca gtttccctga attatatttg   1560
gggcaaaga ttgtcccctc tgctgttctc tgaggccgct cagcacagaa gaaggatgag   1620
ggggctcagc ggggggagct ggcaccttcc tggagcctcc agccagtcct gtcctccctc   1680
gccctaccaa gagggcacct gaggagactt tggggacagg gcaggggcag ggagggaaac   1740
tgaggaaatc ttccattcct cccaacagct caaaattagg ccttgggcag gggcagggag   1800
agctgctgag cctaaagact ggagaatctg ggggactggg agtgggggtc agagaggcag   1860
attccttccc ctcccgtccc ctcacgctca aacccccact tcctgcccca ggctggcgcg   1920
gggcactttg tacaaatcct tgtaaatacc ccacaccctc ccctctgcaa aggtctcttg   1980
```

-continued

```
aggagctgcc gctgtcacct acggtttta agttattaca ccccgaccct cctcctgtca   2040

gccccctcac ctgcagcctg ttgcccaata aatttaagag agtccccccc tccccaatgc   2100

tgaccctagg attttccttc cctgccctca cctgcaaatg agttaaagaa gaggcgtggg   2160

aatccaggca gtggttttc ctttcggagc ctcggttttc tcatctgcag aatgggagcg   2220

gtgggggtgg gaaggtaagg atggtcgtgg aagaaggcag gatggaactc ggcctcatcc   2280

ccgaggcccc agttcctata tcgggccccc cattcatcca ctcacactcc cagccaccat   2340

gttacactgg actctaagcc acttcttact ccagtagtaa atttattcaa taaacaatca   2400

ttgacccaaa aaaaaaaaaa aaaaaaaggc cacatgtgct cgagctgcag gtcgcggccg   2460

ctaga                                                               2465
```

<210> SEQ ID NO 34
<211> LENGTH: 2280
<212> TYPE: DNA
<213> ORGANISM: Homo sapiens

<400> SEQUENCE: 34

```
cactgttggc ctactggcac ttttttaaat gccactgggg gttatttttg ctttccttgg     60

cccccaccaa tttatacatc tccattttct gacctctgga ctaactggtt gctcagcaag    120

gttctgaagg agagtttctt gcattggaca ggcccagtct tctcccatca ttgccctgct    180

gtgactccaa agaaaggagc ttcttgctga cagtgccctg tggagcaagg ctgtgtttcc    240

taccccacac ggtgctcagt gggtgccagc cctcagtgtg gctttgtgat tgctgcccta    300

aaggagaatg ctctttcctt cctcactggt actgcctgct gttttctaag cattgctcct    360

gcacagacat ggagtcccag ccccagcaag gctcttctgt tcccatctgt tgacaatgtc    420

ttgtggagca tttttgctga ggaaaaggtc acttgtaaac agaggagaaa gggaaagagt    480

acaaagccct aagtttattg taagtgaaaa ctgagggaat tcctgtcttc tttaggagta    540

atgattcata gatctagata ggtggaaata tcattcaaaa tagtcacttg agctcacaaa    600

aaaagcaagg aagaattctc atgtcctttg tcttccttct gtagccatta actgctgaat    660

ccatgtgagg aagacaggct tcccttcctt ccccctcctt agtgattttt tctttaacag    720

cataagtaaa gaggactttc tggttcattt ttgtttgttt tgttttgttt tgttttgttt    780

acaggtgagg tcttgctgtg ttgcccaggc tggagtgcgg tggccattca cagatgctat    840

catagcacac tacagcctcc aactcttggg ctcaagcatc acgcctagca gtttctggtt    900

cctttaacag caaaaggaaa gagaggttct gattcttacc tcagggtttt ttggttgttc    960

attgtttttg tttttgtttt tgttttgaca ctgcagagca caaggctaaa ggttacagct   1020

gagatctttg gaaccaaagg cagagcaagc agagcccgtt gtctgggccc cacaccactg   1080

caggcaggtg gatagaagtg cggcccctct catagtatgc ccataagtca gggcataggg   1140

cagaactacc tgtcatgttg ctacaccatc ctgtcttctc agcatctcct tgcctgtttt   1200

ctttatcagt ccaaaggaaa acaacagcag caaaatctgt ttttaaaatg tcttatatga   1260

acatatatca aatatccatg cgctgaaacc cacataccat cacttggcaa ttttttagaa   1320

taagacccca ttattatcta ttgctataaa cctagccagt tctcttgctc ttctgtattt   1380

tcctatttcc ctgccatcat ctgctatttc tgccacttct cttagactcc ttgtctgcaa   1440

agcccaagct agaactcact gtctatggca gaaggacatc cagagcccat tctggagttt   1500

tgtttttttcc ttctgccaga tgctttgtgt cctgtcttcc ttcctcctca tatttctgtt   1560
```

-continued

```
tctcatttgt gttcagtttt gtgcagcatt gctagcactg cttttgtgac cagaaaaggc   1620

cataacatgg tccaggatca tcattcttct gactctagat gggacacttg acagtgactt   1680

gaaacatttg catattcagg aatgcatgag atttcaagag agcctacagt atgaaatcat   1740

tttcacaaaa taagcagctt gcttctgaaa tgctgtcttt cccagtagct actcacctgc   1800

ctctggtggc tgggattcag atgccacaaa actgtcagta tctatagacc aggtctgtgc   1860

cacctcctct ctcctctgtg ctcagtgagg aggcagtaaa tgaagttaca ggctagcaca   1920

atacctaact catgtttccc agtacacctg tagatattac tgtactttta tgttctcaag   1980

aaataagttg ttgcctattc agtgttacag atttctttgt ttctttttaa ttaaaataca   2040

agaagcagct gaggaaaggg agacaaggta ttttatttct gactgatttt agaaaaaact   2100

tgtgtacatg tgtttggaac tgttgaaatg ccaagttttc tgtataagtg tttttgtaat   2160

taaactttca gattttcttt gttttttaag aagttgatgt gcttgtttga catttgtctc   2220

attaaaactt ttctacgttg aaaaaaaaaa aaaaaaaggc cacatgtgct cgagctgcag   2280
```

<210> SEQ ID NO 35
<211> LENGTH: 2404
<212> TYPE: DNA
<213> ORGANISM: Homo sapiens

<400> SEQUENCE: 35

```
cactgttggc ctactgggca catgcgcaaa ctgcggacgg ggaactgggc tccctagccc     60

tggcgttttt ggtgttgctg tcccagccag aatcgcgtct ggccggtggg aagccgggaa    120

ctccagcccc ctgtaggaga ggagaaagga gcgagatcat gatacatggt gatggcttgc    180

agagtcgtaa acaaaagaag acacatggga cttcaacaac tttcatcatt cgcggaaaca    240

ggaagaactt tcctaggccc actaaaatca tccaaattta ttatagatga agaatgtcat    300

gaaagtgtat taatcagttc aacagtaagg cttcttgaaa gtttggattt aaccagtgca    360

gtgggacaac ttctcaatga agcagttcaa gcacaaaaca acacatatag aactggaatc    420

agtactcttt tgtttcttgt tggtgcttgg agcagtgcag ttgaagaatg tcttcatctt    480

ggtgtcccca tttccataat agtatcagta atgtcagaag gcttaaactt ttgtagtgaa    540

gaggtagttt ctcttcatgt acctgttcac aatatatttg actgtatgga cagcacaaaa    600

acattttctc aacttgaaac atttagtgta agtttgtgtc cttttctaca ggtcccttca    660

gatactgatt tgatagagga attgcatggt ctcaaagatg ttgcctctca aacactgacc    720

atttccaacc tttctgggag acctcttaaa tcatatgaat tatttaaacc tcagacaaag    780

gttgaagcag ataacaacac atcacgaact ctgaaaaaca gcctgcttgc agatacctgc    840

tgcagacagt caatactaat ccacagtagg cattttaata ggacagataa tactgaaggg    900

gtaagcaaac cagatggatt tcaagaacat gttacagcta ctcacaaaac ttacagatgt    960

aatgatttgg tagagttggc agtaggcttg agtcatggag atcacagcag catgaagtta   1020

gtagaagaag cagtacagct gcaatatcag aatgcttgtg tgcaacaagg caactgtaca   1080

aaaccattta tgtttgacat ttcaagaatt ttcacttgct gtctaccagg cttacctgaa   1140

acttcttctt gtgtttgtcc aggatatatc actgttgtgt cagtatctaa taatcctgtg   1200

atcaaggaat tgcagaatca gcctgtgcga atagttctca ttgagggtga cctcacagag   1260

aattaccgcc acctgggatt taataagtct gcaaatatta aaacagtatt agatagcatg   1320

cagcttcaag aagacagctc agaagaactg tgggcaaatc acgtgttaca ggtgttaatc   1380

cagttcaagg tgaaccttgt cctggtacaa ggaaatgtgt ccgaacgctt aattgaaaaa   1440
```

-continued

```
tgtataaaca gtaagcggtt ggtaatcggc tcagtgaatg gcagtgtgat gcaggctttt   1500
gcagaggctg caggagcagt acaggtggcc tacattacac aagtgaatga agattgtgtg   1560
ggtgacgggg tctgcgtgac cttctggaga agcagccctt tggatgttgt agataggaac   1620
aacagaatcg caatcttatt aaaaacagaa ggaattaatt tggttacggc cgtgctcact   1680
aacccagtta ctgcacagat gcaaatcaaa gaagataggt tctggacatg tgcctatcgt   1740
ttgtattatg ctctaaaaga ggaaaaggtc ttccttggag gtggtgcagt tgaatttttg   1800
tgtcttagct gtcttcatat tcttgcagag caatctctga aaaaaagaaa accatgcctg   1860
ctcagggtgg ctgcataata cttcctcttg gctggcttca tctctggcaa tatacagacc   1920
aactgtgctt aaattcctgg caaatggatg gcagaaatac ctttcaactc tcctatataa   1980
cactgccaat tactcatcag aatttgaagc cagcacatac attcaacatc atctgcaaaa   2040
tgccacagac tctggccctc cttcatctta catcttgaat gaatatagta aactaaatag   2100
tagaattttt aattcagaca tttcaaataa actggagcag attccgagag tttatgacgt   2160
tgttacacca aagattgagg cgtggcgccg agcattggat ttagtattgt tagtacttca   2220
gacagacagt gaaataatta ctggacatgg acacacacag ataaattcac aggaattaac   2280
gggctttcta tttttgtagt gttactggct aagtctttgg aaaataattt ttcataatat   2340
gtcatgctaa taataaatat attgatagcc aaaaaaaaaa aaaaaaaagg ccacatgtgc   2400
tcga                                                                 2404
```

<210> SEQ ID NO 36
<211> LENGTH: 1690
<212> TYPE: DNA
<213> ORGANISM: Homo sapiens

<400> SEQUENCE: 36

```
cactgttggc ctactgggac tcaaagataa ggcttaggcc cctctagcca aagggccctg     60
cccagatgcc ttccttgtac tggaaactgg cccaagtggg gcagaaggcg ttgtcagtgg    120
ggttaagaag ggacggtccc agggtccatg ctagaccagt tggaaagttt tgaagtcagg    180
aaaagacgtt tttgtatcaa gggatttttta gcagttaatg gtggtggatt tttaaaggtc    240
aggggaataa agtctggggc atggggagtg cagaccaagt tactgaactg cacaggcaaa    300
attaggaagg ttattttatg agtcaaaaca tactacagac aagctaccaa aaattatttg    360
ttaaaaaatg caacaagaca aataaaaaga gaaataatca tctgtttata tttctaataa    420
aggagcaaaa tataaaaata ggacctgcta agagacattt tccattctaa ttcacgattc    480
acttttccaa ggacagcctt caactgtcac cacacagctg ggggggagtc atttcttaac    540
aagggatgcc tcttgggata gaactaggga gttttaaatc tttacttgat catcttttat    600
tttcttttcc actttttcct tttttctctc tctctgtgtc ctagacttcc attgcattta    660
tatttaatgt ttatttctga gaatcaagca gtatattttt cctaaatgaa acataaatta    720
tattcctatt cattagatag gttcctagga acaatgccaa ttaatccatt gtttaagtag    780
taacttgaat gtttttctat atccctccag ctttgttgat agtggcgggt tttgtacaat    840
tggagggagc cctcagagcc ttctggggga ggagaggaac tgtccttaat ccatcaccac    900
taccataggg caaagccagc aggtgtggcc ctgtgagggg ctgtacagat gggatgtggc    960
caggagaaca gagccccacc tggaccacct gacccctcgg gattccaccc ctgtcatcgt   1020
ggggatgttc ctatatggga gaaagttggg ttaaatcaaa aaagaggcca cgcccaggtg   1080
```

-continued

```
taatcagagc caacctggtg ggctgggtct atcacaagac ataactgatg ctgaacatga   1140

acaaagataa aaactgtttg gagggttttt gagttgtttt tcttatgttg ttgggtgggg   1200

tataccagca taaactctaa agataaaatc tatgttagat tgtcaatcaa ctgtgttttt   1260

gaacagcata attgtgtagc agcacattgc aaaaatgcat tcatccaaag cgacacatgt   1320

ggcaacgtag accacgccag tgaaataagc cccttcgtga tcacctgact ccagttctcc   1380

gtgtgctcca ttggctgcgg ctgcaggagg aagatgcctg acagccctca tgctctccgc   1440

agggggggcgc tcacaaagat gccaggggtg tttattgtgt ttattttttt aattactaaa   1500

atcagtagct aagaaagggt ccttgaagcc tcctaacctg ggttggacct ttgaaaaata   1560

tatttgtagc acatattata gatggaaaga agaagatatt tatttatacc tgtgatgcca   1620

attgtcatta aaaggctttt catggcttga caagtcaaaa aaaaaaaaaa aaaggccaca   1680

tgtgctcgag                                                          1690
```

<210> SEQ ID NO 37
<211> LENGTH: 2963
<212> TYPE: DNA
<213> ORGANISM: Homo sapiens

<400> SEQUENCE: 37

```
cactgttggc ctactggaag taattgtccg tgtcaggaag gtaggcgtgc caagccgcgg     60

ctctgcggag aaaccacgac caccgcggcc gccggaaacc caaagcgctc cagagcgtcc    120

ccgggtggcc gggcagcacc agggacagcg cccgggactc cactggggac cggctcctgg    180

gcttcccagc gtcgcgggta gaggtacagc tgctccgtgt gccgcaggct ccagattctc    240

gccaccccac ccctccctca gaaactcgga ctgctctcgt ctgccgtgtg gttctctttt    300

cttccgaaag gccagtgtct tatctctcca cttcaagtcc agaggacttg ctcagtctcc    360

tccccttaag tcatttccac catcctcagg cagctgtggg aagccgagag tcctggactg    420

ttcgtccggg tgccagcgct ggcagtccca gtccgtccgg tgcagcagcc cggcgcattc    480

ccctctctcc ctccctcttg ctctccctcc ctttctgtct tcctctcttt cctcctctac    540

tgctccctcc ctctcttgcc tcttaagttt cctgcaccgt gaatccaact gtgccaagcc    600

ttggctcccg cgaaccaatc ctgagcgcga cccgggcact gggacggcga ctccgccaaa    660

gctggacgag gcagccggac ccgtctgcgc tcgagcatgg agacggagcg cctgggaggg    720

cacgtccggg gcgctggaga cgccaggccc gagtagcttc tccatggagc ctgcccagag    780

cggtcccttc tcgcaggatt cgccccaagt cctgtgcggc tgctgagagc gctccttgct    840

ctgtaaagtg gatgtcaggt ggatctatgt ttctgaagga acaaagactc aaagaaggca    900

ccgccaagga agtttgagac gcgggagaat gcaggctgcg tgctggtacg tgcttttcct    960

cctgcagccc accgtctact tggtcacatg tgccaattta acgaacggtg gaaagtcaga   1020

acttctgaaa tcaggaagca gcaaatccac actaaagcac atatggacag aaagcagcaa   1080

agacttgtct atcagccgac tcctgtcaca gacttttcgt ggcaaagaga atgatacaga   1140

tttggacctg agatatgaca ccccagaacc ttattctgag caagacctct gggactggct   1200

gaggaactcc acagaccttc aagagcctcg gcccagggcc aagagaaggc ccattgttaa   1260

aacgggcaag tttaagaaaa tgtttggatg gggcgatttt cattccaaca tcaaaacagt   1320

gaagctgaac ctgttgataa ctgggaaaat tgtagatcat ggcaatggga catttagtgt   1380

ttatttcagg cataattcaa ctggtcaagg gaatgtatct gtcagcttgg taccccctac   1440

aaaaatcgtg gaatttgact tggcacaaca aaccgtgatt gatgccaaag attccaagtc   1500
```

-continued

```
ttttaattgt cgcattgaat atgaaaaggt tgacaaggct accaagaaca cactctgcaa   1560
ctatgaccct tcaaaaacct gttaccagga gcaaacccaa agtcatgtat cctggctctg   1620
ctccaagccc tttaaggtga tctgtattta catttccttt tatagtacag attataaact   1680
ggtacagaaa gtgtgccctg actacaacta ccacagtgac acaccttact ttccctcggg   1740
atgaaggtga acatgggggt gagactgaag cctgaggaat taaaggtcat atgacagggc   1800
tgttacctca aagaagaagg tcacatctgt tgcctggaat gtgtctacac tgctgctctt   1860
gtcaactggc tgcaaaatac actagtggaa aacactctga tgtaatttct gcccagtcag   1920
cttcatccct cagtataatt gtaaatcatc acagattttg aagtcacacc tgaagacatg   1980
ctctcacata tagaggtaca caaacacacc gtcatgcaca tttcagcttg cgtctatcat   2040
gattcctgtt gagagggctt tcattgtctg actcataatg gttcaggatc aactatcatc   2100
aaacggaagg attaactaga cagagaatgt ttctaacagt tgctgttatg gaaatctctt   2160
ttaaagtctt gagtacatgc taatcaataa tctccactca tgcattccta ctgcttggag   2220
tagctgtact ggtaaatact actgtaggag tatctgcttg ttaaaatgga aaaatgtgtc   2280
tttagagctc agtattcttt attttacaaa cacaacaaaa tgtagtaact tttttccagc   2340
atacagtagg cacattcaaa gtggtccaag atggctcttt tttctttgaa aggggcctgt   2400
tctcagtaaa gatgagcaaa catttggaat ttacatgtgg gcagacattg ggataacaac   2460
tttcatcacc aatcattgga cttttgtgaa gtcgacacca gctaaggctg cttaaaataa   2520
gttctgatca ttatataaga agggaaatgc ctggcagaca ccatgtaagt tataagtgtc   2580
tgtcttatct ttactacaca tattgtaaca aattcaatat cctagtcttc atttgtatga   2640
atggtttgta ttgtacatag tttaaccaag tgttatttga gctgcttatt aatattaact   2700
tgtacttgtc tctctgcttg ttattggtta agaaaaaagg atatgaggaa ttcattttat   2760
caatgtagct gtgaaggcca ttaaaaagac aaacttaatg tacagagcat ttattcagat   2820
caagtattgt tgaaagctat acatatacaa cattacagtc tgtctgtatt tagatatttt   2880
atttctggaa aaaatgaaat gtacataaaa ataaaacact taaagttgag tttcaaaaaa   2940
aaaaaaaaaa ggccacatgt gct                                           2963
```

<210> SEQ ID NO 38
<211> LENGTH: 2262
<212> TYPE: DNA
<213> ORGANISM: Homo sapiens

<400> SEQUENCE: 38

```
ctactgggga aaaaaaaaaa aaacaagatg acgacgacaa ccacaaaaaa aattgacatc     60
agatgaaatg aaaaaaaaaa aaaacaaaaa aaactaaagg aaggagaaag ctgtaaaaat    120
cactggcatt cgtggggcca ctccccaccc aagctccacg tgtgtccgtc tgtgctcctg    180
gcctctgggg gaccagctgg gacatgaact tgtctgccag gcccccgtcg cgtgctgaac    240
ggtgttagtt tgtaggtaac gcacacaccc cacacctaag gtgtctgcat cctcctgcca    300
acgcatgggc tccacgtggt gtgctcgctg gctgtcgtga ctgtcagctg tctcttggga    360
ggggctgtgg gggcccgctg ggctgcctcc tttcccgcta gttgtgcctg agagttgctg    420
ttgttcctgc tttcccttcc cttcctttca tcccctgaag ggctaggtgt gggttttccg    480
tgcccggtat ccccacacac ccagcacgga caacccttcg gcagagccca ggccggcccc    540
tcacccccctg gagtattgaa actggagtcc cgtccccaag gccttcagag atgcccctac    600
```

-continued

```
acacccaggg ctccagctct ggtccttctg ggggagtaaa gtgcaaagag gggcacagct    660
tagttttggg cctctcgccg agcaagagac agcactgctg gctacagctc caacacagcc    720
agctgtggca agaggactct gcctgggctg gcccccctcc tgtgtgaggt gtctgtccct    780
tctctgctgg ccagcagcag atgcactggc agctcccaac cctgtttccg cccctcggcc    840
ctcccccagc ctgttcggct tctctgcagc ccgcaagggg gagcagactt ttgacaaagg    900
actgcgggcc tcgctcaagt ccctgagccc ccagctgaag ctgggagggg aggccaggct    960
ttgtgtctgg gcatattcgt ctgctgatgg ggtttgggga agcctggggc ttggggtttg   1020
gtcgggtggt gcagctagtg gcagagcggg atcagaggtg gtggctgccc agcttctggg   1080
ctgagacaag ggtctgtgca ggggtttact gaagtgggag tgcctttgga atctgggccg   1140
ggagcagaag ggagcaaaag ctacagtggg agccagccta gggcacatgg gaggcgtgag   1200
ggcagtgctg cccgtgcagt gtcaggtgtg ccagtgcctt ggcgggctgc agtgcgtgtg   1260
agggcacctt ctaggtgggc cagggatgca gctatggaga taaggcgggc tggggacaga   1320
aacaggtggg cacagggccc aggacaccag cggatggagg gcagggtcta gccctgtgct   1380
cctgagcgtc ggctgcctgg gttcgaggcg gtgggtcccc ggccccttgt gatggtgtgt   1440
accatggggg agctcgggga cagggcaagc ccgagcatgg tggggctgca gggtgggtct   1500
gaagccaggt tgggtggggg tggtcacaag ccctgactgc agagggtcag gggctcctgc   1560
cccagtgcct gcccactttc aattcacatt gctttcaaca aggattttct ttatcttccc   1620
ctacaaatca agccaaggga ggggcacaga atggggaaca ggacacagga tcctaaactc   1680
caaggggact gtccaccgat gaacactcag agtggacacc atcttccgtc cacgctgtgc   1740
ccaggacagc tgtccccatc catgaacaca gggtaaacat ctgccgggct ccgcaccagt   1800
ggctccctgg gccatgggac agcggcaggg ctcaccacgg acagcacgtg gcccagcagc   1860
cggccaccct ggcgtcctgg ggcctcctcc cctcctctcc ctctcacctt gtcacctcca   1920
cggagctgcc tgtctgggat aatttgggga tttttttct gggggataat tcttttgcat   1980
gacccctaaa gagcaagcca caccggtctg ctagctaggt gtccgcggtg tggtggtggc   2040
ggccgctggc cagcgctgca aggggtcggc tgcccacggt gctggctggc ctcccctcct   2100
ctctcttttt gctgagtttc attgtctttt ctttctgagc cttgtaagtg tacaaaaatt   2160
attcttattt tgttctgtct cgggaaactg caaataaaag aaaaacagga caaaaaaaaa   2220
aaaaaaaaaa aaaaaaaaaa aaaaaaaaag gccacatgtg ct                      2262
```

<210> SEQ ID NO 39
<211> LENGTH: 3250
<212> TYPE: DNA
<213> ORGANISM: Homo sapiens

<400> SEQUENCE: 39

```
cactgttggc ctactgggaa atggcatttt tttggaactc agcttacaca caaattctgc     60
tagcaggagg aaagggtatt gtggctttcc gttgttaaaa tgcggaggta gagttggaaa    120
acaatcaaaa gaaatgttcc tctcattttt tggaccaaat gaacaaatct agcatttgtt    180
tttgagagaa taaatactct tcaaaaagaa cagaaactgt tctcaaaatc tttgaagtat    240
gtcactgatc ctttaaccag tagttggaga agcaagtatc ctactgacaa acacaggctt    300
tgtggggttg aaagccgatc ataagtttac aaagactgat tggcctttg gcttgtgact    360
aatgcctggc actgacacag aggaggctct taatcgacac agccacatat attttaagta    420
aaaatgcttg ttctcaaaga aattaatttt tttgcctagt accctctttc gggttaaaag    480
```

-continued

```
aatgcattgc tcaggatgta aataacatta ataattctgt caaagtgaca tcattttctg    540
taatggtata gggaaacgga ttatttgggg agaaggattc tcgttatttg tttcttagag    600
atttttcttt taataattaa tttaatttgc cagttgtaaa agcacaagag atcatatgaa    660
taagaacaat gttcctaatg gccttctaat tacagggtct gtgttttgta gtactaacat    720
taaagccaac atgtttctta ttcatacagt aaaaaatatc tattctcaag acctgatcca    780
gaccctgcat tcatatttga tatcagggta tgaagacccc ctacaatccc cctccctcca    840
aaaaccatcc tgacctgctg gctaatgcct gaacttctcc tcctaggctt ggtttcctta    900
attcagttct atatttattg agttgctact gcttcagtca catatcagac atggcattag    960
cgctctgagt cacctgtata ttcttccatg tgccagggac tttctgctct gatccttgct   1020
gaaatgaaac ctctgaggtt tcatccataa gtaatacttt agtggctcta cttcagttct   1080
ttctaggcaa agatattagg atattaatag ctgaggagag gggtaaaggc cagtacctgt   1140
gtaagaaaat gtgcacgatt ggaagagacc acagagaagt tttcctagct tcacaattac   1200
agaggcccca ctttgtccac tagttgtagg gataaaagga taccattgct tgaacccctg   1260
tggttctctg agtagttggc atgctttctc catccttctt aagactgtgg agtgtgtgaa   1320
agtacttcag gcagaagtgt ctgacttcca tctataactg agtgaaacaa agaatagcct   1380
ttgcttcttc cagacaccct ctgggaactc tccgctagct caagtgcact ccttcagcaa   1440
gcgcagtgaa gccctttca aatgcagtca tgtgcagaac cccccatata caaagcagag    1500
ggaagtgggg ttgctccaga gcccctgttc ctcaccactc ctctgtgccc tgcagaggct   1560
ctggtccatg atgctgtgcc ctggttgagg acactgacca cagaggtact ttggtggttg   1620
tcacaaatgc tgttctccac tcatgaagat ggactgttta gcactgtttt cacatctgcg   1680
gactcaaaag tcaaataact tagacaatgt gagtcttggc tttgccaata acaagaaaca   1740
atgaatgcta tgaggtgaat gtttgtgtcc ccccaaaatt catatgttga agcctaaatc   1800
tctgatgtga tggcattagg atgtggtgtc tttgaaagtt gattaagtca tgaggttaag   1860
ccctattgga tgggattagt gcctttagga agaggccccg gggagctgtc ttgccctatt   1920
ctactgtggg tggacatagc aagaaattat ctgtgaacca aaaagtaggt cttcatcaga   1980
catggaatct gccagcacct tggcctttga tttcccagcc tccagaattg tgacaagtaa   2040
atttctgtta tgttaccctg tttatggtac tttgttataa cagcctgaat agactaagag   2100
aatggagaag taacttagct gctgtagacc ccactttact catctataga acatttgatt   2160
ttagagaggt gtaaaaaagt taacatatga aaagtgccta gtacagagcg agccctctgt   2220
aaagagtagt tgtcatttta aaattaaata aaacttaatc ccaaatgaca cagaattctt   2280
ccattttagg ggaaaaatac aaaatcaaca gatttaatga gggctgcaaa atacttgaca   2340
atctcttcat catttaatca ctttttcacc cattcttaac ccctgttgtt attagtagtt   2400
ctgtaccaaa tcatatatgt catcactgtg cccctttttg ctatagacaa aacgtttttc   2460
atgtgtggtg atgcaaatgt ggactttagg gatactaatg taataatgag ccagaagtta   2520
atgaacagga aactgaacaa gaatggggca gacaacttgg caccagagat ggctgcgggg   2580
caggaagtat aaactaagca tgtccaaaaa aggggaagtg attcggaaga ccgtaagggt   2640
gagctagaca aggggctgct tctggatcca ctgagaacag actagactgc atgccgaagg   2700
caaaacataa atgcaagtcc ctctcctcac agcacacaaa tagagtttgt gatgaagtgc   2760
ccattttcct tcccattgca caagtagtct gtgtacaatt tacctaagcc cttggatatg   2820
```

-continued

```
tctattttgt ttattcttgg ttcaaatgca ttcgttctat catctagaaa attacacatt   2880

ccttcaaggc agggacagtg tcatttgctt tatatccctt ttaatatcct tgacttccat   2940

ctgggtgcaa agcaacattc agcaggaaaa tggaagccac tttaggaatt ttgaacaagg   3000

aaatatactg gaaaagctgg aactgcaaca gggagaaaga ggggtgttgg aggaacataa   3060

aggaagaaga ggtgatcccc agattcgaag cagttagccc ttctgggcag gagcccatga   3120

gcttgttcct gaaagtccaa gtgggttggt gacacttgag tttgactgtg agttcactca   3180

agagctgctg tctcaaaaaa ggaaaaaaaa aaaaaaaaaa aaaaaaaggc cacatgtgct   3240

cgagctgcag                                                          3250


<210> SEQ ID NO 40
<211> LENGTH: 6638
<212> TYPE: DNA
<213> ORGANISM: Homo sapiens

<400> SEQUENCE: 40

ctctcccgcc gcgcctccgc ctgcccgccc ccgccggccg aggctgggct gcgggaggcg     60

gccgggcggc ccgagcttcg ctagggcgac caaaacaaag gcagcatccg ggctgggtg    120

gatgcaaaca accatgaaag actgggttct cgctctcccc ggctctgctg ctgctgctgc    180

tgccgccgcc gccgctgctc ctcctcctgc cgccgccgct agggctccgc tgtgaggggg    240

aagcaggggc gcagctgctg ggcgtgcatc cgaaaggtga gagccagaga gcgagcagag    300

ggggcgggca ggccacgaaa atgtcctcgg ccgtggggcc ccgcggtcct cgcccaccca    360

cggtgcctcc ccccatgcaa gagctgcccg acctgagcca cctgaccgaa gaggagagga    420

acattatcat ggcagtgatg gaccggcaga aggaagagga ggaaaaagaa gaagccatgc    480

tcaagtgtgt tgtcagggac atggcgaagc ctgctgcctg caaaacacca agaaatgctg    540

aaaaccagcc ccaccaacct tcaccgagat tgcatcaaca gtttgaaagc tataaggaac    600

aagtgagaaa aataggggaa gaagcgcggc gttaccaggg cgagcacaaa gacgatgctc    660

cgacttgtgg aatctgtcat aaaacaaagt ttgctgatgg gtgcggtcat ctctgctcct    720

attgtcgcac taagttctgt gcgcgctgcg gaggccgcgt gtctctacgg tcaaacaacg    780

aggacaaagt ggttatgtgg gtatgcaatt tatgtcgaaa gcaacaagaa atcttaacca    840

aatctggggc atggttcttt ggaagtggcc ctcagcagac aagtcaggat ggaaccctga    900

gtgatacagc tacaggtgct ggctctgagg taccaagaga aaagaaagca cgactccaag    960

agcgatcgcg gtctcagaca cccctgagca cagcagctgc ctcctcccag gatgctgctc   1020

ctcccagcgc accaccagac aggagcaaag gggctgagcc ctcgcagcaa gccttggggc   1080

ctgaacagaa gcaggcttca tccaggtcta gaagtgaacc tcctagagag agaaagaaga   1140

ccccagggct ttccgagcag aatggcaaag gagccctgaa gagcgagcgg aaacgcgtgc   1200

caaagacctc agcgcagccc gtggaggggg ccgtcgaaga acgggagcgc aaagaaaggc   1260

gggaaagccg aaggcttgag aaagggcgat cacaggatta cccagacacg ccggaaaaac   1320

gggatgaggg caaagcggcg gatgaggaaa agcaaagaaa agaggaggat tatcagacca   1380

ggtaccgcag cgacccgaac ctggctcggt acccggtgaa accgccgcct gaggagcagc   1440

agatgcgcat gcacgcccgg gtgtcccgcg ccaggcacga gcggcgccac agcgacgtgg   1500

cgctcccgcg caccgaggcg ggcgcggcgc tgccggaggg caaggccggc aaacgcgcgc   1560

cggcggcagc cagggcctcg ccgccggact cgccgcgggc ttactcggct gagagaactg   1620

cggagaccag ggcgccgggc gccaagcagc taacgaacca cagcccgccg gcgcccagac   1680
```

-continued

```
atgggccggt tcccgcagaa gccccggagc tcaaagccca ggagcccctc aggaagcaga   1740
gccgcctgga ccccagctcg gcggtcctca tgctgcggaa cgactctttg agctcagacc   1800
agtccgagtc ggtgcggccg tccccgccca agccgcaccg gtccaagaga ggcggcaaga   1860
agcggcagat gtcggtgagc agctctgagg aggagggcgt gtcgacgccc gagtacacca   1920
gctgcgagga cgtggagctg gagagcgaga gcgtcagcga gaaaggtgat ttggattatt   1980
actggttgga tcctgccacg tggcacagcc gggagacatc acctattagt tcgcatcctg   2040
taacgtggca accatctaaa gagggggacc gattaattgg acgtgttatt cttaacaaga   2100
gaacaaccat gcccaaagac tcaggtgcat tgctgggtct gaaagttgtt ggaggaaaaa   2160
tgactgactt aggacgactt ggtgctttca tcaccaaagt aaagaagggt agcctagcag   2220
atgtagttgg acacctaaga gcaggggatg aagttctaga atggaatggt aaacccctgc   2280
cgggagctac aaatgaagaa gtttacaaca ttattttaga atcaaaatca gaacctcaag   2340
ttgaaattat tgtttcaagg cctattggtg acattccccg gattcctgag agctcccacc   2400
ctccactgga gtccagttca agttcctttg aatctcagaa gatggaaagg ccttccattt   2460
ctgttatttc tccaacaagt cctggagctc taaaagatgc cccacaagtc ttaccagggc   2520
aactttctgt gaagttgtgg tatgataaag tgggacacca gctgattgta aatgttctgc   2580
aagcaacaga tctacctgct agagtagatg gacgtcctcg aaatccctat gtaaaaatgt   2640
attttcttcc agatagaagt gataaaagta aaaggaggac caaaacagta aagaaaatac   2700
tagaaccaaa atggaatcaa acttttgtct attcacatgt acatcgtaga gattttagag   2760
aacgaatgtt agaaataact gtgtgggacc aaccaagagt gcaagaagaa gaaagtgaat   2820
ttcttggaga gatcctcata gaattggaga cagcgctttt agatgatgaa ccgcattggt   2880
ataaacttca gacacatgat gagtcttcac tacctctgcc tcagccatca cctttcatgc   2940
caaggcgaca tattcatgga gaaagctcta gcaaaaagct acaaagatct cagcgaatca   3000
gtgatagtga catctcagat tatgaggttg atgatggtat tggcgtagtt cctccagtag   3060
gctataggtc tagtgctaga gaaagtaaat ctacaacatt aactgtgcca gaacagcaaa   3120
gaacaactca tcaccgctca cgttcagtat ctcctcatcg cggcaatgat cagggaaagc   3180
cgcgttcacg tttaccaaat gtgccattac agaggagttt agatgaaatt catccaacaa   3240
gaaggtcacg ttctccaacc agacaccatg atgcctcccg aagtccagtt gatcatagaa   3300
ccagagatgt ggatagtcag tatttatcag aacaagacag tgagcttctt atgctgccca   3360
gagcaaaacg aggacgaagt gcagaatgcc tacatactac caggtaaata cagggatttg   3420
gtaatggtga ctgtgtgtga tgactctctt tccattctat tattcttccg tctctccctt   3480
agtggtatta ttacaagcaa gtcaaataaa tttcccaagt atttgaaatt tgttttgttt   3540
tatattgagg ttatggaaaa ggttccaaat atatttcagt tccgattcag gctgactgct   3600
ttgccatctg tagattcaaa aatccagaga ctagtgggcc tctctgggac tgtttgcgtt   3660
cctaaaactg aggaaccagt ttctgcaatt aaaattctaa atgctcactg tgagtgcccc   3720
caactttccc acacatattc ctgtctagtc acaagaggtc taatctgtgt atggcagtgt   3780
cattgtttca taattgtaag tttgctctgt tttagccttt tttaatttcc ttttagaatt   3840
tattgttgtt tatattctgt ttgcttttga taaaatcttt aacagttcac ttttaatggc   3900
tgagcttcag cttctttctt gatgaaaagt gaagatattc aacctgatct taactatcct   3960
agcccaccag ttgtcagaaa tgctgcagta caaactttcc cacaaaggca tataacagta   4020
```

-continued

```
tgaatgcctc tttagaagcg acaaaagata taatttttgc ttctaaattg gagcttagag   4080
cctgatgctt tatgttaatc tcattacatc tttaatttca tatccaagta aaacttctta   4140
cagattactc atggaacata ttctataaat acttaatgta tatttgaaat gaatatagaa   4200
gttaaggaag tagtaagtca gtgaaacaaa ctaacacaaa ataatcgaac tcaaatattt   4260
tagccaataa aaagcaagag gaaagagaaa gaaagaggta ttaccgcagt acttgggatg   4320
caaagacaaa tgcatgattt attatgtctg tgtgtaatat gtagttctgc ccaataatgc   4380
aaacaaaatt gggctaataa aaattgtttg aactttttac agtctgaagt tatactactc   4440
ataactactg ccatgtttgc ttggagtgcc acaggaaaaa atcgaggaaa tattagttct   4500
gcttgctgag aaaaaaatgt aaaatcatgc atattgtaaa aacctactga aggtcaaagc   4560
atgaactatc caggtttatt attacttgtt cttgacaaac agtttcttaa aataatggtt   4620
tatttactaa ttctgaaagt tttctcacac tcctcttgat gtgactaaag cttcaaaaga   4680
aataaaaaac atgcacacaa aacaaacaca aaaaaaatcc ttatatttta agctacttag   4740
tgtgtgcctg gcactcagtg tgtgaatatt tctaggatac tcacaccagt ggtctaaata   4800
taataactaa aaatattttt ctttccctta ttttgtactt gtaaaatatt atatacttat   4860
ataatattat ataatagttg catcatttta tataatctta tacttaagat tggtgctttg   4920
ctaataattc tgagctccac aagtcctatt taatagtctc tgtatgttga ctttgcattt   4980
cctgatttaa gcaaataatc atatttgtat gtatacaatt taaaaataaa tgagtattca   5040
gcgaggcaga taacatcctg tggacaggta ctacgacaat aagataggga gtggaaggaa   5100
gctgagctag ccaaatgtgt cagtgcgaaa catatgtcac cagtgtcttt tctccttcct   5160
gtctttcatt ctctaatgtg taatgctaaa agtatggaga tagagacaac atgagttcaa   5220
aaatacgtgc atgtatgtat atataatctc ttctgtgttt atattcatgt atttataaaa   5280
acattaattt atatctgtat aaaaatgaat gtcaaaatgt gtacatataa ataaccacaa   5340
ctttatatgg atatatcaat aatatagttt ggtttcatat aaactatgga cacttattat   5400
ttctataact atccatggct aaaatctaaa gctttcaaaa tacatcatac catgttcact   5460
taggacttat aaaaataaaa tctgaggatt tactagtctc tagtaaacat aaggaaaata   5520
acatttattt aataacaagc acagtgttaa atatttaatg tactttgtca atttcctgac   5580
aataattata tgttatgaat attattatcc tgattttaga gatgaggaaa aaagctacga   5640
aagtttattt tacgactaat agagtaagga ttcaaaatca gatctatttg atatcttctg   5700
tttaactagt ttttccaaaa atatgaaaac ttgtcctatg agatgtttca ccaataagag   5760
tttttgtgag tcaaatacat tttggaaact ttgcaactga aagtgtctac cttgaaattt   5820
aatacacaca gcatattaaa gtcatgttct aaagaaatct gtatgtttag tttcttttct   5880
cccaaattgt ttaatttccc aaccttttt tagtaaaacg tgtctcgagg aagtggtagt   5940
atagagaaaa tgctatagtt gccttactgt atcctactgt gtcctaaata ttgtgtacat   6000
gttaccacac acccctgtta agtggaagtt atttcccaca ttttgtggat gtagaaacag   6060
gcttggagac ttaatcgaat tacccaggtc acagccaata agtggcaaag ccaaggcagg   6120
aacttgaaca ttcagactat aaattttgtg ctattttcta gctgtttccc attctatgtt   6180
gatcccattc ttgaaaaaaa aatcactttt gaagcaatgc ttagaaaagt tttatagcaa   6240
cctattacta aagatatttg cctgaggtta ggagttgaaa agaagagtcg actgtctaga   6300
aaggaggcta aatccttagt ttcagtaaaa tttgtcctca acttgtactt aataaggagg   6360
aagctgaagc gggcagatca cttgaggtca ggagtttgag accagtgtgg ccaacatggt   6420
```

-continued

```
gaaaccccgt ctctactaaa acacacacac acacacacac acacacacac acacacacaa   6480

attaggtggg catggtggca ggtgcttgta atcccagcta cttgggaggc tgagagagga   6540

gatttgcttg aacccaggag gcagaggttg cagtgagcca agatcacacc attgcactcc   6600

agcctagata acaagagtga gactctgtct caaaaaag                           6638
```

<210> SEQ ID NO 41
<211> LENGTH: 782
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (8)..(9)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (42)..(42)
<223> OTHER INFORMATION: a, t, c, g, unknown or other
<220> FEATURE:
<221> NAME/KEY: modified_base
<222> LOCATION: (48)..(48)
<223> OTHER INFORMATION: a, t, c, g, unknown or other
<220> FEATURE:
<221> NAME/KEY: modified_base
<222> LOCATION: (102)..(102)
<223> OTHER INFORMATION: a, t, c, g, unknown or other
<220> FEATURE:
<221> NAME/KEY: modified_base
<222> LOCATION: (312)..(312)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (473)..(473)
<223> OTHER INFORMATION: a, t, c, g, unknown or other
<220> FEATURE:
<221> NAME/KEY: modified_base
<222> LOCATION: (500)..(500)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (531)..(531)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:

-continued

<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (619)..(619)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (636)..(636)
<223> OTHER INFORMATION: a, t, c, g, unknown or other
<220> FEATURE:
<221> NAME/KEY: modified_base
<222> LOCATION: (639)..(640)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (669)..(670)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (699)..(699)
<223> OTHER INFORMATION: a, t, c, g, unknown or other
<220> FEATURE:
<221> NAME/KEY: modified_base
<222> LOCATION: (716)..(717)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (723)..(723)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (749)..(750)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (762)..(762)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other

<400> SEQUENCE: 41

```
ggngcttnng ngtggctttc atggcgccat tttttcttna antagcangg ggcccggtga      60
gacaatacaa acaggtaagg tttcgtttac ctgtgagggt antatatgct ccccactcca     120
gaacactaca aaacggccag acaagtctat accaaattgc gtcttttgaa gaggccattt     180
ttctctttct cagaaaaggc attggacacc attcgccact ttgtttagaa ataaattagt     240
ctggtatgga ttggttaata ggtccaacaa ctgaacaaag ctgacagagg gtatattcta     300
attgccaagc anaattatat ctaaattttt tggaaatatt ttctatgact gttcttttgc     360
tgagactcaa gggaancatc aacaaaacaa ctccctgtcc cactcccatc atgtgtgaga     420
tttcctcaan gattttctgg agttgcgata ttagactata ngcgtctgct tanacttatt     480
tattctgtcc atccattggn tttactaatc gtaaaaagtc tagggcaanc nttactcatt     540
taacctcatc atgctccaag ttgagtnaaa aagaactggc aactttttta tccaaatttn     600
ccagtaaagn aacctaaant ctgnaatagg ngnganttnn aaaagtcana atccttgcat     660
ccaattnann tactggttca atcttcctnc gtctttaant aattcaggga ttatcnntnc     720
ccnccaanaa tgccngtcac nttnaaaann attgagtncc tnaangnaaa ggtttcccan     780
tt                                                                   782
```

<210> SEQ ID NO 42
<211> LENGTH: 772
<212> TYPE: DNA
<213> ORGANISM: Homo sapiens
<220> FEATURE:
<221> NAME/KEY: modified_base
<222> LOCATION: (3)..(5)
<223> OTHER INFORMATION: a, t, c, g, unknown or other
<220> FEATURE:
<221> NAME/KEY: modified_base
<222> LOCATION: (7)..(9)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
<222> LOCATION: (39)..(40)

-continued

<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (645)..(645)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other
<220> FEATURE:
<221> NAME/KEY: modified_base
<222> LOCATION: (656)..(656)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (747)..(747)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other

<400> SEQUENCE: 42
ggnnntnnng tgtggctttt ttngnccttt tttttctcnn gtagcaggan gacccggtga 60
gacaatacat acaggtaagg tttcgtttac ctgtgagggt agtatatgct ccccactcca 120
gaacactaca aaacggccag acaagtctat accaaattgc gtcttttgaa gaggccattt 180
ttctctttct cagaaaaggc attggacacc attcgccact ttgtttagaa ataaattagt 240
ctggtatgga ttggttaata ggtccaacaa ctgaacaaag ctgacagagg gtatattcta 300
attgccaagc aaaattatat ctaaattttt tggaaatatt ttctatgact gttcttttgc 360
tgagactcaa gggaagcaaa aacaaaacaa ctccctgtcc cactcccatc atgtgtgaga 420
tttcctcaaa gattttctgg agttgcgata ttagactata ggcgtctgct tatacttatt 480
tattctgtcc atccattggt tttactaatc gtaaaagtct aagggcaacc gtaactcatt 540
tatcctcatc atgctccaat gagtaaaaag aactggcaac tttttatcca atttaccaat 600
taagaaccta aatctgaaat angaggattt tgcacagtca taaancntgc atccanttca 660
atactggtca atcctcctcc ntccttaaat taattccngg gtnatccttc ccctcccaaa 720
aatgccngta actttcaaaa gattgantcc cttaaagtta aanattccca aa 772

<210> SEQ ID NO 43
<211> LENGTH: 782
<212> TYPE: DNA
<213> ORGANISM: Homo sapiens -continued
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (7)..(8)
<223> OTHER INFORMATION: a, t, c, g, unknown or other
<220> FEATURE:
<221> NAME/KEY: modified_base
<222> LOCATION: (21)..(21)
<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (71)..(71)
<223> OTHER INFORMATION: a, t, c, g, unknown or other
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (94)..(94)
<223> OTHER INFORMATION: a, t, c, g, unknown or other
<220> FEATURE:
<221> NAME/KEY: modified_base
<222> LOCATION: (104)..(104)
<223> OTHER INFORMATION: a, t, c, g, unknown or other
<220> FEATURE:
<221> NAME/KEY: modified_base
<222> LOCATION: (107)..(107)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (178)..(178)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (195)..(195)
<223> OTHER INFORMATION: a, t, c, g, unknown or other
<220> FEATURE:
<221> NAME/KEY: modified_base
<222> LOCATION: (258)..(258)
<223> OTHER INFORMATION: a, t, c, g, unknown or other
<220> FEATURE:
<221> NAME/KEY: modified_base
<222> LOCATION: (316)..(316)
<223> OTHER INFORMATION: a, t, c, g, unknown or other
<220> FEATURE:
<221> NAME/KEY: modified_base
<222> LOCATION: (332)..(332)
<223> OTHER INFORMATION: a, t, c, g, unknown or other
<220> FEATURE:
<221> NAME/KEY: modified_base
<222> LOCATION: (339)..(340)
<223> OTHER INFORMATION: a, t, c, g, unknown or other
<220> FEATURE:
<221> NAME/KEY: modified_base
<222> LOCATION: (344)..(344)

-continued

<223> OTHER INFORMATION: a, t, c, g, unknown or other
<220> FEATURE:
<221> NAME/KEY: modified_base
<222> LOCATION: (346)..(346)
<223> OTHER INFORMATION: a, t, c, g, unknown or other
<220> FEATURE:
<221> NAME/KEY: modified_base
<222> LOCATION: (352)..(352)
<223> OTHER INFORMATION: a, t, c, g, unknown or other
<220> FEATURE:
<221> NAME/KEY: modified_base
<222> LOCATION: (368)..(368)
<223> OTHER INFORMATION: a, t, c, g, unknown or other
<220> FEATURE:
<221> NAME/KEY: modified_base
<222> LOCATION: (389)..(389)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (405)..(405)
<223> OTHER INFORMATION: a, t, c, g, unknown or other
<220> FEATURE:
<221> NAME/KEY: modified_base
<222> LOCATION: (422)..(422)
<223> OTHER INFORMATION: a, t, c, g, unknown or other
<220> FEATURE:
<221> NAME/KEY: modified_base
<222> LOCATION: (432)..(432)
<223> OTHER INFORMATION: a, t, c, g, unknown or other
<220> FEATURE:
<221> NAME/KEY: modified_base
<222> LOCATION: (435)..(435)
<223> OTHER INFORMATION: a, t, c, g, unknown or other
<220> FEATURE:
<221> NAME/KEY: modified_base
<222> LOCATION: (443)..(443)
<223> OTHER INFORMATION: a, t, c, g, unknown or other
<220> FEATURE:
<221> NAME/KEY: modified_base
<222> LOCATION: (463)..(463)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (493)..(493)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (504)..(505)
<223> OTHER INFORMATION: a, t, c, g, unknown or other
<220> FEATURE:
<221> NAME/KEY: modified_base
<222> LOCATION: (510)..(510)
<223> OTHER INFORMATION: a, t, c, g, unknown or other
<220> FEATURE:
<221> NAME/KEY: modified_base
<222> LOCATION: (516)..(517)
<223> OTHER INFORMATION: a, t, c, g, unknown or other
<220> FEATURE:
<221> NAME/KEY: modified_base
<222> LOCATION: (546)..(546)
<223> OTHER INFORMATION: a, t, c, g, unknown or other
<220> FEATURE:
<221> NAME/KEY: modified_base
<222> LOCATION: (549)..(549)
<223> OTHER INFORMATION: a, t, c, g, unknown or other
<220> FEATURE:
<221> NAME/KEY: modified_base -continued
<222> LOCATION: (554)..(554)
<223> OTHER INFORMATION: a, t, c, g, unknown or other
<220> FEATURE:
<221> NAME/KEY: modified_base
<222> LOCATION: (560)..(560)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (573)..(573)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (584)..(584)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (608)..(608)
<223> OTHER INFORMATION: a, t, c, g, unknown or other
<220> FEATURE:
<221> NAME/KEY: modified_base
<222> LOCATION: (626)..(626)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (659)..(660)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (743)..(743)
<223> OTHER INFORMATION: a, t, c, g, unknown or other
<220> FEATURE:
<221> NAME/KEY: modified_base
<222> LOCATION: (745)..(746)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (760)..(761)
<223> OTHER INFORMATION: a, t, c, g, unknown or other
<220> FEATURE:

-continued

<221> NAME/KEY: modified_base
<222> LOCATION: (768)..(768)
<223> OTHER INFORMATION: a, t, c, g, unknown or other

<400> SEQUENCE: 43
ggggntnngt gtggctttta naggcctttt ttgtnatant ctcaaggggc ctccattata 60
ttccaangcc ngcctncccc aacttgtgct gatnttttaa ggangtnccc aagagtatga 120
agcagggtgc ttttgtccct ttctctcctc cctagtaatt ccctcctccn tatcccanag 180
ccangtaacc acccntcaaa tgaaccattc ctttttgctt tcatcaatgg tctctgtgaa 240
gttggggtcg ttgttcanga tggcggcgtc cgcgctctct gccgactccg ccccctttgc 300
ttcgttggta tggtangtgc ccttgtggcg gnacatgtnn cggntnagga anaccagggt 360
gcacaggntg gtgaaaatca ccacagcant gncgcctcca atganagccg agtttctgtt 420
gnctccattt cntanagctt ggncttgtcc tggattatat ggnaaatccg cactgggntg 480
aatccaagtg atncaggntg ccannggtcn agtggnngac gacatggggg agagggtcaa 540
cgggcnaang cccncagttn ggnctccaac aangtcnccc tggnatgtgg accttcagnc 600
ngaagggntt tgtccgcctc aaaggncggc ctttnaaggg ggccattttg ggttgaacnn 660
ggactcctgg atagggtaac cagtgaaanc ctggggtgtt ngatttgggg aaaccctttg 720
gncaaatttt ccccggtttc aanannggttt tnccaagnan ngagcgantt tgggagaatt 780
gt 782

<210> SEQ ID NO 44
<211> LENGTH: 762
<212> TYPE: DNA
<213> ORGANISM: Homo sapiens
<220> FEATURE:
<221> NAME/KEY: modified_base
<222> LOCATION: (3)..(11)
<223> OTHER INFORMATION: a, t, c, g, unknown or other
<220> FEATURE:
<221> NAME/KEY: modified_base
<222> LOCATION: (29)..(29)
<223> OTHER INFORMATION: a, t, c, g, unknown or other
<220> FEATURE:
<221> NAME/KEY: modified_base
<222> LOCATION: (41)..(41)
<223> OTHER INFORMATION: a, t, c, g, unknown or other
<220> FEATURE:
<221> NAME/KEY: modified_base
<222> LOCATION: (70)..(70)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (595)..(595)
<223> OTHER INFORMATION: a, t, c, g, unknown or other
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (627)..(627)
<223> OTHER INFORMATION: a, t, c, g, unknown or other -continued
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (645)..(645)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (671)..(671)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (702)..(702)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 44
ggnnnnnnnn ntgtggcctt tttttgccnt tttttgtgat nagtctcaag aatattccat 60
tatattccan cgcctgcctc ccccaacttg tgctgatatt ttaaggatgt gctcaagagt 120
atgaagcagg gtgcttttgt ccctttctct cctccctagt aattccctcc tccctatccc 180
atagccaagt agccacccct caaatgagcc attccttttt gctttcatca atggtctctg 240
tgaagttggg gtcgttgttc atgatggcgg cgtccgcgct ctctgccgac tccgccccct 300
ttgcttcgtt ggtatggtag gtgcccttgt ggcggaacat gtaccggatc aggaagacca 360
gggtgcacag gatggtgaaa atcaccacag caatgacgcc tccaatgata gccgagtttc 420
tgttgactcc atttcttata gcttggcctt gtcctggatt atatggaaaa tccgcactgg 480
gctgaatcca ggtgatccaa gtgccaaggg tcggtggcgg acgacatggg ggaaagggtc 540
agcggcgaag gcccgcaatt ggnctccaac aactcgccct ggatgtggac gtnanccgan 600
gggtttgtcc gcctcaaggn ggccttnana agggcgatnt gggtnaactg gnctctggan 660
aagnaancaa ntgaatccct ggggtgttgn atttggnaat cncctgggca antttccccg 720

-continued gttccaanaa cttttcccaa aaagagcgac ttgggaaaat tt 762

<210> SEQ ID NO 45
<211> LENGTH: 793
<212> TYPE: DNA
<213> ORGANISM: Homo sapiens
<220> FEATURE:
<221> NAME/KEY: modified_base
<222> LOCATION: (3)..(6)
<223> OTHER INFORMATION: a, t, c, g, unknown or other
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (22)..(22)
<223> OTHER INFORMATION: a, t, c, g, unknown or other
<220> FEATURE:
<221> NAME/KEY: modified_base
<222> LOCATION: (38)..(38)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (51)..(51)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (64)..(64)
<223> OTHER INFORMATION: a, t, c, g, unknown or other
<220> FEATURE:
<221> NAME/KEY: modified_base
<222> LOCATION: (68)..(68)
<223> OTHER INFORMATION: a, t, c, g, unknown or other
<220> FEATURE:
<221> NAME/KEY: modified_base
<222> LOCATION: (72)..(72)
<223> OTHER INFORMATION: a, t, c, g, unknown or other
<220> FEATURE:
<221> NAME/KEY: modified_base
<222> LOCATION: (78)..(79)
<223> OTHER INFORMATION: a, t, c, g, unknown or other
<220> FEATURE:
<221> NAME/KEY: modified_base
<222> LOCATION: (83)..(83)
<223> OTHER INFORMATION: a, t, c, g, unknown or other
<220> FEATURE:
<221> NAME/KEY: modified_base
<222> LOCATION: (88)..(89)
<223> OTHER INFORMATION: a, t, c, g, unknown or other
<220> FEATURE:
<221> NAME/KEY: modified_base
<222> LOCATION: (93)..(93)
<223> OTHER INFORMATION: a, t, c, g, unknown or other
<220> FEATURE:
<221> NAME/KEY: modified_base
<222> LOCATION: (96)..(96)
<223> OTHER INFORMATION: a, t, c, g, unknown or other
<220> FEATURE:
<221> NAME/KEY: modified_base
<222> LOCATION: (133)..(133)
<223> OTHER INFORMATION: a, t, c, g, unknown or other
<220> FEATURE:
<221> NAME/KEY: modified_base
<222> LOCATION: (145)..(145)
<223> OTHER INFORMATION: a, t, c, g, unknown or other -continued
<220> FEATURE:
<221> NAME/KEY: modified_base
<222> LOCATION: (147)..(147)
<223> OTHER INFORMATION: a, t, c, g, unknown or other
<220> FEATURE:
<221> NAME/KEY: modified_base
<222> LOCATION: (150)..(150)
<223> OTHER INFORMATION: a, t, c, g, unknown or other
<220> FEATURE:
<221> NAME/KEY: modified_base
<222> LOCATION: (152)..(152)
<223> OTHER INFORMATION: a, t, c, g, unknown or other
<220> FEATURE:
<221> NAME/KEY: modified_base
<222> LOCATION: (154)..(154)
<223> OTHER INFORMATION: a, t, c, g, unknown or other
<220> FEATURE:
<221> NAME/KEY: modified_base
<222> LOCATION: (158)..(158)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (172)..(173)
<223> OTHER INFORMATION: a, t, c, g, unknown or other
<220> FEATURE:
<221> NAME/KEY: modified_base
<222> LOCATION: (180)..(180)
<223> OTHER INFORMATION: a, t, c, g, unknown or other
<220> FEATURE:
<221> NAME/KEY: modified_base
<222> LOCATION: (205)..(205)
<223> OTHER INFORMATION: a, t, c, g, unknown or other
<220> FEATURE:
<221> NAME/KEY: modified_base
<222> LOCATION: (210)..(210)
<223> OTHER INFORMATION: a, t, c, g, unknown or other
<220> FEATURE:
<221> NAME/KEY: modified_base
<222> LOCATION: (212)..(212)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (222)..(223)
<223> OTHER INFORMATION: a, t, c, g, unknown or other
<220> FEATURE:
<221> NAME/KEY: modified_base
<222> LOCATION: (226)..(226)
<223> OTHER INFORMATION: a, t, c, g, unknown or other
<220> FEATURE:
<221> NAME/KEY: modified_base
<222> LOCATION: (230)..(230)
<223> OTHER INFORMATION: a, t, c, g, unknown or other
<220> FEATURE:
<221> NAME/KEY: modified_base
<222> LOCATION: (233)..(234)
<223> OTHER INFORMATION: a, t, c, g, unknown or other
<220> FEATURE:
<221> NAME/KEY: modified_base
<222> LOCATION: (244)..(245)
<223> OTHER INFORMATION: a, t, c, g, unknown or other
<220> FEATURE:
<221> NAME/KEY: modified_base
<222> LOCATION: (265)..(265)
<223> OTHER INFORMATION: a, t, c, g, unknown or other
<220> FEATURE:
<221> NAME/KEY: modified_base
<222> LOCATION: (273)..(273)
<223> OTHER INFORMATION: a, t, c, g, unknown or other
<220> FEATURE:
<221> NAME/KEY: modified_base
<222> LOCATION: (279)..(279)

-continued

<223> OTHER INFORMATION: a, t, c, g, unknown or other
<220> FEATURE:
<221> NAME/KEY: modified_base
<222> LOCATION: (284)..(284)
<223> OTHER INFORMATION: a, t, c, g, unknown or other
<220> FEATURE:
<221> NAME/KEY: modified_base
<222> LOCATION: (288)..(288)
<223> OTHER INFORMATION: a, t, c, g, unknown or other
<220> FEATURE:
<221> NAME/KEY: modified_base
<222> LOCATION: (290)..(291)
<223> OTHER INFORMATION: a, t, c, g, unknown or other
<220> FEATURE:
<221> NAME/KEY: modified_base
<222> LOCATION: (306)..(309)
<223> OTHER INFORMATION: a, t, c, g, unknown or other
<220> FEATURE:
<221> NAME/KEY: modified_base
<222> LOCATION: (323)..(323)
<223> OTHER INFORMATION: a, t, c, g, unknown or other
<220> FEATURE:
<221> NAME/KEY: modified_base
<222> LOCATION: (325)..(325)
<223> OTHER INFORMATION: a, t, c, g, unknown or other
<220> FEATURE:
<221> NAME/KEY: modified_base
<222> LOCATION: (341)..(341)
<223> OTHER INFORMATION: a, t, c, g, unknown or other
<220> FEATURE:
<221> NAME/KEY: modified_base
<222> LOCATION: (382)..(383)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (401)..(401)
<223> OTHER INFORMATION: a, t, c, g, unknown or other
<220> FEATURE:
<221> NAME/KEY: modified_base
<222> LOCATION: (413)..(413)
<223> OTHER INFORMATION: a, t, c, g, unknown or other
<220> FEATURE:
<221> NAME/KEY: modified_base
<222> LOCATION: (425)..(425)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (443)..(444)
<223> OTHER INFORMATION: a, t, c, g, unknown or other
<220> FEATURE:
<221> NAME/KEY: modified_base
<222> LOCATION: (448)..(448)
<223> OTHER INFORMATION: a, t, c, g, unknown or other
<220> FEATURE:
<221> NAME/KEY: modified_base
<222> LOCATION: (451)..(452)
<223> OTHER INFORMATION: a, t, c, g, unknown or other
<220> FEATURE:
<221> NAME/KEY: modified_base
<222> LOCATION: (454)..(455)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (467)..(467)
<223> OTHER INFORMATION: a, t, c, g, unknown or other
<220> FEATURE:
<221> NAME/KEY: modified_base -continued
<222> LOCATION: (471)..(471)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (519)..(519)
<223> OTHER INFORMATION: a, t, c, g, unknown or other
<220> FEATURE:
<221> NAME/KEY: modified_base
<222> LOCATION: (541)..(541)
<223> OTHER INFORMATION: a, t, c, g, unknown or other
<220> FEATURE:
<221> NAME/KEY: modified_base
<222> LOCATION: (545)..(546)
<223> OTHER INFORMATION: a, t, c, g, unknown or other
<220> FEATURE:
<221> NAME/KEY: modified_base
<222> LOCATION: (550)..(550)
<223> OTHER INFORMATION: a, t, c, g, unknown or other
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (561)..(561)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (569)..(571)
<223> OTHER INFORMATION: a, t, c, g, unknown or other
<220> FEATURE:
<221> NAME/KEY: modified_base
<222> LOCATION: (586)..(586)
<223> OTHER INFORMATION: a, t, c, g, unknown or other
<220> FEATURE:
<221> NAME/KEY: modified_base
<222> LOCATION: (589)..(591)
<223> OTHER INFORMATION: a, t, c, g, unknown or other
<220> FEATURE:
<221> NAME/KEY: modified_base
<222> LOCATION: (608)..(608)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:

-continued

<221> NAME/KEY: modified_base
<222> LOCATION: (686)..(688)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (736)..(736)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (750)..(750)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (754)..(754)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other
<220> FEATURE:
<221> NAME/KEY: modified_base
<222> LOCATION: (761)..(763)
<223> OTHER INFORMATION: a, t, c, g, unknown or other
<220> FEATURE:
<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other
<220> FEATURE:
<221> NAME/KEY: modified_base
<222> LOCATION: (786)..(788)
<223> OTHER INFORMATION: a, t, c, g, unknown or other

<400> SEQUENCE: 45
ggnnnntntc ntgtggcttt tntggccctt ttttgtgnta aagncacaca nggccnactc 60
atanattnca antcatgnng tcnggaannt gtnctnaata tctgtagagt gtgccaccca 120
tctcaaacat ganttacatt tgcangnatn cncncctnac tgtgtaaatn tnnctgctgn 180

-continued

```
accagtgaac aaagtgctga gtcangagcn angcaantca tnntgnccan tannacggga    240

cacnngctgc atcctcggtc ctcanccccct cangctgcnc tggnctcnan nttccgccct   300

ctccannnng ctcagggacc ggnancgtcc ttctccattc ncgaatttgc atggctctta    360

gaaaggtagg aggcaacgat gnntgtcatc antgaacgga ntgcacctca aantttgcca    420

tgtgnttggn agaacaattt ctnnttangt nnanntcnca tgtgcanctt naggatanca    480

ccatttantg atcaatactg gttaacatta agtggtacnt atcgctttaa aaatcaggga    540

ntcgnncaan anatcangac ntncacagnn nagttaacat cacagnccnn nttcgggact    600

tgtgggtnaa angtgganaa tcctcacctc ttggccatng tttgactttg ggattgggaa    660

ttcaacnaga gctctgccaa nggcannntt gggagaatcn gggtnttctc ccacaattgg    720

ggggntggcc aangtntngg nggncntaan angnttntcc nnnaaanggg cccacttgtn    780

cggcannntt ttg                                                       793
```

<210> SEQ ID NO 46
<211> LENGTH: 774
<212> TYPE: DNA
<213> ORGANISM: Homo sapiens
<220> FEATURE:
<221> NAME/KEY: modified_base
<222> LOCATION: (3)..(10)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (499)..(499)
<223> OTHER INFORMATION: a, t, c, g, unknown or other
<220> FEATURE:
<221> NAME/KEY: modified_base
<222> LOCATION: (594)..(594)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (675)..(675)
<223> OTHER INFORMATION: a, t, c, g, unknown or other
<220> FEATURE:
<221> NAME/KEY: modified_base
<222> LOCATION: (683)..(683)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (691)..(693)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (730)..(730)

-continued

<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (769)..(770)
<223> OTHER INFORMATION: a, t, c, g, unknown or other
<220> FEATURE:
<221> NAME/KEY: modified_base
<222> LOCATION: (774)..(774)
<223> OTHER INFORMATION: a, t, c, g, unknown or other

<400> SEQUENCE: 46
ggnnnnnnnn tgtggccttt ttttgccntt ttttttttc ataaaaccat gtttattcaa 60
aaaaatctat tcacgaaagt ctggaaagcg taataaatat ctgtacagtg gccacccatc 120
tcaaacatga attacaaagc aggaacataa aaatgatgtg taaacataac tgctgagcca 180
gtgaacaaag tgctgagtca ggagcgaggc agagaagcgt gctcagtaga acggcacaga 240
tgctgcagcc tccgtcctca gcccctcaag ctgcgctgga gtccaccttc cgccctctcc 300
acaccgctca gggaccggca gcgtccttct ccattctcga atttgcatga cgcttagaaa 360
ggtaggaggc agcaaaacgt gtcagaaatg aacggagtgc aaatcaaact ttgccatgtg 420
cttgagagaa tcagtaaagc gttaggtaaa aatcccaagt gcagctttag gataacacca 480
tttaatgaac aatactggnt aacattaagt actattaacg ctttaaaatt caaacaatct 540
tccaaacatc aatacataca cagttagttt aaaatcacaa gcaaatcggg cctntagggt 600
aaaagtggaa atccccaact ccttgcccaa ggtttgacnt tgggatggga ttcaacaaaa 660
gctctcccac tgganattgg ganaatcang nnnttccccc acatnggggg ggtngcaagg 720
gaaaggnggn ccctntaggg gggggcaaca aagggggcca ctggnggtnn gtcn 774

<210> SEQ ID NO 47
<211> LENGTH: 2415
<212> TYPE: DNA
<213> ORGANISM: Homo sapiens

<400> SEQUENCE: 47
aattcctcga gcactgttgg cctactggag tgcgagatcc gctgctgctg aggagaggag 60
cgtcaacagc agcaccatgg tagctcaaca gaagaacctt gaaggctatg tgggatttgc 120
caatctccca aatcaagtat acagaaaatc ggtgaagaga ggttttgaat tcacgcttat 180
ggtagtgggt gaatctggat tgggaaagtc gacattaatc aactcattat tcctcacaga 240
tttgtattct ccagagtatc caggtccttc tcatagaatt aaaaagactg tacaggtgga 300
acaatccaaa gttttaatca aagaaggtgg tgttcagttg ctgctcacaa tagttgatac 360
cccaggattt ggagatgcag tggataatag taattgctgg cagcctgtta tcgactacat 420
tgatagtaaa tttgaggact acctaaatgc agaatcacga gtgaacagac gtcagatgct 480
tgataacagg gtgcagtgtt gtttatactt cattgctcct tcaggacatg gacttaaacc 540
attggatatt gagtttatga agcgtttgca tgaaaaagtg aatatcatcc cacttattgc 600
caaagcagac acactcacac cagaggaatg ccaacagttt aaaaaacaga taatgaaaga 660
aatccaagaa cataaaatta aaatatacga atttccagaa acagatgatg aagaagaaaa 720
taaacttgtt aaaaagataa aggaccgttt acctcttgct gtggtaggta gtaatactat 780

-continued

```
cattgaagtt aatggcaaaa gggtcagagg aaggcagtat ccttggggtg ttgctgaagt    840
tgaaaatggt gaacattgtg attttacaat cctaagaaat atgttgataa gaacacacat    900
gcaggacttg aaagatgtta ctaataatgt ccactatgag aactacagaa gcagaaaact    960
tgcagctgtg acttataatg gagttgataa caacaagaat aaagggcagc tgactaagag   1020
ccctctggca caaatggaag aagaaagaag ggagcatgta gctaaaatga agaagatgga   1080
gatggagatg gagcaggtgt ttgagatgaa ggtcaaagaa aaagttcaaa aactgaagga   1140
ctctgaagct gagctccagc ggcgccatga gcaaatgaaa aagaatttgg aagcacagca   1200
caaagaattg gaggaaaaac gtcgtcagtt cgaggatgag aaagcaaact gggaagctca   1260
acaacgtatt ttagaacaac agaactcttc aagaaccttg gaaaagaaca agaagaaagg   1320
gaagatcttt taaactctct attgaccacc agttaacgta ttagttgcca atatgccagc   1380
ttggacatca gtgtttgttg gatccgtttg accaatttgc accagtttta tccataatga   1440
tggatttaac agcatgacaa aaattatttt tttttttgtt cttgatggag attaagatgc   1500
cttgaattgt ctagggtgtt ctgtacttag aaagtaagag ctctaagtac ctttcctaca   1560
ttttcttttt ttattaaaca gatatcttca gtttaatgca agagaacatt ttactgttgt   1620
acaatcatgt tctggtggtt tgattgttta caggatattc caaaataaaa ggactctgga   1680
agattttcat tgaggataaa ttgccataat atgatgcaaa ctgtgcttct ctatgataat   1740
tacaatacaa aggttccatt cagtgcagca tatacaataa tgtaatttag tctaacacag   1800
ttgaccctat tttttgacac ttccattgtt taaaaataca catggaaaaa aaaaaaccct   1860
atatgcttac tgtgcaccta gagctttttt ataacaacgt ctttttgttt gtttgttttg   1920
gattctttaa atatatatta ttctcattta gtgccctctt tagccagaat ctcattactg   1980
cttcattttt gtaataacat ttaatttaga tattttccat atattggcac tgctaaaata   2040
gaatatagca tctttcatat ggtaggaacc aacaaggaaa ctttccttta actccctttt   2100
tacactttat ggtaagtagc aggggggggaa atgcatttat agatcatttc taggcaaaat   2160
tgtgaagcta atgaccaacc tgtttctacc tatatgcagt ctctttattt tactagaaat   2220
gggaatcatg gcctcttgaa gagaaaaaag tcaccattct gcatttagct gtattcatat   2280
attgcatttc tgtatttttt gtttgtattg taaaaaattc acataataaa cgatgttgtg   2340
atgtaaaaaa aaaaaaaaaa aaaaaaaaaa aggccacatg tgctcgagct gcaggtcgcg   2400
gccgctagac tagtc                                                     2415
```

<210> SEQ ID NO 48
<211> LENGTH: 2362
<212> TYPE: DNA
<213> ORGANISM: Homo sapiens

<400> SEQUENCE: 48

```
gaattcctcg agcactgttg gcctactggg gtggctggcg gaaacgggaa cgtgcagccg     60
cgggtgcagg agtcctgggg catggcgggg gcggggcagg gggaggcgcg cacagaacag    120
gctggggcat ccctcgccct ggctctttga gcccggacca gacagagatg tgataatgga    180
tcatcatgtt tctaccatca agcctcgaag aatccaaaac caaaatgtca ttcaccgctt    240
ggaacgccgg cggatcagtt caggcaaggc aggtacccac tggcaccaag tccgagtgtt    300
ccatcagaat gtcttcccca acttcacagt tgtcaacgtt gaaaagcctc cttgtttctt    360
gcgtaaattc tcacctgatg gacgctactt tattgctttt tcttcagacc agacatctct    420
```

-continued

```
tgaaatctat gagtaccagg gctgccaggc agcagaggac ctactgcagg gatacgaagg    480

agaaatcctg tccaatggca atgaccagcg gtcagtgaat atccggggcc ggctctttga    540

acgctttttt gtcctgctgc acattaccaa tgttgcggcc aatggtgagc acctgaaccg    600

ggagtgtagt ctcttcactg atgactgccg ctgtgtcatc gtgggctcag ctgcctacct    660

cccagatgag cctcaccctc catttttga ggtatatcgg aacagtgaat cagtgacccc    720

caacccacgg tcccctctag aagactattc cctccatatc attgaccttc acaccggccg    780

cttatgtgat acacgcacgt tcaagtgtga caaggtggtc ttgtcacaca accaagggct    840

gtacttgtac aaaaacatcc tggccatctt gtctgtgcaa caacagacca tccatgtctt    900

ccaggtgact cctgaaggca ctttcattga tgtgcggacc attggccgct tttgctatga    960

ggatgacctg ctcactgtgt cagctgtttt ccctgaggta cagcgggaca gtcagacagg   1020

catggccaat ccctttaggg atcctttcat caattccctc aaacaccggt tgctggtata   1080

tttgtggcgc cgggcagaac aggatggtag tgcaatggcc aagaggcgct tcttccagta   1140

ttttgaccaa ctgcggcagc tgcgaatgtg gaaaatgcag cttctggatg aaaaccacct   1200

gtttatcaag tacactagtg aggatgtagt aacactgcga gtcacagatc catcacaggc   1260

atctttcttt gtggtgtaca atatggtgac gacagaggtg attgctgtgt ttgagaatac   1320

atcagatgag cttttggagc tctttgagaa cttctgtgac ctttttcgta atgctaccct   1380

gcacagtgaa gttcagtttc cctgctcagc ttctagcaac aattttgcaa ggcagatcca   1440

gcgccggttc aaagacacta ttataaatgc caagtatgga gggcacacag aggcagtacg   1500

ccggctgctg ggtcagctcc ccatcagtgc tcagtcttac agcggtagcc cctatctgga   1560

tttgtctctc ttcagttatg atgacaagtg ggtatctgtc atggagcggc ccaagacttg   1620

tggagatcac ccaatcaggt tctatgcccg ggactcgggc ctgctcaagt ttgagatcca   1680

ggcggggtta ctgggccgcc ccatcaacca cacagtgcga cgccttgttg ccttcacctt   1740

tcaccctttt gagcctttcg ctatttctgt gcagaggact aatgctgagt atgttgtcaa   1800

cttccatatg cgacactgct gcacgtaggt gcctcaccag agccagatta tctggtcttc   1860

caagactttg ccacccactt atctcagtgg actccaaagc aaaagctccc gactactagc   1920

tctgttagtt ccagcctgct atacctcaga tgggagagag ccagagagat gagtgagggt   1980

ggctcaacct aatggaattt ttaaattgta tacaatactg ctactgattg ttataatatc   2040

ctcttgcgtt ttccctgtgg gaatgcccag cattaattaa gtccatttca tttttgcttt   2100

actttgcatt tgattgctgt gaagatgaaa gcattagact tttatcccct tcatgtcact   2160

tcttcggcat tatggtttgc atctgaaagc agttaaatct tgtttactga tgagaatgac   2220

atacatcctt tccatttagc tcataagcac ggctatcttt ttaagagaaa aataaagcca   2280

tggtattttc atacttaaaa aaaaaaaaaa aaaaaaaagg ccacatgtgc tcgagctgca   2340

ggtcgcggcc gctagactag tc                                             2362
```

```
<210> SEQ ID NO 49
<211> LENGTH: 1865
<212> TYPE: DNA
<213> ORGANISM: Homo sapiens

<400> SEQUENCE: 49

aattcctcga gcactgttgg cctactggtt ttgagctttt tgtgtataca caatcccaaa     60

ctggaagaaa ttttaaaaaa aggaatcctg ctgtgaaagg tatatattac tctagatttt    120

tcttactgta aatattgtaa gattgtaata ctgtcgatat tttattaacc aacaaatgtt    180
```

-continued

```
aatctatgtg aaatcagact tattttaaat gtgcttctta tttactgtgt gtggtccctg    240
ttgctgacag tattaagtta tattctgatg taagattaac tttattaaag aatgtaaaca    300
ttaatgtttc cttatgggaa aacaaataaa gtataaagaa gacaattctt ttcattgaaa    360
tatactgtgt atttacactt gctagaccca gcaccactta taaatttagt acactgttca    420
gaattttagt taacacagct gacatggttg tgctctgttt gaaagtctaa gaataggtat    480
tgttggaata tacagtttgt atttgtctgc tgtgaatcat aatcttgaaa tttctaatca    540
agtttgtaaa atttttatag tgaaacattt taatgacaat ttaaaaattt atcttctcta    600
aagaatggtc aaaacaatat cctttcagaa atagaattgt tctttaatat ctttccaaaa    660
tgactttggt taaatggacc agatgtatat tagttaaaat ttaggactaa gttgttgata    720
ttctttgagt ttacaagtta atccttattg gagatgtgcc aatatacagt tagaatatca    780
ttaatttgca ctgtttgggg accccattta agaatgctga attttgccaa ctaagaagta    840
agcaaatgca atttaaaaag taaatttgag cattctgtat taaatatgtg cagttattat    900
cacatgaaga aacgcagtgt gtcgggctgt aatattacca tatttgctgt catgttctcc    960
catctcagtg ctgggaaatc accatgtgga aaccaagcaa acgtgttgtg catcagccgg   1020
cttgagtttg ttcaatatca aagctgaaaa ctagcgaggt ctgctgtact gcttattgaa   1080
gtattgtgat tattttaggc attgattctt acaaaatata tactgtaaca gtatactttg   1140
tacagattta aattttattt gaaaaaatga aataaagtag gcaaaagaat aaagatgttt   1200
atttttcatg tgactgtata atcagatcag tcttttgttt cagtgctttt tgggggaagg   1260
ggtctggttg cgatcttgga tttttttttt ttttgatagg tggaaacttt ttaggactca   1320
gtagcaggta tacttatgct tatgaattgg ctgcaagcat taagtgtgct ctcatactag   1380
agaactctat cttctatttt attttaaggt aggtttgctt atttttaaaa atgttatgtg   1440
aatggcctcc ctatcctggc atactgggtc atttaaaaaa ttctctggtg gtatgacagt   1500
gaacctagcc atcatgttga agagaaggga aaccttttcc caaagatcat gctccattct   1560
catggaaggt tttttgtttt ctgtcagtta caataaaaaa aatgtaatta tcatggatac   1620
atactagtta tacatactta tggggtacat gtaacatttt gaaacaagcg tacaatgtac   1680
tgattaaatc aggatgattg gggtatccat cacctgaagt atgtataatt tcttcgtttt   1740
aggaacattc taattccact cttagttatt tgaaatatat aataaattat ttttaatagt   1800
taaaaaaaaa aaaaaaaaaa aaggccacat gtgctcgagc tgcaggtcgc ggccgctaga   1860
ctagt                                                               1865
```

<210> SEQ ID NO 50
<211> LENGTH: 3457
<212> TYPE: DNA
<213> ORGANISM: Homo sapiens

<400> SEQUENCE: 50

```
gcactgttgg cctactggga gctgaggccc gcgtcgatcc tgggttggag gaggtggcgg     60
ccgctgaggc tgcggcgtga agacggcggg catggtgggg cgggagaaag agctctctat    120
acactttgtt cccgggagct gtcggctggt ggaggaggaa gttaacatcc ctaataggag    180
ggttctggtt actggtgcca ctgggcttct tggcagagct gtacacaaag aatttcagca    240
gaataattgg catgcagttg gctgtggttt cagaagagca agaccaaaat ttgaacaggt    300
taatctgttg gattctaatg cagttcatca catcattcat gattttcagc cccatgttat    360
```

-continued

```
agtacattgt gcagcagaga gaagaccaga tgttgtagaa aatcagccag atgctgcctc    420
tcaacttaat gtggatgctt ctgggaattt agcaaaggaa gcagctgctg ttggagcatt    480
tctcatctac attagctcag attatgtatt tgatggaaca aatccacctt acagagagga    540
agacatacca gctcccctaa atttgtatgg caaaacaaaa ttagatggag aaaaggctgt    600
cctggagaac aatctaggag ctgctgtttt gaggattcct attctgtatg ggaagttgga    660
aaagctcgaa gaaagtgctg tgactgttat gtttgataaa gtgcagttca gcaacaagtc    720
agcaaacatg gatcactggc agcagaggtt ccccacacat gtcaaagatg tggccactgt    780
gtgccggcag ctagcagaga agagaatgct ggtaagaagg attcctgagt cctgtcttag    840
cgaaggtccg ctttgtcttt tccatgcttg aactttcaca gctgtacttg gagtgttact    900
gagtgaaagc caaaagtgct tttttaaaac taggagacca aacaaaagta gtttacatat    960
acactgtatt catgaagaat aaaaatatta tgctcttctg tttgaattta tttcttatgt   1020
actatagatc ccatcatttc ttttattgca aagtgttagg aaacttcaaa ataatcatct   1080
aaggtctttt aagaagatac tctttggggg ctgggcgtga tggctcacac ctgtaatccc   1140
agcacatttg aaaaagttgg tattaaatat aatatccata caaagaaaga tgagactgat   1200
ttagtttaga atattaatag gatgaccaca gttttttaat atatgagaat tatattttgt   1260
aatatataac atgacaatat ttaagaaagt ttagctcaac ttgaaaaatg gttctattaa   1320
gtttttgttg tagcttggga taattaaaaa tactcattaa attgtactgt tttcataaaa   1380
atttgtaatg ctttttata ttcccactaa ttaagtaaaa ttggagcctt tttttgattt   1440
taaaaattct taaggtttaa attctagaaa ttgctctttt aagtgttttg ctaagagtat   1500
tggtaggaat ttgattttag atatcttgtg gagacctttc cagaaaaaga gggttgcctt   1560
ttagttcctg gaccttattt taagtaagct ttttggtcaa acctattcta ctcagctcaa   1620
aaagttgaaa ctattgaatt tattgtgtca tcgttcttag gatccatcaa ttaagggaac   1680
ctttcactgg tctggcaatg aacagatgac taagtatgaa atggcatgtg caattgcaga   1740
tgccttcaac ctccccagca gtcacttaag acctgtaagt acatggctgt aaaaaccttt   1800
aggtccattg ctatggtata tattattgct gtgttgggta acttcatttc tcagtactaa   1860
tcaaagtgaa ctttgcttgt atgctggctg ttcatagtgc tacttttctc taaattatca   1920
tctgtagaga agatcatgag tattgaagtt tgtagaaaat gtattattgt cttgatcatg   1980
acaggcattt ggtttatttt tccagggatg atcaaatcag atttcttaca ctaagagcaa   2040
aaataagtag caaatataaa acctcaaaat gggcaggcac aatggctcat gcctgtaatc   2100
ccaacacttt gggaggctga cgcaggagga tcccttgagc ccaggaattt gagactagcc   2160
tgggcaatgg agggagatct catctctgtt taaaaatata tacatattta aaaaaaggtc   2220
agggggaaca aagccctcaa aatatagcct ttcacttact tttgattttt ttgtgtttat   2280
ctttctttaa agattactga cagccctgtc ctaggagcac aacgtccgag aaatgctcag   2340
cttgactgct ccaaattgga gaccttgggc attggccaac gaacaccatt tcgaattgga   2400
atcaaagaat cactttggcc tttcctcatt gacaagagat ggagacaaac ggtctttcat   2460
tagtttattt gtgttgggtt cttttttttt ttaaatgaaa agtatagtat gtggcacttt   2520
ttaaagaaca aaggaaatag ttttgtatga gtactttaat tgtgactctt aggatctttc   2580
aggtaaatga tgctcttgca ctagtgaaat tgtctaaaga aactaaaggg cagtcatgcc   2640
ctgtttgcag taatttttct ttttatcatt ttgtttgtcc tggctaaact tggagtttga   2700
gtatagtaaa ttatgatcct taaatatttg agagtcagga tgaagcagat ctgctgtaga   2760
```

-continued

```
cttttcagat gaaattgttc attctcgtaa cctccatatt ttcaggattt ttgaagctgt   2820

tgaccttttc atgttgatta ttttaaattg tgtgaaatag tataaaaatc attggtgttc   2880

attatttgct ttgcctgagc tcagatcaaa atgtttgaag aaaggaactt tatttttgca   2940

agttacgtac agtttttatg cttgagatat ttcaacatgt tatgtatatt ggaacttcta   3000

cagcttgatg cctcctgctt ttatagcagt ttatggggag cacttgaaag agcgtgtgta   3060

catgtatttt ttttctaggc aaacattgaa tgcaaacgtg tatttttta atataaatat   3120

ataactgtcc ttttcatccc atgttgccgc taagtgatat ttcatatgtg tggttatact   3180

cataataatg ggccttgtaa gtcttttcac cattcatgaa taataataaa tatgtactgc   3240

tggcatgtaa tgcttagttt tcttgtattt acttcttttt ttaaatgtaa ggaccaaact   3300

tctaaactaa ttgttctttt gttgctttaa tttttaaaaa ttacattctt ctgatgtaac   3360

atgtgataca tacaaaagaa tatagtttaa tatgtattga aataaaacac aataaaatta   3420

acacttaaaa aaaaaaaaaa aaaggccaca tgtgctc                            3457
```

<210> SEQ ID NO 51
<211> LENGTH: 2158
<212> TYPE: DNA
<213> ORGANISM: Homo sapiens

<400> SEQUENCE: 51

```
cactgttggc ctactggata tttcatttag tgatgtatta ttgttattag ttgcattaaa     60

acaagccaag atggattagg tagacctcca cgttgtactt ccagtttcgt catgttatgg    120

tcttgggggt gcaggaattc ccaggtttcc ttgaggtgaa atctgaaagc tgagaaatat    180

agcacagctc acaaggaaga agtggataaa acagtgtcct cagagcagcc agggaatcct    240

aacccctgac gatcttcagt gaggcatttg gtactccaac ctgttgtgcc ttagccctga    300

gccccagtct gtgaggtgca tatggtccta gctaataggt cagtgggaaa agggagaaat    360

aataaacgag gctgtgtgta aacttacgtg taggaaacag gttaagctgt tctgccctgt    420

tgcatgcaga gagtagtctg aatgctattg ccacagtggt tttattttta ttgtgtgatg    480

taaccatatg ccaatttttt tctttgacta ttgactcact attttataat gcatccttct    540

ggcaataatg aaataaaaat tagtaaacag aagtaactgt ttaatgaaaa tgaagtattt    600

gtatttctat ttatcaagaa agaaaagacg aacctgtggc atgcagagag tagtctgaat    660

gctattgcca cagtggtttt atttttattg tgtgatgtaa ccatatgcca atttttttct    720

ttgactattg actcactatt ttataatgca tccttctggc aataatgaaa taaaaattag    780

taaacagaag taactgttta atgaaaatga agtatttgta tttctattta tcaagaaaga    840

aaagacgaac ctgtggccga gcacgggggc tcacgcctgc ctcggcctcc caaaatgctg    900

agattacagg tgtgagccac cacgcccggc cttctctgta ttttcttgaa gtttgctgag    960

cttccttaaa accctgagtt ctctgcaaga agaaggatga tgacttatgg tgcctctcac   1020

tggtgaggtc caccttttct gcaattttga gcacagtcca aggccttgga aaagctttgt   1080

ttcttgagtc tctcaaataa gaacaacaac attagctttt ctgggagggc caatggctgt   1140

gctgtgatgg ggcatggatg ctttctcaga ggtactttcc ccctaagctt taggcacgtc   1200

tgaccatttc ttctgctttg gtccagtgct ttcctcatga tttagactct ggatgaaggt   1260

gtttttgaag taggtttact tgctgctgtc atcctgtgtc acctcactct ctgtggcctg   1320

gaagtgcagg gtttcaggcc tggctgtggg cggccattat atgacaaagg gttcagcgtc   1380
```

-continued

```
ccctgcatct ggtatgatgc cctctctggt tttaccacct ttagtcatca ttttacttgg   1440

ggtgtggaca tatttgttcc aggagcttcc ccaccctcta caacttattg gagggataaa   1500

ttgtcctaat gttttcttct ggtgttttta accatgaaat cttagacctg gagtagattt   1560

ggttaccaaa tagcttaagg agagaggaca taatatttga tttatgtaag atccaggaaa   1620

tgaggaaagg cacggtgcca tgagctgtgc ttccagccag accttattaa ctttcacaat   1680

tctttatgca aaagagacaa cttccagatg ttgctaatgg aggtatctca tgacctagag   1740

acaaaaccag gagcagcttc cttctatttc tccaaatcca aaaacgattg ctagggagtt   1800

agaccatggc ccagctctgc tttgagaaag ggaattttgc ttttgagatg attgaagtgc   1860

tttaaattcc tcagctgaga aatgagagat gtacagataa tgagacacac ggaggctttg   1920

ccgcatcaga cttcatgagc ttggagaaca tgcaggtgct cttctgacct cttagctgtt   1980

tgtcaggttt ctatgaccag gcaggtgtta ccagcactaa tgtttaggga ttcagctata   2040

ttttagcttc atttttatga tccttttttt ttccagcctg ggcaacaaga gcgaaactgt   2100

ctcaaaaaaa aaaaaaaaaa aggccacatg tgctcgagct gcaggtcgcg gccgctag     2158
```

<210> SEQ ID NO 52
<211> LENGTH: 2142
<212> TYPE: DNA
<213> ORGANISM: Homo sapiens

<400> SEQUENCE: 52

```
gcactgttgg cctactggat taaaattaga aaagttgtgc ctttctcaag atgtgcacac     60

agtcagttgc aaaaccaaat ttgggattga tctcctgatt cctggtctga tatgttatcc    120

attactccat gaacagaaag atagaggtca tttctatgca gagaaaaaca aatgagctgt    180

gtcattgcag aaatgttctg catggtttgc tgccatctgt cttaaagctc aatctggact    240

cctaggaatt gggactgctg agctgcattt agatggacca tgtggacagg gcacagaaaa    300

tcctttattt ggagggcttg gttatttccc tatatggaaa ataaaggata caaaatattt    360

atgacaagat taagagccta gagctataga atttttgaga tctgacatcc tgttttgtaa    420

gattctggcc ctacatgtct ttttgttaga cttgctgtat tttatgtttg ttaaaacaca    480

gttggagaac aacagtaaac attgcttttg gaagaagaaa attataaagc agacagggca    540

ctggaatgga agtcactata ttctaacccc aactgtgata tattatgtgc ttttggatgc    600

tgcacactct gggggctgca gtttccttat tggataaaat caatgttgga aactaagatc    660

tcttgaagct ccctgaagat ttgctcagtc aacttcacat ggctttttga aatttaatac    720

ctttaaccag aaatgctctc ccaggttacc ttaagtcctc ttgtccaata tccgtgtggt    780

agcccctgta agcatttggg tttgtgatcc ctgatatcca gttccctttc agctttgtca    840

ttcaatgatg ctacaacaga aggattcagt gttagtagct ttgtggagca aagttttcaa    900

agtattgatt tattctgttg aaattgtgaa aacaaaggcc ttaaagctgt atctgtgcaa    960

caaaaatcta atataaactc agaattcttc tctaggcata ttgtttgttg tggtaatgat   1020

atagttgaaa acttttggaa aaataattta agactagaaa ttaggaattc ttcaggttaa   1080

agaaacatat gtcattgaat gtaattaagg ttatatgaag attatcagaa aaattgcacc   1140

aaaatgtgat caataatagc tttttcttgg ttgattgtct ctaagcatcc tttccaaatt   1200

atgtcaatac tgttctgcaa agtttggaga aaaactaaaa gatgtatacc aagaaatcca   1260

tgctggtaca ttgtaattta acctcctatt tttcctgaaa agtcactctt tagactaaaa   1320

aaagttcatc attgtgaggc atcactacag ttttataatt tttttcactg agtctttctc   1380
```

-continued aatttaatat taaagggctt ttaagattta tcctccatgt gaaatttggg gctttatatt 1440
ctataggcct ttcttgaaaa tccaaatttc atatgaaaaa ctagaaaact gatgttggga 1500
attatttgtg tgaattcagt gaagtgtacc agttgacagc aagtcattct gggtgatata 1560
atcgttctca tcctcaatca gctgacataa aacaattctt tggagtccaa ttgaactcct 1620
tcaccagaga tggctgttga acttttaata gtttctgaaa ataaaataat caagcattta 1680
tttctcagga gcttaatata aatttcttct gttttatttt atctaggcat ttttattgaa 1740
ttgtacttga tttgattttc tgactcttct atgagaatgg ctttttactt gtaagtttca 1800
ctcaaattga cattttgata gtataacaca ttaatgaaat tcctagaaca gaggctatgt 1860
tctttgaaaa aaaatattga cagagtacac taaagggaca ttttaaagtg catttgattt 1920
cttttgcagc ttgataacat atttggtgat gtttggtagc tcccaaagct atactttcca 1980
gtaacatgtc cagatgagat ttgacaatgt tgcaatacat ctttccatat ctagatttat 2040
gtatgcaaat taagttcttg gcagtctatg aaaaccacaa aactcttatc tcccagccta 2100
acaaaaaaaa aaaaaaaaag gccacatgtg ctcgagctgc ag 2142

<210> SEQ ID NO 53
<211> LENGTH: 846
<212> TYPE: DNA
<213> ORGANISM: Homo sapiens
<220> FEATURE:
<221> NAME/KEY: modified_base
<222> LOCATION: (3)..(5)
<223> OTHER INFORMATION: a, t, c, g, unknown or other
<220> FEATURE:
<221> NAME/KEY: modified_base
<222> LOCATION: (7)..(10)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (14)..(15)
<223> OTHER INFORMATION: a, t, c, g, unknown or other
<220> FEATURE:
<221> NAME/KEY: modified_base
<222> LOCATION: (17)..(18)
<223> OTHER INFORMATION: a, t, c, g, unknown or other
<220> FEATURE:
<221> NAME/KEY: modified_base
<222> LOCATION: (22)..(25)
<223> OTHER INFORMATION: a, t, c, g, unknown or other
<220> FEATURE:
<221> NAME/KEY: modified_base
<222> LOCATION: (33)..(33)
<223> OTHER INFORMATION: a, t, c, g, unknown or other
<220> FEATURE:
<221> NAME/KEY: modified_base
<222> LOCATION: (48)..(48)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (762)..(762)
<223> OTHER INFORMATION: a, t, c, g, unknown or other
<220> FEATURE:
<221> NAME/KEY: modified_base
<222> LOCATION: (808)..(808)
<223> OTHER INFORMATION: a, t, c, g, unknown or other
<220> FEATURE:
<221> NAME/KEY: modified_base
<222> LOCATION: (820)..(820)

-continued

<223> OTHER INFORMATION: a, t, c, g, unknown or other
<220> FEATURE:
<221> NAME/KEY: modified_base
<222> LOCATION: (828)..(828)
<223> OTHER INFORMATION: a, t, c, g, unknown or other
<220> FEATURE:
<221> NAME/KEY: modified_base
<222> LOCATION: (845)..(846)
<223> OTHER INFORMATION: a, t, c, g, unknown or other

<400> SEQUENCE: 53
ggnnngnnnn gngnngnntt tnnnngggcc cgnatcctcg agcactgntg gcctactggg 60
agtagctcag ctcctattcc tgggaagcct ggaacgggga cttttgaaaa taactgcagc 120
ggcattcggg ttagggtccg tgctctccgc ctgcgccagg acagggtgaa gtggtcgggg 180
cgagcagagg gtgcgaaggt gcgggtgctg gtgcctcgca gcaggaggga gccccggctg 240
cgccgcgcga ctccctcttt ggccctcgga gcgcagcacc cggcggacaa gcggcgggac 300
gccaggacgc ggcgagcaag atctctcgtg gaagaggaag accaacacat gaaattgtcc 360
cttggaggca gcgaaatggg cctctcatcc catttgcagt cttccaaggc aggacctaca 420
cgcatcttta ccaagcaata cccacagttc tgtggtgtta cagggctttg accagcttcg 480
acttgaagga ttgctttgtg atgtgaccct gatgccaggt gacacagatg atgctttccc 540
tgtgcataga gtcatgatgg catctgctag tgattacttc aaggctatgt tcacagaatg 600
aaagaacaag atttaatgtg cattaaactt catggtgtga gcaaagtcgg tctaaggaaa 660
attattgatt tcatttatac tgcaaagctt tctcctaata tggacaacct tcaagacacc 720
tggaanctgc caatttccta cagattctgc cagttttgga cntctgtaaa gtgttcccaa 780
aaccggggtc actttaacaa ctgtgttnaa tttggccggn ttgcaaanac tacaaatcta 840 accgnn 846

<210> SEQ ID NO 54
<211> LENGTH: 836
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (6)..(9)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (720)..(720)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other -continued
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (798)..(798)
<223> OTHER INFORMATION: a, t, c, g, unknown or other
<220> FEATURE:
<221> NAME/KEY: modified_base
<222> LOCATION: (803)..(803)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (816)..(816)
<223> OTHER INFORMATION: a, t, c, g, unknown or other
<220> FEATURE:
<221> NAME/KEY: modified_base
<222> LOCATION: (836)..(836)
<223> OTHER INFORMATION: a, t, c, g, unknown or other

<400> SEQUENCE: 54
ggntgnnnnt gggctttttt tggnctttga cattaaaagt ttttattggn cacaaaaaga 60
taaaacatgg aagttgaatt tactgagcaa aagcagctct ccaggtgaag ctgctatact 120
ttgtgctaaa taaccttatg aactgagtat acagaataca tataatatgc aagttacctc 180
aacagcaaag gagaaggagt agaatacagt ttttgaagat aaaatctggt caagtgacaa 240
attttgttgc tcaaaatttc tagcccttat ccacctaaat tctgtatggt tctacatata 300
tgcattcagt atgtgcatac tgaattccca ttttaatgga agctgctttt tggaagaatt 360
ctttttaatt tcacatttct ttgatgtgcc actcaatttt taaaaaaatt atatttgaca 420
tatgtgcatg tgtgtatgtg tatgtatgta tacacacttt aaaaacacca aacccttgtt 480
tataagtaga gggttcatgc tgctttttaa attaatatta gtgaatttaa gctacttctc 540
ctgtgtgtct aggaaacttt gtgttctcaa tgcacccaca cagtcaagtg ggttgacaga 600
tatgtcaaaa atacnttatg aaaagaggga ggtagctcat gcgagttggc aaccttttgt 660
gtaatggttc ctgttcaagc angctgcctc cctttgacat cctacagtca aagatgaaan 720
gggaaacttt tacntgaagc ctantggagc acaagttgta canttacaat aatccacctt 780
caacttggct tatggggntt acnaangtaa ggatgncaaa taccttacac caatan 836

<210> SEQ ID NO 55
<211> LENGTH: 3415
<212> TYPE: DNA
<213> ORGANISM: Homo sapiens

<400> SEQUENCE: 55
gaattcctcg agcactgttg gcctactggt tcggcttcca gactcagagg gagttattgc 60
agcaccagga gctccatgtc cctagcggca aacttcccag agaaagtgac atggaacact 120
ctccaagtgc aactgaagac agcttacagc cagccacaga cttattgacc agaagcgaac 180
ttccccagag ccaaaaggcc atgcagacta aagatgcgag ctctgacaca gagctggaca 240
agtgtgagaa aaagactcag ctctttctca cgaaccagag accagagata cagcctacaa 300
caaataaaca aagcttttct tacacaaaaa taaagtctga gccctctagc ccaagacttg 360

-continued

```
cctcatctcc agttcagcct aatattgggc cttctttccc tgtgggccct ttcctatctc    420
agttttcttt cccccaagat atcaccatgg tccctcaagc ttcagagatc ttagctaaga    480
tgtctgaact ggtgcatcgg cgactgaggc atggcagtag tagctaccct cccgtcattt    540
acagcccttt gatgcccaag gggctactt gttttgagtg taacataaca ttcaataatt    600
tggataatta tctagtgcac aaaaagcatt attgcagcag ccgatggcag cagatggcta    660
agtccccaga gttccctagt gtgtcagaaa agatgcctga agctttgagt cccaacactg    720
gccaaacctc cataaacctt ctcaacccag ctgctcattc tgctgatcct gagaatccac    780
ttcttcaaac atcttgcatc aattcttcca ctgtcttaga tttaattggg ccaaatggga    840
agggccatga caaggacttt tccactcaaa ctaagaagct ctccacctcc agtaacaatg    900
atgacaaaat taatggaaaa cctgttgatg tgaaaaatcc cagtgtcccc ttagtggatg    960
gggaaagtga cccaaataag actacctgtg aagcttgcaa cattaccttc agccggcacg   1020
aaacatacat ggtccacaaa cagtattact gtgctacacg ccacgaccct ccactgaaga   1080
ggtctgcttc caacaaagtg cctgccatgc agagaaccat gcgcacacgc aagcgcagaa   1140
agatgtatga gatgtgccta cctgagcagg aacaaaggcc tccactggtt cagcagagat   1200
ttcttgacgt agccaacctc aataatcctt gtacctccac tcaagaaccc acagaagggc   1260
taggagagtg ctaccaccca agatgtgata tctttccagg aattgtctct aaacacttgg   1320
aaacttctct gacgatcaac aagtgtgttc cagtttccaa atgtgatact actcattcca   1380
gtgtttcctg cctagagatg gacgtgccca tagatctcag caaaaagtgt ttatctcagt   1440
ctgagcggac gaccacgtct cccaaaaggc tgctggacta tcacgagtgc actgtgtgca   1500
agatcagttt caataaggta gaaaactatc tggcccacaa gcagaatttc tgcccggtta   1560
ctgcacatca gcgtaatgac ctgggtcaac tggacggcaa agtgtttccg aatccagaaa   1620
gcgaacgaaa cagccctgat gtcagctacg aaagaagcat aataaaatgt gagaaaaatg   1680
ggaatttgaa gcagccttcc cccaatggaa acttattttc atcccaccta gcaaccctgc   1740
aaggcttgaa ggtctttagt gaagctgctc agctcattgc tacaaaagaa gaaaacagac   1800
atttgtttct tccacaatgc ctttaccctg gagcaataaa gaaagcaaaa ggagccgacc   1860
agctttctcc atattatgga atcaagccaa gtgattatat ttctggttct cttgtcatcc   1920
ataacactga catcgagcaa agcagaaatg cagaaaatga atctcctaaa ggccaggctt   1980
cctcaaatgg gtgtgctgcg ctgaagaaag attctctgcc attgttgccc aaaaatcgag   2040
gaatggtaat agtgaatggt ggactgaaac aagatgagag acctgctgcc aacccacagc   2100
aagagaacat ttcccagaat cctcagcacg aagacgacca caaatctccc tcgtggatct   2160
ctgagaaccc attagctgcc aatgagaatg tctcaccagg agttccctca gcagaggaac   2220
agttgtctag tatagcaaaa ggtgtgaatg gttccagcca ggctccaacc agtgggaaat   2280
attgccggct atgtgatatc cagttcaaca acctttcaaa ctttataact cacaagaagt   2340
tttattgctc atcacatgca gcagaacatg tcaaatgaac taactaaaca tcagtcacct   2400
ttggtatcag tgtttagtat gttgttctaa ccagtccaga aaaaaaaata agctgtttga   2460
attacatctg ggcaatcagg agataattca ttatggctga gttgaagact taaggtgtaa   2520
tttcattaca gtccattagt aaagtgtatt attggtgcca ttttcaaaaa aattaattta   2580
ttttaccagc agtattcata gctgtggtta tgttattttt tatttaaaaa ctttatatta   2640
aagtcatttg taatgttatt gtatagttat tgtgtagcac atatggtttg cactgtatag   2700
tagcttttaa agaaaatagt cacaatacag aaaagcattt tagaaatagc ttcaaaagca   2760
```

-continued

```
cttgtgtatc ttgatttttt cttatatgct gttgcagata tatgtatatg ctaaaatata   2820
acttgcaaag atgttctaaa tacacatgct ataagttcgc cttaagattt caattcttgg   2880
ataatcaggc tctgtttgca ctttatattt tagcagatac agtctcttag tcactaggct   2940
ttgcatttgt atgtagctgt atgtttccgt ccattttctt aatcctgaac ctgtatgtta   3000
aatgaagatg gcaatttttt tcttgtatag tacttgtatt ttctttcgct gatgcagctc   3060
tgtctcaatt tttaaacctt tgctgttaaa tgcaatactt tataaagaat gaacaaaatt   3120
actggaagca gtattgtaag taatgaggta gtattaatca gttttatctt ttgaaaggca   3180
cagtctaaat cgaaacccta aactcaatgc tgcaagtatg aatttaattc atatataaga   3240
tctatttaaa tataagagta gcaatactgc acctggtgat cacaaagata atgttctact   3300
tctgatagaa ataatttctc aacaaatgtt gttactatgc atgtatatgg atggaataaa   3360
attccagatt gttggaaaaa aaaaaaaaaa aaggccacat gtgctcgagc tgcag        3415
```

<210> SEQ ID NO 56
<211> LENGTH: 1829
<212> TYPE: DNA
<213> ORGANISM: Homo sapiens

<400> SEQUENCE: 56

```
gaattcctcg agcactgttg gcctactggg gcgcagggcg tgtacagcgc cgccgcgctc     60
ttctcgctca cggtcagcct ggacgacagg aactcctcgc gctacgtcat ccgcattgac    120
caggatgggc tcaccctgcc agagaggacc ctgtacctcg ctcaggatga ggacagtgag    180
aagatcctgg cagcatacag ggtgttcatg gagcgagtgc tcagcctcct gggtgcagac    240
gctgtggaac agaaggccca agagatcctg caagtggagc agcagctggc caacatcact    300
gtgtcagagt atgacgacct acggcgagat gtcagctcca tgtacaacaa ggtgacgctg    360
gggcagctgc agaagatcac cccccacttg cggtggaagt ggctgctaga ccagatcttc    420
caggaggact tctcagagga agaggaggtg gtgctgctgg cgacagacta catgcagcag    480
gtgtcgcagc tcatccgctc cacaccccac cgggtcctgc acaactacct ggtgtggcgc    540
gtggtggtgg tcctgagtga acacctgtcc ccgccattcc gtgaggcact gcacgagctg    600
gactggatgg acgccgagac cagggctgct gctcgggcca agctccagta catgatggtg    660
atggtcggct acccggactt cctgctgaaa cccgatgctg tggacaagga gtatgagttt    720
gaggtccatg agaagaccta cttcaagaac atcttgaaca gcatccgctt cagcatccag    780
ctctcagtta agaagattcg gcaggaggtg gacaagtcca cgtggctgct cccccccacag    840
gcgctcaatg cctactatct acccaacaag aaccagatgg tgttccccgc gggcatcctg    900
cagcccaccc tgtacgaccc tgacttccca cagtctctca actacggggg catcggcacc    960
atcattggac atgagctgac ccacggctac gacgactggg ggggccagta tgaccgctca   1020
gggaacctgc tgcactggtg gacggaggcc tcctacagcc gcttcctgcg aaaggctgag   1080
tgcatcgtcc gtctctatga caacttcact gtctacaacc agcgggtgaa cgggaaacac   1140
acgcttgggg agaacatcgc agatatgggc ggcctcaagc tggcctacca cgcctatcag   1200
aagtgggtgc gggagcacgg cccagagcgc ccacttcccc ggctcaagta cacacatgac   1260
cagctcttct tcattgcctt tgcccagaac tggtgcatca agcggcggtc gcagtccatc   1320
tacctgcagg tgctgactga caagcatgcc cctgagcact acagggtgct gggcagtgtg   1380
tcccagtttg aggagtttgg ccgggctttc cactgtccca aggactcacc catgaaccct   1440
```

-continued

```
gcccacaagt gttccgtgtg gtgagcctgg ctgcccgccc gcacgccccc actgcccccg   1500

cacgaatcac ctcctgctgg ctaccggggc aggcatgcac ccggtgccag ccccgctctg   1560

ggcaccacct gccttccagc ccctccagga cccggtccgc ctgctgcccc tcacttcagg   1620

aggggcctgg agcagggtga ggctggactt tgggggctg tgagggaaat atactggggt   1680

ccccagattc tgctctaagg gggccagacc ctctgccagg ctggattgta cgggccccac   1740

cttcgctgtg ttcttgctgc aaagtctggt caataaatca ctgcactgtt aaaaaaaaaa   1800

aaaaaaggcc acatgtgctc gagctgcag                                     1829
```

<210> SEQ ID NO 57
<211> LENGTH: 778
<212> TYPE: DNA
<213> ORGANISM: Homo sapiens
<220> FEATURE:
<221> NAME/KEY: modified_base
<222> LOCATION: (5)..(6)
<223> OTHER INFORMATION: a, t, c, g, unknown or other
<220> FEATURE:
<221> NAME/KEY: modified_base
<222> LOCATION: (10)..(10)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (26)..(26)
<223> OTHER INFORMATION: a, t, c, g, unknown or other
<220> FEATURE:
<221> NAME/KEY: modified_base
<222> LOCATION: (38)..(38)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (52)..(53)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (60)..(61)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (71)..(72)
<223> OTHER INFORMATION: a, t, c, g, unknown or other
<220> FEATURE:
<221> NAME/KEY: modified_base
<222> LOCATION: (77)..(78)
<223> OTHER INFORMATION: a, t, c, g, unknown or other
<220> FEATURE:
<221> NAME/KEY: modified_base
<222> LOCATION: (87)..(88)
<223> OTHER INFORMATION: a, t, c, g, unknown or other -continued
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (93)..(94)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (111)..(111)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (121)..(121)
<223> OTHER INFORMATION: a, t, c, g, unknown or other
<220> FEATURE:
<221> NAME/KEY: modified_base
<222> LOCATION: (125)..(125)
<223> OTHER INFORMATION: a, t, c, g, unknown or other
<220> FEATURE:
<221> NAME/KEY: modified_base
<222> LOCATION: (130)..(131)
<223> OTHER INFORMATION: a, t, c, g, unknown or other
<220> FEATURE:
<221> NAME/KEY: modified_base
<222> LOCATION: (138)..(138)
<223> OTHER INFORMATION: a, t, c, g, unknown or other
<220> FEATURE:
<221> NAME/KEY: modified_base
<222> LOCATION: (140)..(141)
<223> OTHER INFORMATION: a, t, c, g, unknown or other
<220> FEATURE:
<221> NAME/KEY: modified_base
<222> LOCATION: (144)..(144)
<223> OTHER INFORMATION: a, t, c, g, unknown or other
<220> FEATURE:
<221> NAME/KEY: modified_base
<222> LOCATION: (147)..(147)
<223> OTHER INFORMATION: a, t, c, g, unknown or other
<220> FEATURE:
<221> NAME/KEY: modified_base
<222> LOCATION: (150)..(150)
<223> OTHER INFORMATION: a, t, c, g, unknown or other
<220> FEATURE:
<221> NAME/KEY: modified_base
<222> LOCATION: (155)..(155)
<223> OTHER INFORMATION: a, t, c, g, unknown or other
<220> FEATURE:
<221> NAME/KEY: modified_base
<222> LOCATION: (158)..(158)
<223> OTHER INFORMATION: a, t, c, g, unknown or other
<220> FEATURE:
<221> NAME/KEY: modified_base
<222> LOCATION: (161)..(161)
<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (174)..(174)
<223> OTHER INFORMATION: a, t, c, g, unknown or other
<220> FEATURE:
<221> NAME/KEY: modified_base
<222> LOCATION: (178)..(178)
<223> OTHER INFORMATION: a, t, c, g, unknown or other
<220> FEATURE:
<221> NAME/KEY: modified_base
<222> LOCATION: (183)..(183)

-continued

<223> OTHER INFORMATION: a, t, c, g, unknown or other
<220> FEATURE:
<221> NAME/KEY: modified_base
<222> LOCATION: (187)..(187)
<223> OTHER INFORMATION: a, t, c, g, unknown or other
<220> FEATURE:
<221> NAME/KEY: modified_base
<222> LOCATION: (191)..(191)
<223> OTHER INFORMATION: a, t, c, g, unknown or other
<220> FEATURE:
<221> NAME/KEY: modified_base
<222> LOCATION: (197)..(197)
<223> OTHER INFORMATION: a, t, c, g, unknown or other
<220> FEATURE:
<221> NAME/KEY: modified_base
<222> LOCATION: (199)..(200)
<223> OTHER INFORMATION: a, t, c, g, unknown or other
<220> FEATURE:
<221> NAME/KEY: modified_base
<222> LOCATION: (202)..(203)
<223> OTHER INFORMATION: a, t, c, g, unknown or other
<220> FEATURE:
<221> NAME/KEY: modified_base
<222> LOCATION: (205)..(206)
<223> OTHER INFORMATION: a, t, c, g, unknown or other
<220> FEATURE:
<221> NAME/KEY: modified_base
<222> LOCATION: (208)..(208)
<223> OTHER INFORMATION: a, t, c, g, unknown or other
<220> FEATURE:
<221> NAME/KEY: modified_base
<222> LOCATION: (211)..(211)
<223> OTHER INFORMATION: a, t, c, g, unknown or other
<220> FEATURE:
<221> NAME/KEY: modified_base
<222> LOCATION: (213)..(213)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (225)..(227)
<223> OTHER INFORMATION: a, t, c, g, unknown or other
<220> FEATURE:
<221> NAME/KEY: modified_base
<222> LOCATION: (232)..(232)
<223> OTHER INFORMATION: a, t, c, g, unknown or other
<220> FEATURE:
<221> NAME/KEY: modified_base
<222> LOCATION: (234)..(234)
<223> OTHER INFORMATION: a, t, c, g, unknown or other
<220> FEATURE:
<221> NAME/KEY: modified_base
<222> LOCATION: (242)..(242)
<223> OTHER INFORMATION: a, t, c, g, unknown or other
<220> FEATURE:
<221> NAME/KEY: modified_base
<222> LOCATION: (256)..(256)
<223> OTHER INFORMATION: a, t, c, g, unknown or other
<220> FEATURE:
<221> NAME/KEY: modified_base
<222> LOCATION: (270)..(270)
<223> OTHER INFORMATION: a, t, c, g, unknown or other
<220> FEATURE:
<221> NAME/KEY: modified_base
<222> LOCATION: (280)..(280)
<223> OTHER INFORMATION: a, t, c, g, unknown or other
<220> FEATURE:
<221> NAME/KEY: modified_base
<222> LOCATION: (282)..(282)
<223> OTHER INFORMATION: a, t, c, g, unknown or other
<220> FEATURE:
<221> NAME/KEY: modified_base
<222> LOCATION: (293)..(293)
<223> OTHER INFORMATION: a, t, c, g, unknown or other
<220> FEATURE:
<221> NAME/KEY: modified_base -continued
<222> LOCATION: (306)..(307)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (312)..(312)
<223> OTHER INFORMATION: a, t, c, g, unknown or other
<220> FEATURE:
<221> NAME/KEY: modified_base
<222> LOCATION: (318)..(318)
<223> OTHER INFORMATION: a, t, c, g, unknown or other
<220> FEATURE:
<221> NAME/KEY: modified_base
<222> LOCATION: (327)..(327)
<223> OTHER INFORMATION: a, t, c, g, unknown or other
<220> FEATURE:
<221> NAME/KEY: modified_base
<222> LOCATION: (338)..(339)
<223> OTHER INFORMATION: a, t, c, g, unknown or other
<220> FEATURE:
<221> NAME/KEY: modified_base
<222> LOCATION: (344)..(344)
<223> OTHER INFORMATION: a, t, c, g, unknown or other
<220> FEATURE:
<221> NAME/KEY: modified_base
<222> LOCATION: (347)..(347)
<223> OTHER INFORMATION: a, t, c, g, unknown or other
<220> FEATURE:
<221> NAME/KEY: modified_base
<222> LOCATION: (358)..(359)
<223> OTHER INFORMATION: a, t, c, g, unknown or other
<220> FEATURE:
<221> NAME/KEY: modified_base
<222> LOCATION: (367)..(367)
<223> OTHER INFORMATION: a, t, c, g, unknown or other
<220> FEATURE:
<221> NAME/KEY: modified_base
<222> LOCATION: (372)..(373)
<223> OTHER INFORMATION: a, t, c, g, unknown or other
<220> FEATURE:
<221> NAME/KEY: modified_base
<222> LOCATION: (387)..(387)
<223> OTHER INFORMATION: a, t, c, g, unknown or other
<220> FEATURE:
<221> NAME/KEY: modified_base
<222> LOCATION: (390)..(390)
<223> OTHER INFORMATION: a, t, c, g, unknown or other
<220> FEATURE:
<221> NAME/KEY: modified_base
<222> LOCATION: (394)..(396)
<223> OTHER INFORMATION: a, t, c, g, unknown or other
<220> FEATURE:
<221> NAME/KEY: modified_base
<222> LOCATION: (400)..(400)
<223> OTHER INFORMATION: a, t, c, g, unknown or other
<220> FEATURE:
<221> NAME/KEY: modified_base
<222> LOCATION: (404)..(404)
<223> OTHER INFORMATION: a, t, c, g, unknown or other
<220> FEATURE:
<221> NAME/KEY: modified_base
<222> LOCATION: (411)..(411)
<223> OTHER INFORMATION: a, t, c, g, unknown or other
<220> FEATURE:
<221> NAME/KEY: modified_base
<222> LOCATION: (414)..(414)
<223> OTHER INFORMATION: a, t, c, g, unknown or other
<220> FEATURE:
<221> NAME/KEY: modified_base
<222> LOCATION: (416)..(418)
<223> OTHER INFORMATION: a, t, c, g, unknown or other
<220> FEATURE:
<221> NAME/KEY: modified_base
<222> LOCATION: (428)..(428)
<223> OTHER INFORMATION: a, t, c, g, unknown or other
<220> FEATURE:

-continued

<221> NAME/KEY: modified_base
<222> LOCATION: (439)..(440)
<223> OTHER INFORMATION: a, t, c, g, unknown or other
<220> FEATURE:
<221> NAME/KEY: modified_base
<222> LOCATION: (447)..(447)
<223> OTHER INFORMATION: a, t, c, g, unknown or other
<220> FEATURE:
<221> NAME/KEY: modified_base
<222> LOCATION: (452)..(452)
<223> OTHER INFORMATION: a, t, c, g, unknown or other
<220> FEATURE:
<221> NAME/KEY: modified_base
<222> LOCATION: (454)..(455)
<223> OTHER INFORMATION: a, t, c, g, unknown or other
<220> FEATURE:
<221> NAME/KEY: modified_base
<222> LOCATION: (465)..(465)
<223> OTHER INFORMATION: a, t, c, g, unknown or other
<220> FEATURE:
<221> NAME/KEY: modified_base
<222> LOCATION: (468)..(469)
<223> OTHER INFORMATION: a, t, c, g, unknown or other
<220> FEATURE:
<221> NAME/KEY: modified_base
<222> LOCATION: (476)..(476)
<223> OTHER INFORMATION: a, t, c, g, unknown or other
<220> FEATURE:
<221> NAME/KEY: modified_base
<222> LOCATION: (480)..(481)
<223> OTHER INFORMATION: a, t, c, g, unknown or other
<220> FEATURE:
<221> NAME/KEY: modified_base
<222> LOCATION: (486)..(487)
<223> OTHER INFORMATION: a, t, c, g, unknown or other
<220> FEATURE:
<221> NAME/KEY: modified_base
<222> LOCATION: (489)..(490)
<223> OTHER INFORMATION: a, t, c, g, unknown or other
<220> FEATURE:
<221> NAME/KEY: modified_base
<222> LOCATION: (494)..(495)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (502)..(503)
<223> OTHER INFORMATION: a, t, c, g, unknown or other
<220> FEATURE:
<221> NAME/KEY: modified_base
<222> LOCATION: (512)..(512)
<223> OTHER INFORMATION: a, t, c, g, unknown or other
<220> FEATURE:
<221> NAME/KEY: modified_base
<222> LOCATION: (516)..(517)
<223> OTHER INFORMATION: a, t, c, g, unknown or other
<220> FEATURE:
<221> NAME/KEY: modified_base
<222> LOCATION: (533)..(534)
<223> OTHER INFORMATION: a, t, c, g, unknown or other
<220> FEATURE:
<221> NAME/KEY: modified_base
<222> LOCATION: (537)..(537)
<223> OTHER INFORMATION: a, t, c, g, unknown or other
<220> FEATURE:
<221> NAME/KEY: modified_base
<222> LOCATION: (541)..(542)
<223> OTHER INFORMATION: a, t, c, g, unknown or other
<220> FEATURE:
<221> NAME/KEY: modified_base
<222> LOCATION: (544)..(545)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other -continued
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (557)..(559)
<223> OTHER INFORMATION: a, t, c, g, unknown or other
<220> FEATURE:
<221> NAME/KEY: modified_base
<222> LOCATION: (565)..(565)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (570)..(570)
<223> OTHER INFORMATION: a, t, c, g, unknown or other
<220> FEATURE:
<221> NAME/KEY: modified_base
<222> LOCATION: (576)..(576)
<223> OTHER INFORMATION: a, t, c, g, unknown or other
<220> FEATURE:
<221> NAME/KEY: modified_base
<222> LOCATION: (583)..(583)
<223> OTHER INFORMATION: a, t, c, g, unknown or other
<220> FEATURE:
<221> NAME/KEY: modified_base
<222> LOCATION: (587)..(591)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (596)..(597)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base
<222> LOCATION: (611)..(612)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (626)..(626)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (647)..(647)

-continued

<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (674)..(675)
<223> OTHER INFORMATION: a, t, c, g, unknown or other
<220> FEATURE:
<221> NAME/KEY: modified_base
<222> LOCATION: (681)..(682)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (693)..(694)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (717)..(717)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (736)..(737)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other
<220> FEATURE:
<221> NAME/KEY: modified_base
<222> LOCATION: (759)..(760)
<223> OTHER INFORMATION: a, t, c, g, unknown or other
<220> FEATURE:
<221> NAME/KEY: modified_base
<222> LOCATION: (764)..(764)
<223> OTHER INFORMATION: a, t, c, g, unknown or other
<220> FEATURE:
<221> NAME/KEY: modified_base
<222> LOCATION: (776)..(776)
<223> OTHER INFORMATION: a, t, c, g, unknown or other

<400> SEQUENCE: 57
cctgnnagan antaccnggc acacanaaac acccaaanaa aattttaacn cnnaanattn 60
ncncccnccg nnggggnntt aaaaaannan ctnncccccc cccanaaaca ncancaaaac 120
ncacnaacan nacacatnan naancanccn caaanccnaa naaaanccaa cacnaaanaa 180
ccncaanaca nccaaancnn tnncnnanca nanaacccac anacnnncaa ancncccaaa 240
cnaacacaac caaacnaaac aacaactaan acaacaccan cnataaacca aanatacaaa 300
acaccnntcn cnacaaancc acacganaac acccaaanna cacnaanaac actcaaanna 360

-continued

```
aacaaancac annccaccaa aaaaacntan tacnnnaaan acancaaatc nacnannnca    420

acatcacnat cactcaccnn aaaacanaac ancnntcacc aacanaannc acaaanacan    480

ncctannann accnnacnac cnnaccccac anacannaac aacccacaaa tannccnaca    540

nnanncntca cnacaannnc aacgnantcn caaaanaccc ccncaannnn nanaannaca    600

ccacaacana nnaaaacnan aacnantaac anaaaaanac naaaaanaan accccaatcn    660

caccacaaaa cacnncacaa nncccccana atnncaccct caccncacaa acaaacnacc    720

accacaaaac aaanannaan aaaaaaanca aaaccancnn aatnacaaac aaaacncg      778
```

<210> SEQ ID NO 58
<211> LENGTH: 753
<212> TYPE: DNA
<213> ORGANISM: Homo sapiens
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (343)..(343)
<223> OTHER INFORMATION: a, t, c, g, unknown or other
<220> FEATURE:
<221> NAME/KEY: modified_base
<222> LOCATION: (489)..(489)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (711)..(711)

-continued

<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (718)..(718)
<223> OTHER INFORMATION: a, t, c, g, unknown or other
<220> FEATURE:
<221> NAME/KEY: modified_base
<222> LOCATION: (720)..(720)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other

<400> SEQUENCE: 58
cctttcaggc aagcagtggt ctctagctgt taaaacattt cctttttgga tcacaatagc 60
ttctaaaact gccttngtag taaaggccat cagagaggta atactaaact gtgcatttgc 120
caaataagaa tatgaattgt ataaaagctc atattccaat cctagatcaa atggcaaaag 180
ttctacaaag ttggtttcca tgtttgtata aaagctccga ctgattttat gtattttgct 240
atgaaattac ctttgggtct tataatcagt atacctctac tcaggaatgt gcaaatgatt 300
ttatacagca cgacgctagt accgctctgt atgacagtaa ggntttttt ttttcttctt 360 ttctaaatgg aaagaaaata tccctagtca gaaataaact gacaaattta cattctcctc 420
tcttaaaaaa gtaaataaaa taacattatt caaaacgtga attagctata gacatacaat 480
acaattacnt agatccatat caatacagca cattcaatct ggccaaaaat taatgattac 540
caagccngta tggatgctgc aatttcaaga gagatgtatg taccatggtt agagcntttg 600
naatgcacta tcctacagca gtctggttgg tnaattcang nactttntga gccangggaa 660
aaaaaagtaa cctggttggt tgaaggcttg ganaatcaag ggtganacnt ntnattcngn 720
tnggcngctt tgggccccat taaaaaggcc ggg 753

<210> SEQ ID NO 59
<211> LENGTH: 766
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (15)..(15)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (32)..(33)
<223> OTHER INFORMATION: a, t, c, g, unknown or other -continued
<220> FEATURE:
<221> NAME/KEY: modified_base
<222> LOCATION: (42)..(43)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (59)..(59)
<223> OTHER INFORMATION: a, t, c, g, unknown or other
<220> FEATURE:
<221> NAME/KEY: modified_base
<222> LOCATION: (71)..(71)
<223> OTHER INFORMATION: a, t, c, g, unknown or other
<220> FEATURE:
<221> NAME/KEY: modified_base
<222> LOCATION: (84)..(86)
<223> OTHER INFORMATION: a, t, c, g, unknown or other
<220> FEATURE:
<221> NAME/KEY: modified_base
<222> LOCATION: (95)..(95)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (117)..(117)
<223> OTHER INFORMATION: a, t, c, g, unknown or other
<220> FEATURE:
<221> NAME/KEY: modified_base
<222> LOCATION: (149)..(149)
<223> OTHER INFORMATION: a, t, c, g, unknown or other
<220> FEATURE:
<221> NAME/KEY: modified_base
<222> LOCATION: (162)..(162)
<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (175)..(176)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (189)..(189)
<223> OTHER INFORMATION: a, t, c, g, unknown or other
<220> FEATURE:
<221> NAME/KEY: modified_base
<222> LOCATION: (200)..(200)
<223> OTHER INFORMATION: a, t, c, g, unknown or other
<220> FEATURE:
<221> NAME/KEY: modified_base
<222> LOCATION: (218)..(218)
<223> OTHER INFORMATION: a, t, c, g, unknown or other
<220> FEATURE:
<221> NAME/KEY: modified_base
<222> LOCATION: (221)..(221)
<223> OTHER INFORMATION: a, t, c, g, unknown or other
<220> FEATURE:
<221> NAME/KEY: modified_base
<222> LOCATION: (232)..(232)
<223> OTHER INFORMATION: a, t, c, g, unknown or other
<220> FEATURE:
<221> NAME/KEY: modified_base
<222> LOCATION: (242)..(242)
<223> OTHER INFORMATION: a, t, c, g, unknown or other
<220> FEATURE:
<221> NAME/KEY: modified_base
<222> LOCATION: (259)..(259)

-continued

<223> OTHER INFORMATION: a, t, c, g, unknown or other
<220> FEATURE:
<221> NAME/KEY: modified_base
<222> LOCATION: (275)..(275)
<223> OTHER INFORMATION: a, t, c, g, unknown or other
<220> FEATURE:
<221> NAME/KEY: modified_base
<222> LOCATION: (286)..(286)
<223> OTHER INFORMATION: a, t, c, g, unknown or other
<220> FEATURE:
<221> NAME/KEY: modified_base
<222> LOCATION: (293)..(293)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (313)..(313)
<223> OTHER INFORMATION: a, t, c, g, unknown or other
<220> FEATURE:
<221> NAME/KEY: modified_base
<222> LOCATION: (315)..(315)
<223> OTHER INFORMATION: a, t, c, g, unknown or other
<220> FEATURE:
<221> NAME/KEY: modified_base
<222> LOCATION: (319)..(320)
<223> OTHER INFORMATION: a, t, c, g, unknown or other
<220> FEATURE:
<221> NAME/KEY: modified_base
<222> LOCATION: (330)..(330)
<223> OTHER INFORMATION: a, t, c, g, unknown or other
<220> FEATURE:
<221> NAME/KEY: modified_base
<222> LOCATION: (338)..(338)
<223> OTHER INFORMATION: a, t, c, g, unknown or other
<220> FEATURE:
<221> NAME/KEY: modified_base
<222> LOCATION: (362)..(362)
<223> OTHER INFORMATION: a, t, c, g, unknown or other
<220> FEATURE:
<221> NAME/KEY: modified_base
<222> LOCATION: (373)..(373)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (394)..(394)
<223> OTHER INFORMATION: a, t, c, g, unknown or other
<220> FEATURE:
<221> NAME/KEY: modified_base
<222> LOCATION: (401)..(402)
<223> OTHER INFORMATION: a, t, c, g, unknown or other
<220> FEATURE:
<221> NAME/KEY: modified_base
<222> LOCATION: (405)..(405)
<223> OTHER INFORMATION: a, t, c, g, unknown or other
<220> FEATURE:
<221> NAME/KEY: modified_base
<222> LOCATION: (409)..(409)
<223> OTHER INFORMATION: a, t, c, g, unknown or other
<220> FEATURE:
<221> NAME/KEY: modified_base
<222> LOCATION: (412)..(412)
<223> OTHER INFORMATION: a, t, c, g, unknown or other
<220> FEATURE:
<221> NAME/KEY: modified_base
<222> LOCATION: (418)..(419)
<223> OTHER INFORMATION: a, t, c, g, unknown or other
<220> FEATURE:
<221> NAME/KEY: modified_base
<222> LOCATION: (425)..(425)
<223> OTHER INFORMATION: a, t, c, g, unknown or other
<220> FEATURE:
<221> NAME/KEY: modified_base -continued
<222> LOCATION: (427)..(428)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (435)..(436)
<223> OTHER INFORMATION: a, t, c, g, unknown or other
<220> FEATURE:
<221> NAME/KEY: modified_base
<222> LOCATION: (445)..(445)
<223> OTHER INFORMATION: a, t, c, g, unknown or other
<220> FEATURE:
<221> NAME/KEY: modified_base
<222> LOCATION: (448)..(449)
<223> OTHER INFORMATION: a, t, c, g, unknown or other
<220> FEATURE:
<221> NAME/KEY: modified_base
<222> LOCATION: (453)..(453)
<223> OTHER INFORMATION: a, t, c, g, unknown or other
<220> FEATURE:
<221> NAME/KEY: modified_base
<222> LOCATION: (462)..(464)
<223> OTHER INFORMATION: a, t, c, g, unknown or other
<220> FEATURE:
<221> NAME/KEY: modified_base
<222> LOCATION: (472)..(472)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (481)..(481)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (492)..(492)
<223> OTHER INFORMATION: a, t, c, g, unknown or other
<220> FEATURE:
<221> NAME/KEY: modified_base
<222> LOCATION: (497)..(498)
<223> OTHER INFORMATION: a, t, c, g, unknown or other
<220> FEATURE:
<221> NAME/KEY: modified_base
<222> LOCATION: (501)..(501)
<223> OTHER INFORMATION: a, t, c, g, unknown or other
<220> FEATURE:
<221> NAME/KEY: modified_base
<222> LOCATION: (509)..(509)
<223> OTHER INFORMATION: a, t, c, g, unknown or other
<220> FEATURE:
<221> NAME/KEY: modified_base
<222> LOCATION: (511)..(511)
<223> OTHER INFORMATION: a, t, c, g, unknown or other
<220> FEATURE:
<221> NAME/KEY: modified_base
<222> LOCATION: (519)..(520)
<223> OTHER INFORMATION: a, t, c, g, unknown or other
<220> FEATURE:
<221> NAME/KEY: modified_base
<222> LOCATION: (524)..(525)
<223> OTHER INFORMATION: a, t, c, g, unknown or other
<220> FEATURE:
<221> NAME/KEY: modified_base
<222> LOCATION: (528)..(528)
<223> OTHER INFORMATION: a, t, c, g, unknown or other
<220> FEATURE:
<221> NAME/KEY: modified_base
<222> LOCATION: (532)..(532)
<223> OTHER INFORMATION: a, t, c, g, unknown or other
<220> FEATURE:

-continued

<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (537)..(538)
<223> OTHER INFORMATION: a, t, c, g, unknown or other
<220> FEATURE:
<221> NAME/KEY: modified_base
<222> LOCATION: (540)..(540)
<223> OTHER INFORMATION: a, t, c, g, unknown or other
<220> FEATURE:
<221> NAME/KEY: modified_base
<222> LOCATION: (542)..(546)
<223> OTHER INFORMATION: a, t, c, g, unknown or other
<220> FEATURE:
<221> NAME/KEY: modified_base
<222> LOCATION: (550)..(553)
<223> OTHER INFORMATION: a, t, c, g, unknown or other
<220> FEATURE:
<221> NAME/KEY: modified_base
<222> LOCATION: (556)..(556)
<223> OTHER INFORMATION: a, t, c, g, unknown or other
<220> FEATURE:
<221> NAME/KEY: modified_base
<222> LOCATION: (568)..(569)
<223> OTHER INFORMATION: a, t, c, g, unknown or other
<220> FEATURE:
<221> NAME/KEY: modified_base
<222> LOCATION: (572)..(572)
<223> OTHER INFORMATION: a, t, c, g, unknown or other
<220> FEATURE:
<221> NAME/KEY: modified_base
<222> LOCATION: (574)..(575)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (581)..(582)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (611)..(611)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other
<220> FEATURE:
<221> NAME/KEY: modified_base
<222> LOCATION: (623)..(623)
<223> OTHER INFORMATION: a, t, c, g, unknown or other
<220> FEATURE:
<221> NAME/KEY: modified_base
<222> LOCATION: (625)..(625)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other -continued
<220> FEATURE:
<221> NAME/KEY: modified_base
<222> LOCATION: (635)..(637)
<223> OTHER INFORMATION: a, t, c, g, unknown or other
<220> FEATURE:
<221> NAME/KEY: modified_base
<222> LOCATION: (639)..(640)
<223> OTHER INFORMATION: a, t, c, g, unknown or other
<220> FEATURE:
<221> NAME/KEY: modified_base
<222> LOCATION: (659)..(660)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (668)..(669)
<223> OTHER INFORMATION: a, t, c, g, unknown or other
<220> FEATURE:
<221> NAME/KEY: modified_base
<222> LOCATION: (687)..(688)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (707)..(707)
<223> OTHER INFORMATION: a, t, c, g, unknown or other
<220> FEATURE:
<221> NAME/KEY: modified_base
<222> LOCATION: (711)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (730)..(731)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (749)..(750)
<223> OTHER INFORMATION: a, t, c, g, unknown or other
<220> FEATURE:
<221> NAME/KEY: modified_base
<222> LOCATION: (754)..(755)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 59

-continued

```
gaacaganac acaanaggca aanancanca cnngaaaaat tnnttccaan acacagacnc      60

caaagaaaca ngggggggata agcnnnaagg gcctntatga ccccnccacc ccacacngag     120

caccaccccg aaggggctgg aagccaggng aaccacccaa angggngcct gcagnnctgc     180

ccanctacng cccctcctcn gggaccacac agggacgncg naacagccaa cnccacacat     240

cngccaaaaa agagcaagnc atcaaggcaa gcagncacga ctcaanactc ccnagctgca     300

gaaaaccaan ggngncagnn ggaacagggn aacacacnaa aaaagccaca caaaaaagga     360

anagacaggc aangaccaac caaagaaagg cncnaaggca nncgnaacna cngggaanna     420

caggngnnan aaacnngcca agcanggnnc acnaaaagga cnnncacaga gngaaaangg     480

nggnacccaa ancccnngg nagaacagna nccaccagnn aacnnagnca cnaancnngn      540

gnnnnngacn nnnggngcaa caaaaaannc ananngngac nnggaccaaa ggaaacaanc     600

gnaangcaag naaacaaaaa ncnanccngg ncccnnnann ggcaaccagg gaaagaaann     660

aaanananne cacaaaaggg aaaaaannaa aaanagaaaa aaaanancce nncaccccaa     720

aaaaaaanan naanaggggn gnaaaacann ccannacnaa aaaaac                     766
```

<210> SEQ ID NO 60
<211> LENGTH: 750
<212> TYPE: DNA
<213> ORGANISM: Homo sapiens
<220> FEATURE:
<221> NAME/KEY: modified_base
<222> LOCATION: (42)..(42)
<223> OTHER INFORMATION: a, t, c, g, unknown or other
<220> FEATURE:
<221> NAME/KEY: modified_base
<222> LOCATION: (44)..(45)
<223> OTHER INFORMATION: a, t, c, g, unknown or other
<220> FEATURE:
<221> NAME/KEY: modified_base
<222> LOCATION: (77)..(78)
<223> OTHER INFORMATION: a, t, c, g, unknown or other
<220> FEATURE:
<221> NAME/KEY: modified_base
<222> LOCATION: (103)..(103)
<223> OTHER INFORMATION: a, t, c, g, unknown or other
<220> FEATURE:
<221> NAME/KEY: modified_base
<222> LOCATION: (408)..(408)
<223> OTHER INFORMATION: a, t, c, g, unknown or other
<220> FEATURE:
<221> NAME/KEY: modified_base
<222> LOCATION: (479)..(479)
<223> OTHER INFORMATION: a, t, c, g, unknown or other
<220> FEATURE:
<221> NAME/KEY: modified_base
<222> LOCATION: (522)..(522)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (559)..(559)
<223> OTHER INFORMATION: a, t, c, g, unknown or other
<220> FEATURE:
<221> NAME/KEY: modified_base
<222> LOCATION: (568)..(568)
<223> OTHER INFORMATION: a, t, c, g, unknown or other
<220> FEATURE:
<221> NAME/KEY: modified_base
<222> LOCATION: (578)..(578)
<223> OTHER INFORMATION: a, t, c, g, unknown or other
<220> FEATURE:
<221> NAME/KEY: modified_base
<222> LOCATION: (583)..(583)
<223> OTHER INFORMATION: a, t, c, g, unknown or other -continued
<220> FEATURE:
<221> NAME/KEY: modified_base
<222> LOCATION: (592)..(592)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (673)..(673)
<223> OTHER INFORMATION: a, t, c, g, unknown or other
<220> FEATURE:
<221> NAME/KEY: modified_base
<222> LOCATION: (680)..(680)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (700)..(701)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (716)..(717)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (725)..(726)

-continued

<223> OTHER INFORMATION: a, t, c, g, unknown or other
<220> FEATURE:
<221> NAME/KEY: modified_base
<222> LOCATION: (729)..(730)
<223> OTHER INFORMATION: a, t, c, g, unknown or other
<220> FEATURE:
<221> NAME/KEY: modified_base
<222> LOCATION: (732)..(732)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other

<400> SEQUENCE: 60
aaggaattgt tacagaaaat gcaaatatca gtatttgaaa antnntttcc attacacaga 60
ctccaaagaa acaaggnnga taagcgccgt ggtcctctat ganccccatca ccccacactg 120 agcaccaccc cgaaggggct ggaagccagg tgatccaccc aaatgtgtgc ctgcagtttc 180
tgcccagcta ctgcccctcc tctgggatca cacagggatg tcgtaacagc caactccaca 240
catctgccaa aaaagagcaa gtcatcaagg cgagcagtct cgactcaaga ctccctagct 300
gcagaaaacc aatgttgtca gttgtaacag gttaatatat tatttatgcc acacaaaaaa 360
ggaatagtac aggcaatgat cttccaaaga aagctttaag gcatctgnaa cttctgggaa 420
tttcaggggt tttatcttgc cagcaagctc tactaaagta cttcacagag tgagaaggng 480
gctccaagtc cctttggtga agttggtgcc acctgcttcc tntggcacca agctggggtg 540
gggagctttg gggcttnang aagtcttntg ggacttgncc aanggaacaa gngtctggca 600
tggaaacatt acccttcctt ggtcctgntc nggcaccngg gaagtaancg tagcttgnct 660
ttaaggngaa acnttcatan tnaaaagggn cntttnttcn naanaaaana aacctnnang 720
gnggnnaann tntnccnttt ccaaaaannc 750

<210> SEQ ID NO 61
<211> LENGTH: 756
<212> TYPE: DNA
<213> ORGANISM: Homo sapiens
<220> FEATURE:
<221> NAME/KEY: modified_base
<222> LOCATION: (7)..(7)
<223> OTHER INFORMATION: a, t, c, g, unknown or other
<220> FEATURE:
<221> NAME/KEY: modified_base
<222> LOCATION: (18)..(18)
<223> OTHER INFORMATION: a, t, c, g, unknown or other
<220> FEATURE:
<221> NAME/KEY: modified_base
<222> LOCATION: (47)..(47)
<223> OTHER INFORMATION: a, t, c, g, unknown or other
<220> FEATURE:
<221> NAME/KEY: modified_base
<222> LOCATION: (619)..(619)
<223> OTHER INFORMATION: a, t, c, g, unknown or other
<220> FEATURE:
<221> NAME/KEY: modified_base
<222> LOCATION: (676)..(676)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other -continued
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other

<400> SEQUENCE: 61
gttttgnaaa aatagccncg aaacggtgtt tttaaagttg aggtctngaa gacctggctc 60
ggtttctggg aaggtgggtc ttttgtgatg tggtccccgg gcggtgcact tgggagccat 120
ggcggggcca ggacctctgg cagcgcaggg atggagcccg caggtgatga gcttgggagg 180
tgagttgtgg aggctgcgct cacatcaatg cccagtgccc tccccgaggg gcctggttct 240
ctctccacag gggcgggggga agcacacagg ggacagggag gggtgctggg ttctctctcc 300
tcgggacagg gagcgcagcc aggttctctc tcctcgggac agggtggtgc ccgttgcgtg 360
cattccccag ctgcagccac gagaaacaat ttggagcgga acccgggctc tgacctcccc 420
tcatcctcag ccttccccca gggatgggcc gtgagatgaa tgtggtcacc ggcccaatcc 480
aagggtctat ggccaaaccg cagacccgga ggaagcaggc caggccatct ggggagccgg 540
cttcccttct cttctccctg ctccacaaag ctgtctcatc cagaagccag gcccgcctgt 600
gagcaagggg aggctgcang tgttccttca cctgaagcgt gtgaaagcca acaggcccca 660
ccctggtctc agccgnagcc ccttccagac tcanggggcc aaaccacttt tcacagccat 720
tgtaaccaaa cgtntggcca cactttgntc gactca 756

<210> SEQ ID NO 62
<211> LENGTH: 799
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (34)..(34)
<223> OTHER INFORMATION: a, t, c, g, unknown or other
<220> FEATURE:
<221> NAME/KEY: modified_base
<222> LOCATION: (37)..(37)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (54)..(54)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other
<220> FEATURE:

-continued

<221> NAME/KEY: modified_base
<222> LOCATION: (70)..(72)
<223> OTHER INFORMATION: a, t, c, g, unknown or other
<220> FEATURE:
<221> NAME/KEY: modified_base
<222> LOCATION: (75)..(75)
<223> OTHER INFORMATION: a, t, c, g, unknown or other
<220> FEATURE:
<221> NAME/KEY: modified_base
<222> LOCATION: (78)..(78)
<223> OTHER INFORMATION: a, t, c, g, unknown or other
<220> FEATURE:
<221> NAME/KEY: modified_base
<222> LOCATION: (84)..(84)
<223> OTHER INFORMATION: a, t, c, g, unknown or other
<220> FEATURE:
<221> NAME/KEY: modified_base
<222> LOCATION: (87)..(87)
<223> OTHER INFORMATION: a, t, c, g, unknown or other
<220> FEATURE:
<221> NAME/KEY: modified_base
<222> LOCATION: (94)..(95)
<223> OTHER INFORMATION: a, t, c, g, unknown or other
<220> FEATURE:
<221> NAME/KEY: modified_base
<222> LOCATION: (98)..(98)
<223> OTHER INFORMATION: a, t, c, g, unknown or other
<220> FEATURE:
<221> NAME/KEY: modified_base
<222> LOCATION: (100)..(102)
<223> OTHER INFORMATION: a, t, c, g, unknown or other
<220> FEATURE:
<221> NAME/KEY: modified_base
<222> LOCATION: (107)..(107)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (122)..(122)
<223> OTHER INFORMATION: a, t, c, g, unknown or other
<220> FEATURE:
<221> NAME/KEY: modified_base
<222> LOCATION: (124)..(124)
<223> OTHER INFORMATION: a, t, c, g, unknown or other
<220> FEATURE:
<221> NAME/KEY: modified_base
<222> LOCATION: (127)..(127)
<223> OTHER INFORMATION: a, t, c, g, unknown or other
<220> FEATURE:
<221> NAME/KEY: modified_base
<222> LOCATION: (129)..(130)
<223> OTHER INFORMATION: a, t, c, g, unknown or other
<220> FEATURE:
<221> NAME/KEY: modified_base
<222> LOCATION: (138)..(139)
<223> OTHER INFORMATION: a, t, c, g, unknown or other
<220> FEATURE:
<221> NAME/KEY: modified_base
<222> LOCATION: (143)..(143)
<223> OTHER INFORMATION: a, t, c, g, unknown or other
<220> FEATURE:
<221> NAME/KEY: modified_base
<222> LOCATION: (145)..(145)
<223> OTHER INFORMATION: a, t, c, g, unknown or other
<220> FEATURE:
<221> NAME/KEY: modified_base
<222> LOCATION: (148)..(148)
<223> OTHER INFORMATION: a, t, c, g, unknown or other
<220> FEATURE:
<221> NAME/KEY: modified_base
<222> LOCATION: (151)..(151)
<223> OTHER INFORMATION: a, t, c, g, unknown or other
<220> FEATURE:
<221> NAME/KEY: modified_base
<222> LOCATION: (153)..(155)
<223> OTHER INFORMATION: a, t, c, g, unknown or other -continued
<220> FEATURE:
<221> NAME/KEY: modified_base
<222> LOCATION: (159)..(159)
<223> OTHER INFORMATION: a, t, c, g, unknown or other
<220> FEATURE:
<221> NAME/KEY: modified_base
<222> LOCATION: (163)..(163)
<223> OTHER INFORMATION: a, t, c, g, unknown or other
<220> FEATURE:
<221> NAME/KEY: modified_base
<222> LOCATION: (166)..(167)
<223> OTHER INFORMATION: a, t, c, g, unknown or other
<220> FEATURE:
<221> NAME/KEY: modified_base
<222> LOCATION: (170)..(171)
<223> OTHER INFORMATION: a, t, c, g, unknown or other
<220> FEATURE:
<221> NAME/KEY: modified_base
<222> LOCATION: (173)..(173)
<223> OTHER INFORMATION: a, t, c, g, unknown or other
<220> FEATURE:
<221> NAME/KEY: modified_base
<222> LOCATION: (175)..(175)
<223> OTHER INFORMATION: a, t, c, g, unknown or other
<220> FEATURE:
<221> NAME/KEY: modified_base
<222> LOCATION: (177)..(177)
<223> OTHER INFORMATION: a, t, c, g, unknown or other
<220> FEATURE:
<221> NAME/KEY: modified_base
<222> LOCATION: (183)..(184)
<223> OTHER INFORMATION: a, t, c, g, unknown or other
<220> FEATURE:
<221> NAME/KEY: modified_base
<222> LOCATION: (188)..(189)
<223> OTHER INFORMATION: a, t, c, g, unknown or other
<220> FEATURE:
<221> NAME/KEY: modified_base
<222> LOCATION: (191)..(191)
<223> OTHER INFORMATION: a, t, c, g, unknown or other
<220> FEATURE:
<221> NAME/KEY: modified_base
<222> LOCATION: (199)..(199)
<223> OTHER INFORMATION: a, t, c, g, unknown or other
<220> FEATURE:
<221> NAME/KEY: modified_base
<222> LOCATION: (206)..(206)
<223> OTHER INFORMATION: a, t, c, g, unknown or other
<220> FEATURE:
<221> NAME/KEY: modified_base
<222> LOCATION: (208)..(209)
<223> OTHER INFORMATION: a, t, c, g, unknown or other
<220> FEATURE:
<221> NAME/KEY: modified_base
<222> LOCATION: (211)..(212)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (224)..(226)
<223> OTHER INFORMATION: a, t, c, g, unknown or other
<220> FEATURE:
<221> NAME/KEY: modified_base
<222> LOCATION: (231)..(231)
<223> OTHER INFORMATION: a, t, c, g, unknown or other
<220> FEATURE:
<221> NAME/KEY: modified_base
<222> LOCATION: (233)..(234)
<223> OTHER INFORMATION: a, t, c, g, unknown or other
<220> FEATURE:
<221> NAME/KEY: modified_base
<222> LOCATION: (239)..(239)
<223> OTHER INFORMATION: a, t, c, g, unknown or other
<220> FEATURE:
<221> NAME/KEY: modified_base
<222> LOCATION: (243)..(243)

-continued

<223> OTHER INFORMATION: a, t, c, g, unknown or other
<220> FEATURE:
<221> NAME/KEY: modified_base
<222> LOCATION: (247)..(247)
<223> OTHER INFORMATION: a, t, c, g, unknown or other
<220> FEATURE:
<221> NAME/KEY: modified_base
<222> LOCATION: (250)..(250)
<223> OTHER INFORMATION: a, t, c, g, unknown or other
<220> FEATURE:
<221> NAME/KEY: modified_base
<222> LOCATION: (254)..(254)
<223> OTHER INFORMATION: a, t, c, g, unknown or other
<220> FEATURE:
<221> NAME/KEY: modified_base
<222> LOCATION: (262)..(262)
<223> OTHER INFORMATION: a, t, c, g, unknown or other
<220> FEATURE:
<221> NAME/KEY: modified_base
<222> LOCATION: (265)..(266)
<223> OTHER INFORMATION: a, t, c, g, unknown or other
<220> FEATURE:
<221> NAME/KEY: modified_base
<222> LOCATION: (272)..(272)
<223> OTHER INFORMATION: a, t, c, g, unknown or other
<220> FEATURE:
<221> NAME/KEY: modified_base
<222> LOCATION: (281)..(281)
<223> OTHER INFORMATION: a, t, c, g, unknown or other
<220> FEATURE:
<221> NAME/KEY: modified_base
<222> LOCATION: (288)..(289)
<223> OTHER INFORMATION: a, t, c, g, unknown or other
<220> FEATURE:
<221> NAME/KEY: modified_base
<222> LOCATION: (299)..(299)
<223> OTHER INFORMATION: a, t, c, g, unknown or other
<220> FEATURE:
<221> NAME/KEY: modified_base
<222> LOCATION: (305)..(305)
<223> OTHER INFORMATION: a, t, c, g, unknown or other
<220> FEATURE:
<221> NAME/KEY: modified_base
<222> LOCATION: (307)..(307)
<223> OTHER INFORMATION: a, t, c, g, unknown or other
<220> FEATURE:
<221> NAME/KEY: modified_base
<222> LOCATION: (311)..(313)
<223> OTHER INFORMATION: a, t, c, g, unknown or other
<220> FEATURE:
<221> NAME/KEY: modified_base
<222> LOCATION: (320)..(320)
<223> OTHER INFORMATION: a, t, c, g, unknown or other
<220> FEATURE:
<221> NAME/KEY: modified_base
<222> LOCATION: (326)..(326)
<223> OTHER INFORMATION: a, t, c, g, unknown or other
<220> FEATURE:
<221> NAME/KEY: modified_base
<222> LOCATION: (328)..(328)
<223> OTHER INFORMATION: a, t, c, g, unknown or other
<220> FEATURE:
<221> NAME/KEY: modified_base
<222> LOCATION: (332)..(333)
<223> OTHER INFORMATION: a, t, c, g, unknown or other
<220> FEATURE:
<221> NAME/KEY: modified_base
<222> LOCATION: (342)..(342)
<223> OTHER INFORMATION: a, t, c, g, unknown or other
<220> FEATURE:
<221> NAME/KEY: modified_base
<222> LOCATION: (348)..(350)
<223> OTHER INFORMATION: a, t, c, g, unknown or other
<220> FEATURE:
<221> NAME/KEY: modified_base
<222> LOCATION: (355)..(357)
<223> OTHER INFORMATION: a, t, c, g, unknown or other
<220> FEATURE:
<221> NAME/KEY: modified_base -continued
<222> LOCATION: (369)..(369)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (378)..(378)
<223> OTHER INFORMATION: a, t, c, g, unknown or other
<220> FEATURE:
<221> NAME/KEY: modified_base
<222> LOCATION: (380)..(380)
<223> OTHER INFORMATION: a, t, c, g, unknown or other
<220> FEATURE:
<221> NAME/KEY: modified_base
<222> LOCATION: (382)..(382)
<223> OTHER INFORMATION: a, t, c, g, unknown or other
<220> FEATURE:
<221> NAME/KEY: modified_base
<222> LOCATION: (386)..(389)
<223> OTHER INFORMATION: a, t, c, g, unknown or other
<220> FEATURE:
<221> NAME/KEY: modified_base
<222> LOCATION: (391)..(391)
<223> OTHER INFORMATION: a, t, c, g, unknown or other
<220> FEATURE:
<221> NAME/KEY: modified_base
<222> LOCATION: (394)..(395)
<223> OTHER INFORMATION: a, t, c, g, unknown or other
<220> FEATURE:
<221> NAME/KEY: modified_base
<222> LOCATION: (397)..(397)
<223> OTHER INFORMATION: a, t, c, g, unknown or other
<220> FEATURE:
<221> NAME/KEY: modified_base
<222> LOCATION: (400)..(400)
<223> OTHER INFORMATION: a, t, c, g, unknown or other
<220> FEATURE:
<221> NAME/KEY: modified_base
<222> LOCATION: (404)..(405)
<223> OTHER INFORMATION: a, t, c, g, unknown or other
<220> FEATURE:
<221> NAME/KEY: modified_base
<222> LOCATION: (411)..(411)
<223> OTHER INFORMATION: a, t, c, g, unknown or other
<220> FEATURE:
<221> NAME/KEY: modified_base
<222> LOCATION: (414)..(416)
<223> OTHER INFORMATION: a, t, c, g, unknown or other
<220> FEATURE:
<221> NAME/KEY: modified_base
<222> LOCATION: (419)..(419)
<223> OTHER INFORMATION: a, t, c, g, unknown or other
<220> FEATURE:
<221> NAME/KEY: modified_base
<222> LOCATION: (423)..(423)
<223> OTHER INFORMATION: a, t, c, g, unknown or other
<220> FEATURE:
<221> NAME/KEY: modified_base
<222> LOCATION: (427)..(427)
<223> OTHER INFORMATION: a, t, c, g, unknown or other
<220> FEATURE:
<221> NAME/KEY: modified_base
<222> LOCATION: (432)..(433)
<223> OTHER INFORMATION: a, t, c, g, unknown or other
<220> FEATURE:
<221> NAME/KEY: modified_base
<222> LOCATION: (446)..(446)
<223> OTHER INFORMATION: a, t, c, g, unknown or other
<220> FEATURE:
<221> NAME/KEY: modified_base
<222> LOCATION: (450)..(450)
<223> OTHER INFORMATION: a, t, c, g, unknown or other
<220> FEATURE:
<221> NAME/KEY: modified_base
<222> LOCATION: (455)..(455)
<223> OTHER INFORMATION: a, t, c, g, unknown or other
<220> FEATURE:

-continued

<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (465)..(465)
<223> OTHER INFORMATION: a, t, c, g, unknown or other
<220> FEATURE:
<221> NAME/KEY: modified_base
<222> LOCATION: (477)..(477)
<223> OTHER INFORMATION: a, t, c, g, unknown or other
<220> FEATURE:
<221> NAME/KEY: modified_base
<222> LOCATION: (487)..(487)
<223> OTHER INFORMATION: a, t, c, g, unknown or other
<220> FEATURE:
<221> NAME/KEY: modified_base
<222> LOCATION: (492)..(494)
<223> OTHER INFORMATION: a, t, c, g, unknown or other
<220> FEATURE:
<221> NAME/KEY: modified_base
<222> LOCATION: (496)..(496)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (505)..(505)
<223> OTHER INFORMATION: a, t, c, g, unknown or other
<220> FEATURE:
<221> NAME/KEY: modified_base
<222> LOCATION: (507)..(507)
<223> OTHER INFORMATION: a, t, c, g, unknown or other
<220> FEATURE:
<221> NAME/KEY: modified_base
<222> LOCATION: (509)..(509)
<223> OTHER INFORMATION: a, t, c, g, unknown or other
<220> FEATURE:
<221> NAME/KEY: modified_base
<222> LOCATION: (522)..(525)
<223> OTHER INFORMATION: a, t, c, g, unknown or other
<220> FEATURE:
<221> NAME/KEY: modified_base
<222> LOCATION: (528)..(528)
<223> OTHER INFORMATION: a, t, c, g, unknown or other
<220> FEATURE:
<221> NAME/KEY: modified_base
<222> LOCATION: (530)..(530)
<223> OTHER INFORMATION: a, t, c, g, unknown or other
<220> FEATURE:
<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (540)..(542)
<223> OTHER INFORMATION: a, t, c, g, unknown or other
<220> FEATURE:
<221> NAME/KEY: modified_base
<222> LOCATION: (544)..(546)
<223> OTHER INFORMATION: a, t, c, g, unknown or other
<220> FEATURE:
<221> NAME/KEY: modified_base
<222> LOCATION: (550)..(550)
<223> OTHER INFORMATION: a, t, c, g, unknown or other
<220> FEATURE:
<221> NAME/KEY: modified_base
<222> LOCATION: (558)..(558)
<223> OTHER INFORMATION: a, t, c, g, unknown or other
<220> FEATURE:
<221> NAME/KEY: modified_base
<222> LOCATION: (564)..(564)
<223> OTHER INFORMATION: a, t, c, g, unknown or other
<220> FEATURE:
<221> NAME/KEY: modified_base
<222> LOCATION: (568)..(568)
<223> OTHER INFORMATION: a, t, c, g, unknown or other -continued
<220> FEATURE:
<221> NAME/KEY: modified_base
<222> LOCATION: (574)..(574)
<223> OTHER INFORMATION: a, t, c, g, unknown or other
<220> FEATURE:
<221> NAME/KEY: modified_base
<222> LOCATION: (580)..(580)
<223> OTHER INFORMATION: a, t, c, g, unknown or other
<220> FEATURE:
<221> NAME/KEY: modified_base
<222> LOCATION: (582)..(582)
<223> OTHER INFORMATION: a, t, c, g, unknown or other
<220> FEATURE:
<221> NAME/KEY: modified_base
<222> LOCATION: (584)..(585)
<223> OTHER INFORMATION: a, t, c, g, unknown or other
<220> FEATURE:
<221> NAME/KEY: modified_base
<222> LOCATION: (589)..(590)
<223> OTHER INFORMATION: a, t, c, g, unknown or other
<220> FEATURE:
<221> NAME/KEY: modified_base
<222> LOCATION: (592)..(592)
<223> OTHER INFORMATION: a, t, c, g, unknown or other
<220> FEATURE:
<221> NAME/KEY: modified_base
<222> LOCATION: (595)..(597)
<223> OTHER INFORMATION: a, t, c, g, unknown or other
<220> FEATURE:
<221> NAME/KEY: modified_base
<222> LOCATION: (604)..(604)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (617)..(617)
<223> OTHER INFORMATION: a, t, c, g, unknown or other
<220> FEATURE:
<221> NAME/KEY: modified_base
<222> LOCATION: (622)..(623)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (637)..(637)
<223> OTHER INFORMATION: a, t, c, g, unknown or other
<220> FEATURE:
<221> NAME/KEY: modified_base
<222> LOCATION: (642)..(642)
<223> OTHER INFORMATION: a, t, c, g, unknown or other
<220> FEATURE:
<221> NAME/KEY: modified_base
<222> LOCATION: (653)..(653)
<223> OTHER INFORMATION: a, t, c, g, unknown or other
<220> FEATURE:
<221> NAME/KEY: modified_base
<222> LOCATION: (656)..(657)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (670)..(671)
<223> OTHER INFORMATION: a, t, c, g, unknown or other
<220> FEATURE:
<221> NAME/KEY: modified_base
<222> LOCATION: (673)..(673)

-continued

<223> OTHER INFORMATION: a, t, c, g, unknown or other
<220> FEATURE:
<221> NAME/KEY: modified_base
<222> LOCATION: (680)..(680)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (698)..(700)
<223> OTHER INFORMATION: a, t, c, g, unknown or other
<220> FEATURE:
<221> NAME/KEY: modified_base
<222> LOCATION: (710)..(711)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(747)
<223> OTHER INFORMATION: a, t, c, g, unknown or other
<220> FEATURE:
<221> NAME/KEY: modified_base
<222> LOCATION: (760)..(761)
<223> OTHER INFORMATION: a, t, c, g, unknown or other
<220> FEATURE:
<221> NAME/KEY: modified_base
<222> LOCATION: (768)..(771)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other
<220> FEATURE:
<221> NAME/KEY: modified_base
<222> LOCATION: (788)..(788)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other

<400> SEQUENCE: 62
ctttggcaaa aagacccgna aanancanaa tatnaanaaa tttttcaaan acanaatttt 60
tcnaaaaacn nnggnaancc ttanaanggg gatnnccnan nnaaacnagg aaanccccat 120
ananatnann tacccaanna aananaanac ncnnntaant acngannaan nanananaaa 180
aannaaanna nccaaaaana aacctnanna nncacaacaa angnnnacaa nannaaaana 240

-continued

```
tanccanaan cacnaaaaca anaannacaa anaaaacaca nataaaanna aaaacaaanc    300

ataananataa nnnacacaan acagananaa annaaaaaag anaaaagnnn actcnnnaac    360

aacaaaaana aaacgnanan tnacannnna ncanncnaan accnnccaaa naannnaana    420

canaaanaac annactatca cacgcncaan actanataca nacancccaa cacaaantaa    480

tcaaaanacc tnnncnanaa actcntnana caaaaaaaaa cnnnnatngn tacanaacan    540

nnannngacn aaaccacnaa cacncaanaa aacncaaacn anannaaann tnatnnnaac    600

aaanaacana gnaatcnacc anngaacata anaacanaaa cnacaaaaca aanaanntaa    660

caacaaanan nanaaccacn tacnaaaaan cncaananann aacacataan nantcaaacc    720

aacaaaanac ctacacanaa tacnanncaa aagaataccn naaacacnnn nataaanata    780

acatacanac ngaaacccg                                                 799
```

<210> SEQ ID NO 63
<211> LENGTH: 796
<212> TYPE: DNA
<213> ORGANISM: Homo sapiens
<220> FEATURE:
<221> NAME/KEY: modified_base
<222> LOCATION: (584)..(584)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (751)..(751)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (784)..(784)
<223> OTHER INFORMATION: a, t, c, g, unknown or other
<220> FEATURE:
<221> NAME/KEY: modified_base
<222> LOCATION: (786)..(786)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other

<400> SEQUENCE: 63

```
gcctgttggc ctactggagc aaaagaagaa gaagaaggag gtgaaggtga agaaggagag     60

gaaaccaaag aagctgaaga ggaggagaag aaagttgaag gtgctgggga ggaacaagca    120

gctaagaaga aagattgaac ccccatttcc ttaattattt caggaataat tctcccgaaa    180

tcaggtcaac cccatcacca accaaccaac cagttgagtt ccagattcta tgtgaattaa    240

aaagtcaata tatgtataat tctgagatga cttaggttgg acattcaatg ttgtgctatg    300

aatttcctct ttatgcagag tatctgtttg cttgcagagt ggctttctgg cttgctgcca    360

gcctgtgcat ggtccacgct tatgagttca ggatctacgg caatgtgaat cattcagatg    420

tttacaataa aaaacaccac atgagtaaat gaattcacta atgttaatgt taaacttcat    480

ggaaaaatag tcctttgaac cttcggtggt tagcaattaa agaccctgag ttatgtgcaa    540
```

-continued

```
taaatagtaa ataaagttat cccgaatgat gtattttttg ctgnggttgg tacttaatta    600

aaatacctta aagatggcac caatataaag tatatccagt ggctattgcc tncaattttt    660

aaaaagttga aattttaaca attccaatac tttttttctt cttcaattgg aaattctgag    720

ggatncagta tgcatgattc ctggggaaat ntttcccaca aaaatttact gntattaaca    780

tgantnaatg ngaaag                                                    796
```

<210> SEQ ID NO 64
<211> LENGTH: 821
<212> TYPE: DNA
<213> ORGANISM: Homo sapiens
<220> FEATURE:
<221> NAME/KEY: modified_base
<222> LOCATION: (13)..(13)
<223> OTHER INFORMATION: a, t, c, g, unknown or other
<220> FEATURE:
<221> NAME/KEY: modified_base
<222> LOCATION: (110)..(110)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (731)..(731)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (789)..(789)
<223> OTHER INFORMATION: a, t, c, g, unknown or other
<220> FEATURE:
<221> NAME/KEY: modified_base
<222> LOCATION: (795)..(797)
<223> OTHER INFORMATION: a, t, c, g, unknown or other
<220> FEATURE:
<221> NAME/KEY: modified_base
<222> LOCATION: (800)..(800)
<223> OTHER INFORMATION: a, t, c, g, unknown or other
<220> FEATURE:
<221> NAME/KEY: modified_base
<222> LOCATION: (811)..(813)
<223> OTHER INFORMATION: a, t, c, g, unknown or other
<220> FEATURE:
<221> NAME/KEY: modified_base
<222> LOCATION: (817)..(817)
<223> OTHER INFORMATION: a, t, c, g, unknown or other

<400> SEQUENCE: 64

```
tttttctta ggntttttac tattttatta tggcacacag gatagaggat ggtacagttt      60

tcttacttca accaagtaat tctcaaagca tccagctatt tccatttggn taaagttact    120

ttttgcacat agcttgcatc tgtttgagac ttaccatgta catcaaccca ggtctagtaa    180

gcagaaatgt gaaaagtttt gtttctgagg agacgcctca tctttacaga agccaataca    240

ctgagagcct tcatagttcc aatccattac catcatggca aggaagcact ttacctattc    300

gcatagcaac atatatttaa ctagaaatag gtggtacaaa gggattaagt aactttaaat    360

ggagaccact ttggtttcag gttaaattaa taacttatag agatcgctaa aaaacaaata    420
```

-continued

```
ttgaatgaaa ttagctgcaa agcaattgtt tcagaacaaa ggcagaatag cagatagtaa    480

tatcatctat atttattcca catcaaatgc aagagcgttc ttaactttac gacagaaagg    540

atacatgggg ccgtgtattt gatgcaatgt ccaaccagtc aagctatcat tgaaatccaa    600

atatttccag tagagacatg cagagcaatg tcaatgtaac atacaagcnt attaccttcc    660

cccttaagtg actcataatt tcattacttg gggctgnagc ttttaaaagg ttaaaaatgt    720

gtaccattaa ntgggattac tttgagggac cagaattncg cttaacaacc cncttaatca    780

tgacctcang gattnnngcn acatgttttc nnnggantgg g                        821
```

<210> SEQ ID NO 65
<211> LENGTH: 738
<212> TYPE: DNA
<213> ORGANISM: Homo sapiens
<220> FEATURE:
<221> NAME/KEY: modified_base
<222> LOCATION: (59)..(59)
<223> OTHER INFORMATION: a, t, c, g, unknown or other
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (89)..(89)
<223> OTHER INFORMATION: a, t, c, g, unknown or other
<220> FEATURE:
<221> NAME/KEY: modified_base
<222> LOCATION: (91)..(91)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (537)..(537)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (720)..(721)
<223> OTHER INFORMATION: a, t, c, g, unknown or other

<400> SEQUENCE: 65

```
ctgtcagtca cattatccca tttcctaggt ctgtctcttt tttctttgca gtttaattnt     60

tagtaaataa gagggnttta agtctcaang ntttggtcag agataaactc agacactgcc    120

tcgatatcac gaagttctca tttataccaa ctcttatctt cacgccaccg tgaattctca    180

tcggcataag gaggaaaaga gatggcacca aaggggaaaa aaatctggtg gtgtaatttg    240

gcatcttcat taagcaagcc atgagcagct tgtgaaatgc ttcatttatg gggccgccag    300

ctgggagaga gaggcgttct cacaatgcct tgaaaatggg aactttgcat cctttaaatt    360

tttccaaact gacttagttt gtttaccttg aatttctggg atggggcaaa tgtgaccttc    420

atgctatagg gcccacgttt ccagatttgg tatggaaaga aggaagaaag tctgaccctc    480

ttgnttttaa gataggcaaa aggaagatga gatagtccat ggttcaccac ccaangncct    540

tctgggcact ggctgggctg acgctgggcc tggttccagc tatgcctacc tttctcttgc    600
```

-continued cataccacac cgttgcttta tgagcattct tttggtaagg ncaagatcaa gataaccttt 660
ttcctttgaa taataggacc agcacctttc ccagtgggcc tttaatggca tctgaatgtn 720
naaagggaaa ccaccctt 738

<210> SEQ ID NO 66
<211> LENGTH: 745
<212> TYPE: DNA
<213> ORGANISM: Homo sapiens
<220> FEATURE:
<221> NAME/KEY: modified_base
<222> LOCATION: (81)..(81)
<223> OTHER INFORMATION: a, t, c, g, unknown or other
<220> FEATURE:
<221> NAME/KEY: modified_base
<222> LOCATION: (84)..(84)
<223> OTHER INFORMATION: a, t, c, g, unknown or other
<220> FEATURE:
<221> NAME/KEY: modified_base
<222> LOCATION: (97)..(98)
<223> OTHER INFORMATION: a, t, c, g, unknown or other
<220> FEATURE:
<221> NAME/KEY: modified_base
<222> LOCATION: (332)..(332)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other

<400> SEQUENCE: 66
tctacgcata ggcatgtgcg tactgggcca taatgcaaaa cttgtcatct tttgctctag 60
attacagttg cagaagttga nggncactat tctaggnnat acctggttga ttattcctgg 120
ggcagacata cagatattga aactgcttta cagcagtgta tgatgatttt aacagtatca 180
tatgcctcat aatgttcact tttgctttca actatcctac aattttcatt aacttttcag 240
aaataccttg caaattgttt ttcatcttgt gctatcaaaa aaatgttctg ccagttgcat 300
tgagtcctta gtatctgtct agaggtgcag anatctccat agcaactcca cagatgagga 360
gggtgggctc ttaccttccc tggccagccc cagaggactc gtaatggcag agctgaggtc 420
acttacctgg ggatggttca tggcttagaa cacaataggt tttcaataaa cattagcttc 480
ttgaacaaat gcatatgtgg aatggcttta ccatttgcaa aaattagggt gtcaatgtgc 540
cagttaatat tacacattca cctatcgatc caccccacac tgcaatgaga acaggggtaa 600
aatatatgca gactgnaccc ttccactgat aggaaaaaat cancacgatc ataactctgc 660
cttgggattt ctgcatgcta ctacagcttn ccaggaangn ccaaagcttt actttgaatt 720
aacgctgaac ttggtttaat tgggg 745

<210> SEQ ID NO 67
<211> LENGTH: 739

-continued

<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (71)..(72)
<223> OTHER INFORMATION: a, t, c, g, unknown or other
<220> FEATURE:
<221> NAME/KEY: modified_base
<222> LOCATION: (87)..(87)
<223> OTHER INFORMATION: a, t, c, g, unknown or other
<220> FEATURE:
<221> NAME/KEY: modified_base
<222> LOCATION: (116)..(116)
<223> OTHER INFORMATION: a, t, c, g, unknown or other
<220> FEATURE:
<221> NAME/KEY: modified_base
<222> LOCATION: (355)..(355)
<223> OTHER INFORMATION: a, t, c, g, unknown or other
<220> FEATURE:
<221> NAME/KEY: modified_base
<222> LOCATION: (623)..(623)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (679)..(679)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (730)..(730)
<223> OTHER INFORMATION: a, t, c, g, unknown or other -continued

<400> SEQUENCE: 67
tnaaaccccc ctgctgttaa gacttgacat tcaatatttt ttgatcacat tctttttttat 60 agcttagcta nnggcaacat ttgtggncat ataaattgca aaagaagctt tctcgngtac 120
atacattttt aaaagcttga aattgatgtg aacttttaaa aacacgtagg atctgtatta 180
cattctacat ctcaaaacaa atttaattaa agtgaatatc attccagtat atacaatatg 240
cctaagaccc agaattggca cactgattta ctagttgaaa atataacagt attcaccaaa 300
cttcaatgta tactttttgg agagaatgaa attacagtat ttcttaattt actgnaatgt 360
catctttgta attatgaatt aacaattcaa tgagaggaga cttggttgat taaattaatg 420
ctggtcctac acattatatc taaaggatct tcgtatatga ctactatctt cttggattat 480
tttaacaggt aaaatatcaa agtggccatt aaaaacagag ttgacttttc accattgctg 540
gttttctggt gagacatgtg gaaaggaagg acaggtggac ttttcaacta actagctctc 600
tgatttttaa taagatcctc aantcttttg gnctnagnta cctatctgtc caanggtaag 660
catatgctta atcactaana cnggtanatc ctgccnttaa naaccttatn aaccaaatnc 720
tggaccntan ggtacaaaa 739

<210> SEQ ID NO 68
<211> LENGTH: 747
<212> TYPE: DNA
<213> ORGANISM: Homo sapiens
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (54)..(54)
<223> OTHER INFORMATION: a, t, c, g, unknown or other
<220> FEATURE:
<221> NAME/KEY: modified_base
<222> LOCATION: (69)..(69)
<223> OTHER INFORMATION: a, t, c, g, unknown or other
<220> FEATURE:
<221> NAME/KEY: modified_base
<222> LOCATION: (81)..(81)
<223> OTHER INFORMATION: a, t, c, g, unknown or other
<220> FEATURE:
<221> NAME/KEY: modified_base
<222> LOCATION: (95)..(95)
<223> OTHER INFORMATION: a, t, c, g, unknown or other
<220> FEATURE:
<221> NAME/KEY: modified_base
<222> LOCATION: (111)..(112)
<223> OTHER INFORMATION: a, t, c, g, unknown or other
<220> FEATURE:
<221> NAME/KEY: modified_base
<222> LOCATION: (444)..(444)
<223> OTHER INFORMATION: a, t, c, g, unknown or other
<220> FEATURE:
<221> NAME/KEY: modified_base
<222> LOCATION: (501)..(501)
<223> OTHER INFORMATION: a, t, c, g, unknown or other
<220> FEATURE:
<221> NAME/KEY: modified_base
<222> LOCATION: (508)..(508)
<223> OTHER INFORMATION: a, t, c, g, unknown or other
<220> FEATURE:
<221> NAME/KEY: modified_base
<222> LOCATION: (538)..(538)
<223> OTHER INFORMATION: a, t, c, g, unknown or other
<220> FEATURE:
<221> NAME/KEY: modified_base
<222> LOCATION: (541)..(541)
<223> OTHER INFORMATION: a, t, c, g, unknown or other
<220> FEATURE:
<221> NAME/KEY: modified_base -continued
<222> LOCATION: (545)..(545)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (661)..(661)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (685)..(685)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other
<220> FEATURE:
<221> NAME/KEY: modified_base
<222> LOCATION: (718)..(718)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (732)..(732)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other -continued

<400> SEQUENCE: 68
aaaacctcca gnaatatttt cacactacct tctattttaa agttcacact tttnattcca 60
gagcagggna tggtcaggcc ngggtgggct ccccnccctc tccccttggc nntggtaacc 120
actggcccca gggactcagc ctgctttcct atccatcccc tcagtagctg tcaccatgca 180
ggttacccct tctgtttctt ctaccactaa ctccatgtct gactgcaagt gaaaggaaca 240
gaagcccaaa cctttgggtt ttaaggagtt tattgctaat ctgtaaaaca gaaagagaca 300
ggagataagc atgacaaaat atagggaaga aatgactttt gcctaaactt ccaattgtgt 360
acaattgaag cctctgcttt atagctctta gcacacctct caaataagaa ggcaagtact 420
gggaaagctc tgaacctgtg gcanaaccac tgatagctgt ggagctattc aaggagtctg 480
ggaatcaagg ggattatcaa nacattgnta gaataaatta atcttactgg atatatanca 540 naaantttc aagcatatgt aaatgctact aataccaaat aattacacct tgttttcttt 600
aaaccggaac tcttaaanat gnctctacaa aanttttga atnggaangg ctgnatgctc 660
naaaaacttn aaaacactac tgganaaaaa aggtctcngg aaggngatga aanccntnac 720
attggaacnt tnatnantta aatnggg 747

<210> SEQ ID NO 69
<211> LENGTH: 726
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (13)..(13)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other
<220> FEATURE:
<221> NAME/KEY: modified_base
<222> LOCATION: (640)..(640)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other

<400> SEQUENCE: 69
tntctgtccc agnctgttga tcttaaaact agttgattta aagagttttt ttgcacatca 60
tttcaattat atttgtgaac ttagaaaggt aacttacaat ctaaccagcc atcatatcat 120
atcctatcag gctagatatc tcaatagtag actgaataca aagctaattt tttttacatg 180
tcaatattgg cacaaactgg aatgaaagaa tagtttgatt cagacctgct ccactatgtg 240
ttgctaaaac acatgctatg agcactccag gaaacactat attttttcca aaaaatatgt 300
gattatatat gttaaagtat agataacatt tcacacttgg atacatatgt gcatttactg 360
tatttcttgg taagcatatt tttgggggaa agtgctgctg atatgataca agtagacaaa 420
atttaaatga aattttgcac attctatgga aaatggtttc tggtaaactg agaaggatat 480

```
taaaataagt ggcttttttc tgggctacca ttattggttg atttctcttt gcaagtgtat    540

agaacctgtc atacattcat gataaggagc actgaaaaat tactcattca aatttnccct    600

gggcacgtaa ggcaaaatat tggccggttg ggatttcaan ggcaagtgac gacgcaattt    660

ccttccagtc agacccccca gnccccccttg ctgggacatg gggangcana aagtcccttg    720

accatc                                                               726
```

<210> SEQ ID NO 70
<211> LENGTH: 854
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (30)..(30)
<223> OTHER INFORMATION: a, t, c, g, unknown or other
<220> FEATURE:
<221> NAME/KEY: modified_base
<222> LOCATION: (35)..(36)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (58)..(58)
<223> OTHER INFORMATION: a, t, c, g, unknown or other
<220> FEATURE:
<221> NAME/KEY: modified_base
<222> LOCATION: (60)..(60)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (81)..(82)
<223> OTHER INFORMATION: a, t, c, g, unknown or other
<220> FEATURE:
<221> NAME/KEY: modified_base
<222> LOCATION: (86)..(86)
<223> OTHER INFORMATION: a, t, c, g, unknown or other
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (93)..(94)
<223> OTHER INFORMATION: a, t, c, g, unknown or other
<220> FEATURE:
<221> NAME/KEY: modified_base
<222> LOCATION: (96)..(97)
<223> OTHER INFORMATION: a, t, c, g, unknown or other
<220> FEATURE:
<221> NAME/KEY: modified_base
<222> LOCATION: (99)..(99)

-continued

<223> OTHER INFORMATION: a, t, c, g, unknown or other
<220> FEATURE:
<221> NAME/KEY: modified_base
<222> LOCATION: (103)..(103)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (108)..(109)
<223> OTHER INFORMATION: a, t, c, g, unknown or other
<220> FEATURE:
<221> NAME/KEY: modified_base
<222> LOCATION: (114)..(115)
<223> OTHER INFORMATION: a, t, c, g, unknown or other
<220> FEATURE:
<221> NAME/KEY: modified_base
<222> LOCATION: (119)..(119)
<223> OTHER INFORMATION: a, t, c, g, unknown or other
<220> FEATURE:
<221> NAME/KEY: modified_base
<222> LOCATION: (122)..(123)
<223> OTHER INFORMATION: a, t, c, g, unknown or other
<220> FEATURE:
<221> NAME/KEY: modified_base
<222> LOCATION: (127)..(127)
<223> OTHER INFORMATION: a, t, c, g, unknown or other
<220> FEATURE:
<221> NAME/KEY: modified_base
<222> LOCATION: (134)..(134)
<223> OTHER INFORMATION: a, t, c, g, unknown or other
<220> FEATURE:
<221> NAME/KEY: modified_base
<222> LOCATION: (159)..(159)
<223> OTHER INFORMATION: a, t, c, g, unknown or other
<220> FEATURE:
<221> NAME/KEY: modified_base
<222> LOCATION: (162)..(162)
<223> OTHER INFORMATION: a, t, c, g, unknown or other
<220> FEATURE:
<221> NAME/KEY: modified_base
<222> LOCATION: (164)..(164)
<223> OTHER INFORMATION: a, t, c, g, unknown or other
<220> FEATURE:
<221> NAME/KEY: modified_base
<222> LOCATION: (172)..(172)
<223> OTHER INFORMATION: a, t, c, g, unknown or other
<220> FEATURE:
<221> NAME/KEY: modified_base
<222> LOCATION: (179)..(179)
<223> OTHER INFORMATION: a, t, c, g, unknown or other
<220> FEATURE:
<221> NAME/KEY: modified_base
<222> LOCATION: (181)..(181)
<223> OTHER INFORMATION: a, t, c, g, unknown or other
<220> FEATURE:
<221> NAME/KEY: modified_base
<222> LOCATION: (185)..(186)
<223> OTHER INFORMATION: a, t, c, g, unknown or other
<220> FEATURE:
<221> NAME/KEY: modified_base
<222> LOCATION: (188)..(188)
<223> OTHER INFORMATION: a, t, c, g, unknown or other
<220> FEATURE:
<221> NAME/KEY: modified_base
<222> LOCATION: (196)..(196)
<223> OTHER INFORMATION: a, t, c, g, unknown or other
<220> FEATURE:
<221> NAME/KEY: modified_base
<222> LOCATION: (198)..(199)
<223> OTHER INFORMATION: a, t, c, g, unknown or other
<220> FEATURE:
<221> NAME/KEY: modified_base
<222> LOCATION: (207)..(208)
<223> OTHER INFORMATION: a, t, c, g, unknown or other
<220> FEATURE:
<221> NAME/KEY: modified_base -continued
<222> LOCATION: (210)..(211)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (227)..(227)
<223> OTHER INFORMATION: a, t, c, g, unknown or other
<220> FEATURE:
<221> NAME/KEY: modified_base
<222> LOCATION: (229)..(229)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (253)..(253)
<223> OTHER INFORMATION: a, t, c, g, unknown or other
<220> FEATURE:
<221> NAME/KEY: modified_base
<222> LOCATION: (259)..(259)
<223> OTHER INFORMATION: a, t, c, g, unknown or other
<220> FEATURE:
<221> NAME/KEY: modified_base
<222> LOCATION: (273)..(274)
<223> OTHER INFORMATION: a, t, c, g, unknown or other
<220> FEATURE:
<221> NAME/KEY: modified_base
<222> LOCATION: (280)..(280)
<223> OTHER INFORMATION: a, t, c, g, unknown or other
<220> FEATURE:
<221> NAME/KEY: modified_base
<222> LOCATION: (287)..(288)
<223> OTHER INFORMATION: a, t, c, g, unknown or other
<220> FEATURE:
<221> NAME/KEY: modified_base
<222> LOCATION: (298)..(298)
<223> OTHER INFORMATION: a, t, c, g, unknown or other
<220> FEATURE:
<221> NAME/KEY: modified_base
<222> LOCATION: (300)..(300)
<223> OTHER INFORMATION: a, t, c, g, unknown or other
<220> FEATURE:
<221> NAME/KEY: modified_base
<222> LOCATION: (302)..(304)
<223> OTHER INFORMATION: a, t, c, g, unknown or other
<220> FEATURE:
<221> NAME/KEY: modified_base
<222> LOCATION: (306)..(306)
<223> OTHER INFORMATION: a, t, c, g, unknown or other
<220> FEATURE:
<221> NAME/KEY: modified_base
<222> LOCATION: (308)..(308)
<223> OTHER INFORMATION: a, t, c, g, unknown or other
<220> FEATURE:
<221> NAME/KEY: modified_base
<222> LOCATION: (313)..(313)
<223> OTHER INFORMATION: a, t, c, g, unknown or other
<220> FEATURE:
<221> NAME/KEY: modified_base
<222> LOCATION: (317)..(317)
<223> OTHER INFORMATION: a, t, c, g, unknown or other
<220> FEATURE:
<221> NAME/KEY: modified_base
<222> LOCATION: (319)..(319)
<223> OTHER INFORMATION: a, t, c, g, unknown or other
<220> FEATURE:
<221> NAME/KEY: modified_base
<222> LOCATION: (325)..(327)
<223> OTHER INFORMATION: a, t, c, g, unknown or other
<220> FEATURE:

-continued

<221> NAME/KEY: modified_base
<222> LOCATION: (331)..(331)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (347)..(348)
<223> OTHER INFORMATION: a, t, c, g, unknown or other
<220> FEATURE:
<221> NAME/KEY: modified_base
<222> LOCATION: (353)..(353)
<223> OTHER INFORMATION: a, t, c, g, unknown or other
<220> FEATURE:
<221> NAME/KEY: modified_base
<222> LOCATION: (364)..(365)
<223> OTHER INFORMATION: a, t, c, g, unknown or other
<220> FEATURE:
<221> NAME/KEY: modified_base
<222> LOCATION: (387)..(387)
<223> OTHER INFORMATION: a, t, c, g, unknown or other
<220> FEATURE:
<221> NAME/KEY: modified_base
<222> LOCATION: (393)..(393)
<223> OTHER INFORMATION: a, t, c, g, unknown or other
<220> FEATURE:
<221> NAME/KEY: modified_base
<222> LOCATION: (396)..(396)
<223> OTHER INFORMATION: a, t, c, g, unknown or other
<220> FEATURE:
<221> NAME/KEY: modified_base
<222> LOCATION: (401)..(401)
<223> OTHER INFORMATION: a, t, c, g, unknown or other
<220> FEATURE:
<221> NAME/KEY: modified_base
<222> LOCATION: (407)..(407)
<223> OTHER INFORMATION: a, t, c, g, unknown or other
<220> FEATURE:
<221> NAME/KEY: modified_base
<222> LOCATION: (412)..(412)
<223> OTHER INFORMATION: a, t, c, g, unknown or other
<220> FEATURE:
<221> NAME/KEY: modified_base
<222> LOCATION: (414)..(414)
<223> OTHER INFORMATION: a, t, c, g, unknown or other
<220> FEATURE:
<221> NAME/KEY: modified_base
<222> LOCATION: (416)..(416)
<223> OTHER INFORMATION: a, t, c, g, unknown or other
<220> FEATURE:
<221> NAME/KEY: modified_base
<222> LOCATION: (422)..(422)
<223> OTHER INFORMATION: a, t, c, g, unknown or other
<220> FEATURE:
<221> NAME/KEY: modified_base
<222> LOCATION: (424)..(425)
<223> OTHER INFORMATION: a, t, c, g, unknown or other
<220> FEATURE:
<221> NAME/KEY: modified_base
<222> LOCATION: (436)..(436)
<223> OTHER INFORMATION: a, t, c, g, unknown or other
<220> FEATURE:
<221> NAME/KEY: modified_base
<222> LOCATION: (444)..(445)
<223> OTHER INFORMATION: a, t, c, g, unknown or other
<220> FEATURE:
<221> NAME/KEY: modified_base
<222> LOCATION: (453)..(454)
<223> OTHER INFORMATION: a, t, c, g, unknown or other
<220> FEATURE:
<221> NAME/KEY: modified_base
<222> LOCATION: (457)..(457)
<223> OTHER INFORMATION: a, t, c, g, unknown or other
<220> FEATURE:
<221> NAME/KEY: modified_base
<222> LOCATION: (465)..(465)
<223> OTHER INFORMATION: a, t, c, g, unknown or other -continued
<220> FEATURE:
<221> NAME/KEY: modified_base
<222> LOCATION: (479)..(479)
<223> OTHER INFORMATION: a, t, c, g, unknown or other
<220> FEATURE:
<221> NAME/KEY: modified_base
<222> LOCATION: (482)..(483)
<223> OTHER INFORMATION: a, t, c, g, unknown or other
<220> FEATURE:
<221> NAME/KEY: modified_base
<222> LOCATION: (485)..(485)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (497)..(497)
<223> OTHER INFORMATION: a, t, c, g, unknown or other
<220> FEATURE:
<221> NAME/KEY: modified_base
<222> LOCATION: (499)..(499)
<223> OTHER INFORMATION: a, t, c, g, unknown or other
<220> FEATURE:
<221> NAME/KEY: modified_base
<222> LOCATION: (505)..(507)
<223> OTHER INFORMATION: a, t, c, g, unknown or other
<220> FEATURE:
<221> NAME/KEY: modified_base
<222> LOCATION: (513)..(514)
<223> OTHER INFORMATION: a, t, c, g, unknown or other
<220> FEATURE:
<221> NAME/KEY: modified_base
<222> LOCATION: (521)..(521)
<223> OTHER INFORMATION: a, t, c, g, unknown or other
<220> FEATURE:
<221> NAME/KEY: modified_base
<222> LOCATION: (524)..(524)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (536)..(536)
<223> OTHER INFORMATION: a, t, c, g, unknown or other
<220> FEATURE:
<221> NAME/KEY: modified_base
<222> LOCATION: (544)..(544)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (554)..(554)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (562)..(562)
<223> OTHER INFORMATION: a, t, c, g, unknown or other
<220> FEATURE:
<221> NAME/KEY: modified_base
<222> LOCATION: (565)..(565)
<223> OTHER INFORMATION: a, t, c, g, unknown or other
<220> FEATURE:
<221> NAME/KEY: modified_base
<222> LOCATION: (574)..(574)

-continued

<223> OTHER INFORMATION: a, t, c, g, unknown or other
<220> FEATURE:
<221> NAME/KEY: modified_base
<222> LOCATION: (580)..(580)
<223> OTHER INFORMATION: a, t, c, g, unknown or other
<220> FEATURE:
<221> NAME/KEY: modified_base
<222> LOCATION: (582)..(585)
<223> OTHER INFORMATION: a, t, c, g, unknown or other
<220> FEATURE:
<221> NAME/KEY: modified_base
<222> LOCATION: (588)..(588)
<223> OTHER INFORMATION: a, t, c, g, unknown or other
<220> FEATURE:
<221> NAME/KEY: modified_base
<222> LOCATION: (591)..(591)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (613)..(613)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (620)..(621)
<223> OTHER INFORMATION: a, t, c, g, unknown or other
<220> FEATURE:
<221> NAME/KEY: modified_base
<222> LOCATION: (627)..(627)
<223> OTHER INFORMATION: a, t, c, g, unknown or other
<220> FEATURE:
<221> NAME/KEY: modified_base
<222> LOCATION: (629)..(630)
<223> OTHER INFORMATION: a, t, c, g, unknown or other
<220> FEATURE:
<221> NAME/KEY: modified_base
<222> LOCATION: (634)..(634)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (651)..(651)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (676)..(676)
<223> OTHER INFORMATION: a, t, c, g, unknown or other
<220> FEATURE:
<221> NAME/KEY: modified_base -continued
<222> LOCATION: (686)..(686)
<223> OTHER INFORMATION: a, t, c, g, unknown or other
<220> FEATURE:
<221> NAME/KEY: modified_base
<222> LOCATION: (690)..(691)
<223> OTHER INFORMATION: a, t, c, g, unknown or other
<220> FEATURE:
<221> NAME/KEY: modified_base
<222> LOCATION: (694)..(695)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (708)..(708)
<223> OTHER INFORMATION: a, t, c, g, unknown or other
<220> FEATURE:
<221> NAME/KEY: modified_base
<222> LOCATION: (710)..(711)
<223> OTHER INFORMATION: a, t, c, g, unknown or other
<220> FEATURE:
<221> NAME/KEY: modified_base
<222> LOCATION: (718)..(719)
<223> OTHER INFORMATION: a, t, c, g, unknown or other
<220> FEATURE:
<221> NAME/KEY: modified_base
<222> LOCATION: (725)..(726)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (755)..(755)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (768)..(768)
<223> OTHER INFORMATION: a, t, c, g, unknown or other
<220> FEATURE:
<221> NAME/KEY: modified_base
<222> LOCATION: (771)..(772)
<223> OTHER INFORMATION: a, t, c, g, unknown or other
<220> FEATURE:
<221> NAME/KEY: modified_base
<222> LOCATION: (775)..(775)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other
<220> FEATURE:

-continued

<221> NAME/KEY: modified_base
<222> LOCATION: (783)..(783)
<223> OTHER INFORMATION: a, t, c, g, unknown or other
<220> FEATURE:
<221> NAME/KEY: modified_base
<222> LOCATION: (793)..(793)
<223> OTHER INFORMATION: a, t, c, g, unknown or other
<220> FEATURE:
<221> NAME/KEY: modified_base
<222> LOCATION: (799)..(799)
<223> OTHER INFORMATION: a, t, c, g, unknown or other
<220> FEATURE:
<221> NAME/KEY: modified_base
<222> LOCATION: (802)..(802)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (809)..(809)
<223> OTHER INFORMATION: a, t, c, g, unknown or other
<220> FEATURE:
<221> NAME/KEY: modified_base
<222> LOCATION: (816)..(816)
<223> OTHER INFORMATION: a, t, c, g, unknown or other
<220> FEATURE:
<221> NAME/KEY: modified_base
<222> LOCATION: (822)..(822)
<223> OTHER INFORMATION: a, t, c, g, unknown or other
<220> FEATURE:
<221> NAME/KEY: modified_base
<222> LOCATION: (825)..(826)
<223> OTHER INFORMATION: a, t, c, g, unknown or other
<220> FEATURE:
<221> NAME/KEY: modified_base
<222> LOCATION: (833)..(833)
<223> OTHER INFORMATION: a, t, c, g, unknown or other
<220> FEATURE:
<221> NAME/KEY: modified_base
<222> LOCATION: (835)..(835)
<223> OTHER INFORMATION: a, t, c, g, unknown or other
<220> FEATURE:
<221> NAME/KEY: modified_base
<222> LOCATION: (838)..(838)
<223> OTHER INFORMATION: a, t, c, g, unknown or other
<220> FEATURE:
<221> NAME/KEY: modified_base
<222> LOCATION: (844)..(844)
<223> OTHER INFORMATION: a, t, c, g, unknown or other
<220> FEATURE:
<221> NAME/KEY: modified_base
<222> LOCATION: (849)..(849)
<223> OTHER INFORMATION: a, t, c, g, unknown or other
<220> FEATURE:
<221> NAME/KEY: modified_base
<222> LOCATION: (852)..(852)
<223> OTHER INFORMATION: a, t, c, g, unknown or other
<220> FEATURE:
<221> NAME/KEY: modified_base
<222> LOCATION: (854)..(854)
<223> OTHER INFORMATION: a, t, c, g, unknown or other

<400> SEQUENCE: 70
acccccctca aattttggna aaacaacccn caggnnccna aaanaaggga acaaananan 60
canacanaaa atttttaaaa nntcancaan ggnncnncnt atncnagnng ggcnnttana 120
annccanaaa accnccccccc aaacacaaca caacaaaanc cnanaaaacc anaccaaanc 180
naaannancc atacantnnc aaaaaannan nttaacnata anataananc accancaccc 240
caaaacaaac canaaaacna aacccaaccc acnnaacaan caaaaannaa aaaatcanan 300
cnnnancnac aanacancna acaannncac nanaacaaaa aaaaccnnca acnaacacca 360
accnnacacc ccaaaccaca acaaaantaa cancanccca nactccnaaa anancnccac 420

-continued

```
cntnnacaaa caaaanaaac aaannacaac aanntanaca acacnacaca acacacaanc    480

annanaanaa aacccancnc aaaannnaca acnnacaaac naanccacna aaaaanacca    540

ccanacncac cnanaanacc cnaanaacaa acancaaacn cnnnntcnaa nanccaaacc    600

nacancaaaa canacnaaan ncaaaanann aaanaacaac nacacnacaa naacnacaca    660

tcacaatacc anacanacaa ccacanatan ncanncnaca caacaacnan nccaaacnna    720

acacnnccnc aancaacnca cacacctnnc cnaanaaaan aanaccanac nnaancnaaa    780

tanaatacaa ccncacacnc anaacnacnt aaccancaca cnacnnacac cananaanat    840

cacncccanc ancn                                                      854
```

```
<210> SEQ ID NO 71
<211> LENGTH: 728
<212> TYPE: DNA
<213> ORGANISM: Homo sapiens
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 71

atgttgccct actgggctgg cggcagtgac aggaggcgcg aacccgcagc gcttaccgcg     60

cggcgccgca ccatggagcc cgccgtgtcg ctggccgtgt gcgcgctgct cttcctgctg    120

tgggtgcgcc tgaaggggct ggagttcgct tatcttcgat atctactact acgtgcgcgc    180

ctgggtggtg ttcaagctca gcagcgctcc gcgcctgcac gagcagcgcg tgcgggacat    240

ccagaagcag gtgcgggaat ggaaggagca gggtagcaag accttcatgt gcacggggcg    300

ccctggctgg ctcactgtct cactacgtgt cgggaagtac aagaagacac acaaaaacat    360

catgatcaac ctgatggaca ttctggaagt ggacaccaag aaacagattg tccgtgtgga    420

gcccttggtg accatgggcc aggtgactgc cctgctgacc tccattggct ggactctccc    480

cgtgttgcct gagcttgatg acctacagtg gggggcttga tcatgggcac aggcatcgaa    540

gtcatcatcc cacaagtacg gcctgttcca acacatctgc actgcttacg agctggtcct    600

gctgatggca gctttgtgcg atgcacttcg tccgaaaact canacctggt ctatgccgta    660

ccctggtcct tgtgggacct ggggttnctg gtgggccgtt ganatccgga tnatccctgc    720

caagaaan                                                             728
```

```
<210> SEQ ID NO 72
<211> LENGTH: 740
<212> TYPE: DNA
<213> ORGANISM: Homo sapiens
<220> FEATURE:
<221> NAME/KEY: modified_base
<222> LOCATION: (8)..(8)
```

-continued

<223> OTHER INFORMATION: a, t, c, g, unknown or other
<220> FEATURE:
<221> NAME/KEY: modified_base
<222> LOCATION: (18)..(18)
<223> OTHER INFORMATION: a, t, c, g, unknown or other
<220> FEATURE:
<221> NAME/KEY: modified_base
<222> LOCATION: (29)..(29)
<223> OTHER INFORMATION: a, t, c, g, unknown or other
<220> FEATURE:
<221> NAME/KEY: modified_base
<222> LOCATION: (573)..(573)
<223> OTHER INFORMATION: a, t, c, g, unknown or other
<220> FEATURE:
<221> NAME/KEY: modified_base
<222> LOCATION: (598)..(598)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (724)..(724)
<223> OTHER INFORMATION: a, t, c, g, unknown or other

<400> SEQUENCE: 72
aattgcantc cctttttnca ggccctttna tttaaacaga agcagcggcc ccacagccac 60
ggggacatgt cttccagaca gtagacacag tgcctgtggc tgtaagagcc tgacagggaa 120
gattcatgcc tttctccttg gcccccatga ccaaagaaga aaataaaaat cacacaccat 180
acactgccac acccatctcc acccctccct ttcagtaata tccaagtatt catccttctg 240
gccaaagaaa ctggctacaa ttctgattct aaagaaaacc ttcatgcagc caagaaactc 300
agggctctgg aggggagagc cttactctga tactttccac atgcactgcc cactggcatc 360
aagtttaact ccatccaaaa ccatcacatg gatggccagg gacaggactg gctacaaaaa 420
aaagccatga actcagctca ccatgctaag aagactgcct ctttccaggc aagattttac 480
tggagcaaca taaccggagg gtgtgattcc aaaatacctt cctttccaag ccccgggttg 540
tggataaggc tggattttgg gtatatgact aanggcgaca gaagctgctg gcatcttntg 600
gncaccgtcc caatggctta aggttggang cttcactggc aaacaatggc actggttaac 660
tagcttcggg taaccattta tntacagcaa gtagaatcat cagttttgac tgggcaagga 720
agcncatggg tcttccttta 740

<210> SEQ ID NO 73
<211> LENGTH: 761
<212> TYPE: DNA
<213> ORGANISM: Homo sapiens
<220> FEATURE:
<221> NAME/KEY: modified_base
<222> LOCATION: (121)..(121)
<223> OTHER INFORMATION: a, t, c, g, unknown or other
<220> FEATURE:
<221> NAME/KEY: modified_base
<222> LOCATION: (722)..(723)
<223> OTHER INFORMATION: a, t, c, g, unknown or other
<220> FEATURE:
<221> NAME/KEY: modified_base
<222> LOCATION: (732)..(732)
<223> OTHER INFORMATION: a, t, c, g, unknown or other -continued
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 73
cactgttggc ctactggaac ttgtaacaca gaattgaact gatactagtt tccttgcctt 60
aaattaatta tatgtcatcc caagggtctc tgttaattct gctttgccaa gcaataatga 120
natctgggtt tggcattaga agtatttcat aattttggtt ttttatttag gtttcctcca 180
catctgtaaa gtgattgatt aaattagagg aggcgtgtag aataaatccc aatcccattg 240
caactggcag agctttataa atctttataa attcagttac aacaaaggag aggatcctac 300
accattagag ccatgccatc aggtgtttgc aagtgacagc tgtagtgtgt tgcctcaaat 360
aataccaagt tataaataat accaagtaat tatcaactca ctcccaaatt taataagata 420
tcaaagtcca aaaggttact taggagtagt cttccgtggg ggaagataaa tttattaaag 480
agtcatgtac tgatcttttt cttgggattt tttttccttt cccagaaaaa aaaattattt 540
tggtgactga tcaattgtaa acaattttct tccttactta caaatcatcc gtcagaaaaa 600
taaaagtgga cttcctttct aagcattaca attagcctgg gcaagaagtg ttatgattgg 660
cttattcttt aagccggctt actttttggg atttgggtga aatggctttt gaaaagaaag 720
tnnatggata gnattaataa ctactttgga tangcttntg c 761

<210> SEQ ID NO 74
<211> LENGTH: 783
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (8)..(13)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:

-continued

<221> NAME/KEY: modified_base
<222> LOCATION: (715)..(715)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (757)..(758)
<223> OTHER INFORMATION: a, t, c, g, unknown or other
<220> FEATURE:
<221> NAME/KEY: modified_base
<222> LOCATION: (761)..(762)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (779)..(779)
<223> OTHER INFORMATION: a, t, c, g, unknown or other

<400> SEQUENCE: 74
gngnnggnnn nnntttgtgg cctttttttt ttttttttct tttcaatcat agtcactctg 60
gtgaatccaa gcataaacag acaaatccaa ctacaactca acagggtgca gatggggagg 120
gcagggcaac atctatgtat atgttcagct gctccagcag aacagacagc atggcttcca 180
gctgggactg ggggaaaaga accatttcca agggggtgtg ttcccctttg tcgggtgtgg 240
agggctgata ctatgcatgt ggagctgagc agcgggctgg gctgtctggg aggttggcag 300
ctacaagcta gggtgcaagt gggggacagc gggactgtgg gcctgccctg ggtgccttgc 360
ccttccatcc tggtgccgca ctgacaacca agacgcccag cctgctgctg tgggctcagc 420
acaggaaggg gccaggcctt ctcaggggaa agggctctct tcatgtcaac aaggcagaaa 480
cacctagggt cacagctgaa cagtgccctg gctcacatct gtgacgggag gaggagacag 540
ggaaccgaat cagatcatga gattcgtggt gagggtccag ttggatgaat ggaactgana 600
gtgaaaagct ggggtcccac tcttgggcct gggactttgc cttccttaat ttaacctcag 660
tatggagtan gnaccttctg naaccaacca gggncattac tggnaaaggg tggtnaagct 720
gggaaattng gacattgnga cctttnataa ggggttnngc nntgattggc tnttacggna 780
aaa 783

<210> SEQ ID NO 75
<211> LENGTH: 761
<212> TYPE: DNA
<213> ORGANISM: Homo sapiens
<220> FEATURE:
<221> NAME/KEY: modified_base
<222> LOCATION: (688)..(688)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other

<400> SEQUENCE: 75
cctcggcact gttggcctac tggatgaata aaacactctt tggtggtgac tgaggcatca 60

-continued

```
ttagaaggcc cagacgattt ccactattca cagcatttcc ttttctcaga aggactcttt    120

atatttccat gtaaatctag atctttggag caattaagat ggaattacaa tttctaggga    180

gcattttaag gaaaatgttt tggctttttc ataattttat gtcttacagt atggaattat    240

aatacgaaaa tctttatatg agttttggct tcttggtatt tgtacttatt caggggaaaa    300

agtctttcga ttacttatgc ctctatagag cttaatttct tgagaaattc aacagtcatt    360

ttcaccagca taattttatc ttaaggaata actaatagga aaagtcagct taattattta    420

aggccctagt ttctacatat aatatattcg atagaaatga aaatctgccg tggaattaac    480

taataagtag taacaataaa cttcatattt agaatgcaaa gtctataaag aataatttta    540

catgatcctc aatatcaact ccagtttaaa aagtggtatt tttaaaacat ttgaaaccaa    600

gtctggttaa tttcaatcag aagatgcaaa tccatacttt tgatctatgg ttgattttgc    660

taataatatt tggaaggaga atgcctanca aggaccaaac cattanattt aaaaatcaaa    720

ccgattcttc atacgctcat agtcccatat gggaatttgg g                        761
```

<210> SEQ ID NO 76
<211> LENGTH: 788
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (8)..(13)
<223> OTHER INFORMATION: a, t, c, g, unknown or other
<220> FEATURE:
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (731)..(731)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (788)..(788)
<223> OTHER INFORMATION: a, t, c, g, unknown or other

<400> SEQUENCE: 76

```
gngnntgnnn nnntttnggg ccttttttttt tttttttgag tctgaaaatt ccatttatta     60

aaacacatac attgtccatg tgggatgaaa atgtgcacat cacattcagg ttttcctgct    120

ttaacatttc tgtagttctc tctttgaaac acacactcca cagatcttat ataggaaaaa    180
```

-continued

```
tgtgaacaac ttttgggctg caaaacatta atgcatacat aacaattcat cattgccaag    240

agcagctaga agcaaatatt aaggaagaaa gacaaagaag tataaaaatt cctaaagaca    300

gcatgcttta ttttctcaaa attccatatg tgactatgag cgtatggaga aatcgtttga    360

tttttaaatt tattgntttg tccttggtag gcaatctcct tcaaatatta ttagcaaaat    420

caaacataga tcaaagtatg tatttgcatc ttctgattga aattaaacag tacttggttt    480

caaatgtttt aaaaataaca ctttttaaac tggagttgat attgaggatc atgtaaaatt    540

attctttata gactttgcat tctaaatatg aagtttattg gtactactta ttagttaatt    600

ccacggcaga ttttcatttc tatcgaatat attatatgta gaaactangg ccttaaataa    660

ttaagctgac ttttcctatt aggtattcct taagataaaa ttatgctggn gaaaatgact    720

gtgaatttct naagaaatta actctataga aggcataagn aatcgaaaga ctttttccct    780

gaataagn                                                             788
```

<210> SEQ ID NO 77
<211> LENGTH: 738
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (597)..(597)
<223> OTHER INFORMATION: a, t, c, g, unknown or other
<220> FEATURE:
<221> NAME/KEY: modified_base
<222> LOCATION: (604)..(604)
<223> OTHER INFORMATION: a, t, c, g, unknown or other
<220> FEATURE:
<221> NAME/KEY: modified_base
<222> LOCATION: (640)..(640)
<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other

<400> SEQUENCE: 77

```
ctactggnat gaaaaggatg agcaaggaga aatgccccaa aggagactga cccggcgcgg     60

tgctggcggg agcgctcaag ggcagcggat ttgttgttgt tgctgttttc ctttgtgggt    120

gtttggtgct tgatttccag aaactctcca gcgacttgga cttcttcttt ttttttttt    180

ctttttagat agaagtgact gtgtggttgg tctctgaggt atttggggga ctctgtattt    240

gctcgtttac gtgttggaaa aaccaagtgg ctttggggtt tcgccctatc ccactccctc    300

tctttcctgc tccattggtt ccttaagaaa tgctatattt tgtgagtgca agctggcttg    360

gggagccctc tcttgtgtaa atgtccccca tgtttctgaa aagtgctgta agtttaagtc    420
```

-continued

```
ccctcacccc cagcactgcc caaacagggg ccaagtgcgc cccaattcca agaatgaagg    480

cagagcgaca acagtgcgga caccccggct gctagcccac ggtgaacccg gcggggttgc    540

ccaccagttg cgaaagcccc ctttctnaag gagcacgcgg acctcggtgg agatctncaa    600

tgangcttaa aggaacccaa ggcctcggcc gggttggggn ttggcctcan tgcattggac    660

ccctggtntt ttccctgaag gctggctcgc gtggccggcn cgggtggtgg gccttccggt    720

tcttgcccna ggaccaat                                                  738
```

<210> SEQ ID NO 78
<211> LENGTH: 785
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (6)..(11)
<223> OTHER INFORMATION: a, t, c, g, unknown or other
<220> FEATURE:
<221> NAME/KEY: modified_base
<222> LOCATION: (40)..(40)
<223> OTHER INFORMATION: a, t, c, g, unknown or other
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (110)..(110)
<223> OTHER INFORMATION: a, t, c, g, unknown or other
<220> FEATURE:
<221> NAME/KEY: modified_base
<222> LOCATION: (115)..(115)
<223> OTHER INFORMATION: a, t, c, g, unknown or other
<220> FEATURE:
<221> NAME/KEY: modified_base
<222> LOCATION: (132)..(132)
<223> OTHER INFORMATION: a, t, c, g, unknown or other
<220> FEATURE:
<221> NAME/KEY: modified_base
<222> LOCATION: (134)..(134)
<223> OTHER INFORMATION: a, t, c, g, unknown or other
<220> FEATURE:
<221> NAME/KEY: modified_base
<222> LOCATION: (154)..(154)
<223> OTHER INFORMATION: a, t, c, g, unknown or other
<220> FEATURE:
<221> NAME/KEY: modified_base
<222> LOCATION: (208)..(208)
<223> OTHER INFORMATION: a, t, c, g, unknown or other
<220> FEATURE:
<221> NAME/KEY: modified_base
<222> LOCATION: (215)..(215)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (239)..(239)
<223> OTHER INFORMATION: a, t, c, g, unknown or other
<220> FEATURE:
<221> NAME/KEY: modified_base
<222> LOCATION: (291)..(291)
<223> OTHER INFORMATION: a, t, c, g, unknown or other
<220> FEATURE:

-continued

<221> NAME/KEY: modified_base
<222> LOCATION: (296)..(296)
<223> OTHER INFORMATION: a, t, c, g, unknown or other
<220> FEATURE:
<221> NAME/KEY: modified_base
<222> LOCATION: (305)..(305)
<223> OTHER INFORMATION: a, t, c, g, unknown or other
<220> FEATURE:
<221> NAME/KEY: modified_base
<222> LOCATION: (320)..(320)
<223> OTHER INFORMATION: a, t, c, g, unknown or other
<220> FEATURE:
<221> NAME/KEY: modified_base
<222> LOCATION: (336)..(336)
<223> OTHER INFORMATION: a, t, c, g, unknown or other
<220> FEATURE:
<221> NAME/KEY: modified_base
<222> LOCATION: (345)..(345)
<223> OTHER INFORMATION: a, t, c, g, unknown or other
<220> FEATURE:
<221> NAME/KEY: modified_base
<222> LOCATION: (370)..(370)
<223> OTHER INFORMATION: a, t, c, g, unknown or other
<220> FEATURE:
<221> NAME/KEY: modified_base
<222> LOCATION: (376)..(377)
<223> OTHER INFORMATION: a, t, c, g, unknown or other
<220> FEATURE:
<221> NAME/KEY: modified_base
<222> LOCATION: (380)..(380)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (406)..(406)
<223> OTHER INFORMATION: a, t, c, g, unknown or other
<220> FEATURE:
<221> NAME/KEY: modified_base
<222> LOCATION: (417)..(417)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (539)..(539)
<223> OTHER INFORMATION: a, t, c, g, unknown or other
<220> FEATURE:
<221> NAME/KEY: modified_base
<222> LOCATION: (543)..(543)
<223> OTHER INFORMATION: a, t, c, g, unknown or other
<220> FEATURE:
<221> NAME/KEY: modified_base
<222> LOCATION: (560)..(560)
<223> OTHER INFORMATION: a, t, c, g, unknown or other
<220> FEATURE:
<221> NAME/KEY: modified_base
<222> LOCATION: (579)..(579)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other -continued
<220> FEATURE:
<221> NAME/KEY: modified_base
<222> LOCATION: (671)..(671)
<223> OTHER INFORMATION: a, t, c, g, unknown or other
<220> FEATURE:
<221> NAME/KEY: modified_base
<222> LOCATION: (687)..(688)
<223> OTHER INFORMATION: a, t, c, g, unknown or other
<220> FEATURE:
<221> NAME/KEY: modified_base
<222> LOCATION: (710)..(712)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (723)..(723)
<223> OTHER INFORMATION: a, t, c, g, unknown or other
<220> FEATURE:
<221> NAME/KEY: modified_base
<222> LOCATION: (761)..(761)
<223> OTHER INFORMATION: a, t, c, g, unknown or other
<220> FEATURE:
<221> NAME/KEY: modified_base
<222> LOCATION: (765)..(767)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other
<220> FEATURE:
<221> NAME/KEY: modified_base
<222> LOCATION: (785)..(785)
<223> OTHER INFORMATION: a, t, c, g, unknown or other

<400> SEQUENCE: 78
gnntgnnnnn nttttgtggc ctttatttga atccctttn ttttttcttt tttttttttt 60
tttttttttt ttttttttag ggccagcgtn tgggctccat ttgatcaggn cagcntttat 120
tagtaggaag cngnaacatt tacaactggt cctngggcag gaaccgggag ggccaccacc 180
cgcggccgcc cacgcgagcc cagccttnag ggganangagc agcgcgtcca atgcnctgng 240
gacaaacccc aacccgcccg aggccctggg ctcctttaag cctcactgga natctncacc 300
gaggncccgc gtgctccctn aggaaagggg gctttngcaa ctggngggca accccgccgg 360
gctttaccgn gggctnncan ccggggtgtc cncactgttg tcgctntgcc ttcattnttg 420
gaattggggc gcacttggcc cctgtttggg cagtgctngg ggtgagggga ctaaactaca 480
gcacttttca aaaacatggg ggacatttac acaagagagg gctccccaag ccagcttgna 540
ctnacaaaat atagcatttn ttaaggaacc aatggagcng gaaagaaagg gantgggata 600
tgggcgaaac cccaaagccc ttgggttttt caacacgtna acnagcnaat tcagattccc 660
caaatcctta nagaccaacc cacagtnnct tttttttaaa aagaaaaaan nnanggaana 720
atncaaatcc cttggaaagt tttgggaatc aaccccccaaa ncccnnnang gaaaaccggn 780 ccccn 785

<210> SEQ ID NO 79
<211> LENGTH: 774
<212> TYPE: DNA

-continued

<213> ORGANISM: Homo sapiens
<220> FEATURE:
<221> NAME/KEY: modified_base
<222> LOCATION: (1)..(3)
<223> OTHER INFORMATION: a, t, c, g, unknown or other
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (15)..(16)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
<220> FEATURE:
<221> NAME/KEY: modified_base
<222> LOCATION: (607)..(607)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (675)..(675)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other

<400> SEQUENCE: 79
nnngagggng gntgnnttcc tttntgaatc ctttgcctgt cggcctactg gcagataaag 60
ccttatgctg cccaccagcc cactaaatgt attaaatacc tgtctctatg tagcttatgt 120
aaaaactcaa tgttgactgt cccgtgtctg ctgcatttaa aagctcattg tgattctatc 180
atcttgctat gccaatgcct tatgttatgg tgtcatgtat ataggccatg gtacaaaagt 240
gactgtcaac tgcttactca acatctagtc agaaaaggtc tgaggcagtg caataacgct 300
tttagtcaaa ctggctcact gttggagtca tttacatctg tgtattcttt accgtaaata 360
ctgaaatagt attttttaac tgttttttca ggcttgtaat aaatatctgt gtcatatcta 420
catagtcaaa atacattgag taattcagtt taaaagtgtt gcctactaac aaactaaaga 480
gaaacatcta ctgattttcc atataattgc ttattttcat tgccaatgta gacctgcctg 540
gaatggtgtc tttcaccact atcatgtgta aaataaaggg aggctattgt ggtgaatttt 600
cacctgnctg acattagctc tttcactagc aaaaggatgt ccatcctnaa aagtgacctg 660
ctacccgagg tccantttca aaaggcatct taatttaatt ttgctccaaa attnaaaatg 720
ggtgnctcca aacttacctn tgtagacttt taaaggccag cattgggggg gaag 774

<210> SEQ ID NO 80
<211> LENGTH: 784
<212> TYPE: DNA
<213> ORGANISM: Homo sapiens -continued
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (10)..(11)
<223> OTHER INFORMATION: a, t, c, g, unknown or other
<220> FEATURE:
<221> NAME/KEY: modified_base
<222> LOCATION: (31)..(33)
<223> OTHER INFORMATION: a, t, c, g, unknown or other
<220> FEATURE:
<221> NAME/KEY: modified_base
<222> LOCATION: (40)..(40)
<223> OTHER INFORMATION: a, t, c, g, unknown or other
<220> FEATURE:
<221> NAME/KEY: modified_base
<222> LOCATION: (47)..(47)
<223> OTHER INFORMATION: a, t, c, g, unknown or other
<220> FEATURE:
<221> NAME/KEY: modified_base
<222> LOCATION: (513)..(513)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (637)..(637)
<223> OTHER INFORMATION: a, t, c, g, unknown or other
<220> FEATURE:
<221> NAME/KEY: modified_base
<222> LOCATION: (663)..(663)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (754)..(754)
<223> OTHER INFORMATION: a, t, c, g, unknown or other

<400> SEQUENCE: 80
gnagtggttn natttggtgg ccttttttga nnnccctttn ttttttnttt tcatttacac 60
atttattttc tatctcgctt attctaccag actgaaatgg agaacaatgc cagcaatttt 120
atagacattt tgacataaag taaacaagta ttttgatgtt gaacaattgt acagactact 180
acatgcatat aggtatgctg attggtgcag aaatattgag ttgatcaaca aaactattaa 240
tacgaaatca catttccttt ttatggagtt aaaatgcagc agatatggga acattgatac 300
aaacaccatt aaatggcaga aaaaggcatt gtagtaacga tgcaggatgg acagctgaac 360
aaacacgagt atgctaactc atatcctgtc tacaaaactg aaataagaac attttgtatg 420
caaatagaat gaaagaaagc atgttgaggc aggtgaatga gactagacaa caagacttaa 480

-continued

```
ccacttatgt ttaagcttct attgagagtt tgnattaaaa gtatttcaac atggtataaa    540

gaagaaatgc taatgctatt atgtgtgtgg ccaggatagg ataattcaat tgngaattca    600

taaataatga aatactgatg gggcttcttt ttcctgnagc attcagagca tcatagacta    660

gtntgnaaan ccttttaaac cctggaggtt atnaaaggca ataatgcttn atgcgactgt    720

cctagaaatc taataccntg tttacttaaa aatngggaaa tggttactta ccatttccat    780

agga                                                                  784
```

<210> SEQ ID NO 81
<211> LENGTH: 782
<212> TYPE: DNA
<213> ORGANISM: Homo sapiens
<220> FEATURE:
<221> NAME/KEY: modified_base
<222> LOCATION: (2)..(8)
<223> OTHER INFORMATION: a, t, c, g, unknown or other
<220> FEATURE:
<221> NAME/KEY: modified_base
<222> LOCATION: (10)..(10)
<223> OTHER INFORMATION: a, t, c, g, unknown or other
<220> FEATURE:
<221> NAME/KEY: modified_base
<222> LOCATION: (12)..(19)
<223> OTHER INFORMATION: a, t, c, g, unknown or other
<220> FEATURE:
<221> NAME/KEY: modified_base
<222> LOCATION: (25)..(27)
<223> OTHER INFORMATION: a, t, c, g, unknown or other
<220> FEATURE:
<221> NAME/KEY: modified_base
<222> LOCATION: (540)..(540)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (644)..(644)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (659)..(659)
<223> OTHER INFORMATION: a, t, c, g, unknown or other
<220> FEATURE:
<221> NAME/KEY: modified_base
<222> LOCATION: (711)..(711)
<223> OTHER INFORMATION: a, t, c, g, unknown or other
<220> FEATURE:
<221> NAME/KEY: modified_base
<222> LOCATION: (729)..(730)
<223> OTHER INFORMATION: a, t, c, g, unknown or other
<220> FEATURE:
<221> NAME/KEY: modified_base
<222> LOCATION: (739)..(739)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (778)..(778)
<223> OTHER INFORMATION: a, t, c, g, unknown or other

<400> SEQUENCE: 81

```
gnnnnnnntn gnnnnnnnnt tggannncct tgagcactgt tggcctactg gtttaatctc     60

attttctcct aaagttcttc tcttcaatat gatctgcaaa gggttgaaag tgctgtcctc    120

caaaccaggc gtaagaaagt ggttacagat aaagcaagta aatccattaa agaagaaatg    180

ggaagatctg ttgtgtgcct tatctgaccc agcattatcg ctggaggggga agtgcttata    240

gggaaggaag agaagtttgg tcaattgatg cagtctcagt atgatgacag ctggtgactt    300

cctgagggtt attcatcaca cttcagcagg gtgatgtttt caaagcctgc gtgtgaccat    360

gtcactcctc tgttctccag cgctttcaaa ataaaactga aatccgtctc agagggccag    420

tctcagagta tcccctgcca gccccatcct tcactgctca gcagtcacct ccttccccct    480

cctcatcctt ttgaggtctc ttctgatcct tcaggggcca gcttctctcc gtcccatggn    540

tggttgccta tgctgatccc ctacatggat cttcggtcac cttcatcact cttacctggg    600

tagtctcttc ctggncttta tccaagtcaa cttcgcttct gcangaatgc ctgncttgna    660

accttaagtc cttctggtcc cctcttaaaa cactggctat tctcctggga ngcagtaatt    720

ccagtagtnn attgcatcnt ttgnaacncg ttttgattaa tgcccgtggt ttccctanaa    780

ct                                                                   782
```

```
<210> SEQ ID NO 82
<211> LENGTH: 788
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (9)..(11)
<223> OTHER INFORMATION: a, t, c, g, unknown or other
<220> FEATURE:
<221> NAME/KEY: modified_base
<222> LOCATION: (28)..(30)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (778)..(778)
<223> OTHER INFORMATION: a, t, c, g, unknown or other

<400> SEQUENCE: 82
```

```
gnnggggtnn nttggtggcc tttttgannn cctttctgac tgcntttcat taacttcctt     60

taaaacgctt ttcttttggg tcaaatgaca catctgacat ttctttggtt tcttgaaact    120

tctacaccca ccttccactt attagacaat tacctatagg gactctactg atactagtgg    180

gcttggggag gtccccaaat gctggtggga ccctgatccc ggcaggtgtc caggctcttg    240

acaccgtctc aagaaggaat tcaaggatga gtcaggcaac agtggaagta cagagattta    300
```

-continued

```
taacaacggg aaaagtacac actcaagaaa gggggagtgt aggcggactc aagagagcac    360

catgcctaag gggatttggg gctgctacct ttatgtgttt ctttagccaa ggggtggaat    420

acttatgaaa attcctggga aagggtggaa atttcttaga attgtgatgc catccatttt    480

tacaccaaac gtaggtattc tcggaattca tggtgctggt cacctaggac ctcgtgatat    540

gctcattaac atggtaagtc actcattaac atcccaagtc acaagtgact tangatgtta    600

acaaacacat cacgagggcc taagtgaatc ctagtcaaat tcagcaccat gttgggtcca    660

cttgggctta accagcttgg gccatgcccc gggttttnaa ggatctgatc aagccacaag    720

cctttaagca tttgaaactg ntatctggat tttttttttt taaaaacacg ttttggtntg    780

tgcaggct                                                             788
```

```
<210> SEQ ID NO 83
<211> LENGTH: 780
<212> TYPE: DNA
<213> ORGANISM: Homo sapiens
<220> FEATURE:
<221> NAME/KEY: modified_base
<222> LOCATION: (2)..(7)
<223> OTHER INFORMATION: a, t, c, g, unknown or other
<220> FEATURE:
<221> NAME/KEY: modified_base
<222> LOCATION: (10)..(19)
<223> OTHER INFORMATION: a, t, c, g, unknown or other
<220> FEATURE:
<221> NAME/KEY: modified_base
<222> LOCATION: (25)..(27)
<223> OTHER INFORMATION: a, t, c, g, unknown or other
<220> FEATURE:
<221> NAME/KEY: modified_base
<222> LOCATION: (33)..(33)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (659)..(659)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (747)..(747)
<223> OTHER INFORMATION: a, t, c, g, unknown or other
<220> FEATURE:
<221> NAME/KEY: modified_base
<222> LOCATION: (764)..(764)
<223> OTHER INFORMATION: a, t, c, g, unknown or other

<400> SEQUENCE: 83

gnnnnnnttn nnnnnnnnnt tggannncct tgngcactgt tggcctactg ggatcctgtt     60

tgacattttt atggctgtat ttgtaaactt aaacacacca gtgtctgttc ttgatgcagt    120

tgctatttag gatgagttaa gtgcctgggg agtccctcaa aaggttaaag ggattcccat    180

cattggaatc ttatcaccag ataggcaagt ttatgaccaa acaagagagt actggcttta    240

tcctctaacc tcatattttc tcccacttgg caagtccttt gtggcattta ttcatcagtc    300

agggtgtccg attggtccta gaacttccaa aggctgcttg tcatagaagc cattgcatct    360

ataaagcaac ggctcctgtt aaatggtatc tcctttctga ggctcctact aaaagtcatt    420
```

-continued

```
tgttacctaa acttatgtgc ttaacaggca atgcttctca gaccacaaag cagaaagaag    480

aagaaaagct cctgactaaa tcagggctgg gcttagacag agttgatctg tagaatatct    540

ttaaaggaga gatgtcaact ttctgcacta ttcccagcct ctgctcctcc tgctaccctc    600

ttcccttcct ctctccttca cttnacccac aatcttgaaa aacttncttt ctcttctgng    660

aacatcattg gccagatcca ttttcaatgg nctggattct tttaatttcc tttcaacttg    720

aaagaaactg gacattaggc actatgnggt gggtactgcc ctantggtca agtgcctctt    780
```

<210> SEQ ID NO 84
<211> LENGTH: 792
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (5)..(6)
<223> OTHER INFORMATION: a, t, c, g, unknown or other
<220> FEATURE:
<221> NAME/KEY: modified_base
<222> LOCATION: (8)..(12)
<223> OTHER INFORMATION: a, t, c, g, unknown or other
<220> FEATURE:
<221> NAME/KEY: modified_base
<222> LOCATION: (34)..(34)
<223> OTHER INFORMATION: a, t, c, g, unknown or other
<220> FEATURE:
<221> NAME/KEY: modified_base
<222> LOCATION: (207)..(207)
<223> OTHER INFORMATION: a, t, c, g, unknown or other
<220> FEATURE:
<221> NAME/KEY: modified_base
<222> LOCATION: (521)..(521)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (661)..(661)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (784)..(784)
<223> OTHER INFORMATION: a, t, c, g, unknown or other

<400> SEQUENCE: 84

```
gnngnngnnn nnttggtggc cttttttttt tccntttttt ttttttttcc tttagtcttt     60
```

-continued

```
taatgttagc cttttaatat tttccaataa gtgctttcaa ctcagcaata tacatatcat    120

gctttcctca ttattattga tccatcaata aatatacaaa aaccagagga agggtgtgct    180

ctgaaaagtc aaagtaacaa taacagnggt cattgtacag cacaagaatg aacaatgggc    240

tattctttga aaactcaaaa caaatgattt acacaaagac atatctataa cataaaggtg    300

aatggaccat gttattctta ttcttaagta cattttgctt ttccagataa gtcaaatgtt    360

tcctctctcc tactcctctg atataacagt attgaatgaa tgttggctac aaaatcaatt    420

cttggtgttg ttatgaatct caatataaaa cttttggaaa ggttctgcta gaaaagccaa    480

ttctaccagg cttgaaatat ggattcgaag atgtcttttg nctcttttga tttttcactc    540

agagctaatt ttaagggaag tcttcaggag acacaaaaga tttacaattg caagaaaaat    600

tacatcttta gctcttaagg tgctttgcna aataattaaa tggtgggcct ttacttttat    660

naaganccag tttaaatgac ttaacccaag tcacctgnaa atcattggna aaaatggccg    720

ggtagncaaa ctgggcnttc caaagttccc cccttgaaat caagggagtg ggaatccatc    780

ttanttcctt aa                                                         792
```

<210> SEQ ID NO 85
<211> LENGTH: 787
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (7)..(7)
<223> OTHER INFORMATION: a, t, c, g, unknown or other
<220> FEATURE:
<221> NAME/KEY: modified_base
<222> LOCATION: (12)..(13)
<223> OTHER INFORMATION: a, t, c, g, unknown or other
<220> FEATURE:
<221> NAME/KEY: modified_base
<222> LOCATION: (16)..(19)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (31)..(31)
<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (750)..(750)
<223> OTHER INFORMATION: a, t, c, g, unknown or other -continued
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (755)..(755)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (771)..(771)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other

<400> SEQUENCE: 85
gngnngnggg gnnttnnnnt tgnattcctt nagcactgtt ggcctactgg gaattacaca 60
tcctcttgtt cttaaaaaag caagtgtctt tcgtgttgga ggacaaaatc ccctaccatt 120
ttcacgttgt gctactaaga gatctcaaat attagtcttt gtccggaccc ttccatagta 180
caccttagcg ctgagactga gccagcttgg gggtcaggta ggtagaccct gttagggaca 240
gagcctagtg gtaaatccaa gagaaatgat cctatccaaa gctgattcac aaacccacgc 300
tcacctgaca gccgagggac acgagcatca ctctgctgga cggaccatta ggggccttgc 360
caaggtctac cttagagcaa acccagtacc tcagacagga aagtcgggct ttgaccacta 420
ccatatctgg tagcccattt tctaggcatt gtgaataggt aggtagctag tcacactttt 480
cagaccaatt caaactgtct atgcacaaaa ttccgtgggc ctagatggag ataatttttt 540
ttcttctcag ctttatgaag agaagggaaa ctgnctagga ttcagctgaa ccaccaggaa 600
cctggcaaca tcacgattta agctaagggt gggangctaa cgaagtctac tcctctttgn 660
aaatcaagga attggttaaa atgggattgg caatccttta aataaagatg aacttgggtt 720
caagnccaat gggaattatt ttgggttggn ancanaacan cangnacctt naaaatntta 780
agccaag 787

<210> SEQ ID NO 86
<211> LENGTH: 789
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (8)..(12)
<223> OTHER INFORMATION: a, t, c, g, unknown or other
<220> FEATURE:
<221> NAME/KEY: modified_base
<222> LOCATION: (32)..(32)

-continued

<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (46)..(46)
<223> OTHER INFORMATION: a, t, c, g, unknown or other
<220> FEATURE:
<221> NAME/KEY: modified_base
<222> LOCATION: (201)..(201)
<223> OTHER INFORMATION: a, t, c, g, unknown or other
<220> FEATURE:
<221> NAME/KEY: modified_base
<222> LOCATION: (595)..(595)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (657)..(657)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (695)..(695)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (766)..(766)
<223> OTHER INFORMATION: a, t, c, g, unknown or other
<220> FEATURE:
<221> NAME/KEY: modified_base
<222> LOCATION: (783)..(783)
<223> OTHER INFORMATION: a, t, c, g, unknown or other

<400> SEQUENCE: 86
gnngnggnnn nnttggtggc cttttttttt tnccnttttt tttttntttt tttatgtata 60
aacaggtacc agttttgatt ttatttaatc atttcataca ttaacataca tgacacatca 120
aaatgagaaa tgcacagttt aaccgttcaa cagctggcct tacttcaaaa gaacactata 180
ttcatattaa acatttacag nctttccatc taactttaca catgtcctaa atcattttcc 240
agcacttctc acatagaagt ctagttttgc tctttaaaat caccatctgt atcacccccta 300 gtagacgcga gggtttcccc aattacatgc tgaagagagc cagccaccac cccacctaaa 360
gacatccaag cagctccaga gcctgcctcc gaggccaccc cttcgccacg gcagtctcga 420
ttccaagaac tgattatctg acactagtga accagcacta aaggctgtag gatgtgacta 480
catcacagtt ccagaaggaa gggggaccat ggccaagaga agccctaaat gacagaagct 540
cattaaaacc aagtccccca aaccttctga aacatcgtta gcaaggagct actgntttcc 600

-continued tttcttaaac atggtttggg gcatgacaca ctntggaagt ggtgaactgg tacacanttg 660
gggngngggg acattaacat caaaaactac tgngngnaac ttgagaaagn ctgattaaag 720
attcaatggt ttctaaaact aactcaaatc ggtgaccaga cttttnccag tttattacaa 780 tgngggtgg 789

<210> SEQ ID NO 87
<211> LENGTH: 766
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (523)..(523)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other

<400> SEQUENCE: 87
cactgttngc ctactggctt tttttcagcc caggggcccg gcgcacgaaa cctgtttggg 60
aggttatggg atgataaacc caatcctgaa gccctaagtg acagttcaga gcgtcttttc 120
tcctttggcg tcatcgcaga tgttcaattt gcagacttag aagatggctt taatttccaa 180
ggaaccaggc ggcgatacta cagacatagt cttcttcact tacagggtgc cattgaagac 240
tggaataatg aaagcagcat gccctgttgt gtccttcagc ttggagatat catcgatgga 300
tataatgcac agtataatgc atccaaaaag tccctagaac ttgttatgga catgttcaag 360
aggcttaaag ttccagttca tcatacatgg ggaaaccatg aattctataa cttcagtaga 420
gagtatttaa cacactctaa acttaacact aagtttctag aagatcagat tgtcatcatc 480
ctgagaccat gccttcagaa gattattatg cttatcattt tgnaccattc cctaaattcc 540
gggtcatttt acttgatgca tatgacttga gtgtcttggg ccgtggatca gtcttcttca 600
aaatacgagc agtgnatgaa gatattgagg gagcacaatc caaatacgga ctgaatagtc 660
ctcaaggact tctgagcccc agtttgtcca gttaatggag gattcaagcc aagaacagtt 720
aactgggtga atgaaggcta ccattctntg acccaancaa gaaaag 766

<210> SEQ ID NO 88
<211> LENGTH: 785
<212> TYPE: DNA
<213> ORGANISM: Homo sapiens
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (14)..(14)

<223> OTHER INFORMATION: a, t, c, g, unknown or other
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (503)..(503)
<223> OTHER INFORMATION: a, t, c, g, unknown or other
<220> FEATURE:
<221> NAME/KEY: modified_base
<222> LOCATION: (665)..(665)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (785)..(785)
<223> OTHER INFORMATION: a, t, c, g, unknown or other

<400> SEQUENCE: 88
gaannccttt ngantttttnt actaaacaat gagacagagg atttttattt ttttgtttag 60
gagggacaaa cacaaagctc attttctatc aagttaaaat aaattagact aacaatggaa 120
ggctctttct ttcttgtaat tcataattct atctggaact ctgcctctcc ctttcaacat 180
cattttgtca ggatagacat gaactgtgcc aaaggcttgg ctgtctggag ctgtttcaat 240
aactccttct aggttgacgt ggtatacacc aaaaggatcc tcagagtagc caccatcatg 300
ggtgtgacca gcaaagaaac acaccacaca ctcatgagac caaatgactg ccagggcatc 360
tctgtagttc caggccaggc acacattgtc agaggcgtcc gggtaaatgg gaagatggct 420
cacaatcacc accttttctt ggtttgtgtc agagaatgtt agcacttcat tcaaccagtt 480
tagctggtct tggctgaatc ctncattaaa ctggacaaac tggggctcaa aaagtccttg 540
aggactattc aagttccgta tttggatggg ctcctcaata tcttcataca ctggtcggat 600
tttggagaaa actgatccac gcccaagaca cttaaagcat atgcatcaag taaaatgaac 660
ccggnattta gggaatggtc caaaatggat agccttaata aancttttga aagcattggg 720
cttaaggatg atgtncaatc tggacctttt anaaacttaa gggttaaant taaaaggggg 780 gtaan 785

<210> SEQ ID NO 89
<211> LENGTH: 717
<212> TYPE: DNA
<213> ORGANISM: Homo sapiens
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (707)..(707)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other

<400> SEQUENCE: 89
gggcactgtt ggcctactgg tatagttcat gacctggact ttctgtactc ttggaagctg 60
ggctccttaa aggaggcctc tagtgaacac ctttatctcc atgtccctct tagagcccag 120
agagctgccc ataggcattt tccagaattc ctcatgtcac ctagttcaat ttccattaac 180
tcagatcagc cattgtgatt caccatttgt caggctctca ggtttaacaa aacctactat 240
caccatcatc cttcaacagc cacagtctga attgagccaa catttttttt tctttgagaa 300
agaagtggac tggggcacaa cttttagtct gaggggagct agtggaaatc tagacaatag 360
aagtcatcga tagcagcttt tcctcaaatg tgtgactcct caggggctaa actgctctta 420
gcttagaatt atgctttact agagatctag cagataagtg ggttaatcac taccatcctg 480
taactagtta tatagcttcc agacatgagg gagacatcaa acagggatgg aagcaacccc 540
aaggatatgc aagaagggca tgatgaaccc ccttcctctg gcaggagaac aaggccaacc 600
aagggacaga ctggaaagca cttagatggt taaggaggag aaaggggaac ctttgccagt 660
ccttggcttt tgccaagtca agccagttnt ccgntgcttg naanctntaa cgcagna 717

<210> SEQ ID NO 90
<211> LENGTH: 726
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (656)..(656)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:

-continued

<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other

<400> SEQUENCE: 90
ttttnctttt tggtgtttct ctcttttatt taaaaacagt gcttcattac catgtgcaaa 60
ggctgaggca gtgctcctcc ttcgcttaga gtttataaaa gccagcaaca tgatcaataa 120
tttatacaca tggagagtaa tacaaaaaaa taaggaataa aagctaaaga tctaactact 180
ccgaccttca caattccagc tacttgataa taataagagt aacccaatga atactgtatg 240
gtctgaaagc tactatacaa tatgattctt aacgagaagg gaagggaatt agagactgtc 300
acaaagccct gggatgcttc tctggagtta gcagggaaac aggaccctgg gcaagcagct 360
cgggtgtcct aggaagtgat tctgggggag gacgggaggg gagagagaag gctaggtggt 420
cgattacaca agcatcccat gtaatgcccc catgccccaa aggtacctgt tttgccatgg 480
caatgggagg ggctggagga acagcatgtt gcatgtaggg atggtccggt ccctgccatg 540
gggagtgggg agaagaggag aggttctgtg gcattttgag ccttgcaaag atttggactg 600
aaaagctcan agactcangt aggtcaacct gtcanggaca agtacacttc aacggntntc 660
ttctcgcttt gcagccctac ttacgcgtgt nagccccaag nttgnttcaa cttttcacaa 720 gcagan 726

<210> SEQ ID NO 91
<211> LENGTH: 722
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other

<400> SEQUENCE: 91
ggcactgcng gcctactggc ttcacaatat tctttatttc tctgtctctg tctctctctc 60
tcaagtcaga gtgtacaaca gtaagcaaag tttggcctct gttctcgcgt gaaatcaagt 120
taacatgctc cacctgttga tatgtttgta agagaaatct catgtatatg cacatatgca 180
gaatttctgc tctttgcttc tcaggaaatc tcttttctcc aatgtaggaa gaacacatta 240
aaatgaataa gtcatgttat ttttagaaaa cagaaaagca aataaatgtg tgaatagaat 300
atgcactgtt tctgtgcttg aaacattgaa cattgaatat tgattgaaag gccaccatga 360
actttgaaag accactgtgt tcagagaact gtgatagaaa ctaaaagagt ataaaaagat 420
gtgatacttt catttttgag aggtttacag tgggatgcag aaaaaaagaa acctgtaaat 480
gtgaatggca gtgtgtttgg ttagtgccta ctggctatat aaaattgctt ttggatgtgt 540
ttcatgattc cttataaaac gaagacttaa taagtttact tggcagctga tgggcaaagt 600
tttaaaaaaa atcaaatgag ttttttggtt tcctttaagc agttcctggc aatgctttct 660
ttttttttat ttcaaacaga tgantttttta aaacaatgat tgcatttaga accttcaaga 720
ag 722

-continued

<210> SEQ ID NO 92
<211> LENGTH: 724
<212> TYPE: DNA
<213> ORGANISM: Homo sapiens
<220> FEATURE:
<221> NAME/KEY: modified_base
<222> LOCATION: (696)..(696)
<223> OTHER INFORMATION: a, t, c, g, unknown or other

<400> SEQUENCE: 92

```
tttccctttt ttcggaactg taaggttctt aacttctcca atagtgcacg gctctgaaaa     60

gtacttttag aaagcagttc caacatttct tttcaggcag ttcttaagaa tgttggaatg    120

tgaacaacaa caaaaaaaag ttgcttcaac cacagcctgc actctgcatt tggcccgcaa    180

gcactgctga cgttgcagaa taaataccaa tgacaccaca agcaacttga aaaaattttt    240

tggactgaca aagctcacat tatgcaacac ttaattgagt atatttcttc acatagagag    300

aaacagcaca gtggtcacag ggtaaaatcc agtgaattga atatactggg cattttaatt    360

gcagaaaatt gtgcattcct gccatcattg tttataataa ctacatacac gtgctgcatt    420

aaaccagttc tgagtttaag acctaaatga accagactca gacacacaga ctgctttcct    480

actccctact gccatcatag actaaacaag tatcagtcat gaataaaaca tcaaggtgaa    540

atataaatat acacatcgcc cttctcaaaa gtatcatggc aaaggccctt acacataata    600

aaactgcttg gtgcatctct tatgggaaga cacagagtac agacagctgt gctagtcctg    660

gctcaagagt ccagccttta ttaacccaaa gcttanggcc taagcccctt tgacaccaag    720

gaag                                                                 724
```

<210> SEQ ID NO 93
<211> LENGTH: 758
<212> TYPE: DNA
<213> ORGANISM: Homo sapiens
<220> FEATURE:
<221> NAME/KEY: modified_base
<222> LOCATION: (522)..(522)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (688)..(688)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:

-continued

<221> NAME/KEY: modified_base
<222> LOCATION: (724)..(724)
<223> OTHER INFORMATION: a, t, c, g, unknown or other
<220> FEATURE:
<221> NAME/KEY: modified_base
<222> LOCATION: (730)..(730)
<223> OTHER INFORMATION: a, t, c, g, unknown or other
<220> FEATURE:
<221> NAME/KEY: modified_base
<222> LOCATION: (739)..(739)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 93
cactgttggc ctactggaat tattcagttg cggagacctg tttgagaaaa aaaactcttt 60
gtcttcttta atcaagtgtt gtattgtctg tggcactgtt ttaaatgaaa gacaattaaa 120
ttgctttgct gttttataca ttgttgtctt taatcactag tctaaactct atgtttttat 180
gaaagcatct ttaaattttt tttcttagct gttctttctt gtttgtggta taacctttct 240
gtaccatctt ttggttctgt ggaaatgccc ttaataacac ataggattag gactaaattt 300
tggagatggg taagtttgag caaagagtca gtcaacacag gggaggattt ttgaaatttt 360
atctctaaaa acagttttcc aattcagagt ttttaaaacc cttttaaaaa tatagttagt 420
tttcagtggt ttcttttact tttaagtgtt ttttacacttg gaagtcagat atctaaaaat 480
agggaatggt cttttgctat tttaagatct ctactaaaat gnaatctgta gtgtttcttg 540
gttcagagca tatcttaaaa gatcagacag gggcatttgg ggccctcttc ccatccactg 600
ctttcactca anggaaaata agactcttgg tctgcaaatc tggctntggc anaaatgggc 660
tactggtttn cntggggacc ntttaagnan tatggtggaa gaccgttttc ctcagtggaa 720
accnggtccn aagctttcng gtaaanaagc ctatgacn 758

<210> SEQ ID NO 94
<211> LENGTH: 758
<212> TYPE: DNA
<213> ORGANISM: Homo sapiens
<220> FEATURE:
<221> NAME/KEY: modified_base
<222> LOCATION: (539)..(539)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (590)..(590)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base -continued
<222> LOCATION: (616)..(616)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (625)..(625)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (644)..(644)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (655)..(656)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (675)..(676)
<223> OTHER INFORMATION: a, t, c, g, unknown or other
<220> FEATURE:
<221> NAME/KEY: modified_base
<222> LOCATION: (680)..(682)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (705)..(708)
<223> OTHER INFORMATION: a, t, c, g, unknown or other
<220> FEATURE:
<221> NAME/KEY: modified_base
<222> LOCATION: (715)..(715)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (733)..(734)
<223> OTHER INFORMATION: a, t, c, g, unknown or other
<220> FEATURE:

-continued

<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (756)..(757)
<223> OTHER INFORMATION: a, t, c, g, unknown or other

<400> SEQUENCE: 94
ttttttttta attttttgta gagatgggtc ttgaactctt gggcttaagc gatcctcccg 60
cctcagcctc ctgaagtgtt gggattacag gtgtgagcca catgccaggc ccgaaagttt 120
gtatataaca tacatgaaca tgtctcacca aaacccccaa gctccaaata ttcaaatgaa 180
aattgttcat aaatataaaa cataccctgg aactttgcta tcatattcaa tatcctgaag 240
ttttatttag ggtaaaactt tccatcctga attctgtcaa caaggtttag ttactttaaa 300
actctcatta aatagcagtc tcacctataa agcatatatt catataggtt aaaatattct 360
attgctagaa aacctatggc tcatgtttat ctactgataa agcccaaaag tcttgacttt 420
tcagagaatg gcttttaagt tcactgaggc ttcataacag atgctttttc atttcctatc 480
ataaagagag caggatttta ctatacaggt ggcatattac tggtcaatcc agctatggnt 540
acagcacttt agaccaaacc ggngcanttt tacaaaccac acattgtaan ggttttgaac 600
atttnggana caggtnctgg anatntaant tggtattacc cttntattcc anagnntttc 660
ccttttacna acttnncccn nngaagnagt cccttcncgn ttcannnnac ccttnatttt 720
anctngntnc aanntttttgg naantncntt ttnccnnc 758

<210> SEQ ID NO 95
<211> LENGTH: 747
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (686)..(686)
<223> OTHER INFORMATION: a, t, c, g, unknown or other
<220> FEATURE:
<221> NAME/KEY: modified_base -continued
<222> LOCATION: (692)..(692)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other

<400> SEQUENCE: 95
ngagcactgt tggcctactg gtactagagg tgctaagtta gaacactagg cttttattga 60
ggcaggtttt aatattgata gatgcttttt gtttggtttg tttcttctgg gagagaatgg 120
aggacttaag tagaagtagc tactgataac agactttcta gtagcagttt ccactccacg 180
gttacctttt tagtttcata gtatcttttc acaaagtatt acaaataagc tagattctcc 240
cagtttggga atgcaagttt gctacatttt tagcctggca atatttgtgt aggtattgcc 300
ttattggaaa ttctggaaac ctgatactgc aacctgcaat gtaggatgtt tgtatggcat 360
ttaaaggtaa tggtgatgtt tattattcta tactttgcat tctgtgagag taattttcac 420
tctgtcttaa gtgtgagtaa gcctcttcta aaaatcttgt tcttgccaag aaatttataa 480
atcacatacg aagacgtctg ttgctaacag ttaactttat gaggtaacta tatccttcta 540
tttctctgga ctcattttta aaaaatatgc cgaatctgca tactggttaa ggtagtatat 600
aagtttatga gagaagtgga nagctttctt ccttgaaaag tcggtatttg gtgagatcca 660
tttgcctnac anaaaggtgt ccccantcca tncccattgn cagataataa atattttgag 720
aaaagngcct aaacagctgn aatctta 747

<210> SEQ ID NO 96
<211> LENGTH: 768
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (678)..(678)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 96
ttntttttct tttttaaaaa cccagtagtt ttatttcaaa gtataaattt caggcttgct 60
ggacaaaacc ccactacagg taacacttat acagacacca ctctactata catttaaaaa 120
agaaaaacac acacacgcac gcacacacac acacaaacct tcaaaaccct aataaaaata 180
gggccacttg ctggagccca gtttgtatta gacattagga aggtcttact tacattgtct 240

-continued

```
tattatttac actttcaatt gcaataaaga aaaattagga tgcaagtttc ttacaaagga    300

tttttatatt taattttaaa atggctgata aaatactaaa gccagaatcc ccaaaaggtg    360

tttgattgcc cagttacctt atttacaaaa caaaacaaaa caaaaacaga caaaaacaaa    420

gacctcaaaa aaataataaa gacggcattt aaatatgggt acttagctga ctctacaaat    480

aaaaaacaaa gaaaagttta ttttaacatg gtaaattatt gaaaatgaga aaacaaaaca    540

tgtgtttgca ttatcctatt cctccccatt ggctggctca aggggatgaa tgagtttcaa    600

ggaattagga caagtctggc acactaacaa acgcttcatg agaattgctg atttttgngt    660

gtccaaaagt taaaaatnat aataattaaa aaaatagggc atttgccagt aaaaatagta    720

agggangnag gaatcacaca tcgggtttag aggtatttga tattgcaa                 768
```

```
<210> SEQ ID NO 97
<211> LENGTH: 750
<212> TYPE: DNA
<213> ORGANISM: Homo sapiens
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (627)..(627)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (679)..(679)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other

<400> SEQUENCE: 97
```

```
cgagcactgt tggcctactg gatcgtataa aatcttatgt ggaagccaaa cattaaactg     60

gtaaaaatca tttcaggttg agggtgtatg ttggtgggta cgaagtggtt tcagagcttc    120

cctctcagtt ttcccagtgt tccccaaaga ctcctaggac acctcggggg agctcagggg    180

acccaatgca gcacaactag aggccccagc ctccacactg cctggtgggg gggtctagac    240

tgaatcgtga aatcacccta tctatgggct gtgtgtccag ttgttggggt gaggtctggg    300

gagtggggga tgcaagtggt ggagggaatg aaaggaggga gggaaacttc cagtgcctca    360

tcattcaccc tccccataga tggcacctgg gctccccggg gctgggtcag gctctgagtg    420

acagccattg aagagaagcc agcctccagg aaatttctcc agcatgactg ggcatcctct    480

ctcctagcca aatatatcag agctttgagg aaaatgggct tctggccagg ccacactcgt    540

ccttaggaag agctggttca tctgaggaat ctttttgtag acaggtgctg gtccttgaan    600

ggtangtccg ctgagcttgc gccatanaat gcctacacca ctggcatcct ttagtcctgc    660

tgaagggang gactaactnc tggnaatttt cgtttggtga tcaataaagg ttggtggatt    720

ggcaagtgcc acctggataa ttctacanna                                     750
```

-continued

<210> SEQ ID NO 98
<211> LENGTH: 760
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (575)..(575)
<223> OTHER INFORMATION: a, t, c, g, unknown or other
<220> FEATURE:
<221> NAME/KEY: modified_base
<222> LOCATION: (591)..(591)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (686)..(686)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other

<400> SEQUENCE: 98

```
ttttttttnt ttgtgagggg gaccgagttt tgctctttcc acccaggctg gagtacaatg     60

gtgcaatctt ggctcactgc aacctccgcc tgtcaggttc aagtgattct cctgcctcag    120

cctcccgagt agctgagatt acaggcacac aacaccgtgc ccagctaact tctatatttt    180

tagtagaaac ggggtttcac catgttggcc aggttggtct ctaacttctg acctcaagtg    240

atccaccccc cttcagcctc tcaaagtgct aggattacag gcgtgagcca tcgcgcccag    300

cctgtaataa ttcttaaaaa caatcaacat tataaaaaat aaaaattgta gggtaccatg    360

aaaccaagct gattgttctt cccaggggag gaggaagggc cagagaggat ttggaaggta    420

ttatccagca caggttaggt ttgatcagtc agtggatgct gctgggttgg aaactggatt    480

ttccatctac cagtgcacac tcagccctca gtattcttag agcacatgag gaaaaaaaat    540

cactattaag ctttaatttc cagagccctt actgngtgct ttgtgcaatg nactttattc    600

tnacaacaac ccagagatgt aagnattttt agcccatttg acagatgang aaattgatgc    660

cagaaangat aagaaacttg cttaanggta catagatggg gaaggcaagc ttgcangggt    720

agaaaccaag cccgttggtg aatcctaata ataatgggcc                          760
```

<210> SEQ ID NO 99
<211> LENGTH: 781
<212> TYPE: DNA
<213> ORGANISM: Homo sapiens
<220> FEATURE:
<221> NAME/KEY: modified_base
<222> LOCATION: (543)..(543)

-continued

<223> OTHER INFORMATION: a, t, c, g, unknown or other
<220> FEATURE:
<221> NAME/KEY: modified_base
<222> LOCATION: (650)..(660)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (781)..(781)
<223> OTHER INFORMATION: a, t, c, g, unknown or other

<400> SEQUENCE: 99
cactgttggc ctactggatt aatttactcg cagttgctgc tgctcaggaa gagagacaag 60
gaatatttta acagaatcaa ggcatagaag aatcaccatt ttatttgagc ctctaatcag 120
agtcagacca gtagagaaat taaataagat tagaaaactc tgtactgaaa gctgctgatg 180
cttcaaaaat gaaaacaaga tctcacaact ctccctgtta gttgaaaata tatcaatttg 240
ctctgaaagg attcagctgc ctagtgttgc cattactaac ataaacatat ggctcatatt 300
tccatccaga gaaattaatg ctaaattggt gcctcgctaa catcagatac actgtattat 360
gcttaaatat attcagtaaa atgtggaaag gggtattaac aacgacaaca aaaagatgga 420 ttttttttt ctcacaatca cagttgctaa tccagtggga gatgtttgag agagttttgt 480
tcaacatcac agtgagagtg cctagggaaa tcagaaaatt acaatggatt cccctttgat 540
tgnaataagt gttgattttc tccatgagtt ggttatcctg tctagtgatt tgatggtgaa 600
cttttctaaa taaatagccc tttcccttcg gtgtcggtaa aaaaaaaaan nnnnnnnnnn 660
aaaaaaaaag gccacatgtg ctcgaactgc aggtcgnggn ccgttagact agtctaagag 720
aaaaaccttc canacttncc ctgaacctga acnttaaaag gatgccattg gtggtggtaa 780 n 781

<210> SEQ ID NO 100
<211> LENGTH: 776
<212> TYPE: DNA
<213> ORGANISM: Homo sapiens
<220> FEATURE:
<221> NAME/KEY: modified_base
<222> LOCATION: (302)..(302)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (558)..(558)
<223> OTHER INFORMATION: a, t, c, g, unknown or other
<220> FEATURE:
<221> NAME/KEY: modified_base -continued
<222> LOCATION: (700)..(700)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (773)..(773)
<223> OTHER INFORMATION: a, t, c, g, unknown or other

<400> SEQUENCE: 100
tttttttttt tttaccgaca ccggaggggga aagggctatt tatttagaaa agttcaccat 60
caaatcacta gacaggataa acaactcatg gagaaaatca acacttatta caatcaaagg 120
ggaatccatt gtaattttct gatttcccta ggcactctca ctgtgatgtt gaacaaaact 180
ctctcaaaca tctcccactg gattagcaac tgtgattgtg agaaaaaaaa aatccatctt 240
tttgttgtcg ttgttaatac ccctttccac attttactga atatatttaa gcataataca 300
gngtatctga tgttagcgag gcaccaattt agcattaatt tctctggatg gaaatatgag 360
ccatatgttt atgttagtaa tggcaacact aggcagctga atcctttcag agcaaattga 420
tatattttca actaacaggg agagttgtga gatcttgntt tcatttttga agcatcagca 480
gctttcagta cagagttttc taatcttatt taatttctct actggtctga ctctgattag 540
aggctcaaat aaaatggnga ttcttctatg ccttgattct ggtaaaatat tccttggctc 600
tcttcctgag cagcagcaac tgcgagtaaa ttaatccagt aggccaacag gctcgaggaa 660
ttccgcagct tttaaagcag aagtacactt ccgtcaaggn ctanaagtaa aggcaccatc 720
cctgnggagc cagtctttgg anttgnacca ccaccggatc cgggaccgga aanaat 776

<210> SEQ ID NO 101
<211> LENGTH: 740
<212> TYPE: DNA
<213> ORGANISM: Homo sapiens
<220> FEATURE:
<221> NAME/KEY: modified_base
<222> LOCATION: (6)..(6)
<223> OTHER INFORMATION: a, t, c, g, unknown or other
<220> FEATURE:
<221> NAME/KEY: modified_base
<222> LOCATION: (16)..(16)
<223> OTHER INFORMATION: a, t, c, g, unknown or other
<220> FEATURE:
<221> NAME/KEY: modified_base
<222> LOCATION: (106)..(106)
<223> OTHER INFORMATION: a, t, c, g, unknown or other
<220> FEATURE:
<221> NAME/KEY: modified_base
<222> LOCATION: (594)..(594)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (681)..(681)

-continued

<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other

<400> SEQUENCE: 101
actgtnggcc tactgncaga tgaactaggt cagatccctt ggaaagattg aatatagaat 60
tttaatggca tcaaatagtt ctgtccttcc atattagaca attatntttc aaccgaagtc 120
acattttgga gaagactcta taccagaatc ttagtaagag ctttttattc tctgtgtagt 180
agtaggatag ctttttgggg gtgttttcct ggtttttcca aattgctaca attttaacaa 240
ttatgatcat gaatagcaaa aagaaagaaa acatcactca gaagtgaaga aaagcgcttg 300
gtcagacaca aaagcccagt cacaaaggtt aaaataacca tcattttgtg agccttttta 360
caatgcacta gacaccgtga ggtgtgcatc atctccatcc ctcacagcag cactgaaggg 420
tagatgatat tattcccagc atcctattgc tatccagagg gaaaggaggc ttagccaacg 480
ggctgcaaac attccaattc cttttcctga gatggacgca tgaactctct tggcccaaag 540
gcattaaata ttccggccat gtaacccgat gccccttctt ggaattcaga gctnccctgc 600
aacctgctgg gtatcatttg gcttctatca cangctggca acggtgagaa gtacacatgg 660
gtcacgctca tgtaaatatt ncagaccata tggcangtgg gatttctcac tgnaaatgaa 720
cacattggct ttggtctata 740

<210> SEQ ID NO 102
<211> LENGTH: 742
<212> TYPE: DNA
<213> ORGANISM: Homo sapiens
<220> FEATURE:
<221> NAME/KEY: modified_base
<222> LOCATION: (68)..(68)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (500)..(500)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other

<400> SEQUENCE: 102
ttttcttttt ctttggaggt caccatttct gagctggaaa gttaggactc attggatgat 60

-continued

```
catgaatnca taagaaggta gaaatcggtg aagggcccac tattaaccta tcatttagaa    120

atgattttca tgggtcattt attaagagcc catggaaaga gttctgcaaa gatccctgaa    180

agaaatgcag ctcttgccca gtcatcacct tttacggttg agaaagttga agctcagaga    240

aattataaac tccaccaagt tttgtacagg ttagtagcag agtctaaagt ctgctgtttt    300

acccttattt tggtgttcct ttaacacgta ttattgtaca tctactgtcc taggaactga    360

gcaaattaca tttgttgttt accccaaact ttgatattag gaaagaaaaa aacatgtatc    420

ttaaaacaac gaaaggaaga tctgtttcct ttttcatctt ttgtgcattt gccctctttc    480

tagnttctta agtttaatgn ttcttttttta gtaacctata ggacattgca ctaggcctga    540

aggagaaaga cattttgggc tgcagtgaca agaaagtgat agtttaatgc aagggttccc    600

caaaatggta tgagaagctt ctattttaca ttttattttc attggtggnt ttttggtttt    660

aaagatggng aagtggggca aaaagtggaa ntttccactg gaagngaatt ttgggctttt    720

ttactgggat tcaangggaa ga                                             742
```

<210> SEQ ID NO 103
<211> LENGTH: 734
<212> TYPE: DNA
<213> ORGANISM: Homo sapiens
<220> FEATURE:
<221> NAME/KEY: modified_base
<222> LOCATION: (6)..(6)
<223> OTHER INFORMATION: a, t, c, g, unknown or other
<220> FEATURE:
<221> NAME/KEY: modified_base
<222> LOCATION: (15)..(15)
<223> OTHER INFORMATION: a, t, c, g, unknown or other

<400> SEQUENCE: 103

```
ctgtcngcct actgntccac aacagaaaat agactgaatt taaaaaaatt gatgattatg     60

aaaaatttgg tgatttccag aaatatgagt ttactcgttt aaaatagatg actcagtata    120

gaatttcatg tgataatgtt tttcattagt attcatgatc tgatcctaga aatatttttc    180

tcgtgttttt tttttttcca aacaatttat tttagattgc aactagtaga taattgcttt    240

atgttttagg gaaaagaatc gcttaattat tgtaatccct caaacacaat attggaactt    300

ttaccatgac catttctaat gccagcccca caatatagct gaatcttgcc atcaagctta    360

ctatctaagg aatctcagtc ttcttttcta gtttatgaac tacggtaatt gaaaaaaggg    420

atttccaaaa gataattgta ttgattaatc caatttctgg gttgagcata aggttgtaaa    480

ttggagatca ttcatataaa ttgaatacaa agggagaatt ttttttaagt cttttttttga    540

catattaaat gatttatgct gaactcctaa aagctttcca gccccacaga gcttcaatag    600

atgtctaatg gagcctgaat gccagctcta tttttggtgc ttatccagta ggtgggaaac    660

ctttaacagt aggatgagtc tttggttccg ttccatggaa aagctcatgg gctaacattt    720

atgacttcta atgt                                                      734
```

<210> SEQ ID NO 104
<211> LENGTH: 738
<212> TYPE: DNA
<213> ORGANISM: Homo sapiens
<220> FEATURE:
<221> NAME/KEY: modified_base
<222> LOCATION: (587)..(587)
<223> OTHER INFORMATION: a, t, c, g, unknown or other
<220> FEATURE:
<221> NAME/KEY: modified_base
<222> LOCATION: (600)..(600)

-continued

<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (653)..(653)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (721)..(721)
<223> OTHER INFORMATION: a, t, c, g, unknown or other

<400> SEQUENCE: 104
ccttttaaga ggtggggtct tgctatatca ccatggctgc agcgatcctg gactcaaggg 60
agtggctggg actaaaggcg tgcaccaccg cacctggctt taaattctcc cttttcctgc 120
tttgtgtgag tgagataagc agtatgcatg agaagatctt agagtaagaa agtcaaagaa 180
gacgacagtg atttgagctg cttcattgtt tggccccaaa gccaggcaga cctcatagtt 240
ctagcagcca ggatcctggt gttaatcagt gtcaataact taattttagt gttttgctct 300
tttcctgagt cagcagttag tttccatgat ttttacctga attctttggt tatcgggtct 360
ttaatctgcg ttgaggattt agtgtgttgg gagagtctgc tgcttgtgcc aaggcttcct 420
gctgctccag gccagtttag cagtgtgacc actgctcacc atcagctgac ggagcttcag 480
tccctgtgct ccagccttgt tccccggaca cctgctaagg ccaacagcta gatattcagc 540
acctgtctga ccagataccg ttcctacaga ggcatctgct actttgnatg cacaagcttn 600
cacatgttgc tataatctgn tccaatgncc tactccttgg tggtgatttt ctncaattct 660
caatggccag cctttcattg gcccaatgca actggccctg atntgncang tncaacaggg 720
nttttcagat actagaag 738

<210> SEQ ID NO 105
<211> LENGTH: 27
<212> TYPE: RNA
<213> ORGANISM: Artificial Sequence
<220> FEATURE:
<223> OTHER INFORMATION: Description of Artificial Sequence: Synthetic
RNA sequence

<400> SEQUENCE: 105
agcaucgagu cggccuuggc cuacugg 27

<210> SEQ ID NO 106
<211> LENGTH: 42
<212> TYPE: DNA

-continued

```
<213> ORGANISM: Artificial Sequence
<220> FEATURE:
<223> OTHER INFORMATION: Description of Artificial Sequence: Adapter-
      primer

<400> SEQUENCE: 106

gcggctgaag acggcctatg tggccttttt tttttttttt tt                        42


<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 107

agcatcgagt cggccttgtt g                                               21


<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 108

gcgctgaaga cggcctatgt                                                 20
```